(12) United States Patent
Hutt et al.

(10) Patent No.: US 12,269,881 B2
(45) Date of Patent: *Apr. 8, 2025

(54) ANTIGEN BINDING PROTEINS SPECIFICALLY BINDING MAGE-A

(71) Applicant: Immatics Biotechnologies GmbH, Tuebingen (DE)

(72) Inventors: Meike Hutt, Tuebingen (DE); Felix Unverdorben, Tuebingen (DE); Sebastian Bunk, Tuebingen (DE); Dominik Maurer, Tuebingen (DE); Martin Hofmann, Tuebingen (DE); Gabriele Pszolla, Tuebingen (DE); Sara Yousef, Tuebingen (DE); Claudia Wagner, Tuebingen (DE); Frank Schwoebel, Tuebingen (DE); Heiko Schuster, Tuebingen (DE)

(73) Assignee: Immatics Biotechnologies GmbH, Tübingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/538,242

(22) Filed: Dec. 13, 2023

(65) Prior Publication Data

US 2024/0117068 A1    Apr. 11, 2024

Related U.S. Application Data

(63) Continuation of application No. 18/483,174, filed on Oct. 9, 2023, now abandoned, which is a continuation of application No. 16/943,779, filed on Jul. 30, 2020, now Pat. No. 11,840,577.

(60) Provisional application No. 62/905,782, filed on Sep. 25, 2019, provisional application No. 62/882,131, filed on Aug. 2, 2019.

(30) Foreign Application Priority Data

Aug. 2, 2019 (DE) .......................... 102019121007.0

(51) Int. Cl.
| | |
|---|---|
| *C07K 16/28* | (2006.01) |
| *A61K 39/00* | (2006.01) |
| *A61P 35/00* | (2006.01) |
| *C07K 14/725* | (2006.01) |
| *C07K 16/30* | (2006.01) |
| *C07K 16/46* | (2006.01) |

(52) U.S. Cl.
CPC ........ *C07K 16/2809* (2013.01); *A61K 39/461* (2023.05); *A61K 39/4632* (2023.05); *A61K 39/464486* (2023.05); *A61P 35/00* (2018.01); *C07K 14/7051* (2013.01); *C07K 16/30* (2013.01); *C07K 16/468* (2013.01); *C07K 2317/24* (2013.01); *C07K 2317/32* (2013.01); *C07K 2317/55* (2013.01); *C07K 2317/565* (2013.01); *C07K 2317/567* (2013.01); *C07K 2317/622* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,179,338 | A | 12/1979 | Gordon |
| 4,301,144 | A | 11/1981 | Iwashita et al. |
| 4,496,689 | A | 1/1985 | Mitra |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 4,861,719 | A | 8/1989 | Miller |
| 4,975,278 | A | 12/1990 | Senter et al. |
| 5,202,238 | A | 4/1993 | Fell et al. |
| 5,204,244 | A | 4/1993 | Fell et al. |

(Continued)

FOREIGN PATENT DOCUMENTS

| | | |
|---|---|---|
| AU | 2003236645 B2 | 6/2009 |
| CL | 2022000252 A1 | 9/2022 |

(Continued)

OTHER PUBLICATIONS

Paul, Fundamental Immunology, 3rd Edition, 1993, pp. 292-295 (Year: 1993).*

(Continued)

*Primary Examiner* — Michael Allen
(74) *Attorney, Agent, or Firm* — McBee, Moore & Vanik IP, LLC

(57) ABSTRACT

The present invention concerns antigen binding proteins specifically binding melanoma associated antigen A (MAGE-A) protein-derived antigens. The invention in particular provides antigen binding proteins which specifically bind to the MAGE-A antigenic peptide comprising or consisting of SEQ ID NO: 1 in a complex with a major histocombatibility (MHC) protein. The antigen binding proteins of the invention contain, in particular, the complementary determining regions (CDRs) of novel engineered T cell receptors (TCRs) that specifically bind to said MAGE-A peptide/MHC complex. The antigen binding proteins of the invention are of use for the diagnosis, treatment and prevention of MAGE-A expressing cancerous diseases. Further provided are nucleic acids encoding the antigen binding proteins of the invention, vectors comprising these nucleic acids, recombinant cells expressing the antigen binding proteins and pharmaceutical compositions comprising the antigen binding proteins of the invention.

8 Claims, 23 Drawing Sheets

Specification includes a Sequence Listing.

(56) References Cited

U.S. PATENT DOCUMENTS

| | | |
|---|---|---|
| 5,208,020 A | 5/1993 | Chari et al. |
| 5,278,056 A | 1/1994 | Bank et al. |
| 5,624,821 A | 4/1997 | Winter et al. |
| 5,731,168 A | 3/1998 | Carter et al. |
| 5,807,706 A | 9/1998 | Carter et al. |
| 5,821,333 A | 10/1998 | Carter et al. |
| 5,882,877 A | 3/1999 | Gregory et al. |
| 6,013,516 A | 1/2000 | Verma et al. |
| 6,018,032 A | 1/2000 | Koike et al. |
| 6,127,175 A | 10/2000 | Vigne et al. |
| 6,464,998 B1 | 10/2002 | Beuzard et al. |
| 6,805,861 B2 | 10/2004 | Stauss |
| 7,429,652 B2 | 9/2008 | Wang et al. |
| 7,642,228 B2 | 1/2010 | Carter et al. |
| 7,695,936 B2 | 4/2010 | Carter et al. |
| 7,811,828 B2 | 10/2010 | Lemmel et al. |
| 8,216,805 B2 | 7/2012 | Carter et al. |
| 9,688,762 B2 | 6/2017 | Igawa et al. |
| 9,791,443 B2 | 10/2017 | Weinschenk et al. |
| 9,791,444 B2 | 10/2017 | Weinschenk et al. |
| 10,106,805 B2 | 10/2018 | Spangenberg et al. |
| 10,538,573 B2 | 1/2020 | Maurer et al. |
| 10,683,495 B2 | 6/2020 | Bunk et al. |
| 11,028,142 B2 | 6/2021 | Baeuerle et al. |
| 11,104,894 B2 | 8/2021 | Bunk et al. |
| 11,464,800 B2 | 10/2022 | Kalra et al. |
| 11,840,577 B2 | 12/2023 | Hutt et al. |
| 2008/0038285 A1 | 2/2008 | Lemmel et al. |
| 2009/0060910 A1 | 3/2009 | Johnson et al. |
| 2010/0034841 A1 | 2/2010 | Nishimura |
| 2011/0027266 A1 | 2/2011 | Lee et al. |
| 2011/0189141 A1 | 8/2011 | Kieback et al. |
| 2011/0257890 A1 | 10/2011 | Weinschenk et al. |
| 2011/0318380 A1 | 12/2011 | Brix et al. |
| 2013/0096016 A1 | 4/2013 | Weinschenk et al. |
| 2013/0273647 A1 | 10/2013 | Sahin et al. |
| 2015/0166661 A1 | 6/2015 | Chen et al. |
| 2015/0337369 A1 | 11/2015 | Davis et al. |
| 2016/0017038 A1 | 1/2016 | Koenig |
| 2016/0187351 A1 | 6/2016 | Weinschenk et al. |
| 2016/0279215 A1 | 9/2016 | Mahr et al. |
| 2017/0267738 A1 | 9/2017 | Maurer et al. |
| 2017/0296641 A1 | 10/2017 | Weinschenk et al. |
| 2017/0342154 A1 | 11/2017 | Igawa et al. |
| 2018/0135039 A1 | 5/2018 | Bunk et al. |
| 2018/0162922 A1 | 6/2018 | Bunk et al. |
| 2018/0208657 A1 | 7/2018 | Jung et al. |
| 2019/0016801 A1 | 1/2019 | Hofmann et al. |
| 2019/0016802 A1 | 1/2019 | Hofmann et al. |
| 2019/0016803 A1 | 1/2019 | Hofmann et al. |
| 2019/0016804 A1 | 1/2019 | Hofmann et al. |
| 2019/0175650 A1 | 6/2019 | Dao et al. |
| 2019/0185539 A1 | 6/2019 | Ogasawara |
| 2019/0192691 A1 | 6/2019 | Barrett et al. |
| 2019/0216852 A1 | 7/2019 | Kalra et al. |
| 2019/0256571 A1 | 8/2019 | Baeuerle et al. |
| 2019/0292520 A1 | 9/2019 | Alpert |
| 2019/0309042 A1 | 10/2019 | Maurer et al. |
| 2019/0336531 A1 | 11/2019 | Stauss et al. |
| 2019/0338012 A1 | 11/2019 | Stauss et al. |
| 2020/0085930 A1 | 3/2020 | Weinschenk et al. |
| 2020/0263162 A1 | 8/2020 | Bunk et al. |
| 2021/0032361 A1 | 2/2021 | Hutt et al. |
| 2021/0032370 A1 | 2/2021 | Pszolla et al. |
| 2021/0041435 A1 | 2/2021 | Ogasawara |
| 2021/0238543 A1 | 8/2021 | Renes et al. |
| 2021/0355478 A1 | 11/2021 | Bunk et al. |
| 2021/0380659 A1 | 12/2021 | Bunk et al. |
| 2022/0080030 A1 | 3/2022 | Johnson et al. |
| 2022/0119479 A1 | 4/2022 | Conroy et al. |
| 2022/0185888 A1 | 6/2022 | Hofmann et al. |
| 2022/0195044 A1 | 6/2022 | Hoffmann et al. |
| 2022/0267406 A1 | 8/2022 | Stauss et al. |
| 2022/0356252 A1 | 11/2022 | Bunk et al. |
| 2023/0203200 A1 | 6/2023 | Pszolla et al. |
| 2023/0348598 A1 | 11/2023 | Hoffmann et al. |
| 2024/0052054 A1 | 2/2024 | Hutt et al. |

FOREIGN PATENT DOCUMENTS

| | | |
|---|---|---|
| EP | 1930433 A1 | 6/2008 |
| EP | 2258719 A1 | 12/2010 |
| EP | 2660250 A1 | 11/2013 |
| EP | 2752198 A1 | 7/2014 |
| EP | 2897981 A1 | 7/2015 |
| EP | 3015477 B1 | 5/2016 |
| EP | 3286210 A1 | 2/2018 |
| EP | 2970484 B1 | 5/2018 |
| EP | 3443001 A2 | 2/2019 |
| EP | 3494138 A1 | 6/2019 |
| EP | 3494984 A1 | 6/2019 |
| EP | 3529267 A1 | 8/2019 |
| EP | 3529352 A2 | 8/2019 |
| EP | 3770168 A1 | 1/2021 |
| EP | 3886872 A1 | 10/2021 |
| EP | 3911298 A1 | 11/2021 |
| EP | 3917955 A1 | 12/2021 |
| JP | 2013126415 A | 6/2013 |
| WO | 8101145 A1 | 4/1981 |
| WO | 8705330 A1 | 9/1987 |
| WO | 8807378 A1 | 10/1988 |
| WO | 9411026 A1 | 5/1994 |
| WO | 9419478 A1 | 9/1994 |
| WO | 9514785 A1 | 6/1995 |
| WO | 9622378 A1 | 7/1996 |
| WO | 9710354 A1 | 3/1997 |
| WO | 200148145 A1 | 7/2001 |
| WO | 2003100432 A2 | 12/2003 |
| WO | 2004044004 A2 | 5/2004 |
| WO | 2004091668 A1 | 10/2004 |
| WO | 2005076009 A1 | 8/2005 |
| WO | 2007032255 A1 | 3/2007 |
| WO | 2008053579 A1 | 5/2008 |
| WO | 2009032661 A1 | 3/2009 |
| WO | 2011044186 A1 | 4/2011 |
| WO | 2011128448 A1 | 10/2011 |
| WO | 2012135345 A1 | 10/2012 |
| WO | 2013026837 A1 | 2/2013 |
| WO | 2013057596 A1 | 4/2013 |
| WO | 2014018863 A1 | 1/2014 |
| WO | 2014043441 A1 | 3/2014 |
| WO | 2014159940 A1 | 10/2014 |
| WO | 2015075939 A1 | 5/2015 |
| WO | 2016107740 A1 | 7/2016 |
| WO | 2016116626 A1 | 7/2016 |
| WO | 2016184592 A1 | 11/2016 |
| WO | 2017070608 A1 | 4/2017 |
| WO | 2017109496 A1 | 6/2017 |
| WO | 2017157972 A1 | 9/2017 |
| WO | 2017158103 A1 | 9/2017 |
| WO | 2018091396 A1 | 5/2018 |
| WO | 2018104407 A1 | 6/2018 |
| WO | 2019012138 A1 | 1/2019 |
| WO | 2019012141 A1 | 1/2019 |
| WO | 2019219709 A1 | 11/2019 |
| WO | 2019235915 A1 | 12/2019 |
| WO | 2020109616 A1 | 6/2020 |
| WO | 2020148372 A1 | 7/2020 |
| WO | 2020157211 A1 | 8/2020 |
| WO | 2020236795 A2 | 11/2020 |
| WO | 2021023657 A1 | 2/2021 |
| WO | 2021073624 A1 | 4/2021 |

OTHER PUBLICATIONS

Bendig M. M. (Methods: A Companion to Methods in Enzymology, 1995; 8:83-93) (Year: 1995).*

Rudikoff et al. (Proceedings of the National Academy of Sciences USA, vol. 79, p. 1979-1983, 1982) (Year: 1982).*

International Search Report Issued in Counterpart Application No. PCT/EP2020/071660 Mailed Oct. 13, 2020.

(56) References Cited

OTHER PUBLICATIONS

Janeway, Jr., Charles A., et al. "Immunobiology" 5th Ed., Garland Science, pp. 117-118, 2001.
Jendeberg, Lena, et al. "Engineering of Fc1 and Fc3 from human immunoglobulin G to analyse subclass specificity for staphylococcal protein A1" Journal of Immunological Methods, vol. 201, pp. 25-34, Feb. 1997.
Jespers, Laurent S., et al. "Guiding the Selection of Human Antibodies from Phage Display Repertoires to a Single Epitope of an Antigen" Bio/Technology, vol. 12, No. 9, pp. 899-903, Sep. 1994.
Jevsevar, Simona, et al. "PEGylation of therapeutic proteins" Biotechnology Journal: Healthcare Nutrition Technology, vol. 5, No. 1, pp. 113-128, Jan. 2010.
Jones, Andrew J.S. "Analysis of polypeptides and proteins" Advanced Drug Delivery Reviews, vol. 10, pp. 29-90, Jan.-Apr. 1993.
Kageyama, et al., "Adoptive Transfer of MAGE-A4 T-cell Receptor Gene-Transduced Lymphocytes in Patients with Recurrent Esophageal Cancer," Clinical Cancer Research, (2015), vol. 21, No. 10: 2268-2277.
Kessler, Jan H., et al. "Efficient Identification of Novel HLA-A*0201-presented Cytotoxic T Lymphocyte Epitopes in the Widely Expressed Tumor Antigen Prame by Proteasome-mediated Digestion Analysis" Journal Exp. Med., vol. 193, No. 1, pp. 73-88, Jan. 2001.
Kirin, Srecko I., et al. "Amino Acid and Peptide Bioconjugates of Copper(II) and Zinc(II) Complexes with a Modified N, N-Bis(2-picolyl)amine Ligand" Inorganic Chemistry, vol. 44, pp. 5405-5415, Jul. 2005.
Knapp, Bernhard, et al. "Variable Regions of Antibodies and T-Cell Receptors May Not be Sufficient in Molecular Simulations Investigating Binding" Journal of Chemical Theory and Computation, vol. 13, pp. 3097-3105, Jun. 2017.
Knies, Diana, et al. "An optimized single chain TCR scaffold relying on the assembly with the native CD3-complex prevents residual mispairing with endogenous TCRs in human T-cells" Oncotarget, vol. 7, No. 16, pp. 21199-21221, Mar. 2016.
Kontermann, Roland E., et al. "Complement recruitment using bispecific diabodies" Nature Biotechnology, vol. 15, No. 7, pp. 629-631, Jul. 1997.
Kontermann, Roland E., et al. "Enzyme immunoassays using bispecific diabodies" Immunothechnology, vol. 3, No. 2, pp. 137-144, Jun. 1997.
Kuwana, Yoshihisa, et al. "Expression of Chimeric Receptor Composed of Immunoglobulin-Derived V Resions and T-Cell Receptor-Derived C Regions", vol. 149, No. 3, pp. 960-968, Dec. 31, 1987.
Lacy, Susan E., et al. "Generation and characterization of ABT-981, adual variable domain immunoglobulin (DVD-IgTM)molecule that specifically and potentlyneutralizes both IL-1aand IL-1b" mAbs, vol. 7, pp. 605-619, May/Jun. 2015.
Lefranc, Marie-Paule, et al. "IMGT unique numbering for immunoglobulin and T cell receptor variable domains and Ig superfamily V-like domains" Developmental & Comparative Immunology, vol. 27, No. 1, pp. 55-77, 2003.
Lefranc, Marie-Paule, et al. "IMGTR, the international ImMunoGeneTics information system(R) 25 years on" Nucleic Acids Research, vol. 43, Database issue D413-D422, Jan. 2015.
Linette, Gerald P. et al., "Cardiovascular toxicity and titin cross-reactivity of affinity-enhanced T cells in myeloma and melanoma", Blood, Aug. 8, 2013, pp. 863-871, vol. 122, No. 6.
Liu, Liqin, et al. "MGD011, A CD19 x CD3 Dual-Affinity Retargeting Bi-specific Molecule Incorporating Extended Circulating Half-life for the Treatment of B-Cell Malignancies" Clinical Cancer Research, vol. 23, No. 6, pp. 1506-1518, Mar. 2017.
Manning et al., "Alanine Scanning Mutagenesis of an αβ T Cell Receptor: Mapping the Energy of Antigen Recognition," Immunity, (1998), vol. 8: 413-425.
Mason, John O., et al. "Transcription Cell Type Specificity is Conferred by an Immunoglobulin VH Gene Promoter That Includes a Functional Consensus Sequence" Cell, vol. 41, pp. 479-487, Jun. 1985.
Merchant, A.M., et al. "An efficient route to human bispecific IgG" Nature Biotechnology, vol. 16, No. 7, pp. 677-681, Jul. 1998.
Merten, Christoph, et al. "Directed Evolution of Retrovirus Envelope Protein Cytoplasmic Tails Guided by Functional Incorporation into Lentivirus Particles" Jounral of Virology, vol. 79, No. 2, pp. 834-840, Jan. 2005.
Miles, John J., et al. "Understanding the complexity and malleability of T-cell recognition" Immunology and Cell Biology, vol. 93, No. 5, pp. 433-441, May 2015.
Mitchell, Rod T., et al. "Intratubular germ cell neoplasia of the human testis: heterogeneous protein expression and relation to invasive potential" Modern Pathology, vol. 27, pp. 255-266, Sep. 2014.
Miyaji, Hiromasa, et al. "Expression of human beta-interferon in Namalwa KJM-1 which was adapted to serum-free medium" Cytotechnology, vol. 3, No. 2, pp. 133-140, Mar. 1990.
Mizukami, Yuji, et al. "Primary T-Cell Lymphoma of the Thyroid" Pathology International, vol. 37, Issue 12, pp. 1987-1995, Dec. 1987.
Moore, Paul A., et al. "Application of dual affinity retargeting molecules to achieve optimal redirected T-cell killing of B-cell lymphoma" Blood, vol. 117, No. 17, pp. 4542-4551, Apr. 2011.
Morgan, A., et al. "The N-terminal end of the CH2 domain of chimeric human IgG1 anti-HLA-DR is necessary for C1q, FcγRI and FcγRIII binding", Immunology, vol. 86, pp. 319-324, Oct. 1995.
Morgan, Richard A., et al. "Cancer Regression in Patients After Transfer of Genetically Engineered Lymphocytes" Science, vol. 314, pp. 126-129, Oct. 6, 2006.
Morrison, Sherie L., et al. "Chimeric human antibody molecules: Mouse antigen-binding domains with human constant region domains" Proc. Natl. Acad. Sci., vol. 81, pp. 6851-6855, Nov. 1984.
Nakatsugawa et al., "Identification of an HLA-A*0201-restricted cytotoxic T lymphocyte epitope from the lung carcinoma antigen, Lengsin," International Journal of Oncology, (2011), vol. 39: 1041-1049.
Needleman, Saul B., et al. "A general Method Applicable to the Search for Similarities in the Amino Acid Sequence of Two Proteins" Journal Molecular Biology, vol. 48, pp. 443-453, Mar. 1970.
Neuberger, M.S., et al. "A hapten-specific chimaeric IgE antibody with human physiological effector function" Nature, vol. 314, pp. 268-270, Mar. 1985.
O'Hare, K., et al. "Transformation of mouse fibroblasts to methotrexate resistance by a recombinant plasmid expressing a prokaryotic dihydrofolate reductase" Proceedings of the National Academy of Sciences, vol. 78, No. 3, pp. 1527-1531, Mar. 1981.
Ohkuri et al., "Identification of novel helper epitopes of MAGE-A4 tumor antigen: useful tool for the propagation of ThI cells" British Journal of Cancer (2009) pp. 1135-1143.
Onuoha, Shimobi C., et al. "Rational Design of Antirheumatic Prodrugs Specific for Sites of Inflammation" Arthritis & Rheumatology, vol. 67, No. 10, pp. 2661-2672, Oct. 2015.
Paul et al., "Fundamental Immunology: Third Edition," Raven Press, pp. 292-295, 1993.
Piccione, Emily C., "A bispecific antibody targeting CD47 and CD20 selectively binds and eliminates dual antigen expressing lymphoma cells" mAbs, vol. 7, No. 5, pp. 946-956, Sep. 2015.
Piepenbrink et al., "The basis for limited specificity and MHC restriction in a T cell receptor interface," Nature Communications, (2013), vol. 4: 1948.
Plebanski, Magdalena, et al. "Induction of peptide-specific primary cytotoxic T lymphocyte responses from human peripheral blood" European Journal of Immunology, vol. 25, No. 6, pp. 1783-1787, Jun. 1995.
Popovic et al., "The only proposed T-cell epitope derived from the TEL-AML 1 translocation is not naturally processed," Blood, (2011), vol. 118, No. 4: 946-954.
Portolano et al., "Lack of Promiscuity in Autoantigen-Specific H and L Chain Combinations as Revealed by Human H and L Chain 'Roulette'," J Immunol., (1993), vol. 150, No. 3: 880-7.
Rader, Christoph. "CARTs take aim at BiTEs" Blood, vol. 117, No. 17, pp. 4403-4404, Apr. 28, 2011.

(56) References Cited

OTHER PUBLICATIONS

Reichmann, Lutz, et al. "Reshaping human antibodies for therapy" Nature, vol. 332, No. 24, pp. 323-327, Mar. 1988.

Reiter, Yoram, et al. "Stabilization of the Fv Fragments in Recombinant Immunotoxins by Disulfide Bonds Engineered into Conserved Framework Regions" Biochemistry, vol. 33, pp. 5451-5459, May 1994.

Rice, Peter, et al. "EMBOSS: The European Molecular Biology Open Software Suite" Trend in Genetics, vol. 16, No. 6, pp. 276-277, Jun. 2000.

Richman, Sarah A., et al. "Structural features of T cell receptor variable regions that enhance domain stability and enable expression as single-chain V-alpha V-beta fragments" Molecular Immunology, vol. 46, pp. 902-916, 2009 (with 4 pp. of Supplementary Fig. 1 attached).

Rudikoff et al., "Single amino acid substitution altering antigen-binding specificity," Proc. Natl. Acad. Sci. USA, vol. 79. pp. 1979-1983, Mar. 1982.

Sarcevic, Bozena, et al. "Expression of Cancer/Testis Tumor Associated Antigens in Cervical Squamous Cell Carcinoma" Oncology, vol. 64, No. 4, pp. 443-449, 2003.

Aggen, David H., et al. "Identification and engineering of human variable regions that allow expression of stable single-chain T cell receptors" Protein Engineering, Design & Selection, vol. 24, No. 4, pp. 361-372, Apr. 2011.

Aleksic, Milos, et al. "Different affinity windows for virus and cancer-specific T-cell receptors: implications for therapeutic strategies" European Journal of Immunology, vol. 42, No. 12, pp. 3174-3179, Dec. 2012.

Almagro, Juan C., et al. "Humanization of antibodies" Frontiers in Bioscience, vol. 13, pp. 1619-1633, Jan. 1, 2008.

Altschul, Stephen F., et al. "Gapped Blast and PSI-Blast: a new generation of protein database search programs" Nucleic Acids Research, vol. 25, No. 17, pp. 3389-3402, 1997.

Atwell, John L., et al. "Design and Expression of a Stable Bispecific scFv Dimer with Affinity for Both Glycophorin and N9 Neuraminidase" Molecular Immunology, vol. 33, No. 17/18, pp. 1301-1312, 1996.

Bell, Jr., Anthony, J. et al. "RD114 envelope proteins provide an effective and versatile approach to pseudotype lentiviral vectors" Experimental Biology and Medicine, vol. 235, pp. 1269-1276, 2010.

Bendig, Mary M. "Humanization of rodent monoclonal antibodies by CDR Grafting" Methods: A Companion to Methods in Enzymology, vol. 8, pp. 83-93, 1995.

BioLegend (OKT3, purified anti-human CD3 antibody, Jun. 12, 2013, 3 pages).

Boder, Eric T., et al. "Yeast Surface Display for Directed Evolution of Protein Expression, Affinity, and Stability" Methods in Enzymology, vol. 328, Article 25, pp. 430-444, 2000.

Bolotin et al., "Next generation sequencing for TCR repertoire profiling: Platform-specific features and correction algorithms," Eur. J. Immunol., (2012), vol. 42: 3073-3083.

Bossi et al., "Examining the presentation of tumor-associated antigens on peptide-pulsed T2 cells," OncoImmunology, (2003), vol. 2:11, e26840.

Brady, Ged, et al. "New cosmid vectors developed for eukaryotic DNA cloning" Gene, vol. 27, No. 2, pp. 223-232, Feb. 1984.

Bridgeman, John S., et al. "Structural and biophysical determinants of alpha beta T-cell antigen recognition" Immunology, vol. 135, No. 1, pp. 9-18, Jan. 2012.

Brinkmann, Ulrich, et al. "The making of bispecific antibodies" mAbs, vol. 9, No. 2, pp. 182-212, Feb./Mar. 2017.

Brown, McKay, et al. "Tolerance to single, but not multiple, amino acid replacements in antibody V-H CDR2: A means of minimizing B cell wastage from somatic hypermutation?" The Journal of Immunology, vol. 156, No. 9, pp. 3285-3291, Jan. 1996.

Bunk, Sebastian, et al. "Abstract 2789: Development of highly potent T-cell receptorbispecifics with picomolar activity against tumor-specificHLA ligands" Cancer Research, vol. 78, Supplement 13, 2018 (Abstract Only).

Bunk, Sebastian, et al. "Effective Targeting of Prame-Positive Tumors with Bispecific TCell-Engaging Receptor (TCER®) Molecules" Blood, vol. 134, Supplement 1, pp. 3368, Nov. 2019.

Cameron, Brian J. et al., "Identification of a Titin-Derived HLA-A1-Presented Peptide as a Cross-Reactive Target for Engineered MAGE A3-Directed T Cells", Science Translational Medicine, Aug. 7, 2013, pp. 197-103, vol. 5.

Caron, Philip C., et al. "Engineered humanized dimeric forms of IgG are more effective antibodies" The Journal of experimental medicine, vol. 176, No. 4, pp. 1191-1195, Oct. 1992.

Carter, P. "Bispecific human IgG by design" Journal Immunol Methods, vol. 248, Issue 1-2, pp. 7-15, Feb. 2001.

Casset, Florence, et al. "A peptide mimetic of an anti-CD4 monoclonal antibody by rational design" Biochemical and Biophysical Research Communications, vol. 307, pp. 198-205, Jul. 2003.

Chervin, Adam S. "Engineering higher affinity T cell receptors using a T cell display system" Journal Immunology Methods, vol. 339, No. 2, pp. 175-184, Dec. 31, 2008.

Cochlovius, Bjorn, et al. "Cure of Burkitt's lymphoma in severe combined immunodeficiency mice by T cells, tetravalent CD3x CD19 tandem diabody, and CD28 costimulation" Cancer research, vol. 60, No. 16, pp. 4336-4341, Aug. 2000.

Colman, P.S. "Effects of amino acid sequence changes on antibody-antigen interactions" Research in Immunology, vol. 145, pp. 33-36, Jan. 1994.

Craig, Ryan B., et al. "Anti-HIV Double Variable Domain Immunoglobulins Binding Both gp41 and gp120 for Targeted Delivery of Immunoconjugates" PLOS One, vol. 7, Issue 10, paper e46778, Oct. 2012.

Database UniProt [Online], Nov. 1, 1995 (Nov. 1, 1995). Uniprot: P43358. Database Accession No. P43358 sequence. XP055374176.

Denardo, David G., et al "Anti-HLA-DR/anti-DOTA Diabody Construction in a Modular Gene Design Platform: Bispecific Antibodies for Pretargeted Radioimmunotherapy" Cancer Biotherapy & Radiopharmaceuticals, vol. 16, No. 6, pp. 525-535, Dec. 2001.

Dengjel, Jorn, et al. "Unexpected Abundance of HLA Class II Presented Peptides in Primary Renal Cell Carcinomas" Clinical Cancer Research, vol. 12, No. 14, Jul. 15, 2006.

Dennis, Mark S., et al. "Albumin Binding as a General Strategy for Improving the Pharmacokinetics of Proteins*" The Journal of Biological Chemistry, vol. 277, No. 38, pp. 35035-35043, Sep. 2002.

Dozier, Jonathan K., et al. "Site-Specific PEGylation of Therapeutic Proteins" International Journal of Molecular Sciences, vol. 16, pp. 25831-25864, Oct. 2015.

Dunbar, James, et al. "Examining Variable Domain Orientations in Antigen Receptors Gives Insight into TCR-Like Antibody Design" PLOS Computational Biology, vol. 10, Issue 9, e1003852, Sep. 2014.

Edelman, Gerald M., et al. The Covalent Structure of an Entire yG Immunoglobulin Molecule* Proceedings of the National Academy of Sciences, vol. 63, No. 1, pp. 78-85, May 1969.

Edge, Albert S. B., et al. "Deglycosylation of Glycoproteins by Trifluoromethanesulfonic Acid" Analytical Biochemistry, vol. 118, pp. 131-137, 1981.

Folch, Geraldine, et al. "The Human T cell Receptor Beta Variable (TRBV) Genes" Experimental and Clinical Immunogenetics, vol. 17, No. 1, pp. 42-54, 2000.

Freeman et al., "Profiling the T-cell receptor beta-chain repertoire by massively parallel sequencing," Genome Research, (2009), vol. 19: 1817-1824.

Ganju, et al., "Similarity between fluorescein-specific T-cell receptor and antibody in chemical details of antigen recognition," Proceedings of the National Academy of Sciences of the United States of America, (1992), vol. 89: 11552-11556.

Garcia et al., "How the T Cell Receptor Sees Antigen—A Structural View," Cell, (2005), vol. 122: 333-336.

Gattioni, Luca, et al. "Adoptive immunotherapy for cancer: building on success" National Review of Immunology, vol. 6, No. 5, pp. 383-393, May 2006.

Gillies, Stephen D., et al. "Expression of cloned immunoglobulin genes introduced into mouse L cells" Nucleic Acids Research, vol. 11, No. 22, pp. 7981-7997, Nov. 1983.

(56) References Cited

OTHER PUBLICATIONS

Goyarts et al., "Point mutations in the B chain CDR3 can alter the T cell receptor recognition pattern on an MHC class I/peptide complex over a broad interface area," Mol Immunol., (1998), vol. 35: 593-607.
Guo, Haiwei, et al. "Protein tolerance to random amino acid change" PNAS, vol. 101, No. 25, pp. 9205-9210, Jun. 22, 2004.
Hickman, Emma S., et al. "Antigen Selection for Enhanced Affinity T-Cell Receptor-Based Cancer Therapies" Journal of Biomolecular Screening, vol. 21, Issue 8, pp. 769-785, Sep. 2016.
Hollinger, Philipp, et al. "Specific killing of lymphoma cells by cytotoxic T-cells mediated by a bispecific diabody" Protein Engineering, vol. 9, No. 3, pp. 299-305, Mar. 1996.
Hu, Hongmin, "Prediction and identification of HLA-A2/A3 restricted CTL epitopes derived from MAGE-4," (2008).
Hudecz, Ferenc. "Synthesis of Peptide Bioconjugates" Methods in Molecular Biology, vol. 298, pp. 209-223, 2005.
International Preliminary Report on Patentability from PCT/EP2018/069151, dated Jan. 14, 2020, 9 pages.
International Preliminary Report on Patentability from PCT/EP2018/069157, dated Jan. 14, 2020, 9 pages.
International Search Report from PCT/EP2018/069151, dated Sep. 14, 2018, 5 pages.
International Search Report from PCT/EP2018/069157, dated Sep. 14, 2018, 5 pages.
International Search Report from PCT/EP2022/062018, dated Sep. 7, 2022, 5 pages.
Scaviner, Dominique, et al. "The Human T Cell Receptor Alpha Variable (TRAV) Genes" Experimental and Clinical Immunogenetics, vol. 17, No. 1, pp. 83-96, 2000.
Schellenberger, V., et al. "A recombinant polypeptide extends the in vivo half-life of peptides and proteins in a tunable manner" Nature Biotechnology, vol. 27, No. 12, pp. 1186-1190, Dec. 2009.
Schlapschy, Martin, et al. "PASylation: a biological alternative to PEGylation for extending the plasma half-life of pharmaceutically active proteins" Protein Eng Des Sel. vol. 26, No. 8, pp. 489-501, Aug. 2013.
Shearman, Clyde W., et al. "Construction, expression and characterization of humanized antibodies directed against the human alpha/beta T cell receptor" Journal of Immunology, vol. 147, No. 12, pp. 4366-4373, Dec. 15, 1991.
Shirakura, et al., "T-cell receptor gene therapy targeting melanoma-associated antigen-A4 inhibits human tumor growth in non-obese diabetic/SCID/ycnull mice," Cancer Science, (2012), vol. 103, No. 1: 17-25.
Shitara, Kenya, et al. "A new vector for the high level expression of chimeric antibodies in myeloma cells" Journal of Immunological Methods, vol. 167, No. 1-2, pp. 271-278, Jan. 1994.
Shopes, Bob. "A genetically engineered human IgG mutant with enhanced cytolytic activity" The Journal of Immunology, vol. 148, No. 9, pp. 2918-2922, May 1992.
Smith, Sheena N., et al. "T Cell Receptor Engineering and Analysis Using the Yeast Display Platform" Methods Mol Biology vol. 1319, pp. 95-141, 2015.
Sommermeyer, Daniel, et al. "Minimal Amino Acid Exchange in Human TCR Constant Regions Fosters Improved Function of TCR Gene-Modified T Cells" The Journal of Immunology, vol. 184, pp. 6223-6231, May 2010.
Spel, Lotte, et al. "Natural killer cells facilitate Prame-specific T-cell reactivity against neuroblastoma" Oncotarget, vol. 6, No. 34, pp. 35770-35781, Oct. 2015.
Tao, Mi-Hua, et al. "Studies of Aglycosylated Chimeric Mouse-Human IgG: Role of carbohydrate in the structure and effector functions mediated by the human IgG constant region" The Journal of Immunology, vol. 143, No. 8, pp. 2595-2601, Oct. 1989.
Thotakura, Nageswara, et al. "Enzymatic Deglycosylation of Glycoproteins" Methods in Enzymology, vol. 138, pp. 350-359, Jan. 1987.
U.S. Appl. No. 18/052,009, filed Nov. 2, 2022.
Urlaub, Gail, et al. "Isolation of Chinese hamster cell mutants deficient in dihydrofolate reductase acitivity" Proc. Natl. Acad. Sci., vol. 77, No. 7, pp. 4216-4220, Jul. 1980.
Van Der Brugen, P., et al. "A Gene Encoding an Antigen Recognized by Cytolytic T Lymphocytes on a Human Melanoma" Science, vol. 254, pp. 1643-1647, Dec. 13, 1991.
Wang, Bao-Zhong, et al. "Incorporation of High Levels of Chimeric Human Immunodeficiency Virus Envelope Glycoproteins into Virus-Like Particles" Journal of Virology, vol. 81, No. 20, pp. 10869-10878, Oct. 2007.
Wei, Hudie, et al. "Structural basis of a novel heterodimeric Fc for bispecific antibody production" Oncotarget, vol. 8, No. 31, pp. 51037-51049, Aug. 2017.
Winkler, Karsten, et al. "Changing the Antigen Binding Specificity by Single Point Mutations of an Anti-p24 (HIV-1) Antibody" Journal of Immunology, vol. 165, No. 8, pp. 4505-4514, Oct. 2000.
Wong, Wing Ki, et al. "Comparative Analysis of the CDR Loops of Antigen Receptors" Frontiers in Immunology, vol. 10, Article 2454, Oct. 2019.
Written Opinion from PCT/EP2022/062018, dated Sep. 7, 2022, 6 pages.
Wu, Chengbin, et al. "Molecular construction and optimization of anti-human IL-1α/β dual variable domain immunoglobulin (DVD-IgTM) molecules" mAbs, vol. 1, No. 4, pp. 339-347, Jul. 2009.
Wu, Chengbin, et al. "Simultaneous targeting of multiple disease mediators by a dual-variable-domain immunoglobulin" Nature Biotechnology, vol. 25, No. 11, pp. 1290-1297, Nov. 2007.
Wu, et al., "Identification of a Novel CD8+ T Cell Epitope Derived from Cancer-Testis Antigen MAGE-4 in Oesophageal Carcinoma," Scandinavian Journal of Immunology, (2011), vol. 74: 561-567.
Zhang, Tong, et al. "Transgenic TCR expression: comparison of single chain with full-length receptor constructs for T-cell function" Cancer Gene Therapy, vol. 11, pp. 487-496, May 2004.
Zheng-Cai, Jia et al., "Identification of Two Novel HLA-A*0201-Restricted CTL Epitopes Derived from MAGE-A4", Clinical and Developmental Immunology, 2010, Article ID 567594.
Zhu, Zhenping, et al. "Identfcation of Heavy Chain Residues in a Humanized Anti-CD3 Antibody Important for Efficient Antigen Binding and T Cell Activation" Journal of Immunology, vol. 155, No. 4, pp. 1903-1910, Aug. 15, 1995.

* cited by examiner

ANTIGEN BINDING PROTEINS SPECIFICALLY BINDING MAGE-A

CROSS-REFERENCE TO RELATED APPLICATIONS

This application is a continuation of U.S. patent application Ser. No. 18/483,174, filed on Oct. 9, 2023, which is a continuation of U.S. patent application Ser. No. 16/943,779, filed on Jul. 30, 2020, now U.S. Pat. No. 11,840,577, issued on Dec. 12, 2023, which claims priority to U.S. Provisional Application No. 62/905,782, filed on Sep. 25, 2019, U.S. Provisional Application No. 62/882,131, filed on Aug. 2, 2019, and German Patent Application No. 102019121007.0, filed on Aug. 2, 2019. Each of these listed applications are incorporated in their entirety herein by reference for all purposes.

REFERENCE TO SEQUENCE LISTING SUBMITTED AS A COMPLIANT XML FILE (.xml)

Pursuant to the EFS-Web legal framework and 37 CFR §§ 1.821-825 (see MPEP § 2442.03(a)), a Sequence Listing in the form of a compliant xml file (entitled "3000058-015004 Sequence-Listing_ST26.xml" created on Dec. 12, 2023, and 243,762 bytes in size) is submitted concurrently with the instant application, and the entire contents of the Sequence Listing are incorporated herein by reference.

BACKGROUND

The present invention concerns antigen binding proteins specifically binding melanoma associated antigen A (MAGE-A) protein-derived antigens. The invention in particular provides antigen binding proteins which specifically bind to the MAGE-A antigenic peptide comprising or consisting of SEQ ID NO: 1 in a complex with a major histocompatibility (MHC) protein. The antigen binding proteins of the invention contain, in particular, the complementary determining regions (CDRs) of novel engineered T cell receptors (TCRs) that specifically bind to said MAGE-A peptide/MHC complex. The antigen binding proteins of the invention are of use for the diagnosis, treatment and prevention of MAGE-A expressing cancerous diseases. Further provided are nucleic acids encoding the antigen binding proteins of the invention, vectors comprising these nucleic acids, recombinant cells expressing the antigen binding proteins and pharmaceutical compositions comprising the antigen binding proteins of the invention.

BACKGROUND OF THE INVENTION

The MAGE-A tumor antigen of the amino acid sequence 'KVLEHVVRV' (SEQ ID NO: 1), also known as MAG-003 peptide, is an HLA-A*02:01-restricted cytotoxic T lymphocyte (CTL) epitope of MAGE-A4 (amino acids 286-294) and MAGE-A8 (amino acids 288-296) (Zheng-Cai J. et al. Clin Dev. Immunol. 2010, 567594). MAGE-A4 and MAGE-A8 are both proteins and members of the MAGE-A gene family. The functions of MAGE-A8 and -A4 are not known, though they may play a role in embryonal development and tumor transformation or aspects of tumor progression. Multiple alternatively spliced variants have been identified for these proteins. The MAGE-A antigen according to SEQ ID NO: 1 belongs to cancer/testis (CT) antigens that are expressed in tumors but not in normal tissues except testis and placenta. The expression of the MAGE-A4 protein and mRNA, for example, has been linked to the development and prognosis of various cancers. Peptides, such as MAGE-A, in particular the MAGE-A4 and/or MAGE-A8 derived peptide 'KVLEHVVRV' (SEQ ID NO: 1), which are presented by molecules of the major histocompatibility complex (MHC), may be bound by TCRs and are, thus a target of, for instance, T cell based immunotherapy. MAGE-A antigens and their epitope peptides have therefore been used in tumor immunotherapy trials.

While advances have been made in the development of molecular-targeting drugs for cancer therapy, there remains a need in the art to develop new anti-cancer agents that specifically target molecules highly specific to cancer cells but not to normal cells.

The present invention thus provides novel antigen binding proteins which are specific for the tumor expressed antigen MAGE-A of SEQ ID NO: 1 in a complex with an MHC protein.

WO 2017/158103 discloses TCRs, more particularly native TCRs, such as the native TCR R7P1D5, that bind to a complex of a MAGE-A antigenic peptide having the amino acid sequence of KVLEHVVRV of SEQ ID NO: 1 and an HLA class I molecule, and their use in the diagnosis, treatment and prevention of cancerous diseases. However, native TCRs specifically binding to MHC presented cancer antigens are often of lower affinity ($K_D$=1-300 µM) when compared to TCRs specifically binding to MHC presented viral antigens. Part of the explanation for this phenomenon seems to be that T cells that develop in the thymus are negatively selected (tolerance induction) on self-peptide-MHC ligands, such that T cells with too high affinity to such self-peptide-MHCs are deleted. This low affinity may be one possible explanation for tumor immune escape (Aleksic et al. 2012, Eur J Immunol. 2012 December; 42(12):3174-9). Therefore, it appears desirable to design TCR variants that bind with higher affinity to cancer antigens for use as antigen recognizing constructs in an adoptive cell therapy (ACT), or as recognition module of a soluble approach, i.e. using bispecific molecules (Hickman et al. 2016, J Biomol Screen. 2016 September; 21(8):769-85).

However, increasing the affinity of TCRs may also increase the risk of side effects. As mentioned above, in nature high affinity TCRs directed against tumor-associated antigens, which are self-proteins, are precluded by thymic selection, to avoid recognition of self-peptides present on normal tissue through cross-reactivity. Accordingly, simply increasing the TCRs affinity for its target sequence is likely to also increase the affinity to similar non cancer-specific peptides and therefore increasing the risk of cross-reactivity and unwanted cytotoxic effects on healthy tissue. That this is not just a theoretic risk has been painfully discovered for engineered TCRs targeting MAGE-A3. In particular, previously published results have shown lethal toxicities in two patients, who were infused with T cells engineered to express a TCR targeting MAGE-A3 cross-reacting with a peptide from the muscle protein Titin, even though no cross-reactivities had been predicted in the pre-clinical studies (Linette G P et al. Blood 2013; 122:863-71, Cameron B J, et al. Sci. Transl. Med. 2013; 5: 197-103). These patients demonstrated that TCR-engineered T cells can have serious and unpredictable off-target and organ-specific toxicities.

Accordingly, there is an unmet medical need to develop and provide TCRs or antigen binding proteins specifically binding to their target with higher affinity, thus allowing to target even a tumor cell or cell lines with reduced expression of the target antigenic peptide, while a high safety profile is maintained due to a low or reduced cross-reactivity with off-target peptides (also referred to as "similar peptides"). In other words, the inventors were able to develop antigen binding proteins which exhibit high binding affinity to their target peptide while maintaining high tumor selectivity.

Furthermore, as shown by the inventors, the MAGE-A specific TCR molecule TCR R7P1D5 shows a relatively low solubility as a single chain construct or in the bispecific format referred to as TCER (in the following "TCER™" molecules or "TCER™"), which comprises a part that specifically binds to a surface molecule on a T cell and that specifically binds to a MHC-peptide complex.

Therefore, despite the advancements in TCR technology, there remains a need for additional cancer therapeutics, particularly those that efficiently target and kill cancer cells. In particular there is the need to develop new antigen binding proteins which are i) selective and specific for the tumor specific MAGE-A peptide of SEQ ID NO: 1 in a complex with an MHC protein having the desired biological activity, ii) have good metabolic, pharmakokinetic, solubility, stability and/or safety profiles, and iii) that can be manufactured in large scale.

Accordingly, in the context of the present invention, the inventors engineered several antigen binding proteins comprising CDR variants derived from said parental TCR R7P1D5. Those antigen binding proteins have an increased binding affinity for the peptide-MHC complex and an increased stability, and/or an increased solubility, making them more suitable for a medical use.

Furthermore, as demonstrated by the inventors these new antigen binding proteins, effectively bind and kill target cancer cells that even have low copy numbers and, advantageously, maintain a high safety profile with a low cross-reactivity to similar peptides.

Furthermore, these new antigen binding proteins, in particular in the form of TCER™ molecules, show a high cytotoxicity against tumor cells. For example, for new antigen binding proteins in the form of TCER™ molecules, the half maximal effective concentration ($EC_{50}$) against NCI-H1755, Hs695T cells and U2OS is in the range of 1 to 300 pM, 1 pM to 100 pM, more particularly, between 1 pM and 20 pM for cells. Furthermore, the $EC_{50}$ of the antigen binding proteins of the present invention is 100-fold, preferably more than 1000-fold higher regarding cell lines of healthy tissue such as primary cell lines versus tumor cell line Hs695T, demonstrating its high safety.

Furthermore, the inventors demonstrated for these new antigen binding proteins, in particular TCER™ molecules, in vivo, significant tumor growth inhibition in a therapeutic mouse model even at low doses.

The present invention thus relates to antigen binding proteins specific for a MAGE-A derived antigenic peptide in a complex with an MHC protein, wherein said antigen binding protein has an increased stability, such as reduced aggregation, during expression and/or purification, for example, in comparison to the native TCR R7P1D5. Furthermore, said antigen binding proteins have a high cytotoxicity, for example against the cell lines NCI-H175, Hs695T cells and U2OS cells.

In summary, the surprising findings of the inventors provide inter alia the following advantages over the art: (i) reduction of cross-reactivity of TCRs or antigen binding proteins with similar peptides on healthy tissues and maintaining high tumor selectivity (ii) increased safety profile of TCRs or antigen binding proteins; (iii) TCRs or antigen binding proteins exerting reduced off target and off-tumor cytotoxicity; and (iv) the provision of improved specific, selective and safe TCRs or antigen binding proteins.

Definitions

The term "antigen binding protein" herein refers to polypeptides or binding proteins that are able to bind to at least one antigen, in particular, an antigen as defined in the context of the present invention. In a preferred embodiment, said antigen binding proteins are capable of binding to two different antigens simultaneously, as it is known from, for example bispecific antibodies. The antigen binding proteins of the present invention comprise at least 6 CDRs as defined in the context of the present invention, which originally derived from a TCR. In a particular embodiment, the antigen binding proteins of the present invention comprise at least one variable alpha domain and at least one variable beta domain as defined in the context of the present invention, which originally derived from a TCR.

A "domain" is a region of a protein defined on the basis of sequence homologies and often related to a specific structural or functional entity. Examples of such domains are the variable light chain domain of the antibody light chain, the variable heavy chain domain of the antibody heavy chain, the $C_{H1}$, $C_{H2}$ and $C_{H3}$ domain (constant domains) of the antibody heavy chain, the variable domain of the α-chain of a TCR or the variable domain of the β-chain of a TCR.

The term "antigen" or "target antigen" as used herein refers to a molecule or a portion of a molecule or complex that is capable of being bound by at least one antigen binding site, wherein said one antigen binding site is, for example, present in a conventional antibody, a conventional TCR and/or in the antigen binding proteins of the present invention.

The antigen that is specifically bound by the antigen binding proteins of the present invention is the MAGE-A antigenic peptide comprising or consisting of the amino acid sequence 'KVLEHVVRV' of SEQ ID NO: 1, more particularly, the MAGE-A antigenic peptide comprising or consisting of the amino acid sequence 'KVLEHVVRV' of SEQ ID NO: 1, in a complex with a MHC protein.

The term "epitope" as used herein comprises the terms "structural epitope" and "functional epitope". The "structural epitope" are those amino acids of the antigen, e.g. peptide-MHC complex, that are covered by the antigen binding protein when bound to the antigen. Typically, all amino acids of the antigen are considered covered that are within 5 Å of any atom of an amino acid of the antigen binding protein. The structural epitope of an antigen may be determined by art known methods including X-ray crystallography or NMR analysis. The structural epitope of an antibody typically comprises 20 to 30 amino acids. The structural epitope of a TCR typically comprises 20 to 30 amino acids. The "functional epitope" is a subset of those amino acids forming the structural epitope and comprises the amino acids of the antigen that are critical for formation of the interface with the antigen binding protein of the invention, either by directly forming non-covalent interactions such as H-bonds, salt bridges, aromatic stacking or hydrophobic interactions or by indirectly stabilizing the binding conformation of the antigen and is, for instance, determined by mutational scanning. Typically, the functional epitope of an antigen bound by an antibody comprises between 4 to 6 amino acids. Typically, the functional epitope of a peptide-MHC complex comprises between 2 to 6 amino acids of the peptide and 2 to 7 amino acids of the MHC molecule. Since MHC I presented peptides typically have a length between 8 to 10 amino acids only a subset of amino acids of each given peptide is part of the functional epitope of a peptide-MHC complex. In the context of the present invention, the epitope, in particular the functional epitope bound by the antigen binding proteins of the present invention comprises or consists of the amino acids of the antigen that are required for formation of the binding interface, therefore the functional epitope comprises at least 3, preferably at least 4 amino acids of the MAGE-A antigenic peptide of SEQ ID NO: 1.

"MAGE-A" or "melanoma associated antigen A" subfamily proteins were the first tumor associated antigens identified at the molecular level (van der Bruggen P, et al. Science. 1991; 254:1643-47). MAGE-A is a sub-family of 12 genes (MAGE-A1 to -A12) located in the q28 region of the X chromosome. Members of the MAGE-A subfamily proteins are normally expressed only in testis or placenta and their restricted expression suggests that they may function in germ cell development. MAGE-A proteins were also detected in the early development of the central nervous system and the spinal cord and brainstem, revealing that MAGE-A proteins may also be involved in neuronal development. The members of this family encode proteins with 50 to 80% sequence identity to each other and all MAGE proteins share the common MAGE homology domain (MHD), a highly conserved domain consisting of approximately 170 amino acids. The biological functions and underlying regulatory mechanism of MAGE-A proteins expression in cancer is still not fully understood.

The "MAGE-A4" or "Melanoma-associated antigen 4" protein is a member of the MAGE-A gene family and has the Uniprot accession number P43358 of SEQ ID NO: 97 (as available on Jul. 8, 2019), MAGE-A4 localization has been described as cytoplasmic. However, MAGE-A4 staining has also been detected in nuclei, with differential distribution between nucleus and cytoplasm in well-differentiated versus less differentiated cancers (Sarcevic B et. al., 2003, Oncology 64, 443-449). MAGE-A4 is used as a male germ cell marker. It is not expressed in gonocytes, but expressed in pre-spermatogonia and mature germ cells (Mitchell et al., 2014, Mod. Pathol. 27, 1255-1266). Expression of the MAGE-A4 protein and mRNA has been linked to the development and prognosis of various cancers.

The "MAGE-A8" or "Melanoma-associated antigen 8" protein is a member of the MAGE-A superfamily and has the Uniprot accession number P43361 of SEQ ID NO: 98 (as available on Jul. 8, 2019).

The "MAGE-A4" and "MAGE-A8" proteins have a sequence identity of 72% as determined by a protein sequence alignment using the BLASTP 2.9.0 algorithm (Stephen F. et al. (1997) Nucleic Acids Res. 25:3389-3402). Furthermore "MAGE-A4" and "MAGE-A8" both comprise the MAG-003 peptide, i.e., KVLEHVVRV (SEQ ID NO: 1).

The "major histocompatibility complex" (MEW) is a set of cell surface proteins essential for the acquired immune system to recognize foreign molecules in vertebrates, which in turn determines histocompatibility. The main function of MHC molecules is to bind to antigens derived from pathogens and display them on the cell surface for recognition by the appropriate T cells. The human MHC is also called the HLA (human leukocyte antigen) complex (often just the HLA). The MHC gene family is divided into three subgroups: class I, class II, and class III. Complexes of peptide and MHC class I are recognized by CD8-positive T cells bearing the appropriate T cell receptor (TCR), whereas complexes of peptide and MHC class II molecules are recognized by CD4– positive-helper-T cells bearing the appropriate TCR. Since both types of response, CD8 and CD4 dependent, contribute jointly and synergistically to the anti-tumor effect, the identification and characterization of tumor-associated antigens and corresponding T cell receptors is important in the development of cancer immunotherapies such as vaccines and cell therapies. The HLA-A gene is located on the short arm of chromosome 6 and encodes the larger, α-chain, constituent of HLA-A. Variation of HLA-A α-chain is key to HLA function. This variation promotes genetic diversity in the population. Since each HLA has a different affinity for peptides of certain structures, greater variety of HLAs means greater variety of antigens to be 'presented' on the cell surface. Each individual can express up to two types of HLA-A, one from each of their parents. Some individuals will inherit the same HLA-A from both parents, decreasing their individual HLA diversity; however, the majority of individuals will receive two different copies of HLA-A. This same pattern follows for all HLA groups. In other words, every single person can only express either one or two of the 2432 known HLA-A alleles.

The MHC class I HLA protein in the context of the present invention may be an HLA-A, HLA-B or HLA-C protein, preferably HLA-A protein, more preferably HLA-A*02.

"HLA-A*02" signifies a specific HLA allele, wherein the letter A signifies the gene and the suffix "*02" indicates the A2 serotype.

In the MHC class I dependent immune reaction, peptides not only have to be able to bind to certain MHC class I molecules expressed by tumor cells, they subsequently also have to be recognized by T cells bearing specific T cell receptors (TCR).

A "TCR" is a heterodimeric cell surface protein of the immunoglobulin super-family, which is associated with invariant proteins of the CD3 complex involved in mediating signal transduction. TCRs exist in αβ and γδ forms, which are structurally similar but have quite distinct anatomical locations and probably functions. The extracellular portion of native heterodimeric αβ TCR and γδ TCR each contain two polypeptides, each of which has a membrane-proximal constant domain, and a membrane-distal variable domain Each of the constant and variable domains include an intra-chain disulfide bond. The variable domains contain the highly polymorphic loops analogous to the complementarity determining regions (CDRs) of antibodies. The use of TCR gene therapy overcomes a number of current hurdles. It allows typically equipping subjects' (patients') own T cells with desired specificities and generation of sufficient numbers of T cells in a short period of time, avoiding their exhaustion. For example, the TCR will be transduced into potent T cells (e.g. central memory T cells or T cells with stem cell characteristics), which may ensure better persistence, preservation and function upon transfer. TCR-engineered T cells will be infused into cancer patients rendered lymphopenic by chemotherapy or irradiation, allowing efficient engraftment but inhibiting immune suppression.

The term "TCR" herein denotes TCRs and fragments thereof, as well as single chain TCRs and fragments thereof, in particular variable alpha and beta domains of single domain TCRs, and chimeric, humanized, bispecific or multispecific TCRs.

"Fragments of a TCR" comprise a portion of an intact or native TCR, in particular the antigen binding region or variable region of the intact or native TCR. Examples of TCR fragments include fragments of the α, β, δ, γ chain, such as $V_\alpha$-$C_a$ or $V_\beta$-$C_\beta$ or portions thereof, such fragments might also further comprise the corresponding hinge region or single variable domains, such as $V_\alpha$, $V_\beta$, $V_\delta$, $V_\gamma$, single chain V$\alpha$V$\beta$ fragments or bispecific and multispecific TCRs formed from TCR fragments. Fragments of a TCR exert identical functions compared to the naturally occurring full-length TCR, i.e. fragments selectively and specifically bind to their target peptide.

"Single chain TCR (scTCR)" herein denotes a protein wherein the variable domains of the TCR, such as the $V_\alpha$ and $V_\beta$ or $V_\delta$ and $V_\gamma$ are located on one polypeptide. Typically, the variable domains are separated by a linker, wherein said linker typically comprises 5 to 20, such as 5 to 15 amino acids.

"Native" as used for example in the wording "native TCR" refers to a wildtype TCR.

In the adoptive cell transfer (ACT) approach, the transgene T cells produced may express a wildtype TCR having wildtype alpha and beta chains, and the transgenic TCR with the alpha and beta chains specific for the respective target antigen-MHC complex. Both the wildtype alpha and beta chains and the transgenic alpha and beta chains are usually still capable of cross-pairing with each other. This undesired possibility of pairing is called "TCR mispairing" and is a recognized problem in the field of TCR (gene) therapy. Mispairing and incorrect pairing between a transgenic TCR α or β chain and an endogenous TCR β or α chain, respectively, may result in a reduced surface expression of the transgenic TCRαβ heterodimer, which in turn reduces the functional avidity of the modified T cells. Furthermore, T cells expressing mispaired TCRs and expanded under high IL-2 conditions were demonstrated to induce graft-versus-host disease (GvHD) in a preclinical model.

Some strategies for the optimization of transgenic TCR α and β pairing to avoid mispairing may include the following: 1. Murinized TCRs: In this approach, human TCRα and β constant chains are replaced by the corresponding murine domains. Although human and murine TCR-C domains show a high degree of homology, small differences affect the stability of TCR/CD3 interactions and hence TCR surface expression levels. 2. Cysteine-modified TCRs: This approach introduces cysteine amino acids at a structurally favorable position, and hence allows the formation of at least one additional disulfide bridge and promotes correct pairing between the two TCR chains. Site-directed mutations of e.g. T48C in the TCR alpha constant chain and S57C in the TCR beta constant chain resulted in a TCR heterodimer linked by two interchain bonds (i.e., an introduced disulfide bridge plus an endogenous transmembrane disulfide bridge (position No. 95 in the alpha constant domain and position No. 131 in the beta constant domain) 3 Domain swapping: Constant domains are swapped between the α and β chains of a tumor-specific T cell receptor, creating a domain-swapped (ds)TCR. When correctly paired, these dsTCR chains retain all domains necessary to recruit CD3 proteins, to express on the T cell surface, and to mediate functional T cell responses upon engaging a target antigen. By contrast, mispaired TCRs containing one dsTCR chain and one wild-type TCR chain lack key domains necessary for CD3 recruitment, export, and signaling, and thus are unable to mediate deleterious autoimmunity. 4. Exclusive TCR heterodimers: In this approach, sterical and electrostatic forces are exploited to facilitate correct pairing between TCR alpha and beta transgenes and at the same time inhibit pairing between exogenous and endogenous TCR alpha and beta chains. One example uses site-directed mutations to introduce an S85R into the alpha constant domain and R88G in the beta constant domain, in order to obtain the required changes in electrostatic charges, and hence generate a reciprocal 'knob-into-hole' configuration, which allegedly minimally distorts secondary and tertiary structures. 5. The use of chimericTCR-CD3ζ chain having each TCR chain fused to a CD3ζ molecule. 6. The use of single-chain TCRs wherein the V alpha chain of a defined TCR is fused to the beta chain using a flexible peptide linker 7 The use of shRNA sequences or zinc finger nucleases to knock down the expression of the endogenous TCR. Another approach, termed "velcro", that is able to pair the two TCR chains with one another due to favorable electrostatic interactions in the heterodimeric state. That is, the two peptides are predominantly unfolded in isolated form but associate preferentially to form a stable parallel, coiled coil heterodimer when mixed. This approach may be applied to produce soluble TCR, in which heterodimeric complex was favored by fusing the peptides to truncated alpha and beta chains respectively.

Native alpha-beta heterodimeric TCRs have an alpha chain and a beta chain. Each alpha chain comprises variable, joining and constant regions, and the beta chain also usually contains a short diversity region between the variable and joining regions, but this diversity region is often considered as part of the joining region. The constant, or C, regions of TCR alpha and beta chains are referred to as TRAC and TRBC respectively (Lefranc, (2001), Curr Protoc Immunol Appendix 1: Appendix 10). Each variable region, herein referred to as alpha variable domain and beta variable domain, comprises three Complementarity Determining Regions (CDRs) embedded in a framework sequence, one being the hypervariable region named CDR3. The alpha variable domain CDRs are herein referred to as CDRa1, CDRa2, CDRa3, and the beta variable domain CDRs are herein referred to as CDRb1, CDRb2, CDRb3. There are several types of alpha chain variable (Valpha) regions and several types of beta chain variable (Vbeta) regions distinguished by their framework, CDR1 and CDR2 sequences, and by a partly defined CDR3 sequence. The Valpha types are referred to in IMGT nomenclature by a unique TRAV number, Vbeta types are referred in IMGT nomenclature to by a unique TRBV number (Folch and Lefranc, (2000), Exp Clin Immunogenet 17(1): 42-54; Scaviner and Lefranc, (2000), Exp Clin Immunogenet 17(2): 83-96; LeFranc and LeFranc, (2001), "T cell Receptor Factsbook", Academic Press). For more information on immunoglobulin antibody and TCR genes see the international ImMunoGeneTics information System®, Lefranc M-P et al (Nucleic Acids Res. 2015 January; 43 (Database issue):D413-22; and imgt.org). A conventional TCR antigen binding site, therefore, includes, usually, six CDRs, comprising the CDR set from each of an alpha and a beta chain variable region, wherein CDR1 and CDR3 sequences are relevant to the recognition and binding of the peptide antigen that is bound to the HLA protein and the CDR2 sequences are relevant to the recognition and binding of the HLA protein.

Analogous to antibodies, "TCR Framework Regions" (FRs) refer to amino acid sequences interposed between CDRs, i.e. to those portions of TCR alpha and beta chain variable regions that are to some extent conserved among different TCRs in a single species. The alpha and beta chains of a TCR each have four FRs, herein designated FR1-a, FR2-a, FR3-a, FR4-a, and FR1-b, FR2-b, FR3-b, FR4-b, respectively. Accordingly, the alpha chain variable domain may thus be designated as (FR1-a)-(CDRa1)-(FR2-a)-(CDRa2)-(FR3-a)-(CDRa3)-(FR4-a) and the beta chain variable domain may thus be designated as (FR1-b)-(CDRb1)-(FR2-b)-(CDRb2)-(FR3-b)-(CDRb3)-(FR4-b).

In the context of the invention, CDR/FR definition in an α or β chain or a γ or δ chain is to be determined based on IMGT definition (Lefranc et al. Dev. Comp. Immunol., 2003, 27(1):55-77; imgt.org). Accordingly, CDR/FR amino acid positions when related to TCR or TCR derived domains are indicated according to said IMGT definition. Preferably, the IMGT position of the CDR/FR amino acid positions of the first variable domain is given in analogy to the IMGT numbering of TRAV5 and/or the IMGT position of the CDR/FR amino acid positions of the second variable domain is given in analogy to the IMGT numbering of TRBV12-4. With respect to gamma/delta TCRs, the term "TCR gamma variable domain" as used herein refers to the concatenation of the TCR gamma V (TRGV) without leader region (L), and TCR gamma J (TRGJ) regions; and the term TCR gamma constant domain refers to the extracellular TRGC region, or to a C-terminal truncated TRGC sequence. Likewise, the term "TCR delta variable domain" refers to the concatenation of the TCR delta V (TRDV) without leader region (L), and TCR delta D/J (TRDD/TRDJ) regions; and the term TCR delta constant domain refers to the extracellular TRDC region, or to a C-terminal truncated TRDC sequence.

In an "antibody" also called "immunoglobulin" two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains or regions, a variable domain ($V_L$) and a constant domain ($C_L$). The heavy chain includes four domains, a variable domain ($V_H$) and three constant domains ($C_{H1}$, $C_{H2}$ and $C_{H3}$, collectively referred to as CH). The variable regions of both light ($V_L$) and heavy ($V_H$) chains determine binding recognition and specificity to the antigen. The constant region domains of the light ($C_L$) and heavy ($C_H$) chains confer important biological properties such as antibody chain association, secretion, trans-placental mobility, complement binding, and binding to $F_c$ receptors ($F_cR$). The Fv fragment is the N-terminal part of the Fab fragment of an immunoglobulin and consists of the variable portions of one light chain and one heavy chain. The specificity of the antibody resides in the structural complementarity between the antibody combining site (synonym to antibody binding site) and the antigenic determinant Antibody combining sites are made up of residues that are primarily from the hypervariable or complementarity determining regions (CDRs). Occasionally, residues from non-hypervariable or FR influence the overall domain structure and hence the combining site. CDRs refer to amino acid sequences that together define the binding affinity and specificity of the natural Fv region of a native immunoglobulin binding site. The light and heavy chains of an immunoglobulin each have three CDRs, designated CDR1-L, CDR2-L, CDR3-L and CDR1-H, CDR2-H, CDR3-H, respectively. A conventional antibody antigen binding site, therefore, includes six CDRs, comprising the CDR set from each of a heavy and a light chain V region.

In the context of the invention, an antibody or immunoglobulin is an IgM, IgD, IgG, IgA or IgE.

"Antibody Framework Regions" (FRs) refer to amino acid sequences interposed between CDRs, i.e. to those portions of immunoglobulin light and heavy chain variable regions that are relatively conserved among different immunoglobulins in a single species. The light and heavy chains of an immunoglobulin each have four FRs, designated FR1-L, FR2-L, FR3-L, FR4-L, and FR1-H, FR2-H, FR3-H, FR4-H, respectively. Accordingly, the light chain variable domain may thus be designated as (FR1-L)-(CDR1-L)-(FR2-L)-(CDR2-L)-(FR3-L)-(CDR3-L)-(FR4-L) and the heavy chain variable domain may thus be designated as (FR1-H)-(CDR1-H)-(FR2-H)-(CDR2-H)-(FR3-H)-(CDR3-H)-(FR4-H).

In the context of the invention, CDR/FR definition in an immunoglobulin light or heavy chain, except of the Fc domain, is to be determined based on IMGT definition (Lefranc et al. Dev. Comp. Immunol., 2003, 27(1):55-77; imgt.org). Accordingly, amino acid sequences of the CDR1, CDR2 and CDR3 of a given variable chain and the amino acid sequences of FR1, FR2, FR3, FR4 and FR5 are indicated according to said IMGT definition.

As it will be understood by the person skilled in the art, the structures of antibodies, in particular the structure of the variable heavy and light chains of antibodies, is similar to the structures of the TCR alpha and beta variable domain structure. Thus, CDRs of a TCR of the present invention can be grafted into conventional antibodies, bispecific antibodies, or multispecific antibodies.

Knowing the amino acid sequence of the CDRs of an antibody, a TCR or an antigen binding protein of the invention, one skilled in the art can easily determine the framework regions, such as the TCR framework regions or antibody framework regions. However, in cases where the CDRs are not indicated, the skilled in the art can first determine the CDR amino acid sequences based on the IMGT definition for TCRs or the IMGT definition for antibodies and then determine the amino acid sequences of the framework regions.

As used herein, a "human framework region" is a framework region that is substantially identical (about 85%, or more, in particular 90%, 95%, 97%, 99% or 100%) to the framework region of a naturally occurring antigen binding protein, such as a naturally occurring human antibody or human TCR.

The term "antibody" denotes antibodies and fragments thereof, as well as single domain antibodies and fragments thereof, in particular a variable heavy chain of a single domain antibody, and chimeric, humanized, bispecific or multispecific antibodies.

A "conventional antibody" as herein referred to is an antibody that has the same domains as an antibody isolated from nature and comprises antibody derived CDRs and framework regions. In analogy, a "conventional TCR" as herein referred to is a TCR that comprises the same domains as a native TCR and TCR derived CDRs and Framework regions.

The term "humanized antibody" refers to an antibody which is completely or partially of non-human origin and which has been modified to replace certain amino acids, in particular in the framework regions of the heavy and light chains, in order to avoid or minimize an immune response in humans. The constant domains of a humanized antibody are mainly human $C_H$ and $C_L$ domains.

Numerous methods for humanization of an antibody sequence are known in the art; see e.g. the review by Almagro & Fransson (2008) Front Biosci. 13: 1619-1633. One commonly used method is CDR grafting, or antibody reshaping, which involves grafting of the CDR sequences of a donor antibody, generally a mouse antibody, into the framework scaffold of a human antibody of different specificity. Since CDR grafting may reduce the binding specificity and affinity, and thus the biological activity, of a CDR grafted non-human antibody, back mutations may be introduced at selected positions of the CDR grafted antibody in order to retain the binding specificity and affinity of the parent antibody. Identification of positions for possible back mutations can be performed using information available in the literature and in antibody databases. An alternative humanization technique to CDR grafting and back mutation is resurfacing, in which non-surface exposed residues of non-human origin are retained, while surface residues are altered to human residues. Another alternative technique is known as "guided selection" (Jespers et al. (1994) Biotechnology 12, 899) and can be used to derive from for example a murine or rat antibody a fully human antibody conserving the epitope and binding characteristics of the parental antibody. A further method of humanization is the so-called 4D humanization. The 4D humanization protocol is described in the patent application US20110027266 A1 (WO2009032661A1) and is exemplified in the following applying the 4D humanization to humanize the rat antibody variable light ($V_L$) and heavy ($V_H$) domains.

For chimeric antibodies, humanization typically involves modification of the framework regions of the variable region sequences.

Amino acid residues that are part of a CDR will typically not be altered in connection with humanization, although in certain cases it may be desirable to alter individual CDR amino acid residues, for example to remove a glycosylation site, a deamidation site, an isomerization site, or an undesired cysteine residue. N-linked glycosylation occurs by attachment of an oligosaccharide chain to an asparagine residue in the tripeptide sequence Asn-X-Ser or Asn-X-Thr, where X may be any amino acid except Pro. Removal of an N-glycosylation site may be achieved by mutating either the Asn or the Ser/Thr residue to a different residue, in particular by way of conservative substitution. Deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in a CDR sequence, it may therefore be desirable to remove the site, typically by conservative substitution to remove one of the implicated residues. Substitution in a CDR sequence to remove one of the implicated residues is also intended to be encompassed by the present invention.

"Fragments of antibodies" comprise a portion of an intact antibody, in particular the antigen binding region or variable region of the intact antibody. Examples of antibody fragments include Fv, Fab, F(ab')2, Fab', dsFv, (dsFv)2, scFv, sc(Fv)2, diabodies, bispecific and multispecific antibodies formed from antibody fragments. A fragment of an antibody may also be a single domain antibody, such as a heavy chain antibody or VHH.

The term "Fab" denotes an antibody fragment having a molecular weight of about 50,000 Dalton and antigen binding activity, in which about a half of the N-terminal side of H chain and the entire L chain, among fragments obtained by treating IgG with a protease, e.g. papain, are bound together through a disulfide bond.

The term "bispecific" in relation to the antigen binding proteins of the present invention refers to antigen binding proteins with at least two valences and binding specificities for two different antigens and thus, comprises two antigen binding sites. The term "valence" refers to the number of binding sites of an antigen binding protein, e.g. a bivalent antigen binding protein relates to an antigen binding protein that has two binding sites. It should be noted, that, the term valence refers to the number of binding sites, wherein those binding sites may bind to the same or different targets, i.e. a bivalent antigen binding protein may be monospecific, i.e. binding one target, or bispecific, i.e. binding two different targets. Targets may be antigens, target peptides, off-targets, i.e. similar peptides or the like.

In the context of the present invention it is preferred that at least one antigen-binding site is derived from a TCR, more particularly, that at least one antigen binding site comprises the TCR derived CDRs as defined in the context of the present invention.

In the context of the present invention for the term "bispecific" it is preferred that at least one specificity of the antigen binding sites is derived from a TCR, more particularly, that at least one antigen binding site comprises the TCR derived CDRs as defined in the context of the present invention. Accordingly, "bispecific" in the context of the present invention refers to an antigen binding protein which combines at least one antigen binding site comprising CDRs as defined in context of the present invention, i.e. TCR derived CDRs, and at least one further antigen binding site, wherein said at least one further antigen binding site, may be derived from an antibody and thus comprises antibody CDRs, or from a further TCR and thus comprises the CDRs of a further TCR. However, in a preferred embodiment, the said further antigen binding site, is derived from an antibody and thus comprises antibody CDRs.

The term "format" herein refers to antigen binding protein comprising a specific number and type of domains that are present in said antigen binding protein and the spatial organization thereof.

Many different formats, such as bispecific formats, are described in the art, typically, in the context of antibodies, such formats typically include non-limiting examples, such as, diabodies, Cross-Over-Dual-Variable-Domain (CODV) and/or in the Dual variable domain (DVD) proteins. An overview of these different bispecific antibodies and ways of making them is disclosed in, for example, Brinkmann U. and Kontermann E E MAbs. 2017 February-March; 9(2): 182-212. Particularly, the DVD format is, for example, disclosed in the following scientific articles (Wu C et al. Nat Biotechnol 2007; 25:1290-7; PMID:17934452; Wu C. et al. MAbs 2009; 1:339-47; Lacy S E et al. MAbs 2015; 7:605-19; PMID:25764208; Craig R B et al. PLoS One 2012; 7:e46778; PMID:23056448; Piccione E C et al. MAbs 2015). The CODV is for example disclosed in Onuoha S C et al. Arthritis Rheumatol. 2015 October; 67(10):2661-72 or for example in WO2012/135345, WO2016/116626. Bispecific diabodies are for example described in Holliger P et al. Protein Eng 1996; 9:299-305; PMID:8736497; Atwell J L et al. Mol Immunol 1996; 33:1301-12; PMID:9171890; Kontermann R E, Nat Biotechnol 1997; 15:629-31; PMID: 9219263; Kontermann R E et al. Immunotechnology 1997; 3:137-44; PMID:9237098; Cochlovius B et al. Cancer Res 2000; 60:4336-41; PMID:10969772; and DeNardo D G et al. Cancer Biother Radiopharm 2001; 16:525-35; PMID: 11789029.

"Diabodies" as used in the context of antibodies, typically refer to bivalent molecules composed of two chains, each comprising a VH and VL domain, either from the same or from different antibodies. The two chains typically have the configuration VHA-VLB and VHB-VLA (A and B representing two different specificities) or VLA-VHB and VLB-VHA.

In the context of the present invention, "diabodies (db)" or the "diabody format" herein refers to bivalent molecules composed of two polypeptide chains, each comprising two variable domains connected by a linker ($L_{Db1}$ and $L_{Db2}$), wherein two of the domains are first and second domains as defined in the context of the present invention ($V_1$ and $V_2$) and the other two domains may be TCR derived or antibody derived variable domains ($V_A$, $V_B$). The $V_1$ and $V_2$ domains are located on two different polypeptides and the $V_A$ and $V_B$ domains are located on two different polypeptides and the domains dimerize in a head-to-tail orientation. Accordingly, the orientation may be $V_1$-$L_{Db1}$-$V_A$ and $V_B$-$L_{Db2}$-$V_2$, $V_2$-$L_{Db1}$-$V_A$ and $V_B$-$L_{Db2}$-$V_1$, $V_1$-$L_{Db1}$-$V_B$ and $V_A$-$L_{Db2}$-$V_2$ or $V_2$-$L_{Db1}$-$V_B$ and $V_A$-$L_{Db2}$-$V_1$. In order to allow the domains to dimerize head to-tail the linker, i.e. $L_{Db1}$ and $L_{Db1}$, can be identical or different and are short linkers. A short linker is a linker that is typically between 2 to 12, 3 to 13, such as 3, 4, 5, 6, 7, 8, 9 amino acids long, for example 4, 5 (Brinkmann U. and Kontermann E E (MAbs. 2017 February-March; 9(2): 182-212) or 8 amino acids long, such as 'GGGS' of SEQ ID NO: 100, 'GGGGS' of SEQ ID NO: 101 or 'GGGSGGGG' of SEQ ID NO: 96.

The "dual-variable-domain immunoglobulin (DVD-Ig™)" format was initially described in 2007 by Wu C. et al. (Nat Biotechnol. 2007 November; 25(11):1290-7). In this format, the target-binding variable domains of a, typically, second monoclonal antibody (B) are typically fused to a conventional antibody (A) (comprising the domains $V_{LA}$ and $V_{HA}$), wherein the light chain of the conventional antibody (A) thus comprises an additional light chain variable domain ($V_{LB}$) and the heavy chain of the conventional antibody (A) comprises an additional heavy chain variable domain ($V_{HB}$). The DVD-Ig™ as described in the art, is thus typically composed of two polypeptide chains, one heavy chain comprising $V_{HB}$-L-$V_{HA}$-$C_{H1}$-$C_{H2}$-$C_{H3}$ and one light chain comprising $V_{LB}$-L-$V_{LA}$-$C_L$. The domain pairs $V_{LA}$/$V_{HA}$ and $V_{LA}$/$V_{LA}$ are thus pairing in parallel.

In the context of the present invention, the "dual-variable-domain Ig format" refers to a protein comprising two polypeptide chains, each comprising two variable domains connected by a linker ($L_1$, $L_3$), wherein two of the domains are first and second domains as defined in the context of the present invention ($V_1$ and $V_2$) and the other two domains are antibody derived heavy and light chain variable domains ($V_{HA}$ and $V_{HB}$). In the DVD-Ig format in the context of the present invention the polypeptide chains have, for example the organization $V_1$-$L_1$-$V_{HA}$-$L_2$-$C_{H1}$-$C_{H2}$-$C_{H3}$ and $V_2$-$L_3$-$V_{LA}$-$L_4$-$C_L$ or $V_2$-$L_1$-$V_{HA}$-$L_2$-$C_{H1}$-$C_{H2}$-$C_{H3}$ and $V_1$-$L_3$-$V_{LA}$-$L_4$-$C_L$. The connecting linkers $L_1$ and $L_3$ are preferably between 5 to 20 amino acid residues long, such as 5 to 15 amino acid residues, and/or the connecting linkers $L_2$ and $L_4$ may be present or absent.

The "crossover dual-variable domain-Ig-like proteins" as described in the art in the context of antibodies represents a format in which two $V_H$ and two $V_L$ domains are linked in a way that allows crossover pairing of the variable $V_H$-$V_L$ domains, which are arranged either (from N- to C-terminus) in the order $V_{HA}$-$V_{HB}$ and $V_{LB}$-$V_{LA}$, or in the order $V_{HB}$-$V_{HA}$ and $V_{LA}$-$V_{LB}$.

In the context of the present invention, the "crossover dual-variable domain-Ig-like protein" refers to a protein comprising two polypeptide chains, each comprising two variable domains connected by a linker ($L_1$, $L_2$, $L_3$ and $L_4$), wherein two of the domains are first and second domains as defined in the context of the present invention ($V_1$ and $V_2$) and the other two domains are antibody derived heavy and light chain variable domains ($V_{HA}$, $V_{HB}$). In the CDVD-Ig format in the context of the present invention the polypeptide chains have, for example the organization $V_1$-$L_1$-$V_{HA}$-$L_2$-$CH_1$-$C_{H2}$-$C_{H3}$ and $V_{LA}$-$L_3$-$V_2$-$L_4$-$C_L$, $V_2$-$L_1$-$V_{HA}$-$L_2$-$C_{H1}$-$C_{H2}$-$C_{H3}$ and $V_{LA}$-$L_3$-$V_1$-$L_4$-$C_L$, $V_{HA}$-$L_1$-$V_1$-$L_2$-$C_{H1}$-$C_{H2}$-$C_{H3}$ and $V_2$-$L_3$-$V_{LA}$-$L_{DVD3}$-$C_L$ or $V_{HA}$-$L_1$-$V_2$-$L_2$-$C_{H1}$-$C_{H2}$-$C_{H3}$ and $V_1$-$L_3$-$V_{LA}$-$L_4$-$C_L$. In this CDVD format, the linkers ($L_1$ to $L_4$) are typically of different length, including all-glycine linkers and linkers as described herein below in the section linkers. For example, $L_1$ is 3 to 12 amino acid residues in length, $L_2$ is 3 to 14 amino acid residues in length, $L_3$ is 1 to 8 amino acid residues in length, and $L_4$ is 1 to 3 amino acid residues in length, or $L_1$ is 5 to 10 amino acid residues in length, $L_2$ is 5 to 8 amino acid residues in length, $L_3$ is 1 to 5 amino acid residues in length, and $L_4$ is 1 to 2 amino acid residues in length or $L_1$ is 7 amino acid residues in length, $L_2$ is 5 amino acid residues in length, $L_3$ is 1 amino acid residues in length, and $L_4$ is 2 amino acid residues in length.

"At least one" herein refers to one or more of the specified objects such as 1, 2, 3, 4, 5 or 6 or more of the specified objects. For example, at least one binding site herein refers to 1, 2, 3, 4, 5 or 6 or more binding sites.

A sequence "at least 85% identical to a reference sequence" is a sequence having, over its entire length, 85%, or more, in particular 90%, 91%, 92%, 93%, 94%, 95%, 96%, 97%, 98% or 99% sequence identity with the entire length of a reference sequence.

In the context of the present application, the "percentage of identity" is calculated using a global pairwise alignment (i.e. the two sequences are compared over their entire length). Methods for comparing the identity of two or more sequences are well known in the art. The "needle" program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is for example available on the World Wide Web site and is further described in the following publication (*EMBOSS: The European Molecular Biology Open Software Suite* (2000) Rice, P. Longden, I. and Bleasby, A. Trends in Genetics 16, (6) pp. 276-277). The percentage of identity between two polypeptides, in accordance with the invention, is calculated using the EMBOSS: needle (global) program with a "Gap Open" parameter equal to 10.0, a "Gap Extend" parameter equal to 0.5, and a Blosum62 matrix.

Proteins consisting of an amino acid sequence "at least 80%, 85%, 90%, 95%, 96%, 97%, 98% or 99% identical" to a reference sequence may comprise amino acid mutations such as deletions, insertions and/or substitutions compared to the reference sequence. In case of substitutions, the protein consisting of an amino acid sequence at least 80%, 85%, 90%, 95%, 96%, 97%, 98% or 99% identical to a reference sequence may correspond to a homologous sequence derived from another species than the reference sequence.

"Amino acid substitutions" may be conservative or non-conservative. Preferably, substitutions are conservative substitutions, in which one amino acid is substituted for another amino acid with similar structural and/or chemical properties.

In an embodiment, conservative substitutions may include those, which are described by Dayhoff in "The Atlas of Protein Sequence and Structure. Vol. 5", Natl. Biomedical Research, the contents of which are incorporated by reference in their entirety. For example, in an aspect, amino acids, which belong to one of the following groups, can be exchanged for one another, thus, constituting a conservative exchange: Group 1: alanine (A), proline (P), glycine (G), asparagine (N), serine (S), threonine (T); Group 2: cysteine (C), serine (S), tyrosine (Y), threonine (T); Group 3: valine (V), isoleucine (I), leucine (L), methionine (M), alanine (A), phenylalanine (F); Group 4: lysine (K), arginine (R), histidine (H); Group 5: phenylalanine (F), tyrosine (Y), tryptophan (W), histidine (H); and Group 6: aspartic acid (D), glutamic acid (E). In an aspect, a conservative amino acid substitution may be selected from the following of T→A, G→A, T→V, A→M, A→V, T→G, and/or T→S.

In a further embodiment, a conservative amino acid substitution may include the substitution of an amino acid by another amino acid of the same class, for example, (1) nonpolar: Ala, Val, Leu, Ile, Pro, Met, Phe, Trp; (2) uncharged polar: Gly, Ser, Thr, Cys, Tyr, Asn, Gln; (3) acidic: Asp, Glu; and (4) basic: Lys, Arg, His. Other conservative amino acid substitutions may also be made as follows: (1) aromatic: Phe, Tyr, His; (2) proton donor: Asn, Gln, Lys, Arg, His, Trp; and (3) proton acceptor: Glu, Asp, Thr, Ser, Tyr, Asn, Gln (see, for example, U.S. Pat. No. 10,106,805, the contents of which are incorporated by reference in their entirety).

In another embodiment, conservative substitutions may be made in accordance with Table 1. Methods for predicting tolerance to protein modification may be found in, for example, Guo et al., Proc. Natl. Acad. Sci., USA, 101(25): 9205-9210 (2004), the contents of which are incorporated by reference in their entirety.

TABLE 1

Conservative Amino Acid substitution
Conservative Amino Acid Substitutions

| Amino Acid | Substitutions (others are known in the art) |
|---|---|
| Ala | Ser, Gly, Cys |
| Arg | Lys, Gln, His |
| Asn | Gln, His, Glu, Asp |
| Asp | Glu, Asn, Gln |
| Cys | Ser, Met, Thr |
| Gln | Asn, Lys, Glu, Asp, Arg |
| Glu | Asp, Asn, Gln |
| Gly | Pro, Ala, Ser |
| His | Asn, Gln, Lys |
| Ile | Leu, Val, Met, Ala |
| Leu | Ile, Val, Met, Ala |
| Lys | Arg, Gln, His |
| Met | Leu, Ile, Val, Ala, Phe |
| Phe | Met, Leu, Tyr, Trp, His |
| Ser | Thr, Cys, Ala |
| Thr | Ser, Val, Ala |
| Trp | Tyr, Phe |
| Tyr | Trp, Phe, His |
| Val | Ile, Leu, Met, Ala, Thr |

In another embodiment, conservative substitutions may be those shown in Table 2 under the heading of "conservative substitutions." If such substitutions result in a change in biological activity, then more substantial changes, denominated "exemplary substitutions" in Table 2, may be introduced and the products screened if needed.

TABLE 2

Amino Acid substitution
Amino Acid Substitutions

| Original Residue (naturally occurring amino acid) | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

In some embodiments, the antigen binding protein may include a variant antigen binding protein, wherein said variant antigen binding protein includes a first polypeptide chain (such as an α chain) and a second polypeptide chain (such as a β chain) comprising up to 8, 9, 10, 11, 12, 13, 14, 15, or more amino acid substitutions, preferably in the CDR regions of the first variable domain (such as a Valpha domain) and the second variable domain (such as a Vbeta domain) in comparison to the antigen binding protein from which the variant is derived. In this regard, there may be 1, 2, 3, 4, 5, 6, 7, 8, 9, 10, 11, 12, 13, 14, 15, or more amino acid substitutions in each of the CDR regions of the antigen binding protein or in all of the CDR regions of the first and/or second variable domain Substitutions may be in the CDRs either in the first and/or the second variable domain.

In one embodiment, the variant is a functional variant.

The term "functional variant" as used herein refers to an antigen binding protein having substantial or significant sequence identity or similarity to a parent antigen binding protein, such as those antigen binding proteins containing conservative amino acid substitutions, wherein said functional variant retains the biological activity of the parental antigen binding protein. In an aspect, functional variants encompass, for example, those variants of antigen binding proteins described herein (the antigen binding proteins described herein are then themselves referred to as parent antigen binding proteins) that retain the ability to recognize target cells to a similar extent, the same extent, or to a higher extent, as the parent antigen binding proteins. In reference to the parent antigen binding protein the functional variant can, for instance, have an amino acid sequence that is sequence at least 80%, 85%, 90%, 95%, 96%, 97%, 98% or 99% identical to the amino acid sequence to the parent antigen binding protein.

The functional variant can, for example, comprise the amino acid sequence of the parent antigen binding protein with at least one conservative amino acid substitution. Alternatively, or additionally, the functional variants can comprise the amino acid sequence of the parent antigen binding protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parental antigen binding protein.

The modified TCRs, polypeptides, and antigen binding proteins of the present disclosure (including functional portions and functional variants) can be of any length, i.e., can comprise any number of amino acids, provided that the modified TCRs, polypeptides, or proteins (or functional portions or functional variants thereof) retain their biological activity, e.g., the ability to specifically bind to antigen, detect diseased cells in a host, or treat or prevent disease in a host, etc.

The antigen binding proteins of the present inventions (including functional portions and functional variants) can comprise synthetic amino acids in place of one or more naturally-occurring amino acids. Such synthetic amino acids are known in the art, and may include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

In one embodiment, the antigen binding protein of the present invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The antigen binding protein of the present disclosure can be synthetic, recombinant, isolated, and/or purified.

A "covalent link" herein refers for example to a disulfide bridge or a peptide link or a covalent link via a linker or linker sequence, such as a polypeptide linker.

The term "linker" as used herein refers to one or more amino acid residues inserted between two domains to provide sufficient mobility for the domains, for example in single chain constructs, between the first variable domain and the second variable domain of the antigen binding proteins of the invention and, optionally, between the variable domains of light and heavy chain variable domains, to fold correctly to form the antigen binding site or, in case of bispecific antigen binding proteins, to form the antigen binding site and the at least one further antigen binding site, either in a cross over pairing (in a CODV format or in some of the diabody formats) or in a parallel pairing configuration (for example, in a DVD format) of the antigen binding proteins of the invention.

In some embodiments, a linker consists of 0 amino acid meaning that the linker is absent. A linker is inserted at the transition between variable domains or between variable domains and constant domains, respectively, at the amino acid sequence level. The transition between domains can be identified because the approximate size of the immunoglobulin domains as well as of the TCR domains is well understood. It is known by the skilled in the art, that the precise location of a domain transition can be determined by locating peptide stretches that do not form secondary structural elements such as beta-sheets or alpha-helices as demonstrated by experimental data or can be identified or assumed using techniques of modeling or secondary structure prediction. The term linker used in the context of the present invention refers but is not limited to the linkers referred to as $L_1$, $L_2$, $L_3$, $L_4$, $L_5$ and $L_6$.

A linker, as long as it is not specified otherwise in the respective context, such as $L_1$, $L_2$, $L_3$, $L_4$, $L_5$ and $L_6$, can be from at least 1 to 30 amino acids in length. In some embodiments, a linker, such as $L_1$, $L_2$, $L_3$, $L_4$, $L_5$ and $L_6$, can be 2-25, 2-20, or 3-18 amino acids long. In some embodiments, a linker, such as $L_1$, $L_2$, $L_3$, $L_5$ and $L_6$, can be a peptide of a length of no more than 14, 13, 12, 11, 10, 9, 8, 7, 6, or 5 amino acids. In other embodiments, a linker, such as $L_1$, $L_2$, $L_3$, $L_4$, $L_5$ and $L_6$, can be 5-25, 5-15, 4-11, 10-20, or 20-30 amino acids long. In other embodiments, a linker, such as $L_1$, $L_2$, $L_3$, $L_4$, $L_5$ and $L_6$, can be about, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids long. In a particular embodiment linkers, such as $L_1$, $L_2$, $L_3$, $L_4$, $L_5$ and $L_6$, may be less than 24, less than 20, less than 16, is less than 12, less than 10, for example from 5 to 24, 10 to 24 or 5-10 amino acid residues in length. In some embodiments, said linker is equal to 1 or more amino acid residues in length, such as more than 1, more than 2, more than 5, more than 10, more than 20 amino acid residues in length, more than 22 amino acid residues in length.

Exemplary linkers, such as $L_1$, $L_2$, $L_3$, $L_4$, $L_5$ and $L_6$, comprise or consist of the amino acid sequence selected from the group of amino acids consisting of the amino acid sequences TVAAP (SEQ ID NO: 99), GGGS (SEQ ID NO: 100), GGGGS (SEQ ID NO: 101), GGSGG (SEQ ID NO: 140), TVLRT (SEQ ID NO: 102), TVSSAS (SEQ ID NO: 103), GGGSGGGG (SEQ ID NO:96), GGGGSGT (SEQ ID NO: 148), GGSGGGGSGG (SEQ ID NO: 141), GGGGSGGGGS (SEQ ID NO: 104), GGSGGGGSGGGGSGG (SEQ ID NO: 143), GGGGSAAA (SEQ ID NO: 105), GGGGSGGGGSGT (SEQ ID NO: 155) GGGGSGGGGSGGGGS (SEQ ID NO: 106), GGGGSGGGGSGGGGSGT (SEQ ID NO: 161), GGGGSGGGGSGGGGSGGGGSGT (SEQ ID NO: 163), GGSGGGGSGGGGSGGGGSGG (SEQ ID NO: 144), GGGGSGGGGSGGGGSGGGGSGGGGSGT (SEQ ID NO: 165), GGGGSGGGGSGGGGSGGGGSGGGGSGS (SEQ ID NO: 107), GGSGGGGSGGGGSGGGGSGGGGSGG (SEQ ID NO: 145), GGGGSGGGGSGGGGSGGGGSGGGGS (SEQ ID NO: 108), GSADDAKKDAAKKDGKS (SEQ ID NO: 146), GGQGSGGTGSGGQGSGGTGSGGQGS (SEQ ID NO: 147), TVLSSAS (SEQ ID NO: 109) and GGGGSGGGGSGGGGSGGGGS (SEQ ID NO: 110), in particular GGGSGGGG (SEQ ID NO:96), GGGGSGGGGSGGGGSGGGGS (SEQ ID NO: 110) and GGGGSGGGGSGGGGSGGGGSGGGGS (SEQ ID NO: 108).

The term "$F_c$ domain" as used in the context of the present invention encompasses native $F_c$ domains and $F_c$ domain variants and sequences as further defined herein below. As with $F_c$ variants and native $F_c$ molecules, the term "Fc domain" includes molecules in monomeric or multimeric form, whether digested from whole antibody or produced by other means.

The term "native $F_c$" as used herein refers to a molecule comprising the sequence of a non-antigen binding fragment resulting from digestion of an antibody or produced by other means, whether in monomeric or multimeric form, and may contain the hinge region. The original immunoglobulin source of the native $F_c$ is, in particular, of human origin and can be any of the immunoglobulins, preferably IgG1 or IgG2, most preferably IgG1. Native $F_c$ molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgGA2). One example of a native $F_c$ is a disulfide-bonded dimer resulting from papain digestion of an IgG. The term "native $F_c$" as used herein is generic to the monomeric, dimeric, and multimeric forms. One example of a native $F_c$ amino acid sequence is the amino acid sequence of SEQ ID NO: 111, which is the native $F_c$ amino acid sequence of IGHG1*01.

The "hinge" or "hinge region" or "hinge domain" refers typically to the flexible portion of a heavy chain located between the $C_{H1}$ domain and the $C_{H2}$ domain. It is approximately 25 amino acids long, and is divided into an "upper hinge," a "middle hinge" or "core hinge," and a "lower hinge." A "hinge subdomain" refers to the upper hinge, middle (or core) hinge or the lower hinge. The amino acids sequences of the hinges of an IgG1, IgG2, IgG3 and IgG4 molecule are indicated herein below:

IgG1:
(SEQ ID NO: 114)
$E_{216}$PKSCDKTHTCPPCPAPELLG

IgG2:
(SEQ ID NO: 115)
$E_{216}$RKCCVECPPCPAPPVAGP

IgG3:
(SEQ ID NO: 116)
ELKTPLGDTTHTCPRCPEPKSCDTPPPCPRCPE$_{216}$PKSCDTPPPCPRCP
APELLG

IgG4:
(SEQ ID NO: 117)
$E_{216}$SKYGPPCPSCPAPEFLG.

In the context of the present invention it is referred to amino acid positions in the $F_c$ domain, these amino acid positions or residues are indicated according to the EU numbering system as described, for example in Edelman, G. M. et al., Proc. Natl. Acad. USA, 63, 78-85 (1969).

The term "$F_c$ variant" as used herein refers to a molecule or sequence that is modified from a native $F_c$ but still comprises a binding site for the salvage receptor, F E Rn (neonatal F, receptor). Exemplary $F_c$ variants, and their interaction with the salvage receptor, are known in the art. Thus, the term "$F_c$ variant" can comprise a molecule or sequence that is humanized from a non-human native $F_c$. Furthermore, a native $F_c$ comprises regions that can be removed because they provide structural features or biological activity that are not required for the antigen binding proteins of the invention. Thus, the term "$F_c$ variant" comprises a molecule or sequence that lacks one or more native $F_c$ sites or residues, or in which one or more $F_c$ sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an F, receptor other than a salvage receptor, or (7) antibody-dependent cellular cytotoxicity (ADCC).

Accordingly, in one embodiment the Fc-domain, such as $F_{c1}$ and/or $F_{c2}$, comprises a hinge domain. In one embodiment, the $F_c$-domain is a human IgG $F_c$ domain, preferably derived from human IgG1, IgG2, IgG3 or IgG4, preferably IgG1 or IgG2, more preferably IgG1.

In some embodiments, in particular, when the antigen binding protein comprises two $F_c$ domains, i.e. in the TCER™ format described herein below (such as $F_{c1}$ and $F_{c2}$), the two $F_c$ domains may be of the same immunoglobulin isotype or isotype subclass or of different immunoglobulin isotype or isotype subclass, preferably of the same. Accordingly, in some embodiments $F_{c1}$ and $F_{c2}$, are of the IgG1 subclass, or of the IgG2 subclass, or of the IgG3 subclass, or of the IgG4 subclass, preferably of the IgG1 subclass, or of the IgG2 subclass, more preferably of the IgG1 subclass.

In some embodiments, the $F_c$ domain is a variant $F_c$ domain and thus comprises one or more of the amino acid substitutions described herein below.

In some embodiments, the $F_c$ domain comprises or further comprise the "RF" and/or "Knob-into-hole" mutation, preferably the "Knob-into-hole".

The "RF mutation" generally refers to the amino acid substitutions of the amino acids HY into RF in the $C_{H3}$ domain of $F_c$ domains, such as the amino acid substitution H435R and Y436F in $C_{H3}$ domain as described by Jendeberg, L. et al. (1997, J. Immunological Meth., 201: 25-34) and is described as advantageous for purification purposes as it abolishes binding to protein A. In case the antigen binding protein comprises two $F_c$-domains, the RF mutation may be in one or both, preferably in one $F_c$-domain.

The "Knob-into-Hole" or also called "Knob-into-Hole"-technology refers to amino acid substitutions T366S, $L_{368}$A and Y407V (Hole) and T366W (Knob) both in the $C_{H3}$-$C_{H3}$ interface to promote heteromultimer formation. Those knob-into-hole mutations can be further stabilized by the introduction of additional cysteine amino acid substitutions Y349C and S354C. The "Knob-into-Hole" technology together with the stabilizing cysteine amino acid substitutions has been described in U.S. Pat. Nos. 5,731,168 and 8,216,805.

In the context of the present invention, the "Knob" mutation together with the cysteine amino acid substitution S354C is, for example, present in the $F_c$ domain comprising or consisting of the amino acid sequence of SEQ ID NO: 112 and the "Hole" mutation together with the cysteine amino acid substitutions Y349C is present in the $F_c$ domain comprising or consisting amino acid sequence of SEQ ID NO: 113.

In some embodiments, the $F_c$ domain of one of the polypeptides, for example $F_{c1}$, comprises the amino acid substitution T366W (Knob) in its $C_{H3}$ domain and the Fc domain of the other polypeptide, for example Fa, comprises the amino acid substitution T366S, $L_{368}$A and Y407V (Hole) in its $C_{H3}$ domain, or vice versa.

In some embodiments, the $F_c$ domain of one of the polypeptides, for example $F_{c1}$, comprises or further comprises the amino acid substitution S354C in its $C_{H3}$ domain and the $F_c$ domain of the other polypeptide, for example Fa, comprises or further comprises the amino acid substitution Y349C in its $C_{H3}$ domain, or vice versa.

Accordingly, in some embodiments, the $F_c$ domain of one of the polypeptides, for example $F_{c1}$, comprises the amino acid substitutions S354C and T366W (Knob) in its $C_{H3}$ domain and the $F_c$ domain of the other polypeptide, for example $F_{c2}$, comprises the amino acid substitution Y349C, T366S, $L_{368}$A and Y407V (Hole) in its $C_{H3}$ domain, or vice versa.

This set of amino acid substitutions can be further extended by inclusion of the amino acid substitutions K409A on one polypeptide and F405K in the other polypeptide as described by Wei et al. (Structural basis of a novel heterodimeric $F_c$ for bispecific antibody production, *Oncotarget*. 2017). Accordingly, in some embodiments, the $F_c$ domain of one of the polypeptides, for example $F_{c1}$, comprises or further comprises the amino acid substitution K409A in its $C_{H3}$ domain and the $F_c$ domain of the other polypeptide, for example $F_{c2}$, comprises or further the amino acid substitution F405K in its $C_{H3}$ domain, or vice versa.

In some cases artificially introduced cysteine bridges may improve the stability of the antigen binding proteins, optimally without interfering with the binding characteristics of the antigen binding proteins. Such cysteine bridges can further improve heterodimerization.

Further amino acid substitutions, such as charged pair substitutions, have been described in the art, for example in EP 2 970 484 to improve the heterodimerization of the resulting proteins.

Accordingly in one embodiment, the $F_c$ domain of one of the polypeptides, for example $F_{c1}$, comprises or further comprises the charge pair substitutions E356K, E356R, D356R, or D356K and D399K or D399R, and the $F_c$ domain of the other polypeptide, for example $F_{c2}$, comprises or further comprises the charge pair substitutions R409D, R409E, K409E, or K409D and N392D, N392E, K392E, or K392D, or vice versa.

In a further embodiment, the $F_c$ domain on one or both, preferably both polypeptide chains can comprise one or more alterations that inhibit $F_c$ gamma receptor ($F_c$yR) binding. Such alterations can include $L_{234}$A, $L_{235}$A.

With the inclusion of $F_c$-parts consisting of Hinges, $C_{H2}$ and $C_{H3}$ domains, or parts thereof, into antigen binding proteins, more particularly into bispecific antigen binding proteins the problem of unspecific immobilization of these molecules, induced by $F_c$:$F_c$-gamma receptor ($F_c$gR) interactions arose. $F_c$gRs are composed of different cell surface molecules ($F_c$gRI, $F_c$gRIIa, $F_c$gRIIb, $F_c$gRIII) binding with differing affinities to epitopes displayed by $F_c$-parts of IgG-molecules. As such an unspecific (i.e. not induced by either of the two binding domains of a bispecific molecule) immobilization is unfavorable due to i) influence on pharmacokinetics of a molecule and ii) off-target activation of immune effector cells various $F_c$-variants and mutations to ablate $F_c$gR-binding have been identified. In this context, Morgan et al. 1995, Immunology (The N-terminal end of the $C_{H2}$ domain of chimeric human IgG1 anti-HLA-DR is necessary for C1q, $F_c$yRI and $F_c$yRIII binding) disclose the exchange of the residues 233-236 of human IgG1 with the corresponding sequence derived from human IgG2, i.e. the residues 233P, 234V and 235A and wherein no amino acid is present at position 236, resulting in abolished $F_c$gRI binding, abolished C1q binding and diminished $F_c$gRIII binding. EP1075496 discloses antibodies and other $F_c$-containing molecules with variations in the $F_c$ region (such as one or more of 233P, 234V, 235A and no residue or G in position 236 and 327G, 330S and 331S) wherein the recombinant antibody is capable of binding the target molecule without triggering significant complement dependent lysis, or cell mediated destruction of the target.

Accordingly, in some embodiments, the $F_c$ region comprises or further comprise one or more of the amino acids or deletions selected from the group consisting of 233P, 234V, 235A, 236 (No residue) or G, 327G, 330S, 331S, preferably, the $F_c$ region comprises or further comprises the amino acids 233P, 234V, 235A, 236 (No residue) or G and one or more amino acids selected from the group consisting of 327G, 330S, 331S, most preferably, the $F_c$ region comprises or further comprises the amino acids 233P, 234V, 235A, 236 (No residue) and 331S.

In one further embodiment, the $F_c$ domain comprises or further comprises the amino acid substitution N297Q, N297G or N297A, preferably N297Q.

The amino acid substitution "N297Q", "N297G" or "N297A" refer to amino acid substitutions at position 297 that abrogate the native N-Glycosylation site within the $F_c$-domain. This amino acid substitution further prevents $F_c$-gamma-receptor interaction and decreases the variability of the final protein products, i.e. the antigen binding proteins of the present invention, due to sugar residues as described for example in Tao, M H and Morrison, SL (J Immunol. 1989 Oct. 15; 143(8):2595-601.).

In one further embodiment, in particular when no light chain, the $F_c$ domain comprises or further comprises the amino acid substitution S220C. The amino acid substitution "S220C" deletes the cysteine forming the $C_{H1}$-$C_L$ disulfide-bridge.

In some embodiments, the $F_c$ domain comprises or further comprises at least two additional cysteine residues, for example S354C and Y349C or $L_{242}$C and K334C, wherein S354C is in the $F_c$-domain of one polypeptide, such as $F_{c1}$, and Y349C is in the $F_c$ domain of the other polypeptide, such as Fa, to form a heterodimer and/or wherein $L_{242}$C and K334C are located in the same $F_c$-domain, either in the $F_{c1}$ or $F_{c2}$ of one or both polypeptides to form a intradomain C-C bridge.

By "purified" and "isolated" it is meant, when referring to a polypeptide (i.e. the antigen binding protein of the invention) or a nucleotide sequence, that the indicated molecule is present in the substantial absence of other biological macromolecules of the same type. The term "purified" as used herein in particular means at least 75%, 85%, 95%, or 98% by weight, of biological macromolecules of the same type are present.

An "isolated" nucleic acid molecule that encodes a particular polypeptide refers to a nucleic acid molecule that is substantially free of other nucleic acid molecules that do not encode the subject polypeptide; however, the molecule may include some additional bases or moieties, which do not deleteriously affect the basic characteristics of the composition.

A "domain" may be any region of a protein, generally defined on the basis of sequence homologies and often related to a specific structural or functional entity.

A "recombinant" molecule is one that has been prepared, expressed, created, or isolated by recombinant means.

The term "gene" means a DNA sequence that codes for, or corresponds to, a particular sequence of amino acids which comprises all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription. In particular, the term gene may be intended for the genomic sequence encoding a protein, i.e. a sequence comprising regulator, promoter, intron and exon sequences.

"Affinity" is defined, in theory, by the equilibrium binding between the antigen binding protein and the antigen, in the context of the present invention by the equilibrium binding between the antigen binding protein and its antigen, namely the MAGE-A antigenic peptide comprising or consisting of the amino acid sequence of SEQ ID NO: 1 in a complex with a MHC protein. Affinity may be expressed for example in half-maximal effective concentration ($EC_{50}$) or the equilibrium dissociation constant ($K_D$).

"$K_D$" is the equilibrium dissociation constant, a ratio of $k_{off}/k_{on}$, between the antigen binding protein and its antigen. $K_D$ and affinity are inversely related. The $K_D$ value relates to the concentration of the antigen binding protein and the lower the $K_D$ value, the higher the affinity of the antigen binding protein. Affinity, i.e. the $K_D$ value, can be experimentally assessed by a variety of known methods, such as measuring association and dissociation rates with surface plasmon resonance (SPR) or biolayer interferometry (BLI), as described in more detail herein below in the section 'Antigen binding proteins'.

"Half maximal effective concentration" also called "$EC_{50}$" typically refers to the concentration of a molecule which induces a response halfway between the baseline and maximum after a specified exposure time. $EC_{50}$ and affinity are inversely related, the lower the $EC_{50}$ value the higher the affinity of the molecule. In one example, the "$EC_{50}$" refers to the concentration of the antigen binding protein of the invention which induces a response halfway between the baseline and maximum after a specified exposure time, more particularly, refers to the concentration of the antigen binding protein of the invention which induces a response halfway between the baseline and maximum after a specified exposure time. $EC_{50}$ values can be experimentally assessed by a variety of known methods, using for example a IFN-gamma release assay or a LDH release assay as described in more detail herein below in the section 'Antigen binding proteins'.

"CD3" is a protein complex and is composed of four distinct chains. In mammals, the complex contains a CD3γ chain, a CD3δ chain, and two CD3ε chains. These chains associate with a molecule known as the T cell receptor (TCR) and the ζ-chain to generate an activation signal in T lymphocytes.

"CD28" is also expressed on T cells and can provide co-stimulatory signals, which are required for T cell activation. CD28 plays important roles in T cell proliferation and survival, cytokine production, and T-helper type-2 development.

"CD134" is also termed OX40. CD134/OX40 is being expressed after 24 to 72 hours following activation and can be taken to define a secondary costimulatory molecule.

"4-1BB" is capable of binding to 4-1BB-Ligand on antigen presenting cells (APCs), whereby a costimulatory signal for the T cell is generated.

"CD5" is another example of a receptor predominantly found on T cells, CD5 is also found on B cells at low levels.

"CD95" is a further example of a receptor modifying T cell functions and is also known as the Fas receptor, which mediates apoptotic signaling by Fas-ligand expressed on the surface of other cells. CD95 has been reported to modulate TCR/CD3-driven signaling pathways in resting T lymphocytes.

A "NK cell specific receptor molecule" is, for example, CD16, a low affinity F, receptor and NKG2D.

An example of a receptor molecule that is present on the surface of both T cells and natural killer (NK) cells is CD2 and further members of the CD2-superfamily CD2 is able to act as a co-stimulatory molecule on T and NK cells.

A "transmembrane region" as referred to in (ii) herein above in the context of the present invention may be, for example, a TCR alpha or beta transmembrane domain.

A "cytoplasmic signaling region" may be for example a TCR alpha or beta intracellular domain.

A "diagnostic agent" herein refers to a detectable molecule or substance, such as a fluorescent molecule, a radioactive molecule or any other labels known in the art that provide (either directly or indirectly) a signal.

"Fluorescent molecules" are known in the art include fluorescein isothiocyanate (FITC), phycoerythrin (PE), fluorophores for use in the blue laser (e.g. PerCP, PE-Cy7, PE-Cy5, FL3 and APC or Cy5, FL4), fluorophores for use in the red, violet or uv laser (e.g. Pacific blue, pacific orange).

"Radioactive molecules" include but are not limited radioactive atom for scintigraphic studies such as $I^{123}$, $I^{124}$, $In^{111}$, $Re^{186}$, $Re^{188}$, $Tc^{99}$. Antigen binding proteins of the invention may also comprise a spin label for nuclear magnetic resonance (NMR) imaging (also known as magnetic resonance imaging, MRI), such as iodine-123, indium-111, fluorine-19, carbon-13, nitrogen-15, oxygen-17, gadolinium, manganese or iron.

Such diagnostic agents are may be either directly coupled (i.e., physically linked) to the antigen binding protein or may be indirectly linked.

A "therapeutic agent" herein refers to an agent that has a therapeutic effect. In one embodiment, such a therapeutic agent may be a growth inhibitory agent, such as a cytotoxic agent or a radioactive isotope.

A "growth inhibitory agent", or "anti-proliferative agent", which can be used indifferently, refers to a compound or composition which inhibits growth of a cell, especially a tumor cell, either in vitro or in vivo.

The term "cytotoxic agent" as used herein refers to a substance that inhibits or prevents the function of cells and/or causes destruction of cells. The term "cytotoxic agent" is intended to include chemotherapeutic agents, enzymes, antibiotics, and toxins such as small molecule toxins or enzymatically active toxins of bacterial, fungal, plant or animal origin, including fragments and/or variants thereof, and the various antitumor or anticancer agents disclosed below. In some embodiments, the cytotoxic agent is a taxoid, vincas, taxanes, a maytansinoid or maytansinoid analog such as DM1 or DM4, a small drug, a tomaymycin or pyrrolobenzodiazepine derivative, a cryptophycin derivative, a leptomycin derivative, an auristatin or dolastatin analog, a prodrug, topoisomerase II inhibitors, a DNA alkylating agent, an anti-tubulin agent, a CC-1065 or CC-1065 analog.

The term "radioactive isotope" is intended to include radioactive isotopes suitable for treating cancer, such as $At^{211}$, $Bi^{212}$, $Er^{169}$, $I^{131}$, $I^{125}$, $Y^{90}$, $In^{111}$, $P^{32}$, $Re^{186}$, $Re^{188}$, $Sm^{153}$, $Sr^{89}$, and radioactive isotopes of Lu. Such radioisotopes generally emit mainly beta-radiation. In an embodiment the radioactive isotope is alpha-emitter isotope, more precisely Thorium 227 which emits alpha-radiation.

A "PK modifying moiety" herein refers to a moiety that modifies the pharmacokinetics (PK) of the antigen binding protein of the invention. Accordingly, the moiety modifies in particular the in vivo half-life and distribution of the antigen binding protein of the invention. In a preferred embodiment, the PK modifying moiety increases the half-life of the antigen binding protein. Examples of PK modifying moieties include, but are not limited to, PEG (Dozier et al., (2015) Int J Mol Sci. October 28; 16(10):25831-64 and Jevsevar et al., (2010) Biotechnol J. January; 5(1):113-28), PASylation (Schlapschy et al., (2013) Protein Eng Des Sel. August; 26(8):489-501), albumin (Dennis et al., (2002) J Biol Chem. September 20; 277(38):35035-43), the $F_c$-part of an antibody and/or unstructured polypeptides (Schellenberger et al., (2009) Nat Biotechnol. December; 27(12): 1186-90).

"Half-Life ($T_{1/2}$)" generally refers to the time required for half the quantity of a drug or other substance deposited in a living organism to be metabolized or eliminated by normal biological processes. Half-life in the context of the present invention thus refers to the time required for half the quantity of the antigen binding protein of the invention to be eliminated in, for example, mice. Half-life can be determined by well-known methods in the art. In one example, the half-life is determined as described in detail in Example 10. Accordingly, in one example, the half-life is determined by administering the antigen binding protein of the invention to, for instance, mice, such as hyper immune-deficient NOG mice, for example, by intravenous administration followed by collecting plasma samples, for instance, from the retrobulbar plexus, at different time points, for instance, at time points 0 h, 0.1 h, 2 h, 8 h, 24 h, 48 h, 120 h, 240 h and 360 h. Plasma levels of the antigen binding protein are then determined by techniques known in the art, such as ELISA, using different set ups, such as a $F_c$–$V_L$ assay and a CD3—pMHC assay. Plasma concentrations of the samples are typically obtained by interpolation from the respective standard curves and the half-life is then typically determined by linear regression of the plasma levels obtained at the different time points.

Antigen Binding Proteins

Using the TCR R7P1D5, as disclosed in WO 2017/158103 as starting point, the inventors have designed, produced and tested TCR variable alpha (Valpha) and optionally variable beta (Vbeta) domain variants either in a single-chain (scTCR) format using a yeast screening assay as herein described in example 1 and 2 or in a single chain bispecific TCR construct to further optimize for binding affinity as well as yield and stability of soluble, bispecific scTCR constructs as herein described in example 4. In this way the inventors identified different variants of the variable alpha and optionally beta domain, more particularly different variants of CDRa3 (with 5 variants) of the variable alpha domain which might advantageously be combined with CDRa1, CDRa2, CDRb1, CDRb2 and/or CDRb3 of the parental TCR or with any of the CDR variants discovered for CDRa1 (1 variant), CDRa2 (3 variants), CDRb1 (1 variant), CDRb2 (5 variants) and/or CDRb3 (1 variant) that are variants which are of an advantage for the antigen binding proteins of the invention to bind the target, i.e. a MAGE-A antigenic peptide comprising the amino acid sequence of SEQ ID NO: 1 in a complex with a MHC protein, preferably in complex with HLA-A*02, with a high affinity but also high specificity.

The inventors demonstrated in the examples that the CDRs may be used in TCRs for ACT, single chain TCR constructs as well as in other bispecific formats and, thus, demonstrated in a proof of principle that the identified CDR variants may be used to produce different antigen binding proteins having a high affinity but also a high specificity to the MAGE-A antigenic peptide comprising the amino acid sequence of SEQ ID NO: 1 in a complex with a MHC protein, preferably in complex with HLA-A*02.

Moreover, the inventors discovered that mutating the framework of the TCR variable alpha (Valpha) and variable beta (Vbeta) domain improve binding specificity as well as yield and stability of soluble, bispecific scTCR constructs as herein described in example 4.

In examples 5-8, the inventors designed, expressed and successfully tested in vitro and in vivo efficacy against tumor cell lines, such as antigen binding proteins in the TCER™ format, specifically binding to the human TCR-CD3 complex and to the peptide:MHC complex comprising the MAGE-A peptide of SEQ ID NO: 1 bound to MHC class I molecules, e.g., HLA-A*02:01. For targeting the TCR-CD3 complex, $V_H$ and $V_L$ domains derived from the CD3-specific, humanized antibody hUCHT1 described by Zhu et al. (J Immunol, 1995, 155, 1903-1910) or the alpha/beta TCR-specific antibody BMA031 described in Shearman et al. (J Immunol, 1991, 147, 4366-73) are modified and used in those examples. For targeting the MAGE-A:MHC complex, the Valpha and Vbeta domains comprising the CDRs as herein disclosed may be utilized leading to stability and affinity maturated antigen binding proteins. The same $V_L$ and $V_H$, Valpha and Vbeta domains were further used in a human single chain T cell receptor format further comprising a Fab domain (comprising a $C_{H1}$-Hinge and $C_L$) as described in example 4.

Accordingly, the present invention refers to an antigen binding protein which specifically binds to an MAGE-A antigenic peptide comprising or consisting of the amino acid sequence 'KVLEHVVRV' of SEQ ID NO: 1, wherein said antigenic peptide is in a complex with an MHC protein, the antigen binding protein comprising (a) a first polypeptide chain comprising a first variable domain comprising three complementary determining regions (CDRs) CDRa1, CDRa2 and CDRa3, wherein the CDRa1 comprises or consists of the amino acid sequence '$X_1$SSSTY' SEQ ID NO: 72, wherein $X_1$ is any amino acid, preferably D or E, more preferably E, or an amino acid sequence differing from SEQ ID NO: 72 by at least one amino acid substitution, preferably by one, two or three amino acid substitutions, preferably by one or two amino acid substitutions, such as one amino acid substitution, the CDRa2 comprises or consists of the amino acid sequence 'I$X_1$S$X_2$$X_3$D$X_4$' SEQ ID NO: 73, wherein $X_1$ to $X_4$ is any amino acid, and wherein preferably $X_1$ is F or Y, more preferably Y, $X_2$ is N or S, preferably S, $X_3$ is Q or M, preferably Q, and $X_4$ is M, V, S or Q, preferably S or Q, more preferably Q.

the CDRa3 comprises or consists of the amino acid sequence 'CAE$X_1$$X_2$S$X_3$SKIIF' SEQ ID NO: 77, wherein $X_1$ to $X_3$ is any amino acid, and wherein preferably $X_1$ is A, F or M, more preferably M, preferably $X_2$ is S, T, or N, more preferably T, and preferably $X_3$ is E or A, preferably E, with the proviso that the CDRa3 does not comprise or consist of the amino acid sequence 'CAEYSSASKIIF' (SEQ ID NO: 7) if CDRa1 comprises or consists of the amino acid sequence SEQ ID NO: 5 and CDRa2 comprises or consists of the amino acid sequence SEQ ID NO: 6, preferably with the proviso that the CDRa3 does not comprise or consist of the amino acid sequence TAEYSSASKIIP (SEQ ID NO: 7), or the CDRa3 comprises or consists of the amino acid sequence 'CAE$X_1$$X_2$S$X_3$SKIIF' SEQ ID NO: 77, wherein $X_1$ to $X_3$ is any amino acid, and preferably $X_1$ is $F_c$ M or A, preferably M, and, preferably $X_2$ is S, T, or N, more preferably T, and preferably $X_3$ is E or A, preferably E, and (b) a second polypeptide chain comprising a second variable domain comprising three complementary determining regions (CDRs) CDRb1, CDRb2 and CDRb3, wherein the CDRb1 comprises or consists of the amino acid sequence '$X_1$GHDY' SEQ ID NO: 78, wherein $X_1$ is any amino acid, preferably S or P, more preferably P, or an amino acid sequence differing from SEQ ID NO: 78, by at least one amino acid substitution, preferably by one or two amino acid substitutions, such as one amino acid substitution, the CDRb2 comprises or consists of the amino acid sequence '$FX_1X_2X_3X_4P$' SEQ ID NO: 79, wherein $X_1$ to $X_4$ is any amino acid, preferably $X_1$ is C or N, more preferably C, preferably $X_2$ is Y or N, more preferably Y, preferably $X_3$ is G or N, more preferably G, preferably $X_4$ is H, V, T, A or M, preferably H or T, most preferably T wherein preferably, when $X_1$ is C, the FR3-b amino acid sequence comprises at the amino acid position 66 the amino acid 66C, and the CDRb3 comprises or consists of the amino acid sequence 'CASRA$X_1$TGELFF' SEQ ID NO: 82, wherein $X_1$ is any amino acid, preferably D or N, preferably D or an amino acid sequence differing from SEQ ID NO: 82, by at least one amino acid substitution, preferably by one, two or three amino acid substitutions, preferably by one or two amino acid substitutions, such as one amino acid substitution.

In one particular embodiment, the present invention refers to an antigen binding protein which specifically binds to a MAGE-A antigenic peptide comprising or consisting of the amino acid sequence 'KVLEHVVRV' of SEQ ID NO: 1, wherein said antigenic peptide is in a complex with a MHC protein, the antigen binding protein comprising (a) a first polypeptide chain comprising a first variable domain comprising three complementary determining regions (CDRs) CDRa1, CDRa2 and CDRa3, wherein the CDRa1 comprises or consists of the amino acid sequence SEQ ID NO: 5 or an amino acid sequence differing from SEQ ID NO: 5 by at least one amino acid substitution, preferably by one, two or three amino acid substitutions, preferably by one or two amino acid substitutions, such as one amino acid substitution, the CDRa2 comprises or consists of the amino acid sequence SEQ ID NO: 6 or an amino acid sequence differing from SEQ ID NO: 6 by at least one amino acid substitution, preferably by one, two or three amino acid substitutions, preferably by one or two amino acid substitutions, such as one amino acid substitution, and the CDRa3 comprises or consists of the amino acid sequence 'CAE$X_1X_2$S$X_3$SKIIF' SEQ ID NO: 77, wherein $X_1$ to $X_3$ is any amino acid, and wherein preferably $X_1$ is A, F or M, more preferably M, preferably $X_2$ is S, T or N, more preferably T, and preferably $X_3$ is E or A, preferably E, with the proviso that the CDRa3 does not comprise or consist of the amino acid sequence 'CAEYSSASKIIF' (SEQ ID NO: 7) if CDRa1 comprises or consists of the amino acid sequence SEQ ID NO: 5 and CDRa2 comprises or consists of the amino acid sequence SEQ ID NO: 6, preferably with the proviso that the CDRa3 does not comprise or consist of the amino acid sequence 'CAEYSSASKIIF' (SEQ ID NO: 7), or the CDRa3 comprises or consists of the amino acid sequence 'CAE$X_1X_2$S$X_3$SKIIF' SEQ ID NO: 77, wherein $X_1$ to $X_3$ is any amino acid, and preferably $X_1$ is $F_c$ M or A, preferably M, and, preferably $X_2$ is S,T or N, more preferably T, and preferably $X_3$ is E or A, preferably E, and wherein (b) a second polypeptide chain comprising a second variable domain comprising three complementary determining regions (CDRs) CDRb1, CDRb2 and CDRb3, wherein the CDRb1 comprises or consists of the amino acid sequence SEQ ID NO: 12 or an amino acid sequence differing from SEQ ID NO: 12, by at least one amino acid substitution, preferably by one, two or three amino acid substitutions, preferably by one or two amino acid substitutions, such as one amino acid substitution, the CDRb2 comprises or consists of the amino acid sequence SEQ ID NO: 13 or an amino acid sequence differing from SEQ ID NO: 13 by at least one amino acid substitution, preferably by one, two or three amino acid substitutions, preferably by one or two amino acid substitutions, such as one amino acid substitution, and the CDRb3 comprises or consists of the amino acid sequence SEQ ID NO: 14 or an amino acid sequence differing from SEQ ID NO: 14 by at least one amino acid substitution, preferably by one, two, three or four amino acid substitutions, preferably by one or two amino acid substitutions, such as one amino acid substitution.

In one particular embodiment, the present invention refers to an antigen binding protein, such as a soluble antigen binding protein, which specifically binds to an MAGE-A antigenic peptide comprising or consisting of the amino acid sequence 'KVLEHVVRV' of SEQ ID NO: 1, wherein said antigenic peptide is in a complex with a MHC protein, the antigen binding protein comprising a) a first polypeptide chain comprising a first variable domain comprising three complementary determining regions (CDRs) CDRa1, CDRa2 and CDRa3, wherein the CDRa1 comprises or consists of the amino acid sequence '$X_1$SSSTY' SEQ ID NO: 72, wherein $X_1$ is any amino acid, preferably D or E, more preferably E, or an amino acid sequence differing from SEQ ID NO: 72 by at least one amino acid substitution, preferably by one, two or three amino acid substitutions, preferably by one or two amino acid substitutions, such as one amino acid substitution, the CDRa2 comprises or consists of the amino acid sequence 'IYSSQD$X_1$' SEQ ID NO: 74 wherein $X_1$ is any amino acid, preferably Q, V or S, preferably Q.

the CDRa3 comprises or consists of the amino acid sequence CAEMTSESKIIF' SEQ ID NO:35, or an amino acid sequence differing from SEQ ID NO: 35 by at least one amino acid substitution, preferably by one, two, three or four amino acid substitutions, preferably by one or two amino acid substitutions, such as one amino acid substitution, and (b) a second polypeptide chain comprising a second variable domain comprising three complementary determining regions (CDRs) CDRb1, CDRb2 and CDRb3, wherein the CDRb1 comprises or consists of the amino acid sequence 'X$_1$GHDY' SEQ ID NO: 78, wherein X$_1$ is any amino acid, preferably S or P, more preferably P, or an amino acid sequence differing from SEQ ID NO: 78, by at least one amino acid substitution, preferably by one, two or three amino acid substitutions, preferably by one or two amino acid substitutions, such as one amino acid substitution, the CDRb2 comprises or consists of the amino acid sequence 'FCYGX$_1$P' SEQ ID NO: 81, wherein X$_1$ is any amino acid, preferably H, V, A or T, preferably T, or an amino acid sequence differing from SEQ ID NO: 81 by at least one amino acid substitution, preferably by one or two amino acid substitutions, more preferably one amino acid substitution, and wherein preferably when CDRb2 comprises or consists of the amino acid sequence 'FCYGX$_1$P' SEQ ID NO: 81 the FR3-b amino acid sequence comprises at the amino acid position 66 the amino acid 66C, the CDRb3 comprises or consists of the amino acid sequence 'CASRAX$_1$TGELFF' SEQ ID NO: 82, wherein X$_1$ is any amino acid, preferably D or N, preferably D or an amino acid sequence differing from SEQ ID NO: 82, by at least one amino acid substitution, preferably by one, two, three or four amino acid substitutions, preferably by one or two amino acid substitutions, such as one amino acid substitution.

As indicated herein above, in some embodiments the CDRb2 amino acid sequences comprises at position 57 the amino acid 57C, this amino acid preferably forms a disulfide bridge with a cysteine preferably present at position 66 of the FR3b amino acid sequence. Accordingly, in preferred embodiments, when the CDRb2 amino acid sequence comprises at position 57 the amino acid 57C then the FR3-b amino acid sequence, preferably, comprises at the amino acid position 66 the amino acid 66C and vice versa. In some embodiments, the FR3b amino acid sequence thus comprises preferably an amino acid substitution at this position 66, accordingly, in some related embodiments the FR3b amino acid sequence comprises the amino acid substitution I66C.

In some embodiments, the CDRa1 in the context of the present invention comprises or consists of the amino acid sequence of SEQ ID NO: 5 or SEQ ID NO: 55.

In one embodiment, the CDRa2 in context of the present invention comprises or consists of the amino acid sequence: 'IYSSQDX$_1$' SEQ ID NO: 74 wherein X$_1$ is any amino acid, preferably Q, V or S, more preferably Q, or SEQ ID NO: 6, or an amino acid sequence differing from SEQ ID NO: 74 or SEQ ID NO: 6 by at least one amino acid substitution, such as one, two or three amino acid substitutions, more preferably by one amino acid substitution, preferably CDRa2 comprises or consists of the amino acid sequence 'IYSSQDX$_1$' SEQ ID NO: 74 wherein X$_1$ is any amino acid, preferably Q, V or S, more preferably Q, or an amino acid sequence differing from SEQ ID NO: 74 by at least one amino acid substitution, such as one, two or three amino acid substitutions, more preferably one amino acid substitution.

In some embodiments, the CDRa2 in the context of the present invention comprises or consists of the amino acid sequence selected from the group consisting of the amino acid sequences SEQ ID NO: 6 and SEQ ID NO: 56, 57 and 59, preferably SEQ ID NO: 6 and SEQ ID NO: 56.

In some embodiments, the CDRa3 comprises or consists of the amino acid sequence selected from the group consisting of the amino acid sequences SEQ ID NO: 35, 36, 37, 38, 39 preferably SEQ ID NO: 35.

In some embodiments, the CDRb1 comprises or consists of the amino acid sequence of SEQ ID NO: 12 or SEQ ID NO: 62.

In some embodiments, the CDRb2 comprises or consists of the amino acid sequence:
'FNNNVP' SEQ ID NO: 13, or
'FCYGX$_1$P' SEQ ID NO: 81, wherein X$_1$ is any amino acid, preferably H, V, A or T, more preferably T, and wherein, preferably, when the CDRb2 comprises or consists of the amino acid sequence FCYGX$_1$P' SEQ ID NO: 81 the FR3-b amino acid sequence comprises at the amino acid position 66 the amino acid 66C, or
an amino acid sequence differing from SEQ ID NO: 13 or 81 by at least one amino acid substitution, such as one, two or three amino acid substitutions, more preferably one amino acid substitution.

In some embodiments, the CDRb2 in the context of the present invention comprises or consists of the amino acid sequence selected from the group consisting of the amino acid sequences SEQ ID NO: 13 and SEQ ID NO: 63, 64, 65, 66 and 70, preferably SEQ ID NO: 13 and SEQ ID NO: 65, and wherein preferably when the CDRb2 comprises or consists of the amino acid sequence SEQ ID NO: 63, 64, 65, 66 or 70, the FR3-b amino acid sequence preferably comprises at the amino acid position 66 the amino acid 66C.

In one embodiment the CDRb3 in the context of the present invention comprises or consists of the amino acid sequence of SEQ ID NO: 14 or SEQ ID NO: 71.

In one particular embodiment, the antigen binding protein of the invention comprises
a) a first polypeptide chain comprising a first variable domain comprising three complementary determining regions (CDRs) CDRa1, CDRa2 and CDRa3, wherein
the CDRa1 comprises or consists of the amino acid sequence SEQ ID NO: 5,
the CDRa2 comprises or consists of the amino acid sequence SEQ ID NO: 6, and
the CDRa3 comprises or consists of the amino acid sequence selected from the group consisting of the amino acid sequences SEQ ID NO: 35, 36, 37, 38, 39, preferably SEQ ID NO: 35, 36, 37, 38, more preferably SEQ ID NO: 35 and 38, such as SEQ ID NO: 35 and wherein
(b) a second polypeptide chain comprising a second variable domain comprising three complementary determining regions (CDRs) CDRb1, CDRb2 and CDRb3, wherein
the CDRb1 comprises or consists of the amino acid sequence SEQ ID NO: 12
the CDRb2 comprises or consists of the amino acid sequence SEQ ID NO: 13, and
the CDRb3 comprises or consists of the amino acid sequence SEQ ID NO: 14.

In one particular embodiment, the antigen binding protein comprises
a) a first polypeptide chain comprising a first variable domain comprising three complementary determining regions (CDRs) CDRa1, CDRa2 and CDRa3, wherein
the CDRa1 comprises or consists of the amino acid sequence of SEQ ID NO: 5 or SEQ ID NO: 55, preferably SEQ ID NO: 55,
the CDRa2 comprises or consists of the amino acid sequence selected from the group consisting of the amino acid sequences SEQ ID NO: 56, 57 and 59, preferably, SEQ ID NO: 56 and 59, more preferably SEQ ID NO: 56, the CDRa3 comprises or consists of the amino acid sequence SEQ ID NO:35, (b) a second polypeptide chain comprising a second variable domain comprising three complementary determining regions (CDRs) CDRb1, CDRb2 and CDRb3, wherein CDRb1 comprises or consists of the amino acid sequence SEQ ID NO: 62, CDRb2 comprises or consists of the amino acid sequence selected from the group consisting of the amino acid sequences SEQ ID NO: 63, 64, 65, 66 and 70, preferably SEQ ID NO: 65, and wherein preferably when the CDRb2 comprises or consists of the amino acid sequence SEQ ID NO: 63, 64, 65, 66 or 70, the FR3-b amino acid sequence preferably comprises at the amino acid position 66 the amino acid 66C, and CDRb3 comprises or consists of the amino acid sequence of SEQ ID NO: 14 or SEQ ID NO: 71, preferably SEQ ID NO: 71.

The present invention further refers to antigen binding proteins comprising variants of the CDR amino acid sequences that are disclosed in the context of the present invention, typically variants of CDRa1, CDRa2, CDRa3, CDRb1, CDRb2 and/or CDRb3, such variants may comprise at least one, such as four, three, two, or one, preferably one, two or three amino acid substitutions wherein the preferred number of amino acid substitutions preferably depends on the length of the respective CDR.

Accordingly, in some embodiments, the CDRa1 comprises or consists of an amino acid sequence differing from the herein disclosed CDRa1 amino acid sequences by at least one amino acid substitution, preferably by one, two or three amino acid substitutions, preferably by one or two amino acid substitutions, or only one amino acid substitution, wherein said amino acid substitution is preferably at any of the amino acid positions 28, 29, 36, 37 and 38, more preferably at position 28.

In some embodiments, the CDRa2 comprises or consists of an amino acid sequence differing from the herein disclosed CDRa2 amino acid sequences by at least one amino acid substitution, preferably by one, two or three amino acid substitutions, preferably by one or two amino acid substitutions, or only one amino acid substitution, wherein said amino acid substitution is preferably at position 56 or 65, more preferably at position 65.

In some embodiments, the CDRa3 comprises or consists of an amino acid sequence differing from the herein disclosed CDRa3 amino acid sequences by at least one amino acid substitution, preferably by one, two, three or four amino acid substitutions, preferably by one or two amino acid substitutions, or only one amino acid substitution, wherein said amino acid substitution is preferably at any of the amino acid positions 105, 106, 107, 108, 109, 113, 114, 115, 116 and 117.

In some embodiments, the CDRb1 comprises or consists of an amino acid sequence differing from the herein disclosed CDRb1 amino acid sequences by at least one amino acid substitution, preferably by one, two or three amino acid substitution, preferably by one or two amino acid substitutions, such as one amino acid substitution, wherein said amino acid substitution is preferably at any of the amino acid positions 27, 28, 29, 37 and 38, more preferably 27 and 38.

In some embodiments, the CDRb2 comprises or consists of an amino acid sequence differing from the herein disclosed CDRb2 amino acid sequences by at least one amino acid substitution, preferably by one, two or three amino acid substitutions, preferably by one or two amino acid substitutions, or only one amino acid substitution, wherein said amino acid substitution is preferably at position 56.

In some embodiments, the CDRb3 comprises or consists of an amino acid sequence differing from the herein disclosed CDRb3 amino acid sequences by at least one amino acid substitution, preferably by one, two, three or four amino acid substitution, preferably by one or two amino acid substitutions, or only one amino acid substitution, wherein said amino acid substitution is preferably at any of the amino acid positions 105, 106, 107, 108, 109, 113, 114, 115, 116, 117.

The amino acid substitutions referred to herein above are as defined herein above in the section "definitions", preferably amino acid substitutions are conservative amino acid substitutions. As it will be understood by the skilled in the art, the first variable domain comprising the CDR amino acid sequences as herein defined and the second variable domain comprising the CDR amino acid sequences as herein defined form together an antigen binding site, wherein said antigen binding site binds to the MAGE-A antigenic peptide comprising or consisting of the amino acid sequence 'KVLEHVVRV' of SEQ ID NO: 1 in a complex with an MHC protein. The three complementarity determining regions (CDRs) CDRa1, CDRa2 and CDRa3 are derived from the variable alpha domain of a TCR. Accordingly, as it will be understood by the skilled in the art, in some embodiments, the first variable domain may also be referred to as variable alpha domain In analogy, the three complementarity determining regions (CDRs) CDRb1, CDRb2 and CDRb3 are derived from the variable beta domain of said TCR, and it will thus, further be understood by the skilled in the art, that the second variable domain may also be referred to as variable beta domain. More particularly, a first variable domain comprising the alpha variable framework amino acid sequences and the alpha variable CDRs as defined in the context of the invention, such as the sequence (FR1-a)-(CDRa1)-(FR2-a)-(CDRa2)-(FR3-a)-(CDRa3)-(FR4-a) might be referred to as variable alpha domain and/or a second variable domain comprising the beta variable framework amino acid sequences and the beta variable CDRs as defined in the context of the present invention, such as the sequence (FR1-b)-(CDRb1)-(FR2-b)-(CDRb2)-(FR3-b)-(CDRb3)-(FR4-b) might be referred to as variable beta domain.

In some embodiments, the CDRs may be engrafted in an antibody framework sequence. Accordingly, in one example, the CDRs as defined in the context of the first variable domain might be engrafted in the light chain variable domain, the first variable domain thus comprises or consists of the sequences (FR1-L)-(CDRa1)-(FR2-L)-(CDRa2)-(FR3-L)-(CDRa3)-(FR4-L) and might be referred to as a light chain variable domain. In the same example, the CDRs as defined in the context of the second variable domain might be engrafted in the heavy chain variable domain, the second variable domain thus comprises or consists of the sequences (FR1-H)-(CDRb1)-(FR2-H)—(CDRb2)-(FR3-H)—(CDRb3)-(FR4-H) and might be referred to as a heavy chain variable domain. However, it will also be understood by the skilled in the art, that it is also possible, that the CDRs as defined in the context of the first variable domain might be engrafted in the heavy chain variable domain and that the CDRs as defined in the context of the second variable domain might be engrafted in the light chain variable domain, the considerations above apply mutatis mutandis.

In the context of the present invention, the CDRs of the antigen binding proteins of the invention differ from the CDRs of the native and parental TCR R7P1D5, as disclosed in WO 2017/158103 at least in the amino acid sequence of CDRa3 of said parental TCR R7P1D5. As it will be understood by the skilled in the art, the CDRa3, as defined herein above, does not comprise or consist of the amino acid sequence 'CAEYSSASKIIF' (SEQ ID NO: 7) which is the CDRa3 of the parental TCR R7P1D5.

In one embodiment, the first variable domain and the second variable domain as herein defined in the context of the antigen binding proteins of the invention may comprise an amino acid substitution at position 44 according to the IMGT numbering. In a preferred embodiment, said amino acid at position 44 is substituted with another suitable amino acid, in order to improve pairing. In particular embodiments, preferably in which said antigen binding protein is a TCR, said amino acid substitution improves for example the pairing of the chains (i.e. pairing of α and β chains or pairing of γ and δ in a preferred embodiment, one of or both of the amino acids present at position 44 in the first variable domain ($v_1$44) and the amino acid present at position 44 in the second variable domain ($v_2$44) are substituted into amino acid pairs $v_1$44/$v_2$44 selected from the group of amino acid pairs consisting of $v_1$44D/$v_2$44R, $v_1$44R/$v_2$44D, $v_1$44E/$v_2$44K, $v_1$44K/$v_2$44E, $v_1$44D/$v_2$44K, $v_1$44K/$v_2$44D, $v_1$44R/$v_2$44E; $v_1$44E/$v_2$44R, $v_1$44L/$v_2$44W, $v_1$44W/$v_2$44L, $v_1$44V/$v_2$44W, $v_1$44W/$v_2$44V.

Accordingly, in a further embodiment, the antigen binding protein may further include one of the preferred substitution pairs ($v_1$44/$v_2$44) selected from the group consisting of: $v_1$Q44D/$v_2$Q44R; $v_1$Q44R/$v_2$Q44D; $v_1$Q44E/$v_2$Q44K; $v_1$Q44K/$v_2$Q44E; $v_1$Q44D/$v_2$Q44K; $v_1$Q44K/$v_2$Q44D; $v_1$Q44E/$v_2$Q44R; $v_1$Q44R/$v_2$Q44E; $v_1$Q44L/$v_2$Q44W; $v_1$Q44W/$v_2$Q44L; $v_1$Q44V/$v_2$Q44W; and $v_1$Q44W/$v_2$Q44V; $v_1$W44D/$v_2$Q44R; $v_1$W44R/$v_2$Q44D; $v_1$W44E/$v_2$Q44K; $v_1$W44K/$v_2$Q44E; $v_1$W44D/$v_2$Q44K; $v_1$W44K/$v_2$Q44D; $v_1$W44E/$v_2$Q44R; $v_1$W44R/$v_2$Q44E; $v_1$W44L/$v_2$Q44W; $v_1$W44/$v_2$Q44L; $v_1$W44V/$v_2$Q44W; and $v_1$W44/$v_2$Q44V; $v_1$H44D/$v_2$Q44R; $v_1$H44R/$v_2$Q44D; $v_1$H44E/$v_2$Q44K; $v_1$H44K/$v_2$Q44E; $v_1$H44D/$v_2$Q44K; $v_1$H44K/$v_2$Q44D; $v_1$H44E/$v_2$Q44R; $v_1$H44R/$v_2$Q44E; $v_1$H44L/$v_2$Q44W; $v_1$H44W/$v_2$Q44L; $v_1$H44V/$v_2$Q44W; and $v_1$H44W/$v_2$Q44V; $v_1$K44D/$v_2$Q44R; $v_1$K44R/$v_2$Q44D; $v_1$K44E/$v_2$Q44K; $v_1$K44/$v_2$Q44E; $v_1$K44D/$v_2$Q44K; $v_1$K44/$v_2$Q44D; $v_1$K44E/$v_2$Q44R; $v_1$K44R/$v_2$Q44E; $v_1$K44L/$v_2$Q44W; $v_1$K44W/$v_2$Q44L; $v_1$K44V/$v_2$Q44W; and $v_1$K44W/$v_2$Q44V; $v_1$E44D/$v_2$Q44R; $v_1$E44R/$v_2$Q44D; $v_1$E44/$v_2$Q44K; $v_1$E44K/$v_2$Q44E; $v_1$E44D/$v_2$Q44K; $v_1$E44K/$v_2$Q44D; $v_1$E44/$v_2$Q44R; $v_1$E44R/$v_2$Q44E; $v_1$E44L/$v_2$Q44W; $v_1$E44W/$v_2$Q44L; $v_1$E44V/$v_2$Q44W; and $v_1$E44W/$v_2$Q44V; $v_1$Q44D/$v_2$R44; $v_1$Q44R/$v_2$R44D; $v_1$Q44E/$v_2$R44K; $v_1$Q44K/$v_2$R44E; $v_1$Q44D/$v_2$R44K; $v_1$Q44K/$v_2$R44D; $v_1$Q44E/$v_2$R44; $v_1$Q44R/$v_2$R44E; $v_1$Q44L/$v_2$R44W; $v_1$Q44W/$v_2$R44L; $v_1$Q44V/$v_2$R44W; and $v_1$Q44W/$v_2$R44V; $v_1$W44D/$v_2$R44; $v_1$W44R/$v_2$R44D; $v_1$W44E/$v_2$R44K; $v_1$W44K/$v_2$R44E; $v_1$W44D/$v_2$R44K; $v_1$W44K/$v_2$R44D; $v_1$W44E/$v_2$R44; $v_1$W44R/$v_2$R44E; $v_1$W44L/$v_2$R44W; $v_1$W44/$v_2$R44L; $v_1$W44V/$v_2$R44W; and $v_1$W44/$v_2$R44V; $v_1$H44D/$v_2$R44; $v_1$H44R/$v_2$R44D; $v_1$H44E/$v_2$R44K; $v_1$H44K/$v_2$R44E; $v_1$H44D/$v_2$R44K; $v_1$H44K/$v_2$R44D; $v_1$H44E/$v_2$R44; $v_1$H44R/$v_2$R44E; $v_1$H44L/$v_2$R44W; $v_1$H44W/$v_2$R44L; $v_1$H44V/$v_2$R44W; and $v_1$H44W/$v_2$R44V; $v_1$K44D/$v_2$R44; $v_1$K44R/$v_2$R44D; $v_1$K44E/$v_2$R44K; $v_1$K44/$v_2$R44E; $v_1$K44D/$v_2$R44K; $v_1$K44/$v_2$R44D; $v_1$K44E/$v_2$R44; $v_1$K44R/$v_2$R44E; $v_1$K44L/$v_2$R44W; $v_1$K44W/$v_2$R44L; $v_1$K44V/$v_2$R44W; and $v_1$K44W/$v_2$R44V; $v_1$E44D/$v_2$R44; $v_1$E44R/$v_2$R44D; $v_1$E44/$v_2$R44K; $v_1$E44K/$v_2$R44E; $v_1$E44D/$v_2$R44K; $v_1$E44K/$v_2$R44D; $v_1$E44R/$v_2$R44E; $v_1$E44L/$v_2$R44W; $v_1$E44W/$v_2$R44L; $v_1$E44V/$v_2$R44W; and $v_1$E44W/$v_2$R44V; $v_1$Q44D/$v_2$K44R; $v_1$Q44R/$v_2$K44D; $v_1$Q44E/$v_{244}$K; $v_1$Q44K/$v_2$K44E; $v_1$Q44D/$v_{244}$K; $v_1$Q44K/$v_2$K44D; $v_1$Q44E/$v_2$K44R; $v_1$Q44R/$v_2$K44E; $v_1$Q44L/$v_2$K44W; $v_1$Q44W/$v_2$K44L; $v_1$Q44V/$v_2$K44W; and $v_1$Q44W/$v_2$K44V; $v_1$W44D/$v_2$K44R; $v_1$W44R/$v_2$K44D; $v_1$W44E/$v_{244}$K; $v_1$W44K/$v_2$K44E; $v_1$W44D/$v_{244}$K; $v_1$W44K/$v_2$K44D; $v_1$W44E/$v_2$K44R; $v_1$W44R/$v_2$K44E; $v_1$W44L/$v_2$K44W; $v_1$W44/$v_2$K44L; $v_1$W44V/$v_2$K44W; and $v_1$W44/$v_2$K44V; $v_1$H44D/$v_2$K44R; $v_1$H44R/$v_2$K44D; $v_1$H44E/$v_2$44K; $v_1$H44K/$v_2$K44E; $v_1$H44D/$v_2$44K; $v_1$H44K/$v_2$K44D; $v_1$H44E/$v_2$K44R; $v_1$H44R/$v_2$K44E; $v_1$H44L/$v_2$K44W; $v_1$H44W/$v_2$K44L; $v_1$H44V/$v_2$K44W; and $v_1$H44W/$v_2$K44V; $v_1$K44D/$v_2$K44R; $v_1$K44R/$v_2$K44D; $v_1$K44E/$v_2$44K; $v_1$K44/$v_2$K44E; $v_1$K44D/$v_2$44K; $v_1$K44/$v_2$K44D; $v_1$K44E/$v_2$K44R; $v_1$K44R/$v_2$K44E; $v_1$K44L/$v_2$K44W; $v_1$K44W/$v_2$K44L; $v_1$K44V/$v_2$K44W; and $v_1$K44W/$v_2$K44V; $v_1$E44D/$v_2$K44R; $v_1$E44R/$v_2$K44D; $v_1$E44/$v_2$44K; $v_1$E44K/$v_2$K44E; $v_1$E44D/$v_2$44K; $v_1$E44K/$v_2$K44D; $v_1$E44/$v_2$K44R; $v_1$E44R/$v_2$K44E; $v_1$E44L/$v_2$K44W; $v_1$E44W/$v_2$K44L; $v_1$E44V/$v_2$K44W; and $v_1$E44W/$v_2$Q44V.

In the above, e.g., "$v_1$Q44R/$v_2$Q44D" shall mean, for example, that, in the first variable domain Q44 is substituted by R, while in the second variable domain, Q44 is substituted by D. Additional substitutions and description may be found in U.S. Patent Application No. 2018-0162922.

The inventors of the present invention demonstrated that the CDRs that were initially obtained from TCR alpha and beta variable domains may be used in antigen binding proteins that have different formats than native TCRs. For example, in the experimental section the inventors used the CDRs of the TCR alpha and beta variable domains in the TCER™ format, as described herein below in detail and as shown in the examples (i.e. example 6).

Furthermore, the inventors used the CDRs as defined in the context of the present invention in single chain TCR constructs, such as a bispecific TCR comprising a scTCR, or a Fab stabilized scTCR, comprising a first polypeptide with $V_H$ (CD3)-$C_{H1}$-Valpha-$L_z$-Vbeta and a second polypeptide with $V_L$ (CD3)-$C_L$ wherein $V_H$(CD3), $V_L$ (CD3), Valpha and Vbeta are as defined above and $L_z$ is a linker consisting of the amino acid sequence GGGGSGGGGSGGGGSGGGGSGGGGS of SEQ ID NO: 108 and $C_{H1}$ is the constant domain of the heavy chain and $C_L$ is a constant region of the light chain (example 4).

Accordingly, the skilled in the art understands from these experiments as a proof of principle that the CDRs as herein defined in the context of the present invention may be used in different antigen binding proteins of the invention, and thus, in different formats as herein disclosed. It will be further understood by the skilled in the art, that the binding characteristics of the antigen binding proteins of the invention, demonstrated in the context of one antigen binding format are preferably at least conserved when the format of an antigen binding protein is changed (i.e. at least the CDR amino acid sequences of the first and second variable domain, preferably the amino acid of the first and second variable domains are identical).

As already mentioned above, the binding functionality of the CDRs in the context of the invention may be provided in the framework of an antibody. For example, CDR amino acid sequences as defined in the context of the invention, possibly including additional 3, 2 or 1 N and/or C terminal framework residues, may be directly grafted into an antibody variable heavy/light chain sequence. More particularly, the CDRa1, CDRa2 and CDRa3 domains defined in the context of the present invention may be grafted in the variable heavy chain amino acid sequence and CDRb1, CDRb2 and CDRb3 defined in the context of the present invention may be grafted in the variable light chain amino acid sequence, or vice versa.

As it will also be understood, in some embodiments, within an antibody the variable light chain domain of an antibody may be replaced by the first variable domain as defined in the context of the invention and the variable heavy chain domain may be replaced by the second variable domain as defined in the context of the present invention, or vice versa.

However, in a preferred embodiment, the antigen binding protein further comprises the alpha framework regions and the beta framework regions.

In one embodiment, said first variable domain further comprises one or more framework regions, preferably FR1-a, FR2-a, FR3-a and FR4-a, selected from the group consisting of FR1-a, FR2-a, FR3-a and FR4-a, wherein FR1-a comprises or consists of the amino acid sequence of 'EDVEQSLFLSVREGDSSVINCTYT' SEQ ID NO: 83 or an amino acid sequence at least 85% identical to SEQ ID NO: 83, FR2-a comprises or consists of the amino acid sequence of 'LYWYKQEPGAGLQLLTY' SEQ ID NO: 84 or an amino acid sequence at least 85% identical to SEQ ID NO: 84, FR3-a comprises or consists of the amino acid sequence of 'KQDQRLTVLLNKKDKEILSLRIADTQTGDSAIYF' SEQ ID NO: 85 or 'an amino acid sequence at least 85% identical to SEQ ID NO: 85, FR4-a comprises or consists of the amino acid sequence of 'GSGTRLSIRP' SEQ ID NO: 86 or an amino acid sequence at least 85% identical to SEQ ID NO: 86, and said second variable domain further comprises one or more framework regions, preferably FR1-b, FR2-b, FR3-b and FR4-b, selected from the group consisting of FR1-b, FR2-b, FR3-b and FR4-b, and wherein FR1-b comprises or consists of the amino acid sequence of 'DAGVIQSPRHEVTEMGQEVTLRCKPI' SEQ ID NO: 87 or an amino acid sequence at least 85% identical to SEQ ID NO: 87, FR2-b comprises or consists of the amino acid sequence of IFWYRQTMMRGLELLIY' SEQ ID NO: 88 or an amino acid sequence at least 85% identical to SEQ ID NO: 88

FR3-b comprises or consists of the amino acid sequence of 'IDDSGMPEDRFSAKMPNASFSTLKIQPSEPRDSAVYF' SEQ ID NO: 89 or an amino acid sequence at least 85% identical to SEQ ID NO: 89, or FR4-b comprises or consists of the amino acid sequence of 'GEGSRLTVL' SEQ ID NO: 90 or an amino acid sequence at least 85% identical to SEQ ID NO: 90.

In one embodiment, said first variable domain further comprises one or more framework regions, preferably FR1-a, FR2-a, FR3-a and FR4-a, selected from the group consisting of FR1-a, FR2-a, FR3-a and FR4-a, wherein FR1-a comprises or consists of the amino acid sequence of 'EDVEQSLFLSVREGDSSVINCTYT' SEQ ID NO: 83 or an amino acid sequence at least at least 90% identical to SEQ ID NO: 83;

FR2-a comprises or consists of the amino acid sequence of 'LYWYKQEPGAGLQLLTY' SEQ ID NO: 84 or an amino acid sequence at least 90% identical to SEQ ID NO: 84, FR3-a comprises or consists of the amino acid sequence of 'KQDQRLTVLLNKKDKEILSLRIADTQTGDSAIYF' SEQ ID NO: 85 or 'an amino acid sequence at least 90% identical to SEQ ID NO: 85;

FR4-a comprises or consists of the amino acid sequence of 'GSGTRLSIRP' SEQ ID NO: 86 or an amino acid sequence at least 90% identical to SEQ ID NO: 86;

and said second variable domain further comprises one or more framework regions, preferably FR1-b, FR2-b, FR3-b and FR4-b, selected from the group consisting of FR1-b, FR2-b, FR3-b and FR4-b, and wherein FR1-b comprises or consists of the amino acid sequence of 'DAGVIQSPRHEVTEMGQEVTLRCKPI' SEQ ID NO: 87 or an amino acid sequence at least 90% identical to SEQ ID NO: 87;

FR2-b comprises or consists of the amino acid sequence of 'LFWYRQTMMRGLELLIY' SEQ ID NO: 88 or an amino acid sequence at least 90% identical to SEQ ID NO: 88;

FR3-b comprises or consists of the amino acid sequence of 'IDDSGMPEDRFSAKMPNASFSTLKIQPSEPRDSAVYF' SEQ ID NO: 89 or an amino acid sequence at least 90% identical to SEQ ID NO: 89; or FR4-b comprises or consists of the amino acid sequence of 'GEGSRLTVL' SEQ ID NO: 90 or an amino acid sequence at least 90% identical to SEQ ID NO: 90.

In one embodiment, said first variable domain further comprises one or more framework regions, preferably FR1-a, FR2-a, FR3-a and FR4-a, selected from the group consisting of FR1-a, FR2-a, FR3-a and FR4-a, wherein FR1-a comprises or consists of the amino acid sequence of 'EDVEQSLFLSVREGDSSVINCTYT' SEQ ID NO: 83 or an amino acid sequence at least 95% identical to SEQ ID NO: 83;

FR2-a comprises or consists of the amino acid sequence of 'LYWYKQEPGAGLQLLTY' SEQ ID NO: 84 or an amino acid sequence at least 95% identical to SEQ ID NO: 84, FR3-a comprises or consists of the amino acid sequence of 'KQDQRLTVLLNKKDKHLSLRIADTQTGDSAIYF' SEQ ID NO: 85 or 'an amino acid sequence at least 95% identical to SEQ ID NO: 85;

FR4-a comprises or consists of the amino acid sequence of 'GSGTRLSIRP' SEQ ID NO: 86 or an amino acid sequence at least 95% identical to SEQ ID NO: 86;

and said second variable domain further comprises one or more framework regions, preferably FR1-b, FR2-b, FR3-b and FR4-b, selected from the group consisting of FR1-b, FR2-b, FR3-b and FR4-b, and wherein FR1-b comprises or consists of the amino acid sequence of 'DAGVIQSPRHEVTEMGQEVTLRCKPI' SEQ ID NO: 87 or an amino acid sequence at least 95% identical to SEQ ID NO: 87;

FR2-b comprises or consists of the amino acid sequence of 'LFWYRQTMMRGLELLIY' SEQ ID NO: 88 or an amino acid sequence at least 95% identical to SEQ ID NO: 88;

FR3-b comprises or consists of the amino acid sequence of 'IDDSGMPEDRFSAKMPNASFSTLKIQPSEPRDSAVYF' SEQ ID NO: 89 or an amino acid sequence at least 95% identical to SEQ ID NO: 89; or FR4-b comprises or consists of the amino acid sequence of 'GEGSRLTVL' SEQ ID NO: 90 or an amino acid sequence at least 95% identical to SEQ ID NO: 90.

The antigen binding proteins of the invention, thus, preferably further comprises a constant domain, e.g. an alpha constant domain and/or a beta constant domain, or a gamma and/or delta constant domain as described herein above. Preferably alpha and beta constant domains and/or gamma and delta constant domains comprise further mutations that are not present in native TCRs to enhance pairing of the two transgenic chains, i.e. the alpha and beta chain. For Example, position 48 of the TRAC and at position 57 of TRBC1 or TRBC2 may be substituted by cysteine residues. Further examples for such modifications are described above. Examples for alpha constant domains and beta constant domains comprised in antigen binding proteins of the invention are SEQ ID NO: 8 (alpha constant domain of TCR R7P1D5) and SEQ ID NO: 15 (beta constant domain of TCR R7P1D5).

In one embodiment antigen binding molecules of the present invention comprise a TCR molecule as defined herein above, e.g. a molecule comprising at least one alpha variable domain and one beta variable domain (alpha/beta TCR) or a molecule comprising at least one gamma variable domain or delta variable domain. In other words such TCRs are heterodimeric molecules, namely alpha/beta and gamma/delta heterodimers.

For use in adoptive cell therapy (ACT), an alpha/beta or gamma/delta heterodimeric TCR may be transfected as full-length chains having both cytoplasmic and transmembrane domains into a patient's T cell. Constant domains may comprise suitable mutations, i.e. disulfide bonds, to improved pairing of desired, transgenic alpha/beta or gamma/delta chains and reduce pairing of endogenous alpha/beta or gamma/delta with the respective transgenic chains. The antigen binding proteins of the invention, thus, preferably further comprises a constant domain, e.g. an alpha constant domain and/or a beta constant domain as described herein above. Preferably alpha and beta constant domains comprise further mutations that are not present in native TCRs to enhance pairing of the two chains, i.e. the alpha and beta chain, or the gamma and delta chain, respectively. For Example, position 48 of the TRAC and at position 57 of TRBC1 or TRBC2 are substituted by cysteine residues. Examples for alpha constant domains and beta constant domains comprised in antigen binding proteins of the invention are SEQ ID NO: 8 (alpha constant domain of TCR R7P1D5) and SEQ ID NO: 15 (beta constant domain of TCR R7P1D5).

In a preferred embodiment the TCR comprises an alpha chain comprising an alpha variable domain comprising CDR1alpha, CDR2alpha and CDR3alpha and further comprises an alpha constant domain; and a beta chain comprising a beta variable domain comprising CDR1beta, CDR2beta, CDR3beta and further comprises a beta constant domain. In a further preferred embodiment the alpha variable domain comprises three complementary determining regions (CDRs) CDRa1, CDRa2 and CDRa3, wherein the CDRa1 comprises or consists of the amino acid sequence SEQ ID NO: 5, the CDRa2 comprises or consists of the amino acid sequence SEQ ID NO: 6, and the CDRa3 comprises or consists of the amino acid sequence selected from the group consisting of the amino acid sequences SEQ ID NO: 35, 36, 37, 38, 39, preferably of the amino acid sequences SEQ ID NO: 35, 36, 37, 38, more preferably of the amino acid sequences SEQ ID NO: 35 and 38, such as SEQ ID NO: 35; and the beta variable domain comprises three complementary determining regions (CDRs) CDRb1, CDRb2 and CDRb3, wherein the CDRb1 comprises or consists of the amino acid sequence SEQ ID NO: 12 the CDRb2 comprises or consists of the amino acid sequence SEQ ID NO: 13, and the CDRb3 comprises or consists of the amino acid sequence SEQ ID NO: 14.

In a preferred embodiment the TCR comprises an alpha chain comprising an alpha variable domain comprising CDR1alpha, CDR2alpha and CDR3alpha and further comprises an alpha constant domain; and a beta chain comprising a beta variable domain comprising CDR1beta, CDR2beta, CDR3beta and further comprises a beta constant domain. In a further preferred embodiment the alpha variable domain comprises three complementary determining regions (CDRs) CDRa1, CDRa2 and CDRa3, wherein the CDRa1 comprises or consists of the amino acid sequence SEQ ID NO: 5, the CDRa2 comprises or consists of the amino acid sequence SEQ ID NO: 6, and the CDRa3 comprises or consists of the amino acid sequence SEQ ID NO: 35, and the beta variable domain comprises three complementary determining regions (CDRs) CDRb1, CDRb2 and CDRb3, wherein the CDRb1 comprises or consists of the amino acid sequence SEQ ID NO: 12 the CDRb2 comprises or consists of the amino acid sequence SEQ ID NO: 13, and the CDRb3 comprises or consists of the amino acid sequence SEQ ID NO: 14.

In another preferred embodiment the TCR comprises an alpha chain comprising an alpha variable domain comprising CDR1alpha, CDR2alpha and CDR3alpha and further comprises an alpha constant domain; and a beta chain comprising a beta variable domain comprising CDR1beta, CDR2beta, CDR3beta and further comprises a beta constant domain In a further preferred embodiment the alpha variable domain comprises three complementary determining regions (CDRs) CDRa1, CDRa2 and CDRa3, wherein the CDRa1 comprises or consists of the amino acid sequence SEQ ID NO: 5, the CDRa2 comprises or consists of the amino acid sequence SEQ ID NO: 6, and the CDRa3 comprises or consists of the amino acid sequence SEQ ID NO: 38, and the beta variable domain comprises three complementary determining regions (CDRs) CDRb1, CDRb2 and CDRb3, wherein the CDRb1 comprises or consists of the amino acid sequence SEQ ID NO: 12 the CDRb2 comprises or consists of the amino acid sequence SEQ ID NO: 13, and the CDRb3 comprises or consists of the amino acid sequence SEQ ID NO: 14.

In another preferred embodiment, the variable alpha and beta domains of the TCR further comprises the alpha framework regions and the beta framework regions, respectively.

In one embodiment, said first alpha variable domain further comprises one or more framework regions, preferably FR1-a, FR2-a, FR3-a and FR4-a, selected from the group consisting of FR1-a, FR2-a, FR3-a and FR4-a, wherein FR1-a comprises or consists of the amino acid sequence of 'EDVEQSLFLSVREGDSSVINCTYT' SEQ ID NO: 83, FR2-a comprises or consists of the amino acid sequence of 'LYWYKQEPGAGLQLLTY' SEQ ID NO: 84, FR3-a comprises or consists of the amino acid sequence of 'KQDQRLTVLLNKKDKHLSLRIADTQTGDSAIYF' SEQ ID NO: 85, and FR4-a comprises or consists of the amino acid sequence of 'GSGTRLSIRP' SEQ ID NO: 86, and said second beta variable domain further comprises one or more framework regions, preferably FR1-b, FR2-b, FR3-b and FR4-b, selected from the group consisting of FR1-b, FR2-b, FR3-b and FR4-b, and wherein FR1-b comprises or consists of the amino acid sequence of 'DAGVIQSPRHEVTEMGQEVTLRCKPI' SEQ ID NO: 87, FR2-b comprises or consists of the amino acid sequence of 'LFWYRQTMMRGLELLIY' SEQ ID NO: 88, FR3-b comprises or consists of the amino acid sequence of 'IDDSGMPEDRFSAKMPNASF-STLKIQPSEPRDSAVYF' SEQ ID NO: 89, or FR4-b comprises or consists of the amino acid sequence of 'GEGSRLTVL' SEQ ID NO: 90.

In another preferred embodiment, the TCRs comprising any of the above defined variable domains further comprise the alpha constant domain comprising or consisting of amino acid sequence SEQ ID NO: 8 or a sequence a least 85%, 90% or 95% identical to SEQ ID NO: 8; and the beta constant domain comprising or consisting of amino acid sequence SEQ ID NO: 15 or a sequence a least 85%, 90% or 95% identical to SEQ ID NO: 15.

Variants of the antigen binding proteins as described herein are contemplated and explicitly referred to using the wording "at least 85% identical to a reference sequence" as defined herein above in the section "definitions". For instance, the sequence FR1-a, FR2-a, FR3-a and FR4-a and FR1-b, FR2-b, FR3-b and FR4-b may differ from the reference sequences SEQ ID NO:83, SEQ ID NO: 84, SEQ ID NO:85, SEQ ID NO: 86 SEQ ID NO:87, SEQ ID NO: 88, SEQ ID NO: 89 and SEQ ID NO: 90, as appropriate, by at least one amino acid substitution(s), in particular by at least one conservative amino acid substitution(s) and/or substitution(s) with canonical residues. In particular, the sequences FR1-a, FR2-a, FR3-a and FR4-a and FR1-b, FR2-b, FR3-b and FR4-b of the first and the second variable domain may differ from the reference sequences SEQ ID NO:83, SEQ ID NO: 84, SEQ ID NO:85, SEQ ID NO: 86, SEQ ID NO:87, SEQ ID NO: 88, SEQ ID NO: 89 and SEQ ID NO: 90 by conservative amino acid substitution(s), only.

Modifications and changes may be made in the amino acid sequence of the antigen binding protein of the present invention, and in the corresponding DNA sequences, respectively, and still result in a functional antigen binding protein or polypeptide with desirable characteristics. Modifications may be made in the first or second variable domain, in particular in the framework regions or in the each of the CDRs or in all CDRs comprised in the first and/or second variable domain.

The inventors of the present invention furthermore discovered that by using the framework region of the parental TCR R7P1D5 specific amino acid substitutions in the Framework region of the antigen binding proteins have an advantageous effect. In particular, the amino acid substitutions S19A or S19V, preferably S19V, were crucial for the expression of a soluble single chain TCR construct, in particular in addition to a CDRa2 amino acid sequence comprising at its second amino acid position a Y, i.e. amino acid 57 according to IMGT is a Y (57Y) in CDRa2. Furthermore, the inventors discovered that the amino acid substitutions A48K and $L_{50}P$ in FR2-a, M46P, M47G in FR2-b either alone or in combination increase the expression yield of the soluble antigen binding proteins of the invention. The inventors also showed that I54F in FR2-b increases the expression yield of the soluble antigen binding proteins and, in particular in addition to a CDRb3 amino acid sequence comprising a D in position 109 according to IMGT, increase the stability of the soluble antigen binding proteins. In addition, the inventors found that the I54F substitution in FR2-b significantly improved the specificity of the soluble antigen binding proteins.

Accordingly, in one embodiment, the framework regions of the antigen binding proteins of the invention comprises at least one amino acid substitution, preferably one, two, three, four, five, six, seven, eight, nine or 10, more preferably 1 to 5, 2 to 5, such as 3 or 4 amino acid substitutions selected from the group of amino acid substitutions comprising:
- an amino acid substitution at position 19 in FR1-a, wherein said amino acid substitution is preferably S19A, S19V, more preferably S19V
- an amino acid substitution at position 48 and/or 50 in FR2-a, wherein said amino acid substitution at position 48 is preferably A48K and said amino acid substitution at position 50 is preferably $L_{50}P$,
- an amino acid substitution at position 46, 47 and/or 54 in FR2-b, wherein said amino acid substitution at position 46, 47 and 54 is preferably M46P, M47G and I54F, respectively, wherein preferably said amino acid at position 54 is I54F when the CDRb3 amino acid sequence as defined above comprises at position 109 the amino acid 109D,
- an amino acid substitution at position 66 in FR3-b, wherein said amino acid substitution at position 66 is preferably I66C and wherein preferably said amino acid at position 66 is 66C when the CDRb2 amino acid sequence as defined above comprises at position 57 the amino acid 57C, and wherein the positions of the substitutions are given according to the IMGT nomenclature, and wherein optionally said amino acid substitution is given in comparison to the amino acid sequence of the corresponding framework amino acid sequence of the parental TCR R7P1D5.

In a preferred embodiment, the framework regions of the antigen binding proteins of the invention comprises the amino acid substitutions S19V, A48K, and I54F or S19V, A48K, preferably S19V, A48K, and I54F, wherein the positions of the substitutions are given according to the IMGT nomenclature. In one embodiment, said combination of amino acid substitutions is advantageously further combined with the CDRb3 comprising or consists of the amino acid sequence 'CASRAX$_1$TGELFF' SEQ ID NO: 82, wherein X$_1$ is D, or, according to IMGT numbering, wherein the CDRb3 amino acid comprises at position 109 the amino acid 109D. In a further preferred embodiment, the framework regions of the antigen binding proteins of the invention further comprises the amino acid substitution I66C, wherein preferably FR3-b comprises the amino acid substitution I66C, when the CDRb2 amino acid sequence as defined above comprises at position 57 the amino acid 57C.

Accordingly, in one embodiment, said first variable domain further comprises one or more framework regions, preferably all framework regions, selected from the group consisting of FR1-a, FR2-a, FR3-a and FR4-a, wherein
  FR1-a comprises or consists of the amino acid sequence of 'EDVEQSLFLSVREGDS<u>V</u>VINCTYT' SEQ ID NO: 91 or an amino acid sequence at least 85% identical to SEQ ID NO: 91, wherein preferably said amino acid sequence at least 85% identical to SEQ ID NO: 91 comprises the amino acid 19V (underlined in SEQ ID NO: 91),
  FR2-a comprises or consists of the amino acid sequence of 'LYWYKQEPG<u>K</u>GLQLLTY' SEQ ID NO: 92 or an amino acid sequence at least 85% identical to SEQ ID NO: 92, wherein preferably said amino acid sequence at least 85% identical to SEQ ID NO: 92 comprises the amino acid 48K (underlined in SEQ ID NO: 92) and optionally an amino acid substitution at position 50, preferably $L_{50}P$, FR3-a comprises or consists of the amino acid sequence of 'KQDQRLTVLLNKKDKHLSLRIADTQTGD-SAIYF' SEQ ID NO: 85 or an amino acid sequence at least 85% identical to SEQ ID NO: 85, FR4-a comprises or consists of the amino acid sequence of 'GSGTRLSIRP' SEQ ID NO: 86 or an amino acid sequence at least 85% identical to SEQ ID NO: 86, and said second variable domain further comprises one or more framework regions, preferably framework regions, selected from the group consisting of FR1-b, FR2-b, FR3-b and FR4-b, and wherein FR1-b comprises or consists of the amino acid sequence of 'DAGVIQSPRHEVTEMGQEVTLRCKPI' SEQ ID NO: 87 or an amino acid sequence at least 85% identical to SEQ ID NO: 87, FR2-b comprises or consists of the amino acid sequence of IFWYRQTMMRGLELLFY' SEQ ID NO: 93 or an amino acid sequence at least 85% identical to SEQ ID NO: 93, wherein preferably said amino acid sequence at least 85% identical to SEQ ID NO: 93 comprises the amino acid 54F$_c$ and optionally an amino acid substitution at position 46 and/or 47, wherein said amino acid substitution at position 46 and/or 47 is preferably M46P and/or M47G, respectively, FR3-b comprises or consists of the amino acid sequence of 'IDDSGMPEDRFSAKMPNASFSTLKIQPSEPRD-SAVYF' SEQ ID NO: 89 or an amino acid sequence at least 85% identical to SEQ ID NO: 89, or of the amino acid sequence of 'CDDSGMPEDRFSAKMPNASF-STLKIQPSEPRDSAVYF' SEQ ID NO: 94 or an amino acid sequence at least 85% identical to SEQ ID NO: 94, wherein preferably said amino acid sequence at least 85% identical to SEQ ID NO: 94 comprises the amino acid 66C, and wherein FR3-b preferably comprises or consists of an amino acid sequence at least 85% identical to SEQ ID NO: 94 comprising the amino acid 66C, when the CDRb2 amino acid sequence as defined above comprises at position 57 the amino acid 57C, FR4-b comprises or consists of the amino acid sequence of 'GEGSRLTVL' SEQ ID NO: 90 or an amino acid sequence at least 85% identical to SEQ ID NO: 90.

Variants of the antigen binding proteins as described herein are contemplated and explicitly referred to using the wording "at least 85% identical to a reference sequence" as defined herein above in the section "definitions". For instance, the sequence FR1-a, FR2-a, FR3-a and FR4-a and FR1-b, FR2-b, FR3-b and FR4-b may differ from the reference sequences SEQ ID NO:91, SEQ ID NO: 92, SEQ ID NO: 85, SEQ ID NO: 86, SEQ ID NO: 87, SEQ ID NO:93 and SEQ ID NO: 89 or SEQ ID NO:94, SEQ ID NO: 90, as appropriate, by at least one amino acid substitution(s), in particular by at least one conservative amino acid substitution(s) and/or substitution(s) with canonical residues. In particular, the sequences FR1-a, FR2-a, FR3-a and FR4-a and FR1-b, FR2-b, FR3-b and FR4-b of the first and the second variable domain may differ from the reference sequences SEQ ID NO:91, SEQ ID NO: 92, SEQ ID NO: 85, SEQ ID NO: 86, SEQ ID NO: 87, SEQ ID NO:93 and SEQ ID NO: 89 or SEQ ID NO:94, SEQ ID NO: 90, by conservative amino acid substitution(s), only.

Modifications and changes may be made in the amino acid sequence of the antigen binding protein of the present invention, and in the corresponding DNA sequences encoding them, and still result in a functional antigen binding protein or polypeptide with desirable characteristics.

Accordingly, in one embodiment, the present invention refers to an antigen binding protein comprising (i) a first polypeptide chain comprising a first variable domain comprising the amino acid sequence selected from the group consisting of 'EDVEQSLFLSVREGDSSVINCTYT<u>DSSSTY-</u>LYWYKQEPGAGLQLLTY<u>IFSN</u> MDM<u>KQDQRLTVLLNKKDKHLSLRIADTQTGD-</u>SA<u>IYF</u>CAEMTSESKIIFGSG TRLSIRP' SEQ ID NO: 118, 'EDVEQSLFLSVREGDSSVINCTYT<u>DSSSTY-</u>LYWYKQEPGAGLQLLTY<u>IFSN</u> MDM<u>KQDQRLTVLLNKKDKHLSLRIADTQTGD-</u>SA<u>IYF</u>CAEFTSESKIIFGSGT RLSIRP' 'SEQ ID NO: 119, 'EDVEQSLFLSVREGDSSVINCTYT<u>DSSSTY-</u>LYWYKQEPGAGLQLLTY<u>IFSN</u> MDM<u>KQDQRLTVLLNKKDKHLSLRIADTQTGD-</u>SA<u>IYF</u>CAEFNSESKIIFGSGT RLSIRP' SEQ ID NO: 120, 'EDVEQSLFLSVREGDSSVINCTYT<u>DSSSTY-</u>LYWYKQEPGAGLQLLTY<u>IFSN</u> MDM<u>KQDQRLTVLLNKKDKHLSLRIADTQTGD-</u>SA<u>IYF</u>CAEFSSASKIIFGSGT RLSIRP' SEQ ID NO: 121, 'EDVEQSLFLSVREGDSSVINCTYT<u>DSSSTY-</u>LYWYKQEPGAGLQLLTY<u>IFSN</u> MDM<u>KQDQRLTVLLNKKDKHLSLRIADTQTGD-</u>SA<u>IYF</u>CAEATSESKIIFGSGT RLSIRP' SEQ ID NO: 122, preferably SEQ ID NO: 118 and SEQ ID NO: 121, more preferably SEQ ID NO: 118, or an amino acid sequence at least 85% identical to the amino acid sequence selected from the group consisting of SEQ ID NO 118 to 122 and wherein said amino acid sequence at least 85% identical to the amino acid sequence selected from the group consisting of SEQ ID NO 118 to 122 comprises preferably the amino acid sequence of CDRa1 of SEQ ID NO: 5, CDRa2 of SEQ ID NO: 6 and CDRa3 of SEQ ID NO: 35, 36, 37, 38, 39, in case of SEQ ID NO 118 to 122, respectively, and (ii) a second polypeptide chain comprising a second variable domain comprising the amino acid sequence of SEQ ID NO: 11 or an amino acid sequence at least 85% identical to SEQ ID NO: 11, wherein said amino acid sequence at least 85% identical to the amino acid sequence of SEQ ID NO: 11 comprises preferably the amino acid sequence of CDRb1, CDRb2 and CDRb3 of the SEQ ID NO: 12, 13 and 14, respectively, or (iii) a first polypeptide chain comprising a first variable domain comprising the amino acid sequence 'EDVEQSLFLSVREGDSVVINCTYT<u>DSSSTY-</u>LYWYKQEPGKGLQLLT<u>YIYSS</u> <u>QDQKQDQRLTVLLNKKDKHLSLRIADTQTGD-</u>SA<u>IYF</u>CAEMTSESKIIFGSGT RLSIRP' 'SEQ ID NO: 151 or 'EDVEQSLFLSVREGDSVVINC-TYT<u>ESSSTY</u>LYWYKQEPGKGLQLLTY<u>IYS</u> <u>SQDQKQDQRLTVLLNKKDKHLSLRIADTQTGD-</u>SA<u>IYF</u>CAEMTSESKIIFGSG TRLSIRP' SEQ ID NO: 152, preferably or an amino acid sequence at least 85% identical to the amino acid sequence of SEQ ID NO: 151 or 152 and wherein preferably the amino acid sequence at least 85% identical to the amino acid sequence of SEQ ID NO: 151 preferably comprises the amino acid sequence of CDRa1 of SEQ ID NO: 5, CDRa2 of SEQ ID NO: 56 and CDRa3 of SEQ ID NO: 35, and wherein preferably the amino acid sequence at least 85% identical to the amino acid sequence of SEQ ID NO: 152 preferably comprises the amino acid sequence of CDRa1 of SEQ ID NO: 55, CDRa2 of SEQ ID NO: 56 and CDRa3 of SEQ ID NO: 35 and preferably further comprises the amino acids 19V and/or 48K, and iv) a second polypeptide chain comprising a second variable domain comprising the amino acid sequence DAGVIQSPRHEVTEMGQEVTLRCK-PIPGHDYLFWYRQTMMRGLELLFYC YGTPCDDSGMPEDRESAKMPNASF-STLKIQPSEPRDSAVYFCASRANTGELF FGEGSRLTVL' SEQ ID NO: 149 or 'DAGVIQSPRHEVTEMGQEVTLRCK-PIPGHDYLFWYRQTMMRGLELLFYC YGTPCDDSGMPEDRESAKMPNASF-STLKIQPSEPRDSAVYFCASRADTGELF FGEGSRLTVL' SEQ ID NO: 150, and wherein preferably the amino acid sequence at least 85% identical to the amino acid sequence of SEQ ID NO: 149 preferably comprises the amino acid sequence of CDRb1 of SEQ ID NO: 62, CDRb2 of SEQ ID NO: 65 and CDRb3 of SEQ ID NO: 14, and wherein preferably the amino acid sequence at least 85% identical to the amino acid sequence of SEQ ID NO: 150 comprises the amino acid sequence of CDRb1 of SEQ ID NO: 62, CDRb2 of SEQ ID NO: 65 and CDRb3 of SEQ ID NO: 71, and preferably further comprises the amino acid 54F and/or 66C.

In one embodiment, the antigen binding protein is an antibody or a fragment thereof, or a bispecific antibody or fragment thereof, or a T cell receptor (TCR) or a fragment thereof, or a bispecific T cell receptor (TCR) or fragment thereof. The antibody and TCR and the respective fragments are as defined herein above in the section "definitions".

In one embodiment, the antigen binding protein is of human origin, which is understood as being generated from a human antigen locus and therefore comprising human sequences, in particular, human TCR or antibody sequences.

In one embodiment, the first polypeptide and the second polypeptide are linked together, in particular, via a covalent link.

In one embodiment, the antigen binding protein is a soluble protein.

A "covalent link", "linker sequence" or "polypeptide linker" is as defined herein above in the section "definitions" (see "linker").

In one embodiment the antigen binding protein of the invention further comprises one or more of the following:
(i) one or more further antigen binding sites;
(ii) a transmembrane region, optionally including a cytoplasmic signaling region;
(iii) a diagnostic agent;
(iv) a therapeutic agent; or
(v) PK modifying moiety.

As it is known to the skilled in the art an antigen binding site, for example, in the context of antibodies, is typically formed by 6 CDRs that bind to an antigen.

In the context of the present invention, the one or more further antigen binding site as referred to in (i) herein above is preferably selected from a binding site that binds to an antigen, wherein said antigen is selected from the group consisting of the antigens CD3 (such as the CD3γ, CD3δ, and CD3ε chains), CD4, CD7, CD8, CD10, CD11b, CD11c, CD14, CD16, CD18, CD22, CD25, CD28, CD32a, CD32b, CD33, CD41, CD41b, CD42a, CD42b, CD44, CD45RA, CD49, CD55, CD56, CD61, CD64, CD68, CD94, CD90, CD117, CD123, CD125, CD134, CD137, CD152, CD163, CD193, CD203c, CD235a, CD278, CD279, CD287, Nkp46, NKG2D, GITR, F$_c$εRI, TCRα/β and TCRγ/δ, HLA-DR or to an antigen of an effector cell, preferably CD3, TCRα/β or CD28, more preferably CD3 and TCRα/β.

"CD3" and "CD28" are defined herein above in the section "definitions".

In some embodiments, the one of the one or more further antigen binding sites as referred to in (i) is able to bind a T cell specific receptor molecule and/or a natural killer cell (NK cell) specific receptor molecule. In a particular embodiment, the antigen binding protein forms a complex with the CD3 T cell co-receptor.

In a preferred embodiment, the one of the one or more further antigen binding sites as referred to in (i) is able to bind TCRα/β.

In some embodiments a T cell specific receptor is the CD3 T cell co-receptor.

In some embodiments, the T cell specific receptor is CD28, CD134, 4-1 BB, CD5 or CD95.

"CD134", "4-1 BB", "CD5", "CD95" and "NK cell specific receptor molecule" are defined herein above in the section "definitions". "Transmembrane region", "cytoplasmic signaling region", "diagnostic agent", "therapeutic agent" and "PK modifying moiety" are defined herein above in the section "definitions".

In some embodiments, the antigen binding proteins of the present invention are covalently attached, directly or via a cleavable or non-cleavable linker, to the at least one growth inhibitory agent. An antigen binding protein to which such the at least one growth inhibitory agent is attached may also be referred to as a conjugate.

The preparation of such conjugates, for example immunoconjugates, is described in the application WO2004/091668 or Hudecz, F., Methods Mol. Biol. 298: 209-223 (2005) and Kirin et al., Inorg Chem. 44(15): 5405-5415 (2005), and may by the skilled in the art be transferred to the preparation of antigen binding proteins of the present invention to which such a at least one growth inhibitory agent is attached.

"Linker" in the context of the attachment of at least one growth inhibitory agent, means a chemical moiety comprising a covalent bond or α chain of atoms that covalently attaches a polypeptide to a drug moiety.

The conjugates may be prepared by in vitro methods. In order to link a drug or prodrug to the antibody, a linking group is used. Suitable linking groups are well known in the art and include disulfide groups, thioether groups, acid labile groups, photolabile groups, peptidase labile groups and esterase labile groups. Conjugation of an antigen binding protein of the invention with cytotoxic agents or growth inhibitory agents may be made using a variety of bifunctional protein coupling agents including but not limited to N-succinimidyl pyridyldithiobutyrate (SPDB), butanoic acid 4-[(5-nitro-2-pyridinyl)dithio]-2,5-dioxo-1-pyrrolidinyl ester (nitro-SPDB), 4-(Pyridin-2-yldisulfanyl)-2-sulfobutyric acid (sulfo-SPDB), N-succinimidyl (2-pyridyldithio) propionate (SPDP), succinimidyl (N-maleimidomethyl) cyclohexane-1-carboxylate (SMCC), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl)-hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al (1987). Carbon labeled 1-isothiocyanatobenzyl methyldiethylene triaminepentaacetic acid (MX-DTPA) is an exemplary chelating agent for conjugation of radionucleotide to the antibody (WO 94/11026).

The linker may be a "cleavable linker" facilitating release of the cytotoxic agent or growth inhibitory agent in the cell. For example, an acid-labile linker, a peptidase-sensitive linker, an esterase labile linker, a photolabile linker or a disulfide-containing linker (see e.g. U.S. Pat. No. 5,208,020) may be used. The linker may be also a "non-cleavable linker" (for example SMCC linker) that might led to better tolerance in some cases.

Alternatively, a fusion protein comprising the antibody of the invention and a cytotoxic or growth inhibitory polypeptide may be made, by recombinant techniques or peptide synthesis. The length of DNA may comprise respective regions encoding the two portions of the conjugate either adjacent one another or separated by a region encoding a linker peptide which does not destroy the desired properties of the conjugate.

The antigen binding proteins of the present invention may also be used in Dependent Enzyme Mediated Prodrug Therapy by conjugating the polypeptide to a prodrug-activating enzyme which converts a prodrug (e.g. a peptidyl chemotherapeutic agent, see WO 81/01145) to an active anti-cancer drug (See, for example, WO 88/07378 and U.S. Pat. No. 4,975,278).

In one embodiment the antigen binding protein of the invention further comprises one or more of the following: an enzyme, a cytokine (such as the human IL-2, IL-7 or IL-15), a nanocarrier, or a nucleic acid.

In one preferred embodiment, the antigen binding protein is bispecific. The bispecific antigen binding protein is also herein referred to as "bispecific molecule".

Many different bispecific formats are described in the art and are described herein above in the section "definition" under "formats". Techniques to produce proteins of the different formats are also disclosed in the art cited in the corresponding section and the skilled in the art can thus easily use the CDRs or the variable domains as defined in the context of the present invention in the herein disclosed formats. The production of antigen binding proteins, such as scTCRs or soluble bispecific binding proteins, such as TCER™ are also herein disclosed in the Example section. It will be understood by the skilled in the art that, the light and heavy chain variable domains may be in a parallel orientation and the alpha and beta variable domains may be in a parallel orientation as it is the case in the DVD format, or that the light and heavy chain variable domains may be in a cross orientation and the alpha and beta variable domains may be in a cross orientation as it is the case for example in the CODV format.

Accordingly, the invention further refers to an antigen binding protein comprising two polypeptide chains that form two antigen binding sites (A and B), wherein a first polypeptide chain has a structure represented by the formula:

$$V_3\text{-}L_1\text{-}V_4\text{-}L_2\text{-}C_L \quad [I]$$

wherein $V_3$ is a third variable domain; $V_4$ is a fourth variable domain; $L_1$ and $L_2$ are linkers; $L_2$ may be present or absent; $C_L$ is a light chain constant domain or a portion thereof and present or absent;

and wherein a second polypeptide chain has a structure represented by the formula:

$$V_5\text{-}L_3\text{-}V_6\text{-}L_4\text{-}C_{H1} \quad [II]$$

wherein $V_5$ is a fifth variable domain; $V_6$ is a sixth variable domain; $L_3$ and $L_4$ are linkers; $L_4$ may be present or absent; $C_{H1}$ is a heavy chain constant domain 1 or a portion thereof and is present or absent; and wherein $V_3$ or $V_4$ is a first variable domain as defined herein above and $V_5$ or $V_6$ is a second variable domain as defined herein above, or $V_5$ or $V_6$ is a first variable domain as defined in the context of the present invention and $V_3$ or $V_4$ is a second variable domain as defined herein above, and wherein $V_3$ is the first variable domain and $V_5$ is the second variable domain as defined herein above, and $V_4$ is a light chain variable domain and $V_6$ is a heavy chain variable domain or $V_4$ is a heavy chain variable domain and $V_6$ is a light chain variable domain, or, $V_3$ is the second variable domain and $V_5$ is the first variable domain as defined herein above, and $V_4$ is a light chain variable domain and $V_6$ is a heavy chain variable domain or $V_4$ is a heavy chain variable domain and $V_6$ is a light chain variable domain, or, $V_3$ is the first variable domain and $V_6$ is the second variable domain as defined herein above, and $V_4$ is a light chain variable domain and $V_5$ is a heavy chain variable domain or $V_4$ is a heavy chain variable domain and $V_5$ is a light chain variable domain, or $V_3$ is the second variable domain and $V_6$ is the first variable domain as defined herein above, and $V_4$ is a light chain variable domain and $V_5$ is a heavy chain variable domain or $V_4$ is a heavy chain variable domain and $V_5$ is a light chain variable domain, $V_4$ is the first variable domain and $V_5$ is the second variable domain as defined herein above, and $V_3$ is a light chain variable domain and $V_6$ is a heavy chain variable domain or $V_3$ is a heavy chain variable domain and $V_6$ is a light chain variable domain, or $V_4$ is the second variable domain and $V_5$ is the first variable domain as defined herein above, and $V_3$ is a light chain variable domain and $V_6$ is a heavy chain variable domain or $V_3$ is a heavy chain variable domain and $V_6$ is a light chain variable domain, and wherein the light chain variable domain and the heavy chain variable domain form together one antigen binding site B, and wherein the first and second variable domain as defined herein above form one antigen binding site A. The linkers $L_1$, $L_2$, $L_3$, $L_4$ are defined herein above in the section "definitions". However, in some embodiments some linker lengths might be preferable for a specific format. However, the knowledge concerning linker lengths and their amino acid sequences belongs to the general knowledge of the art, and linkers as well as linker and amino acid sequences for the different formats are part of the state of the art and are disclosed in the here above cited disclosures.

It will be understood by the skilled in the art, that the antigen binding site A, formed the first and second variable domain as defined herein above specifically binds to the MAGE-A peptide/MHC complex as herein described in the context of the present invention.

In a preferred embodiment, $V_3$ is the first variable domain and $V_6$ is the second variable domain as defined in the context of the present invention, and $V_4$ is a light chain variable domain and $V_5$ is a heavy chain variable domain or $V_3$ is the first variable domain and $V_6$ is the second variable domain as defined in the context of the present invention, and $V_4$ is a heavy chain variable domain and $V_5$ is a light chain variable domain.

In one embodiment, the polypeptide of formula [I] further comprises at the C-terminus the polypeptide of formula [I]

a linker ($L_5$) and a $F_c$ domain or portion thereof and/or wherein the polypeptide of formula [II] further comprises at the C-terminus of the polypeptide of formula [II] a linker ($L_6$) and a $F_c$ domain or a portion thereof.

The $F_c$-domain is as defined herein above in the section 'definition'.

In one embodiment, the antigen binding protein comprises two polypeptide chains that form two antigen binding sites (A and B), wherein one polypeptide chain has a structure represented by the formula [III]:

and one polypeptide chain has a structure represented by the formula [IV]:

wherein $V_3$, $L_1$, $V_4$, $L_2$, $C_L$, $V_5$, $L_3$, $V_6$, $L_4$, $C_{H1}$, are as defined herein above, and wherein $L_5$ and $L_6$ are linkers that are present or absent and wherein $F_{C1}$, and $F_{C2}$ are $F_c$-domains and wherein $F_{C1}$ and $F_{C2}$ are the same or different, preferably different. The $F_c$-domain is as defined herein above in the section 'definition'.

In one embodiment, $F_{C1}$ comprises or consists of the amino acid sequence SEQ ID NO: 113 (hole) and $F_{C2}$ comprises or consists of the amino acid sequence SEQ ID NO: 112 (knob), or vice versa, more preferably $F_{C1}$ comprises or consists of the amino acid sequence SEQ ID NO: 113, when $V_4$ or $V_3$ is a heavy chain variable domain and, accordingly, $F_{C2}$ comprises or consists of the amino acid sequence SEQ ID NO: 112, when $V_5$ or $V_6$ is a light chain variable domain, or $F_{C1}$ comprises or consists of the amino acid sequence SEQ ID NO: 112, when $V_4$ or $V_3$ is a light chain variable domain and, accordingly, $F_{C2}$ comprises or consists of the amino acid sequence SEQ ID NO: 113, when $V_5$ or $V_6$ is a heavy chain variable domain.

In one embodiment, the heavy chain variable domain ($V_H$) and the light chain variable domain ($V_L$) form together one binding site B that binds to an antigen selected from the group consisting of CD3 (such as the CD3γ, CD3δ, and CD3ε chains), CD4, CD7, CD8, CD10, CD11b, CD11c, CD14, CD16, CD18, CD22, CD25, CD28, CD32a, CD32b, CD33, CD41, CD41b, CD42a, CD42b, CD44, CD45RA, CD49, CD55, CD56, CD61, CD64, CD68, CD94, CD90, CD117, CD123, CD125, CD134, CD137, CD152, CD163, CD193, CD203c, CD235a, CD278, CD279, CD287, Nkp46, NKG2D, GITR, $F_c$ εRI, TCRα/β and TCRγ/δ, HLA-DR and/or bind to an effector cell.

In a further embodiment, the heavy chain variable domain ($V_H$) and the light chain variable domain ($V_L$) form together one binding site that binds to a T cell specific receptor molecule and/or a natural killer cell (NK cell) specific receptor molecule, wherein the T cell specific receptor molecule and the natural killer cell (NK cell) specific receptor molecule are as defined herein above in the section 'Definition'.

In one embodiment, the light chain variable domain comprises or consists of the amino acid sequence SEQ ID NO: 153 and the heavy chain variable domain comprises or consists of the amino acid sequence SEQ ID NO: 154, or the light chain variable domain comprises or consists of the amino acid sequence SEQ ID NO: 153 and the heavy chain variable domain comprises or consists of the amino acid sequence SEQ ID NO: 156, or the light chain variable domain comprises or consists of the amino acid sequence SEQ ID NO: 157 and the heavy chain variable domain comprises or consists of the amino acid sequence SEQ ID NO: 158, or the light chain variable domain comprises or consists of the amino acid sequence SEQ ID NO: 159 and the heavy chain variable domain comprises or consists of the amino acid sequence SEQ ID NO: 160, or the light chain variable domain comprises or consists of the amino acid sequence SEQ ID NO: 153 and the heavy chain variable domain comprises or consists of the amino acid sequence SEQ ID NO: 162, or the light chain variable domain comprises or consists of the amino acid sequence SEQ ID NO: 153 and the heavy chain variable domain comprises or consists of the amino acid sequence SEQ ID NO: 164.

Preferably, the light chain variable domain comprises or consists of the amino acid sequence SEQ ID NO: 153 and the heavy chain variable domain comprises or consists of the amino acid sequence SEQ ID NO: 154, or the light chain variable domain comprises or consists of the amino acid sequence SEQ ID NO: 153 and the heavy chain variable domain comprises or consists of the amino acid sequence SEQ ID NO: 156, or the light chain variable domain comprises or consists of the amino acid sequence SEQ ID NO: 159 and the heavy chain variable domain comprises or consists of the amino acid sequence SEQ ID NO: 160, or the light chain variable domain comprises or consists of the amino acid sequence SEQ ID NO: 153 and the heavy chain variable domain comprises or consists of the amino acid sequence SEQ ID NO: 162, or the light chain variable domain comprises or consists of the amino acid sequence SEQ ID NO: 153 and the heavy chain variable domain comprises or consists of the amino acid sequence SEQ ID NO: 164, more preferably the light chain variable domain comprises or consists of the amino acid sequence SEQ ID NO: 159 and the heavy chain variable domain comprises or consists of the amino acid sequence SEQ ID NO: 160

As it can be seen from the examples, the inventor of the present invention demonstrated as a proof of principle the use of the CDRs as defined in the context of the present invention, more particular the variable domains as defined herein above, in a TCER™ format (Example).

Accordingly, in one preferred embodiment, the antigen binding protein comprises two polypeptide chains that form two antigen binding sites, wherein one polypeptide chain has a structure represented by the formula [III]:

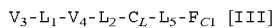

and one polypeptide chain has a structure represented by the formula [IV]:

wherein $L_2$, $C_L$, $L_5$ and $L_4$, $C_{H1}$, $L_6$ are absent, and
wherein $V_3$, $L_1$, $V_4$, $V_5$, $L_3$, $V_6$ are as defined herein above,
preferably, $V_3$ is the first variable domain and $V_6$ is the second variable domain as defined in the context of the present invention, and $V_4$ is a light chain variable domain and $V_5$ is a heavy chain variable domain, or preferably, $V_3$ is the first variable domain and $V_6$ is the second variable domain as defined in the context of the present invention, and $V_4$ is a heavy chain variable domain and $V_5$ is a light chain variable domain, and
preferably, $L_1$ and $L_3$ comprise or consist of the amino acid sequence 'GGGSGGGG' of (SEQ ID NO:96), and preferably $F_{C1}$ comprises or consists of the amino acid sequence SEQ ID NO: 113 and $F_{C2}$ comprises or consists of the amino acid sequence SEQ ID NO: 112, or vice versa, more preferably $F_{C1}$ comprises or consists of the amino acid sequence SEQ ID NO: 113, when $V_4$ is a heavy chain variable domain and, accordingly, $F_{C2}$ comprises or consists of the amino acid sequence SEQ ID NO: 112, when $V_5$ is a light chain variable domain, or more preferably $F_{C1}$ comprises or consists of the amino acid sequence SEQ ID NO: 112, when $V_4$ is a light chain variable domain and, accordingly, $F_{C2}$ comprises or consists of the amino acid sequence SEQ ID NO: 113, when $V_5$ is a heavy chain variable domain, and the light chain variable domain and the heavy chain variable domain form together one antigen binding site preferably which binds to an antigen as defined herein above, preferably, CD3, TCRα/β or CD28, more preferably CD3 or TCRα/β, and wherein the first and second variable domain form one antigen binding site that specifically binds to the MAGE-A antigenic peptide as defined in the context of the present invention.

The antigen binding protein of this embodiment may be referred to as a bispecific TCR, or as a $F_c$-containing bispecific TCR/mAb diabody. The antigen binding protein of this embodiment may be also be referred to as TCER™.

"TCER™" are bispecific T cell Receptors (TCR) which are soluble antigen binding proteins comprising two antigen binding domains, a first and second variable domain as defined in the context of the invention and a further antigen binding domain that is formed by the heavy and light chain variable domain of an antibody, also referred to as recruiter, such as variable light and heavy variable domains directed against CD3 or directed against TCRα/β.

In one preferred embodiment, the antigen binding protein, such as the TCER™ comprises one first polypeptide of formula $V_3$-$L_1$-$V_4$-$L_2$-$C_L$-$L_5$-$F_{C1}$ [III] of the amino acid sequence (SEQ ID NO:135):

EDVEQSLFLSVREGDSVVINCTYTDSSSTYLYWYKQEPGKGLQLLTYIYS

SQDSKQDQRLTVLLNKKDKHLSLRIADTQTGDSAIYFCAEMTSESKIIFG

SGTRLSIRP<u>GGGSGGGG</u>EVQLVQSGAEVKKPGASVKVSCKASGYKFTSYV

MHWVRQAPGQGLEWMGYINPYNDVTKYAEKFQGRVTLTSDTSTSTAYMEL

SSLRSEDTAVHYCARGSYYDYEGFVYWGQGTLVTVSS<u>EPKSSDKTHTCPP</u>

<u>CPAPPVAGPSVFLFPPKPKDTLMISRTPEVTCVVVDVSHEDPEVKFNWYV</u>

<u>DGVEVHNAKTKPREEQYQSTYRVVSVLTVLHQDWLNGKEYKCKVSNKALP</u>

<u>ASIEKTISKAKGQPREPQVCTLPPSRDELTKNQVSLSCAVKGFYPSDIAV</u>

<u>EWESNGQPENNYKTTPPVLDSDGSFFLVSKLTVDKSRWQQGNVFSCSVMH</u>

<u>EALHNHYTQKSLSLSP</u> wherein $L_2$, $C_L$, $L_5$ are absent and which comprises $V_3$ (maturated TCR derived alpha variable domain) of sequence SEQ ID NO: 138 (with the CDRa1, CDRa2, CDRa3 of SEQ ID NO: 5, SEQ ID NO: 59 and SEQ ID NO: 35 in bold), $L_1$ (underlined) of sequence SEQ ID NO: 96, $V_4$ (anti-TCRα/β $V_H$) of sequence SEQ ID NO: 160, and $F_{C1}$ (in italic and underlined) of sequence SEQ ID NO: 113; and one second polypeptide of formula $V_5$-$L_3$-$V_6$-$L_4$-Cm-$L_6$-$F_{c2}$ [IV] of the amino acid sequence (SEQ ID NO: 136):

QIQMTQSPSSLSASVGDRVTITCSATSSVSYMHWYQQKPGKAPKRWIYDT

SKLASGVPSRFSGSGSGTDYTLTISSLQPEDAATYYCQQWSSNPLTFGGG

TKVEIK<u>GGGSGGGG</u>DAGVIQSPRHEVTEMGQEVTLRCKPIPGHDYLFWYR

QTMMRGLELLFYFCYGTPCDDSGMPEDRFSAKMPNASFSTLKIQPSEPRD

SAVYFCASRADTGELFFGEGSRLTVL<u>EPKSSDKTHTCPPCPAPPVAGPSV</u>

<u>FLFPPKPKDTLMISRTPEVTCVVVDVSHEDPEVKFNWYVDGVEVHNAKTK</u>

<u>PREEQYQSTYRVVSVLTVLHQDWLNGKEYKCKVSNKALPASIEKTISKAK</u>

<u>GQPREPQVYTLPPCRDELTKNQVSLWCLVKGFYPSDIAVEWESNGQPENN</u>

<u>YKTTPPVLDSDGSFFLYSKLTVDKSRWQQGNVFSCSVMHEALHNHYTQKS</u>

<u>LSLSP</u> wherein $L_4$, $C_{H1}$, $L_6$ are absent and which comprises $V_5$ (anti-TCRαβ VL) of sequence SEQ ID No: 159, $L_3$ (underlined) of sequence SEQ ID NO: 96, $V_6$ (TCR derived beta variable domain) of sequence SEQ ID NO: 150 (with the CDRa1, CDRa2, CDRa3 of SEQ ID NO: 62, SEQ ID NO: 65, SEQ ID NO: 71 in bold), and $F_{C2}$ (in italic and underlined) of sequence SEQ ID NO: 112, wherein the $F_{C1}$ and $F_{C2}$ sequence comprise a cysteine to serine amino acid substitution (S indicated in bold) since no light chain needs to be connected via said cysteine, amino acid substitutions of the IgG1 hinge region to resemble the IgG2 hinge to abrogate $F_c$-gamma receptor interaction (PVA indicated in bold in positions 233 to 235 and 331S), a N297Q amino acid substitution (Q in bold) to remove the N-Glycosylation site within the $F_c$-part to abrogate $F_c$-gamma-receptor interaction and in addition the hole mutation (Y349C, T366S, $L_{368}$A and Y407V) in case of $F_{C1}$ and the knob mutation (S354C and T366W) in case of $F_{C2}$. Accordingly, in one preferred embodiment, $F_{C1}$ is of sequence SEQ ID NO: 113 and $F_{C2}$ is of sequence SEQ ID NO: 112.

In another preferred embodiment, the antigen binding protein, such as the TCER™, comprises one first polypeptide of formula $V_3$-$L_1$-$V_4$-$L_2$-$C_L$-$L_5$-$F_{C1}$ [III] of the amino acid sequence (SEQ ID NO:136):

QIQMTQSPSSLSASVGDRVTITCSATSSVSYMHWYQQKPGKAPKRWIYDT

SKLASGVPSRFSGSGSGTDYTLTISSLQPEDAATYYCQQWSSNPLTFGGG

TKVEIK<u>GGGSGGGG</u>DAGVIQSPRHEVTEMGQEVTLRCKPIPGHDYLFWYR

QTMMRGLELLFYFCYGTPCDDSGMPEDRFSAKMPNASFSTLKIQPSEPRD

SAVYFCASRADTGELFFGEGSRLTVL<u>EPKSSDKTHTCPPCPAPPVAGPSV</u>

<u>FLFPPKPKDTLMISRTPEVTCVVVDVSHEDPEVKENWYVDGVEVHNAKTK</u>

<u>PREEQYQSTYRVVSVLTVLHQDWLNGKEYKCKVSNKALPASIEKTISKAK</u>

<u>GQPREPQVYTLPPCRDELTKNQVSLWCLVKGFYPSDIAVEWESNGQPENN</u>

<u>YKTTPPVLDSDGSFFLYSKLTVDKSRWQQGNVFSCSVMHEALHNHYTQKS</u>

<u>LSLSP</u> wherein $L_2$, $C_L$, $L_5$ are absent and which comprises $V_3$ (anti-TCRαβ $V_L$) of sequence SEQ ID NO: 159, $L_1$ (underlined) of sequence SEQ ID NO: 96, $V_4$ (TCR derived beta variable domain) of sequence SEQ ID NO: 150 (with the CDRb1, CDRb2, CDRb3 of sequences SEQ ID NO: 62, SEQ ID NO:65, SEQ ID NO: 71 in bold), and $F_{C1}$ (in italic and underlined) of sequence SEQ ID NO: 112; and one second polypeptide of formula $V_5$-$L_3$-$V_6$-$L_4$-Cm-$L_6$-$F_{C2}$ [IV] of the amino acid sequence (SEQ ID NO: 137):

EDVEQSLFLSVREGDSVVINCTYTDSSSTYLYWYKQEPGKGLQLLTYIYS

SQDQKQDQRLTVLLNKKDKHLSLRIADTQTGDSAIYFCAEMTSESKIIFG

SGTRLSIRP<u>GGGSGGGG</u>EVQLVQSGAEVKKPGASVKVSCKASGYKFTSYV

MHWVRQAPGQGLEWMGYINPYNDVTKYAEKFQGRVTLTSDTSTSTAYMEL

SSLRSEDTAVHYCARGSYYDYEGFVYWGQGTLVTVSS*EPKSSDKTHTCPP*

*CPAPPVAGPSVFLFPPKPKDTLMISRTPEVTCVVVDVSHEDPEVKFNWYV*

*DGVEVHNAKTKPREEQYQSTYRVVSVLTVLHQDWLNGKEYKCKVSNKALP*

*ASIEKTISKAKGQPREPQVCTLPPSRDELTKNQVSLSCAVKGFYPSDIAV*

*EWESNGQPENNYKTTPPVLDSDGSFFLVSKLTVDKSRWQQGNVFSCSVMH*

*EALHNHYTQKSLSLSP* wherein $L_4$, $C_{H1}$, $L_6$ are absent and which comprises $V_5$ (maturated TCR derived alpha variable domain) of sequence SEQ ID NO: 151 (with the CDRa1, CDRa2, CDRa3 of SEQ ID NO: 5, SEQ ID NO: 56 and SEQ ID NO: 35 in bold), $L_3$ (underlined) of sequence SEQ ID NO: 96, $V_6$ (anti-TCRαβ $V_H$) of sequence SEQ ID NO: 160, and $F_{C2}$ (in italic and underlined) of sequence SEQ ID NO: 113, wherein the $F_{C1}$ and $F_{C2}$ sequence comprise a cysteine to serine amino acid substitution (S indicated in bold) since no light chain needs to be connected via said cysteine amino acid substitutions of the IgG1 hinge region to resemble the IgG2 hinge to abrogate $F_c$-gamma receptor interaction (PVA indicated in bold in positions 233 to 235 and 331S), a N297Q amino acid substitution (Q in bold) to remove the N-Glycosylation site within the $F_c$-part to abrogate $F_c$-gamma-receptor interaction and in addition the hole mutation (Y349C, T366S, $L_{368}$A and Y407V) in case of $F_{C2}$ and the knob mutation (S354C and T366W) in case of $F_{C1}$. Accordingly, in one preferred embodiment, $F_{C1}$ is of sequence SEQ ID NO: 112 and $F_{C2}$ is of sequence SEQ ID NO: 113.

In another preferred embodiment, the antigen binding protein, such as the TCER™, comprises one first polypeptide of formula $V_3$-$L_1$-$V_4$-$L_2$-$C_L$-$L_5$-$F_{C1}$ [III] of the amino acid sequence (SEQ ID NO:131):

EDVEQSLFLSVREGDSVVINCTYTDSSSTYLYWYKQEPGKGLQLLTYIYS

SQDQKQDQRLTVLLNKKDKHLSLRIADTQTGDSAIYFCAEMTSESKIIFG

SGTRLSIRP<u>GGGSGGGG</u>DIQMTQSPSSLSASVGDRVTITCRASQDIRNYL

NWYQQKPGKAPKLLIYYTSRLHSGVPSRFSGSGSGTDYTLTISSLQPEDI

ATYFCQQGQTLPWTFGQGTKVEIK*EPKSSDKTHTCPPCPAPPVAGPSVFL*

*FPPKPKDTLMISRTPEVTCVVVDVSHEDPEVKFNWYVDGVEVHNAKTKPR*

*EEQYQSTYRVVSVLTVLHQDWLNGKEYKCKVSNKALPASIEKTISKAKGQ*

*PREPQVYTLPPCRDELTKNQVSLWCLVKGFYPSDIAVEWESNGQPENNYK*

*TTPPVLDSDGSFFLYSKLTVDKSRWQQGNVFSCSVMHEALHNHYTQKSLS*

*LSP* wherein $L_2$, $C_L$, $L_5$ are absent and which comprises $V_3$ (maturated TCR derived alpha variable domain) of sequence SEQ ID NO: 151 (with the CDRa1, CDRa2, CDRa3 of SEQ ID NO: 5, SEQ ID NO: 56 and SEQ ID NO: 35 in bold), $L_1$ (underlined) of sequence SEQ ID NO: 96, $V_4$ (anti-TCRαβ $V_L$) of sequence SEQ ID NO: 153, and $F_{C1}$ (in italic and underlined) of sequence SEQ ID NO: 112; and and one second polypeptide of formula $V_5$-$L_3$-$V_6$-$L_4$-Cm-$L_6$-$F_{C2}$ [IV] of the amino acid sequence (SEQ ID NO: 130):

EVQLVQSGAEVKKPGASVKVSCKASGYSFTGYTMNWVRQAPGQGLEWMGL

INPYKGVSTYAQKFQDRVTLTVDKSTSTAYMELSSLRSEDTAVYYCARSG

YYGDSDWYFDVWGQGTLVTVSSGGGSGGGGDAGVIQSPRHEVTEMGQEVT

LRCKPIPGHDYLFWYRQTMMRGLELLFYFCYGTPCDDSGMPEDRFSAKMP

NASFSTLKIQPSEPRDSAVYFCASRADTGELFFGEGSRLTVL*EPKSSDKT*

*HTCPPCPAPPVAGPSVFLFPPKPKDTLMISRTPEVTCVVVDVSHEDPEVK*

*FNWYVDGVEVHNAKTKPREEQYQSTYRVVSVLTVLHQDWLNGKEYKCKVS*

*NKALPASIEKTISKAKGQPREPQVCTLPPSRDELTKNQVSLSCAVKGFYP*

*SDIAVEWESNGQPENNYKTTPPVLDSDGSFFLVSKLTVDKSRWQQGNVFS*

*CSVMHEALHNHYTQKSLSLSP* wherein $L_4$, $C_{H1}$, $L_6$ are absent and which comprises $V_5$ (anti-TCRαβ $V_L$) of sequence SEQ ID NO: 154, $L_3$ (underlined) of sequence SEQ ID NO: 96, $V_6$ (TCR derived beta variable domain) of sequence SEQ ID NO: 151 (with the CDRb1, CDRb2, CDRb3 of sequences SEQ ID NO: 62, SEQ ID NO:65, SEQ ID NO: 71 in bold), and $F_{C2}$ (in italic and underlined) of sequence SEQ ID NO: 113, wherein the $F_{C1}$ and $F_{C2}$ sequence comprise a cysteine to serine amino acid substitution (S indicated in bold) since no light chain needs to be connected via said cysteine amino acid substitutions of the IgG1 hinge region to resemble the IgG2 hinge to abrogate $F_c$-gamma receptor interaction (PVA indicated in bold in positions 233 to 235 and 331S), a N297Q amino acid substitution (Q in bold) to remove the N-Glycosylation site within the $F_c$-part to abrogate $F_c$-gamma-receptor interaction and in addition the hole mutation (Y349C, T366S, $L_{368}$A and Y407V) in case of $F_{C2}$ and the knob mutation (S354C and T366W) in case of $F_{C1}$. Accordingly, in one preferred embodiment, $F_{C1}$ is of sequence SEQ ID NO: 112 and $F_{C2}$ is of sequence SEQ ID NO: 113.

In another preferred embodiment, the antigen binding protein, such as the TCER™, comprises a first polypeptide of formula $V_3$-$L_1$-$V_4$-$L_2$-$C_L$-$L_5$-$F_{C1}$ [III] of the amino acid sequence (SEQ ID NO: 133):

EDVEQSLFLSVREGDSVVINCTYTESSSTYLYWYKQEPGKGLQLLTYIYS

SQDQKQDQRLTVLLNKKDKHLSLRIADTQTGDSAIYFCAEMTSESKIIFG

SGTRLSIRP<u>GGGSGGGG</u>DIQMTQSPSSLSASVGDRVTITCRASQDIRNYL

NWYQQKPGKAPKLLIYYTSRLHSGVPSRFSGSGSGTDYTLTISSLQPEDI

ATYFCQQGQTLPWTFGQGTKVEIK*EPKSSDKTHTCPPCPAPPVAGPSVFL*

-continued

FPPKPKDTLMISRTPEVTCVVVDVSHEDPEVKFNWYVDGVEVHNAKTKPR

EEQYQSTYRVVSVLTVLHQDWLNGKEYKCKVSNKALPASIEKTISKAKGQ

PREPQVYTLPPCRDELTKNQVSLWCLVKGFYPSDIAVEWESNGQPENNYK

TTPPVLDSDGSFFLYSKLTVDKSRWQQGNVFSCSVMHEALHNHYTQKSLS

LSP wherein $L_2$, $C_L$, $L_5$ are absent and which comprises $V_3$ (maturated TCR derived alpha variable domain) of sequence SEQ ID NO: 152 (with the CDRa1, CDRa2, CDRa3 of SEQ ID NO: 55, SEQ ID NO: 56 and SEQ ID NO: 35 in bold), $L_1$ (underlined) of sequence SEQ ID NO: 96, $V_4$ (anti-TCRαβ $V_L$) of sequence SEQ ID NO: 154, and $F_{C1}$ (in italic and underlined) of sequence SEQ ID NO: 112; and one second polypeptide of formula $V_5$-$L_3$-$V_6$-$L_4$-Cm-$L_6$-$F_{C2}$ [IV] of the amino acid sequence (SEQ ID NO: 130):

EVQLVQSGAEVKKPGASVKVSCKASGYSFTGYTMNWVRQAPGQGLEWMGL

INPYKGVSTYAQKFQDRVTLTVDKSTSTAYMELSSLRSEDTAVYYCARSG

YYGDSDWYFDVWGQGTLVTVSSGGGSGGGGDAGVIQSPRHEVTEMGQEVT

LRCKPIPGHDYLFWYRQTMMRGLELLFYFCYGTPCDDSGMPEDRFSAKMP

NASFSTLKIQPSEPRDSAVYFCASRADTGELFFGEGSRLTVLEPKSSDKT

HTCPPCPAPPVAGPSVFLFPPKPKDTLMISRTPEVTCVVVDVSHEDPEVK

FNWYVDGVEVHNAKTKPREEQYQSTYRVVSVLTVLHQDWLNGKEYKCKVS

NKALPASIEKTISKAKGQPREPQVCTLPPSRDELTKNQVSLSCAVKGFYP

SDIAVEWESNGQPENNYKTTPPVLDSDGSFFLVSKLTVDKSRWQQGNVFS

CSVMHEALHNHYTQKSLSLSP wherein $L_4$, $C_{H1}$, $L_6$ are absent and which comprises $V_5$ (anti-TCRαβ $V_L$) of sequence SEQ ID NO: 154, $L_3$ (underlined) of sequence SEQ ID NO: 96, $V_6$ (TCR derived beta variable domain) of sequence SEQ ID NO: 151 (with the CDRb1, CDRb2, CDRb3 of sequences SEQ ID NO: 62, SEQ ID NO:65, SEQ ID NO: 71 in bold), and $F_{C2}$ (in italic and underlined) of sequence SEQ ID NO: 113, wherein the $F_{C1}$ and $F_{C2}$ sequence comprise a cysteine to serine amino acid substitution (S indicated in bold) since no light chain needs to be connected via said cysteine amino acid substitutions of the IgG1 hinge region to resemble the IgG2 hinge to abrogate $F_c$-gamma receptor interaction (PVA indicated in bold in positions 233 to 235 and 331S), a N297Q amino acid substitution (Q in bold) to remove the N-Glycosylation site within the $F_c$-part to abrogate $F_c$-gamma-receptor interaction and in addition the hole mutation (Y349C, T366S, $L_{368}$A and Y407V) in case of $F_{C2}$ and the knob mutation (S354C and T366W) in case of $F_{c1}$. Accordingly, in one preferred embodiment, $F_{C1}$ is of sequence SEQ ID NO: 112 and $F_{C2}$ is of sequence SEQ ID NO: 113.

In one embodiment, the present invention refers to an antigen binding protein comprising i) a first polypeptide of formula $V_3$-$L_1$-$V_4$-$L_2$-$C_L$-$L_5$-$F_{c1}$ [III] comprising or consisting of the amino acid sequence of SEQ ID NO: 127 and the second polypeptide of formula $V_5$-$L_3$-$V_6$-$L_4$-$C_{H1}$-$L_6$-$F_{c2}$ [IV] comprising or consisting of the amino acid sequence of SEQ ID NO: 128, ii) a first polypeptide of formula $V_3$-$L_1$-$V_4$-$L_2$-$C_L$-$L_5$-$F_{c1}$ [III] comprising or consisting of the amino acid sequence of SEQ ID NO: 127 and the second polypeptide of formula $V_5$-$L_3$-$V_6$-$L_4$-$C_{H1}$-$L_6$-$F_{c2}$ [IV] comprising or consisting of the amino acid sequence of SEQ ID NO: 130, iii) a first polypeptide of formula $V_3$-$L_1$-$V_4$-$L_2$-$C_L$-$L_5$-$F_{c1}$ [III] comprising or consisting of the amino acid sequence of SEQ ID NO: 131 and the second polypeptide of formula $V_5$-$L_3$-$V_6$-$L_4$-$C_{H1}$-$L_6$-$F_{c2}$ [IV] comprising or consisting of the amino acid sequence of SEQ ID NO: 130, iv) a first polypeptide of formula $V_3$-$L_1$-$V_4$-$L_2$-$C_L$-$L_5$-$F_{c1}$ [III] comprising or consisting of the amino acid sequence of SEQ ID NO: 133 and the second polypeptide of formula $V_5$-$L_3$-$V_6$-$L_4$-$C_{H1}$-$L_6$-$F_{c2}$ [IV] comprising or consisting of the amino acid sequence of SEQ ID NO: 130, v) a first polypeptide of formula $V_3$-$L_1$-$V_4$-$L_2$-$C_L$-$L_5$-$F_{c1}$ [III] comprising or consisting of the amino acid sequence of SEQ ID NO: 135 and the second polypeptide of formula $V_5$-$L_3$-$V_6$-$L_4$-$C_{H1}$-$L_6$-$F_{c2}$ [IV] comprising or consisting of the amino acid sequence of SEQ ID NO: 136, vi) a first polypeptide of formula $V_3$-$L_1$-$V_4$-$L_2$-$C_L$-$L_5$-$F_{c1}$ [III] comprising or consisting of the amino acid sequence of SEQ ID NO: 137 and the second polypeptide of formula $V_5$-$L_3$-$V_6$-$L_4$-$C_{H1}$-$L_6$-$F_{c2}$ [IV] comprising or consisting of the amino acid sequence of SEQ ID NO: 136, vii) a first polypeptide of formula $V_3$-$L_1$-$V_4$-$L_2$-$C_L$-$L_5$-$F_{c1}$ [III] comprising or consisting of the amino acid sequence of SEQ ID NO: 139 and the second polypeptide of formula $V_5$-$L_3$-$V_6$-$L_4$-$C_{H1}$-$L_6$-$F_{c2}$ [IV] comprising or consisting of the amino acid sequence of SEQ ID NO: 136, viii) a first polypeptide of formula $V_3$-$L_1$-$V_4$-$L_2$-$C_L$-$L_5$-$F_{c1}$ [III] comprising or consisting of the amino acid sequence of SEQ ID NO: 131 and the second polypeptide of formula $V_5$-$L_3$-$V_6$-$L_4$-$C_{H1}$-$L_6$-$F_{c2}$ [IV] comprising or consisting of the amino acid sequence of SEQ ID NO: 142, ix) a first polypeptide of formula $V_3$-$L_1$-$V_4$-$L_2$-$C_L$-$L_5$-$F_{c1}$ [III] comprising or consisting of the amino acid sequence of SEQ ID NO: 133 and the second polypeptide of formula $V_5$-$L_3$-$V_6$-$L_4$-$C_{H1}$-$L_6$-$F_{c2}$ [IV] comprising or consisting of the amino acid sequence of SEQ ID NO: 142, x) a first polypeptide of formula $V_3$-$L_1$-$V_4$-$L_2$-$C_L$-$L_5$-$F_{c1}$ [III] comprising or consisting of the amino acid sequence of SEQ ID NO: 131 and the second polypeptide of formula $V_5$-$L_3$-$V_6$-$L_4$-$C_{H1}$-$L_6$-$F_{c2}$ [IV] comprising or consisting of the amino acid sequence of SEQ ID NO: 136, xi) a first polypeptide of formula $V_3$-$L_1$-$V_4$-$L_2$-$C_L$-$L_5$-$F_{c1}$ [III] comprising or consisting of the amino acid sequence of SEQ ID NO: 133 and the second polypeptide of formula $V_5$-$L_3$-$V_6$-$L_4$-$C_{H1}$-$L_6$-$F_{c2}$ [IV] comprising or consisting of the amino acid sequence of SEQ ID NO: 136, xii) a first polypeptide of formula $V_3$-$L_1$-$V_4$-$L_2$-$C_L$-$L_5$-$F_{c1}$ [III] comprising or consisting of the amino acid sequence of SEQ ID NO: 133 and the second polypeptide of formula $V_5$-$L_3$-$V_6$-$L_4$-$C_{H1}$-$L_6$-$F_{c2}$ [IV] comprising or consisting of the amino acid sequence of SEQ ID NO: 166,
preferably iii) to xi), more preferably iii) and iv).

In an even more preferred embodiment the present invention refers to an antigen binding protein comprising a first polypeptide of formula $V_3$-$L_1$-$V_4$-$L_2$-$C_L$-$L_5$-$F_{c1}$ [III] consisting of the amino acid sequence of SEQ ID NO: 131 and a second polypeptide of formula $V_5$-$L_3$-$V_6$-$L_4$-$C_{H1}$-$L_6$-$F_{c2}$ [IV] consisting of the amino acid sequence of SEQ ID NO: 130; or the present invention refers to an antigen binding protein comprising a first polypeptide of formula $V_3$-$L_1$-$V_4$-$L_2$-$C_L$-$L_5$-$F_{c1}$ [III] consisting of the amino acid sequence of SEQ ID NO: 133 and a second polypeptide of formula $V_5$-$L_3$-$V_6$-$L_4$-$C_{H1}$-$L_6$-$F_{c2}$ [IV] consisting of the amino acid sequence of SEQ ID NO: 130; or the present invention refers to an antigen binding protein comprising a first polypeptide of formula $V_3$-$L_1$-$V_4$-$L_2$-$C_L$-$L_5$-$F_{c1}$ [III] consisting of the amino acid sequence of SEQ ID NO: 135 and a second polypeptide of formula $V_5$-$L_3$-$V_6$-$L_4$-$C_{H1}$-$L_6$-$F_{c2}$ [IV] consisting of the amino acid sequence of SEQ ID NO: 136; or the present invention refers to an antigen binding protein comprising a first polypeptide of formula $V_3$-$L_1$-$V_4$-$L_2$-$C_L$-$L_5$-$F_{c1}$ [III] consisting of the amino acid sequence of SEQ ID NO: 137 and a second polypeptide of formula $V_5$-$L_3$-$V_6$-$L_4$-$C_{H1}$-$L_6$-$F_{c2}$ [IV] consisting of the amino acid sequence of SEQ ID NO: 136; or the present invention refers to an antigen binding protein comprising a first polypeptide of formula $V_3$-$L_1$-$V_4$-$L_2$-$C_L$-$L_5$-$F_{c1}$ [III] consisting of the amino acid sequence of SEQ ID NO: 139 and a second polypeptide of formula $V_5$-$L_3$-$V_6$-$L_4$-$C_{H1}$-$L_6$-$F_{c2}$ [IV] consisting of the amino acid sequence of SEQ ID NO: 136.

It may be also desirable to modify the antigen binding protein of the present invention with respect to effector function, e.g. so as to enhance or reduce antigen-dependent cell-mediated cytotoxicity (ADCC) and/or complement dependent cytotoxicity (CDC) of the antigen binding protein. This may be achieved by introducing one or more amino acid substitutions in an $F_c$ region of the antigen binding protein, herein also called $F_c$-variants in the context with the antigen binding proteins of the present invention. Alternatively, or additionally, cysteine residue(s) may be introduced in the $F_c$ region, thereby allowing interchain disulfide bond formation in this region. The heterodimeric antigen binding protein thus generated may have improved or reduced internalization capability and/or increased complement-mediated cell killing and/or antibody-dependent cellular cytotoxicity (ADCC) (Caron P C. et al. 1992; and Shopes B. 1992).

Another type of amino acid modification of the antigen binding protein of the invention may be useful for altering the original glycosylation pattern of the antigen binding protein, i.e. by deleting one or more carbohydrate moieties found in the antigen binding protein, and/or adding one or more glycosylation sites that are not present in the antigen binding protein. The presence of either of the tripeptide sequences asp aragine-X-serine, and asparagine-X-threonine, where X is any amino acid except proline, creates a potential glycosylation site. Addition or deletion of glycosylation sites to the antigen binding protein is conveniently accomplished by altering the amino acid sequence such that it contains one or more of the above-described tripeptide sequences (for N-linked glycosylation sites).

Another type of modification involves the removal of sequences identified, either in silico or experimentally, as potentially resulting in degradation products or heterogeneity of antigen binding protein preparations. As examples, deamidation of asparagine and glutamine residues can occur depending on factors such as pH and surface exposure. Asparagine residues are particularly susceptible to deamidation, primarily when present in the sequence Asn-Gly, and to a lesser extent in other dipeptide sequences such as Asn-Ala. When such a deamidation site, in particular Asn-Gly, is present in an antigen binding protein of the invention, it may therefore be desirable to remove the site, typically by conservative substitution to remove one of the implicated residues. Such substitutions in a sequence to remove one or more of the implicated residues are also intended to be encompassed by the present invention.

Another type of covalent modification involves chemically or enzymatically coupling glycosides to the antigen binding protein. These procedures are advantageous in that they do not require production of antigen binding protein in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. For example, such methods are described in WO 87/05330.

Removal of any carbohydrate moieties present on the antigen binding protein may be accomplished chemically or enzymatically. Chemical deglycosylation requires exposure of the antigen binding protein to the compound trifluoromethanesulfonic acid, or an equivalent compound. This treatment results in the cleavage of most or all sugars except the linking sugar (N-acetylglucosamine or N-acetylgalactosamine), while leaving the antigen binding protein intact. Chemical deglycosylation is described by Sojahr H. et al. (1987) and by Edge, A S. et al. (1981). Enzymatic cleavage of carbohydrate moieties on antibodies can be achieved by the use of a variety of endo- and exo-glycosidases as described by Thotakura, N R. et al. (1987).

Another type of covalent modification of the antigen binding protein comprises linking the antigen binding protein to one of a variety of non-proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

In one particular embodiment, the antigen binding protein is a TCR. In one particular embodiment, the TCR is a human TCR. Accordingly, in one embodiment, said first variable domain is comprised in a TCR α or γ chain; and/or wherein said second variable domain is comprised in a TCR β or δ chain. In one embodiment, said TCR is an alpha-beta heterodimer and comprises an alpha chain TRAC constant domain sequence and a beta chain TRBC1 or TRBC2 constant domain sequence.

The alpha chain TRAC constant domain sequence and the beta chain TRBC1 or TRBC2 constant domain are in the following, also referred to as TCR constant domain sequences. In one embodiment, the TCR constant domain sequences may be derived from any suitable species, such as any mammal, e.g., human, rat, monkey, rabbit, donkey, or mouse, preferably human. In some preferred embodiments, the TCR constant domain sequences may be slightly modified, for example, by the introduction of heterologous sequences, preferably mouse sequences, which may increase TCR expression and stability. Also, further stabilizing mutations as known from the state of the art (e.g. WO 2018/104407, PCT/EP2018/069151, WO 2011/044186, WO 2014/018863) may be introduced, such as replacement of unfavorable amino acids in the variable regions and/or the introduction of a disulfide bridge between the TCR C domains and the removal of unpaired cysteine.

In particular, the TCR constant domain sequences may be modified by truncation or substitution to delete the native disulfide bond between Cys4 of exon 2 of TRAC and Cys2 of exon 2 of TRBC1 or TRBC2. The alpha and/or beta chain constant domain sequence(s) may also be modified by substitution of cysteine residues for Thr 48 of TRAC and Ser 57 of TRBC1 or TRBC2, the said cysteines forming a disulfide bond between the alpha and beta constant domains of the TCR. TRBC1 or TRBC2 may additionally include a cysteine to alanine mutation at position 75 of the constant domain and an asparagine to aspartic acid mutation at position 89 of the constant domain. The constant domain may additionally or alternatively contain further mutations, substitutions or deletions relative to the native TRAC and/or TRBC1/2 sequences. The term TRAC and TRBC1/2 encompasses natural polymorphic variants, for example N to K at position 4 of TRAC (Bragado et al In! Immunol. 1994 February; 6(2):223-30).

In one embodiment the TCR is chimeric.

A "chimeric TCR" herein refers to a TCR, wherein the TCR chains comprise sequences from multiple species. Preferably, a TCR in the context of the present invention may comprise an α chain comprising a human variable region of an α chain and, for example, a murine constant region of a murine TCR α chain.

In one embodiment the antigen binding protein of the invention is a single chain TCR (scTCR) or a single-chain bispecific antibody. In this embodiment, the first polypeptide and the second polypeptide are covalently linked together, wherein the covalent link are as defined herein above in the section 'Definition'.

A scTCR can comprise a polypeptide of a variable region of a first TCR chain (e.g., an alpha chain) and a polypeptide of an entire (full-length) second TCR chain (e.g., a beta chain), or vice versa. Furthermore, the scTCR can optionally comprise one or more linkers which join the two or more polypeptides together. The linker can be, for instance, a peptide, which joins together two single chains, as described herein. Also provided is such a scTCR of the invention, which is fused to a human cytokine, such as IL-2, IL-7 or IL-15.

In one embodiment said single chain TCR is in one of the single chain formats selected from the group consisting of Valpha-$L_t$-Vbeta, Vbeta-$L_t$-Valpha, Valpha-Ca-$L_t$-Vbeta, Valpha-Cb-$L_t$-Vbeta, Valpha-$L_t$-Vbeta-Cb, Valpha-$L_t$-Vbeta-Ca, Valpha-Ca-$L_t$-Vbeta-Cb, Valpha-Cb-$L_t$-Vbeta-Ca, preferably Valpha-$L_t$-Vbeta, Vbeta-$L_t$-Valpha, wherein Valpha is a first variable domain as defined herein above and wherein Vbeta is a second variable domain as defined herein above, Ca and Cb are TCR alpha and beta constant regions which are present or absent respectively, and $L_t$ is a linker which is present or absent and as defined herein above in the section "definitions".

In one embodiment, such a single chain TCR may further comprise at least one further variable domain, preferably one or two further variable domain(s), either C- or N-terminally linked.

In one embodiment such a further variable domain may be linked via a further linker $L_k$. In one preferred embodiment, the linker $L_k$ is a linker as defined herein above or a $C_{H1}$-Hinge sequence of the amino acid sequence SEQ ID NO: 114.

The invention also includes particles displaying antigen binding proteins of the invention, in particular a TCRs, and the inclusion of said particles within a library of particles. Such particles include but are not limited to phage, yeast, ribosomes, or mammalian cells. Method of producing such particles and libraries are known in the art (for example see WO2004/044004; WO01/48145, Chervin et al. (2008) J. Immuno. Methods 339.2: 175-184).

Furthermore, the inventors of the present invention demonstrated in the examples, in particular in example 3, that the antigen binding proteins of the present invention bind the target antigen, i.e. the MAGE-A antigenic peptide in a complex with a MHC protein, preferably in complex with HLA-A*02, with high specificity, i.e. the antigen binding proteins specifically binds to the identified epitope.

Accordingly, the antigen binding proteins of the present invention specifically bind to a MAGE-A antigenic peptide comprising or consisting of the amino acid sequence 'KVLEHVVRV' of SEQ ID NO: 1, wherein said antigenic peptide is in complex with a MHC protein, preferably in complex with HLA-A*02. More particularly, in one embodiment the antigen binding protein specifically binds to an epitope comprising or consisting of at least three or at least four amino acid positions of the MAGE-A antigenic peptide of SEQ ID NO: 1, preferably, at least 3, at least 4 amino acid positions, preferably at least 3, such as 3 or 4, preferably 3, selected from the group consisting of the amino acid positions 1, 5, 7 and 8 or 1, 3, 5, 7 and 8, in particular 1, 5 and 7 of the amino acid sequence of SEQ ID NO: 1. The determination of the exact epitope might slightly vary depending on the method used and the cut-off values chosen. Due to the property of binding primarily to amino acid positions 1, 5 and 7 the antigen binding proteins of the invention do not significantly bind to the similar peptides NOMAP-1-0320, NOMAP-1-1223 and ODC-001.

In one embodiment, the antigen binding protein of the present invention does not significantly bind to a MAGE-A antigenic peptide variant comprising or consisting of the amino acid sequence of SEQ ID NO: 1, wherein at least one of the positions 1, 5 and 7, at least one of the positions 1, 5, 7 and 8, or at least one of the positions 1, 3, 5, 7 and 8, is substituted, preferably substituted into an alanine.

"Does not significantly bind" in the context of antigen binding proteins of the invention, in particular TCRs or fragments thereof or bispecific TCRs and fragments thereof, such as T cell-expressed antigen binding proteins, denotes, typically in a functional assay, for example, in a TCR activation assay, such as the IFN-gamma release described above, a response, such as signal that is detected for e.g. antigenic peptide variants, that is below 30%, below 25%, below 20%, below 15%, preferably below 30% of the response, i.e. the signal, obtained for the MAGE-A peptide consisting of the amino acid sequence 'KVLEHVVRV' of SEQ ID NO: 1, preferably in the same experimental conditions. "Does not significantly bind" in the context of antigenic peptide variants and in the context of antigen binding proteins of the invention, in particular soluble antigen binding proteins of the invention, denotes, typically in a binding assay, for example biolayer interferometry, a $K_D$ determined for the for antigenic peptide variant that is increased by more than a factor of 3, more than 3.5, more than 4, more than 4.5, more than 5, preferably more than 3, such as 3 to 10, than the $K_D$ determined for the for MAGE-A peptide consisting of the amino acid sequence 'KVLEHVVRV' of SEQ ID NO: 1, preferably in the same experimental conditions, wherein the signal obtained for antigenic peptide variants is preferably a background signal, wherein the antigenic peptide variants or the MAGE-A peptide are in complex with the MHC molecule.

According to the above, in one embodiment, the antigen binding protein of the invention, in particular a soluble antigen binding protein, binds to MAGE-A antigenic peptide variant described herein above in a complex with a MHC protein, preferably in complex with HLA-A*02, with an affinity that is decreased in comparison to the affinity for the specific antigen, i.e. the MAGE-A antigenic peptide as described in the context of the invention in a complex with a MHC protein, preferably in complex with HLA-A*02, and wherein the respective $K_D$ for MAGE-A antigenic peptide variant complex is increased by more than a factor of 3, more than 3.5, more than 4, more than 4.5, more than 5, preferably more than 3, such as 3 to 10. The terms "affinity" and "$K_D$" are defined herein above in the section "definitions".

MHC proteins, in particular a MHC class I and HLA-A*02 proteins are as defined herein above in the section "definitions".

In one embodiment, the antigen binding protein of the invention is characterized as affinity maturated antigen binding protein, which is capable of specifically and optionally selectively binding the MAGE-A antigenic peptide/MHC complex.

The antigen binding proteins of the present invention specifically bind to the MAGE-A antigenic peptide complex as specified herein above, more particularly to the epitope of SEQ ID NO: 1 as defined herein above and can distinguish between its respective target, i.e. the MAGE-A antigenic peptide and other, similar peptides, to which it does not significantly bind.

The term "specificity" or "specifically binds" denotes the capacity of an antigen binding protein to discriminate the target peptide sequence to which its binds ("epitope") from similar epitopes, peptides or proteins, i.e. an antigen binding protein "binds specifically" to a first antigen when it is not significantly cross-reactive to a second.

"Similar peptides" in the context of the present invention may also be referred to as "off-targets" and relates to peptides comprising typically 8 to 16 amino acids in length. The similar peptides in the context of the present invention are typically MHC presented. Furthermore, similar peptides in the context of the present invention comprises or consists of an amino acid sequence that is similar to the amino acid sequence of the MAGE-A antigenic peptide, more particular, peptides that, in comparison to the epitope of the MAGE-A antigenic peptide, comprise an epitope wherein some or all amino acids are identical and/or similar in biochemical/biophysical characteristics of the amino acids, in comparison to the amino acids that constitute the epitope of the corresponding MAGE-A peptide. Due to this sequence similarity, similar peptides might be bound by an antigen binding protein, in this scenario, if, for example, the similar peptide is presented by a MHC protein and, thus bound by an antigen binding protein, for example a TCR, the ability of a given antigen binding protein, such as a TCR, to bind to a similar peptide will not lead to the desired T cell response but may lead to adverse reactions. Such adverse reactions may be "off-tumor" side effects, such as cross-reactivity of a specific TCR which cross-reacted with a peptide in healthy tissues as reported in Lowdell et al., Cytotherapy, published on Dec. 4, 2018, page 7 Similar peptides in the context of the present invention were selected from a database of, for instance, normal tissue-presented HLA-A*02 bound peptides (XPRESIDENT database) based on, for instance, high sequence similarity (similarity BLAST search) to MAG-003. Due to these adverse reactions, antigen binding proteins of the present invention are thus engineered to avoid binding to similar peptides, in particular to the similar peptides listed herein below.

Accordingly, the similar peptides in the context of the present invention are selected from the list consisting of the peptide RABGAP1L-001 consisting of the amino acid sequence of SEQ ID NO: 23, AXIN1-001 consisting of the amino acid sequence of SEQ ID NO: 24, ANDS-001 consisting of the amino acid sequence of SEQ ID NO: 25, TPX2-001 consisting of the amino acid sequence of SEQ ID NO: 26, SYNE3-001 consisting of the amino acid sequence of SEQ ID NO: 27, MIA3-001 consisting of the amino acid sequence of SEQ ID NO: 28, HERC4-001 consisting of the amino acid sequence of SEQ ID NO: 29, PSME2-001 consisting of the amino acid sequence of SEQ ID NO: 30, HEATR5A-001 consisting of the amino acid sequence of SEQ ID NO: 31, CNOT1-003 consisting of the amino acid sequence of SEQ ID NO: 32, TEP1-003 consisting of the amino acid sequence of SEQ ID NO: 33, PITPNM3-001 consisting of the amino acid sequence of SEQ ID NO: 34, ZFC-001 consisting of the amino acid sequence of SEQ ID NO: 129, INTS4-002 consisting of the amino acid sequence of SEQ ID NO: 171, SAMH-001 consisting of the amino acid sequence of SEQ ID NO: 172, PPP1CA-006 consisting of the amino acid sequence of SEQ ID NO: 173, RPL-007 consisting of the amino acid sequence of SEQ ID NO: 174, SETD1A-001 consisting of the amino acid sequence of SEQ ID NO: 175, NOMAP-1-0320 consisting of the amino acid sequence of SEQ ID NO: 176, NOMAP-1-1223 consisting of the amino acid sequence of SEQ ID NO: 177 and ODC-001 consisting of the amino acid sequence of SEQ ID NO: 178, COL6A3-010 consisting of the amino acid sequence of SEQ ID NO: 179, FAM115A-001 consisting of the amino acid sequence of SEQ ID NO: 180, PHTF2-001 consisting of the amino acid sequence of SEQ ID NO: 181 and RPP1-001 consisting of the amino acid sequence of SEQ ID NO: 181.

In one embodiment, the antigen binding proteins of the invention, in particular TCRs or fragments thereof or bispecific TCRs and fragments thereof, such as T cell-expressed antigen binding proteins, do not bind or do not significantly bind to at least 1, such as at least 2, at least 3, at least 4, at least 5, such as 1, 2, 3, 4, 5, preferably at least 3 or 3 or all of the similar peptides selected from the list consisting of RABGAP1L-001, AXIN1-001, AN05-001, TPX2-001, SYNE3-001, MIA3-001, HERC4-001, PSME2-001, HEATR5A-001, CNOT1-003, TEP1-003, PITPNM3-001, preferably HEATR5A-001, HERC4-001 and CNOT1-003, when said similar peptide is in a complex with a MHC protein, preferably in complex with HLA-A*02. This is an important advantage in the context of the present invention since binding to similar peptides, i.e. off-targets, might increase the risk of side effects, accordingly, the fact that the antigen binding proteins of the invention does not cross-react with the herein listed similar peptides makes it a promising anti-cancer treatment.

"Do not significantly bind" may also be referred to as "do not cross-react" in the context of similar peptides and in the context of the antigen binding proteins of the invention, in particular TCRs or fragments thereof or bispecific TCRs and fragments thereof, such as T cell-expressed antigen binding proteins and herein refers, for example, to a functional response that is measured in a functional assay for the antigen binding protein to a similar peptide/MHC in comparison to MAGE-A and wherein the response of the antigen binding protein to similar peptides/MHC is less than 30%, less than 20%, less than 10%, less than 5%, such as 8%, 6%, 5%, preferably 5% of the response of the same antigen binding protein to MAGE-A antigenic peptide/MHC complex in the same experimental setting. In one example, the response is a functional response of T cells expressing said antigen binding protein and determined using an IFN-gamma release assay as described herein above and as described in example 3 and FIG. 5 in the context of the similar peptides.

Furthermore, in one embodiment, the antigen binding protein of the invention, in particular a soluble antigen binding protein of the invention, does not bind or does not significantly bind to at least one similar peptide, such as at least 2, at least 3, at least 4, at least 5, such as 1, 2, 3, 4, 5, preferably at least 3 or 3 or all similar peptides selected from the group of peptides consisting of RABGAP1L-001, AXIN1-001, ANO5-001, TPX2-001, SYNE3-001, MIA3-001, HERC4-001, PSME2-001, HEATR5A-001, CNOT1-003, TEP1-003, PITPNM3-001, INTS4-002, SAMH-001, PPP1CA-006, RPL-007, SETD1A-001, NOMAP-1-0320, NOMAP-1-1223, ODC-001, COL6A3-010, FAM115A-001, PHTF2-001 and RPP1-001 preferably CNOT1-003, SYNE3-001, TPX2-001, PSME2-001, more preferably SYNE3-001, TPX2-001, PSME2-001 when said similar peptide is in a complex with a MHC protein, preferably in complex with HLA-A*02.

In one example, the antigen binding protein of the invention, in particular a soluble antigen binding protein of the invention, does not bind or does not significantly bind to INTS4-002, SAMH-001, PPP1CA-006, RPL-007, SETD1A-001, NOMAP-1-0320, NOMAP-1-1223 and ODC-001, such as INTS4-002, SAMH-001, PPP1CA-006, RPL-007, SETD1A-001 or NOMAP-1-0320, NOMAP-1-1223, ODC-001, COL6A3-010, FAM115A-001, PHTF2-001 and RPP1-001, such as PPP1CA-006, RPL-007 and SETD1A-001, when said similar peptide is in a complex with a MHC protein, preferably in complex with HLA-A*02.

"Does not significantly bind" in the context of similar peptides and in the context of antigen binding proteins, such as soluble antigen binding proteins of the invention, herein is characterized by a decreased affinity, faster dissociation rates and/or lower binding signals, in particular faster dissociation rates and/or lower binding signals. For example, in the context of the present invention the antigen binding protein has a binding response for the at least one similar peptide/MHC complex that is less than 50%, less than 45%, less than 40%, less than 30%, less than 20%, less than 10%, less than 5%, less than 4% or less than 3% of the binding response of the same antigen binding protein to MAGE-A antigenic peptide/MHC complex in the same experimental setting and at the same antigen binding protein concentration and/or, for example, in the context of the present invention the antigen binding protein binds to the at least one similar peptide/MHC complex with an affinity that is decreased in comparison to the affinity for the specific antigen, i.e. the MAGE-A antigenic peptide/MHC complex as described herein and wherein the respective $K_D$ for the respective similar peptide is increased by the factor of 5, 7, 10, 15, 20, 30, 40, 50, 100, 200, 300, 400, 500, 600, 700, 800, 900, 1000, preferably by 5, 7, 10, 15, 20, 30, 40, 50, 100, preferably 20 to 100, more preferably 30 to 100, such as 40 to 100, typically 40 to 50. For example, when the antigen binding protein binds to the complex MAG-003/MHC with a $K_D$ of 1 nM and the antigen binding protein binds to the complex of, for instance, RABGAP1L-001/MHC with a $K_D$ of 100 nM then the antigen binding protein binds to RABGAP1L-001/MHC with a $K_D$ that is increased by a factor of 100 and thus, with an affinity that is decreased by a factor of 100. In these examples, the binding response, the dissociation constants and binding affinities are preferably measured using biolayer interferometry as described in, for example, example 4 and 5. In some further examples, the antigen binding protein binds to the at least one similar peptide/MHC complex with an affinity that is decreased in comparison to the affinity for the specific antigen, i.e. the MAGE-A antigenic peptide/MHC complex as described herein, wherein the respective $K_D$ for CNOT1-003, INTS4-002 and SAMH-001 is increased by a factor of more than 1000, for COL6A3-010, PHTF2-001, RPP1-001 and FAM115A-001 by a factor of more than 500, in comparison to the affinity for the specific antigen, i.e. the MAGE-A antigenic peptide/MHC complex, when for example $K_D$ values were typically measured by biolayer interferometry as described in example 5.

In a further example, the antigen binding protein, such as 114-iso1-BMA(36) or 114-iso2-UCHT1(17), have a binding response for ODC-001, NOMAP-1-0320 and NOMAP-1-1223 in a MHC complex, that is less than 5%, less than 4%, less than 3%, less than 2%, such as less than 1.5%, when measured by biolayer interferometry as described in example 5.

In one embodiment, the antigen binding protein of the invention specifically binds to the MAGE-A antigenic peptide comprising or consisting of the amino acid sequence of SEQ ID NO: 1 and a HLA molecule, preferably HLA-A*02, with a $K_D$ which is ≤100 µM, ≤50 µM, ≤30 µM, ≤25 µM, ≤1 µM, ≤500 nM, ≤100 nM, ≤50 nM, ≤10 nM, preferably 50 pM to 100 µM, 50 pM to 10 µM, 50 pM to 1 µM, more preferably, 50 pM to 500 nM, 50 pM to 100 nM, 50 pM to 50 nM and 50 pM to 10 nM. Accordingly, the antigen binding protein of the invention has an affinity ($K_D$) for the MAGE-A antigenic peptide comprising or consisting of the amino acid sequence of SEQ ID NO: 1 in complex with a HLA molecule, preferably HLA-A*02, which is ≤200 nM, ≤150 nM, ≤120 nM, 110 nM, preferably ≤100 nM, in particular 50 pM to 100 nM, 100 pM to 100 nM, 1 nM to 100 nM. "$K_D$" and "affinity" are as defined herein above in the section "definitions".

Methods to measure the affinity, such as the $K_D$ are known to the skilled in the art and include, for example, surface plasmon resonance and biolayer interferometry. As it is known to the skilled in the art the experimental conditions used for those experiments, such as buffer used, concentration of the protein, may influence the results.

In a related embodiment, the antigen binding protein of the invention, in particular a TCR or fragment thereof or bispecific TCR or fragment thereof, such as T cell-expressed antigen binding proteins, has an affinity ($K_D$) for a complex of the MAGE-A antigenic peptide comprising or consisting of the amino acid sequence of SEQ ID NO: 1 and a HLA molecule, preferably HLA-A*02, which is ≤100 µM, ≤50 µM, ≤30 µM, ≤25 µM, ≤1 µM, preferably ≤25 µM, for instance 500 nM to 100 µM, 500 nM to 50 µM, 500 nM to 25 µM.

In one particular embodiment, the antigen binding protein of the invention is soluble. Soluble antigen binding proteins may include for example, without being limited to it, an antibody or a fragment thereof, or a bispecific antibody or fragment thereof, a TCR fragment or a bispecific TCR or a scTCR. In a related embodiment, the antigen binding protein, which is preferably soluble, binds to a complex of the MAGE-A antigenic peptide comprising or consisting of the amino acid sequence of SEQ ID NO: 1 and a HLA molecule, preferably HLA-A*02, with a $K_D$ which is ≤100 nM, ≤50 nM, ≤10 nM, ≤1 nM, ≤1 nM, for instance 10 pM to 100 nM, 10 pM to 50 nM, 10 pM to 10 nM, in particular 50 pM to 100 nM, 100 pM to 50 nM, 100 pM to 10 nM.

Accordingly, in one example, the antigen binding proteins of the invention are expressed, for instance, as soluble TCER™ described herein above and are analyzed for their binding affinity towards the HLA-A*02/MAG-003 monomers. Typically, measurements are performed, for instance, on an Octet RED384 system using, typically, settings recommended by the manufacturer. Briefly, binding kinetics were, typically, measured at 30° C. and, for instance, 1000 rpm shake speed using, for example, PBS, 0.05% TWEEN® 20 (polysorbate 20), 0.1% BSA as buffer. The antigen binding proteins were either loaded onto biosensors, such as FAB2G or AHC, or analyzed in solution.

In one embodiment, the antigen binding proteins of the invention have an increased affinity, optionally, in comparison to a reference protein.

A "reference protein" herein refers to a protein with which the antigen binding protein of the invention is compared. In one embodiment, the reference protein is directed against the same target, i.e. the MAGE-A antigenic peptide in complex with a MHC protein, as the present protein, more preferably said reference protein is in same format as the antigen binding protein with which it is compared. In one particular embodiment, the reference protein is in same format as the antigen binding protein with which it is compared and the reference protein comprises the CDRs or the alpha and beta variable domains of the parental TCR R7P1D5.

As disclosed herein, the antigen binding proteins of the invention recognizes and/or binds to a complex of the MAGE-A antigenic peptide comprising or consisting of the amino acid sequence 'KVLEHVVRV' of SEQ ID NO: 1 and a HLA molecule, preferably HLA-A*02. The MAG-003 and the HLA molecule are thus present in a major histocompatibility complex (MHC) class I, and, the binding of the antigen binding protein to said complex may elicit an immune response upon binding. In some embodiments, the antigen binding protein of the present invention induces an immune response that is increased in comparison to the immune response that is induced by reference protein.

Accordingly, in one embodiment, the antigen binding protein of the present invention, induces an immune response, preferably, wherein the immune response is characterized by an increase in interferon (IFN) γ levels. Accordingly, in one example the immune response might be characterized by an $EC_{50}$ value that is preferably determined in an IFN-gamma release assay.

In one embodiment the antigen binding protein has a $EC_{50}$ [nM] value, preferably determined by IFN-gamma release, that is lower than the $EC_{50}$ of the reference protein, preferably the antigen binding protein has an $EC_{50}$ [nM] that is 2 times, preferably, 2, 3, 4, 5, 6, 7, 8, times lower, such as 2 to 9 times lower, than the $EC_{50}$ [nM] value of a reference protein and wherein the $EC_{50}$ value is the concentration of half-maximal IFN-gamma release [nM] determined on MHC, preferably HLA-A*02 expressing cells, preferably loaded with the antigenic peptide of SEQ ID NO: 1. In one example, the $EC_{50}$ referred to, is determined by, typically, ELISA, for example, after co-culture of electroporated CD8+ T cells with T2 cells loaded with a serial dilution of the MAGE-A antigenic peptide, preferably the MAGE-A antigenic peptide of SEQ ID NO: 1. Preferably the reference protein is in same format as the antigen binding protein with which it is compared and the reference protein comprises the CDRs or the alpha and beta variable domains of the parental TCR R7P1D5 and wherein the $EC_{50}$ has preferably been determined in the same experimental setting.

In one embodiment, the antigen binding protein has an $EC_{50}$ value, preferably determined by IFN-gamma release assay or LDH release assay, for MAGE-A/MHC complex presenting cells which is less than 100 nM, less than 50 nM, less 10 nM, less than 900 pM, less than 500 pM, less than 300 pM, less than 200 pM, less than 150 pM, less than 100 pM, less than 50 pM, less than 20 pM, less than 10 pM, such as between 0.1 nM and 20 nM, such as 0.5 nM and 15 nM, 0.8 nM and 12 nM, 0.8 nM and 10 nM, 0.8 nM and 10 nM, 0.8 nM and 10 nM or such as between 1 pM and 150 pM, 1 and 100 pM, 1 and 50 pM, 1 and 20 pM, 1 and 20 pM.

In one embodiment, the antigen binding protein is a TCR, and has a $EC_{50}$, preferably determined by IFN-gamma release, for MAGE-A/MHC complex presenting cells which is less than 12 nM, less than 10 nM, less 9 nM, less than 8 nM, less than 6 nM, less than 4 nM, such as between 0.1 nM and 20 nM, such as 0.5 nM and 15 nM, 0.8 nM and 12 nM, 0.8 nM and 10 nM, 0.8 nM and 10 nM, 0.8 nM and 10 nM.

In this embodiment, the $EC_{50}$ is determined using CD8+ T cells (20,000 cells/well) expressing different antigen binding proteins of the invention and by determining levels of released IFN-gamma upon co-culture with T2 cells (20,000 cells/well) loaded with a dilution series of MAG-003 (SEQ ID NO: 1).

In one embodiment the antigen binding protein is a soluble molecule, such as a TCER™, and has a $EC_{50}$ for MAGE-A/MHC complex presenting cells that is less than 200 pM, less than 150 pM, less than 100 pM, less than 50 pM, less than 20 pM, less than 10 pM, between 1 pM and 150 pM, 1 and 100 pM, 1 and 50 pM, 1 and 20 pM, 1 and 20 pM. In this embodiment, the $EC_{50}$ is determined using CD8+ T cells (20,000 cells/well) expressing different antigen binding proteins of the invention and by determining levels of released LDH upon co-culture with tumor cell lines presenting MAG-003 at endogenous levels, preferably the cell line is Hs695T which presents on its surface around 1071 of the MAG-003 peptides in complex with the MHC protein, preferably the cell line is NCI-H1755 which presents on its surface around 3918 of the MAG-003 peptides in complex with the MHC protein, or preferably the cell line is U2OS which presents on its surface around 125 of the MAG-003 peptides in complex with the MHC protein.

The antigen binding proteins of the present invention have a high safety profile.

"Safety profile" herein refers to the capacity to distinguish tumor cells from healthy tissue cells and this is often determined by determining the safety window.

The "safety window" or "therapeutic window" herein refers to a factor that compares the half maximal concentration of a compound that is required for inducing 100% cytotoxicity in a tumor cell line in comparison to the half maximal concentration of a compound that is required for inducing 100% cytotoxicity healthy tissue cells. If for an antigen binding protein of interest the $EC_{50}$ determined for a tumor cell line is 1 pM and the $EC_{50}$ value determined for, for instance, primary cells is 1000 pM then the safety window is 1000 since the $EC_{50}$ for the tumor cell line is 1000 time smaller than the $EC_{50}$ for the primary cells.

In one embodiment, the antigen binding protein of the invention has an $EC_{50}$ for MAGE-A/MHC complex presenting cells that is ≥100, ≥500, ≥1000, ≥2000, ≥3000, ≥4000, ≥5000, ≥6000, ≥8000, ≥10000 higher than the $EC_{50}$ value for healthy cells, such as an $EC_{50}$ for MAGE-A/MHC complex presenting cells that is between 500 and 12000, preferably between 1000 and 10000 higher than the $EC_{50}$ value for healthy cells.

"MAGE-A/MHC complex presenting cells" herein refers to a cell that presents on its surface the MAGE-A peptide/MHC complex, wherein the copy number of said MAGE-A/MHC complex can typically be determined with methods known to the skilled in the art. In one embodiment, the MAGE-A/MHC complex is a target cell such as a cancer cell, wherein the cancer is as defined herein below in the section 'Therapeutic methods and uses'. In the context of the present invention the MAGE-A peptide/MHC complex is over-presented on the cell surface of a MAGE-A/MHC complex presenting cells, in particular a cancer cell, compared to levels of said complex on the surface of cells in in normal (healthy) tissues. By "over-presented" is mean that the MAGE-A/MHC complex is present at a level at least 1.2-fold of the level present in healthy tissue; preferably at least 2-fold, and more preferably between 5-fold to 10-fold the level present in healthy tissue or cells.

In one embodiment, the MAGE-A/MHC complex presenting cell has a MAGE-A/MHC complex copy number of more than 50, more than 80, more than 100, more than 120, more than 150, more than 300, more than 400, more than 600, more than 800, more than 1000, more than 1500, more than 2000, preferably a MAGE-A/MHC copy number of 50 to 2000, such as 80 to 2000, such as 100 to 2000, for example 120 to 2000.

"Copy number" herein refers to the number of MAGE-A/MHC complex as defined in the context of the present invention that are present on the cell surface of a cell, such as a MAGE-A/MHC presenting cell, for example a cancer cell, or a healthy cell. Copy numbers of a proteincan be determined by a variety of art known methods including FACS analysis of diseased cells with fluorescently labeled antigen binding proteins.

"Healthy cells" herein refers to cells that are no cancer cells, preferably healthy cells herein refers to cells of the tissue surrounding the MAGE-A/MHC presenting cells, cells of the tissue surrounding the MAGE-A/MHC complex presenting cancer cells. However, in some cases also healthy cells might express and present at their surface the MAGE-A/MHC complex. Typically in healthy cells in the context of the present invention, as it will be understood by the skilled in the art, the MAGE-A/MHC complex is present in smaller amounts (copy numbers) than in a cancer cell.

Healthy cells are preferably selected from the group consisting of Astrocytes, GABANeurons, Cardiomyocytes, Cardiac Microvascular Endothelial cells, Chondrocytes, Coronery Artery Endothelial cells, Dermal Microvascular Endothelial cells, Mesenchymal stem cells, Nasal Epithelial cells, Peripheral Blood Mononuclear cells, Pulomary Artery Smooth Muscle cells, preferably GABANeurons, Cardiomyocytes, Cardiac Microvascular Endothelial cells, chondrocytes, Coronary Artery Endothelial cells, Nasal Epithelial cells, Peripheral Blood Mononuclear cells, Pulomary Artery Smooth Muscle cells.

In one embodiment, the antigen binding protein has an $EC_{50}$ for MAGE-A/MHC complex presenting cells that is ≥1000, ≥15000, ≥9000 times higher than the $EC_{50}$ value for healthy cells, preferably healthy cells selected from the group consisting of Astrocytes, GABANeurons, Cardiomyocytes, Cardiac Microvascular Endothelial cells, chondrocytes, Coronary Artery Endothelial cells, Derman Microvascular Endothelial cells, Mesenchymal stem cells, Nasal Epithelial cells, Peripheral Blood Mononuclear cells, Pulmonary Fibroblasts, Tracheal Smooth Muscle Cells, Epidermal Keratinocytes, Renal Cortical Epithelial cells and Pulmonary Artery Smooth Muscle cells, preferably Astrocytes, GABANeurons, Cardiomyocytes, Cardiac Microvascular Endothelial cells, chondrocytes, Coronary Artery Endothelial cells, Dermal Microvascular Endothelial cells, Mesenchymal stem cells, Nasal Epithelial cells, Peripheral Blood Mononuclear cells and Pulmonary Artery Smooth Muscle cells, more preferably GABANeurons, Cardiomyocytes, Cardiac Microvascular Endothelial cells, chondrocytes, Coronary Artery Endothelial cells, Nasal Epithelial cells, Peripheral Blood Mononuclear cells, Pulomary Artery Smooth Muscle cells.

In one preferred embodiment, the antigen binding protein has an $EC_{50}$ for MAGE-A/WIC complex presenting cells that is ≥9000 or ≥10000 times higher than the $EC_{50}$ value for healthy cells, wherein preferably said healthy cells are selected from the group consisting of iPSC-derived Astrocytes, iGABANeurons, iCardiomyocytes, Osteoblasts, Pulmonary Fibroblasts, Tracheal Smooth Muscle Cells and Epidermal Keratinocytes and Renal Cortical Epithelial cells.

Accordingly, in one embodiment, the healthy cells have a MAGE-A/MHC complex copy number of less than 50, less than 20, less than 10, preferably less than 10 MAGE-A/MHC complex copy number, preferably a MAGE-A/MHC complex copy number between 0 and 10.

In one embodiment, the antigen binding protein of the invention has an $EC_{50}$ for MAGE-A/MHC complex presenting cells that is ≥100, ≥500, ≥1000, ≥2000, ≥3000, ≥4000, ≥5000, ≥6000 higher than the $EC_{50}$ value for similar peptide/MHC presenting cells, such as an $EC_{50}$ for MAGE-A/MHC complex presenting cells that is between 500 and 12000, preferably 1000 and 12000 higher than the $EC_{50}$ value for similar peptide/MHC presenting cells.

A "similar peptide" is defined herein above.

A similar peptide/MHC presenting cell is thus a cell that presents on its cell surface similar peptide/MHC complex. In one embodiment, the similar peptide/MHC presenting cells have a copy number of a similar peptide/MHC that is more than 10, more than 20, more than 40, more than 50, more than 80, more than 100, more than 120, more than 150, more than 300, more than 400, more than 500, more than 800, preferably a similar peptide/MHC copy number of 50 to 1000, such as 50 to 8000, such as 50 to 500, for example 100 to 500.

The present invention provides antigen binding proteins that are able to induce tumor regression in vivo, more particularly complete regression under the tested conditions. Antigen binding proteins were prepared and evaluated at different doses against measurable HS695T tumor xenografts implanted in female NOG mice engrafted with human PBMC (see example 7). TCER™ targeting MAG-003 (SEQ ID NO: 127 and 130, group 3; SEQ ID NO: 135 and 136, group 4) induced complete remission of the Hs695T tumor in all mice at Day 18 until the end of the study at Day 25 compared to basal levels of 86 mm$_3$ (group 3) and 80 mm$^3$ (group 4) at the day of randomization.

Accordingly, in one embodiment, the antigen binding protein of the present invention inhibits or reduces tumor growth, more particularly, the antigen binding protein of the present invention reduces the mean tumor volume of a tumor by more than 80%, more than 85%, more than 90%, more than 92, more than 94, more than 96, more than 98, more than 99%, such as 95% to 100%, 96% to 100%, 98% to 100%, such as 98%, 99% or 100%, preferably 100%, wherein said tumor is of a cancer as defined herein below in the section 'Therapeutic methods and uses'. In one example, the antigen binding protein induces complete remission in a cancer tumor, wherein the cancer is as defined herein below, for example in the human tumor cell line HS695T.

In one embodiment, the half-life ($T_{1/2}$) of the antigen binding protein of the invention is between 6 to 7 days, such as 6 or 7 days.

As it can be further seen from the examples, in particular example 1 and FIG. 1, the native TCRs, such as the native TCR R7P1D5, could not be expressed in a soluble format neither in yeast nor in in the CHO cells. Contrary to this, the antigen binding proteins of the present invention, in particular TCER™ molecules, preferably the herein described preferred TCER™ molecules are not only soluble but can also be expressed in CHO cells in a transient expression in amounts that are >10 mg/L(cell culture), >20 mg/L or even 40 mg/L. Accordingly, in one embodiment, the antigen binding protein of the present invention can be expressed in a host cell with high yields, wherein preferably the host cell is CHO cell and wherein preferably the yield is more than 10, more than 15, 18, 20, 22, 24, 26, 28, 30, 35, 40, 45 mg/L(cell culture), such as 5 to 50, 5, to 45, 5 to 40, 5 to 35, 10 to 35, 10 to 30, 10 to 25, 10 to 20 mg/L(cell culture). In one example the antigen binding protein has been expressed in transiently transfected CHO-S cells wherein the cells are cultured at T=0 in a density of $4\times10^6$/mL at 37° C. in a medium of GE Healthcare™ in a total volume of 320 mL After one day feed solution (CellBoost 7a and b) was added and the temperature was lowered to 32° C. The cells and thus the antigen binding protein was harvested after a total culture time of 12 days and three feeds in total.

As it can be further seen from the examples, the inventors demonstrated, for instance in example 4 and 5, that the antigen binding proteins of the invention have an improved stability, in comparison to a reference protein, for instance, in comparison to an antigen binding protein comprising the CDRs of the native TCR R7P1D5 and preferably the Framework regions of said native TCR R7P1D5.

Accordingly, in one embodiment, the antigen binding proteins of the invention have an improved stability, optionally, in comparison to a reference protein. In the context of the present invention, an improved stability refers for example to an increased physical stability when exposed to thermal stress. The newly developed antigen binding proteins of the invention can thus better withstand stress conditions, especially thermal stress than the reference antigen binding protein.

The term "stability" in the context of the present invention refers to physical stability and can be evaluated qualitatively and/or quantitatively using various analytical techniques that are described in the art and are reviewed in for example Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). In the context of the present invention, those methods refer in particular to the evaluation of aggregate formation (for example using size exclusion chromatography, by measuring turbidity, and/or by visual inspection. In order to measure stability a sample which comprises the antigen binding protein of the invention may be tested in a stability study, wherein a sample is exposed for a selected time period to a stress condition followed by quantitative and optionally qualitative analysis of the chemical and physical stability using an adequate analytical technique.

In one embodiment, the antigen binding proteins of the present invention are physical stable, for instance, when exposed to stress condition for a certain period of time, such as when exposed for, for instance, 14 days, to a temperature of 40° C.

"Physical stability" refers substantially, in the context of the present invention, to an antigen binding protein having no signs of aggregation, precipitation and/or denaturation.

Methods to access the physical stability are for example size exclusion chromatography (SEC), dynamic light scattering (DLS), light obscuration (LO) and color and clarity, for example, determined by visual inspection.

"No signs of aggregation" means, for example, that a sample comprising the antigen binding protein, after having been exposed to a stress condition, such as, to a temperature of 40° C. for 14 days in a buffer, such as PBS, has a monomer content of more than 80%, more than 86%, more than 88%, more than 90%, more than 92%, more than 94%, more than 96%, more than 97%, more than 98%, more than 99%, such as a monomer content of 94% to 99%, 95% to 99%, 96% to 99%, 97% to 99% monomer content, when measured by SEC, such as SEC-HPLC, in a buffer, such as PBS.

Accordingly, in one embodiment, the antigen binding proteins of the present invention have a reduced aggregation, for example, in comparison to a reference protein when exposed to a stress condition.

For size exclusion chromatography (SEC), a difference of 1%, 2%, 3%, 4%, preferably 1 or 2%, such as 2%, of the monomer content is considered as significantly different in the context of the invention under the tested conditions depending on the column used, operating pressure, and velocity of the buffer.

This means, when the reference antigen binding protein has a monomer content of 96% and the antigen binding protein of the invention has a monomer content of 97%, the monomer content of the antigen binding protein of the invention is significantly different and thus significantly increased in comparison to the reference antigen binding protein, when measured in the same conditions.

In one embodiment, the antigen binding proteins of the present invention have a reduced aggregation when exposed to a stress condition, more particularly the antigen binding proteins of the present invention have less than 10%, less than 4%, less than 3%, less than 2% aggregation when the aggregates induced by the stress are measured before and after the exposure to said stress condition.

Nucleic Acids, Vectors and Recombinant Host Cells

A further object of the invention relates to an isolated nucleic acid sequence comprising or consisting of a sequence encoding an antigen binding protein of the invention which is as defined herein above.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid of the invention.

Such vectors may comprise regulatory elements, such as a promoter, enhancer, terminator and the like, to cause or direct expression of said polypeptide upon administration to a subject. Examples of promoters and enhancers used in the expression vector for animal cell include early promoter and enhancer of SV40 (Mizukami T et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like. Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO95/14785, WO96/22378, U.S. Pat. Nos. 5,882,877, 6,013,516, 4,861,719, 5,278,056 and WO94/19478.

The term "viral vector" refers to a nucleic acid vector construct that includes at least one element of viral origin and has the capacity to be packaged into a viral vector particle, and encodes at least an exogenous nucleic acid. The vector and/or particle can be utilized for the purpose of transferring any nucleic acids into cells either in vitro or in vivo. Numerous forms of viral vectors are known in the art.

The term "virion" is used to refer to a single infective viral particle. "Viral vector", "viral vector particle" and "viral particle" also refer to a complete virus particle with its DNA or RNA core and protein coat as it exists outside the cell. For example, a viral vector may be selected from adenoviruses, poxviruses, alphaviruses, arenaviruses, flaviviruses, rhabdoviruses, retroviruses, lentiviruses, herpesviruses, paramyxoviruses, or picornaviruses.

Viruses may refer to natural occurring viruses as well as artificial viruses. Viruses in accordance to some embodiments of the present invention may be either an enveloped or non-enveloped virus. Parvoviruses (such as AAVs) are examples of non-enveloped viruses. In a preferred embodiment, the viruses may be enveloped viruses. In preferred embodiments, the viruses may be retroviruses and in particular lentiviruses. Viral envelope proteins that can promote viral infection of eukaryotic cells may include HIV-1 derived lentiviral vectors (LVs) pseudotyped with envelope glycoproteins (GPs) from the vesicular stomatitis virus (VSV-G), the modified feline endogenous retrovirus (RD114TR), and the modified gibbon ape leukemia virus (GALVTR). These envelope proteins can efficiently promote entry of other viruses, such as parvoviruses, including adeno-associated viruses (AAV), thereby demonstrating their broad efficiency. For example, other viral envelop proteins may be used including Moloney murine leukemia virus (MLV) 4070 env (such as described in Merten et al., J. Virol. 79:834-840, 2005; the content of which is incorporated herein by reference), RD114 env, chimeric envelope protein RD114pro or RDpro (which is an RD114-HIV chimera that was constructed by replacing the R peptide cleavage sequence of RD114 with the HIV-1 matrix/capsid (MA/CA) cleavage sequence, such as described in Bell et al. Experimental Biology and Medicine 2010; 235: 1269-1276; the content of which is incorporated herein by reference), baculovirus GP64 env (such as described in Wang et al. J. Virol. 81:10869-10878, 2007; the content of which is incorporated herein by reference), or GALV env (such as described in Merten et al., J. Virol. 79:834-840, 2005; the content of which is incorporated herein by reference), or derivatives thereof.

A further object of the present invention relates to a host cell which has been transformed, transduced or transfected with a nucleic acid and/or a vector according to the invention.

The term "transformation" originally refers to a naturally occurring process of gene transfer into a host cell which involves absorption of the genetic material, such as nucleic acids, for instance, DNA or RNA, by a cell through cell membrane, so that the host cell will express the introduced gene or sequence to produce a desired substance, typically a protein or enzyme coded by the introduced gene or sequence. There are two types called as natural transformation and artificial or induced transformation. The artificial or induced method of transformation is done under laboratory condition and is typically referred to as transfection.

A host cell that receives and expresses foreign nucleic acids, such as DNA or RNA, by the process of a transformation has been "transformed".

The term "transfection" refers to a mode of gene transfer involving creation of pores on the cell membrane of the host cell enabling the host cell to receive the foreign genetic material. Typically transfection refers to a transformation of eukaryotic cells, such as insect or mammalian cells. Chemical mediated transfection involves use of, for instance, calcium phosphate or cationic polymers or liposomes. Non-chemical mediated transfection methods are typically electroporation, sonoporation, impalefection, optical transfection or hydro dynamic delivery. Particle based transfection uses gene gun technique where a nanoparticle is used to transfer the nucleic acid to host cell or by another method called as magnetofection. Nucleofection and use of heat shock are the other evolved methods for successful transfection. A host cell that receives foreign nucleic acids via a transfection method has been "transfected".

The term "transduction" is generally understood to relate to the transfer of foreign nucleic acids, such as DNA or RNA, into a cell by a virus or viral vector. A host cell that receives and expresses foreign nucleic acids, such as DNA or RNA, by a virus or viral vector has been "transduced".

In some embodiments, cells may be transduced using the methods described in US20190216852, the content of which is hereby incorporated by reference in its entirety.

The nucleic acids of the invention may be used to produce a recombinant antigen binding protein of the invention in a suitable expression system.

The nucleic acids of the invention may be used to produce a recombinant antigen binding protein of the invention in a suitable expression system.

The term "expression system" means a host cell and compatible vector under suitable conditions, e.g. for the expression of a protein coded for by foreign DNA carried by the vector and introduced to the host cell.

Common expression systems include E. coli host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like. In some embodiments, the YB2/0 cell may be preferred, since ADCC activity of chimeric or humanized antibodies is enhanced when expressed in this cell.

The invention also pertains to a host cell comprising an antigen recognizing construct in accordance with the invention. Specifically, the host cell of the invention comprises a nucleic acid, or a vector as described herein above. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. For purposes of producing an antigen binding protein, such as a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood leukocyte (PBL) or a peripheral blood mononuclear cell (PBMC). More preferably, the host cell is a T cell. The T cell can be any T cell, such as a cultured T cell, e.g., a primary T cell, or a T cell from a cultured T cell line, e.g., Jurkat, SupT1, etc., or a T cell obtained from a mammal, preferably a T cell or T cell precursor from a human patient. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, CD4-positive and/or CD8-positive, CD4-positive helper T cells, e.g., Th1 and Th2 cells, CD8-positive T cells (e.g., cytotoxic T cells), tumor infiltrating cells (TILs), memory T cells, naive T cells, and the like. Preferably, the T cell is a CD8-positive T cell or a CD4-positive T cell. The host cell preferably is a tumor reactive T cell specific for MAGEA4 and/or MAGEA8 expressing tumor cells.

According to the above, in one embodiment, the invention refers to a host cell comprising the antigen binding protein of the invention which is defined herein above, or the nucleic acid, or the vector of the invention, wherein said host cell preferably is a) a lymphocyte, such as a T lymphocyte or T lymphocyte progenitor cell, for example a CD4 or CD8 positive T cell or b) a cell for recombinant expression, such as a Chinese Hamster Ovary (CHO) cell.

In particular, for expression of some of the antigen binding proteins of the invention the expression vector may be either of a type in which a gene encoding the first polypeptide, such as an antibody heavy chain or an alpha chain, and a gene encoding a second polypeptide, such as an antibody light chain or a beta chain, exists on separate vectors or of a type in which both genes exist on the same vector (tandem type). In respect of easiness of construction of antigen binding protein expression vector, easiness of introduction into animal cells, and balance between the expression levels of antibody H and L chains in animal cells, humanized antibody expression vector of the tandem type is preferred (shitara K et al. J Immunol Methods. 1994 Jan. 3; 167(1-2):271-8). Examples of tandem type humanized antibody expression vector include pKANTEX93 (WO 97/10354), pEE18 and the like.

In one embodiment such recombinant host cells can be used for the production of at least one antigen binding protein of the invention Methods of Producing Antigen Binding Proteins of the Invention The present invention also relates to a method of producing the antigen binding protein as defined herein above, comprising
  a. providing a suitable host cell,
  b. providing a genetic construct comprising a coding sequence encoding the antigen binding protein of the invention,
  c. introducing said genetic construct into said suitable host cell, and
  d. expressing said genetic construct by said suitable host cell, and optionally
  e. selecting the cells which express and/or secrete said antibody.

The antigen binding protein of the invention is as defined herein above in the corresponding section.

"Genetic construct" herein denotes nucleic acids that allow expression of the coding region in a host, and thus refers to nucleic acids, such as vectors, described herein above or RNA.

In one embodiment, the method may further comprise a step of cell surface presentation of said antigen recognizing construct on said suitable host cell.

In other preferred embodiments, the genetic construct in b) comprises a nucleic acid encoding the antigen binding proteins of the invention. Such nucleic acids are as defined herein above in the section 'nucleic acid, vectors and recombinant host cells'.

In a related embodiment, the genetic construct is an expression construct comprising a promoter sequence operably linked to said coding sequence.

In a related embodiment, the genetic constructs are introduced into the suitable host using transformation, transduction or transfection. Transformation, transduction or transfection are as defined in the section herein above.

Desirably, the transfection system for introducing the genetic construct into said suitable host cell is a retroviral or lentiviral vector system as described herein above in the section nucleic acid, vectors and recombinant host cells. Such systems are well known to the skilled artisan.

In one embodiment, the method further comprises the isolation and purification of the antigen binding protein from the host cell and, optionally, reconstitution of the antigen binding protein in a T cell.

An antigen binding protein of the invention may be produced by any technique known in the art, such as, without limitation, any chemical, biological, genetic or enzymatic technique, either alone or in combination.

In some particular embodiments, the antigen binding proteins of the invention have an antibody or immunoglobulin like framework.

Standard techniques for production of polypeptides, such as antibodies or fragments thereof and TCRs or fragments thereof, are known in the art and these techniques can be transferred by the skilled in the art to the antigen binding proteins of the present invention. For instance, they can be synthesized using well-known solid phase method, in particular using a commercially available peptide synthesis apparatus (such as that made by Applied Biosystems, Foster City, California) and following the manufacturer's instructions. Alternatively, antigen binding proteins of the invention, such as antibodies or fragment thereof and TCRs or fragments thereof, can be synthesized by recombinant DNA techniques as is well-known in the art. For example, fragments can be obtained as DNA expression products after incorporation of DNA sequences encoding the desired (poly) peptide into expression vectors and introduction of such vectors into suitable eukaryotic or prokaryotic hosts that will express the desired polypeptide, from which they can be later isolated using well-known techniques.

In one example, i.e. in case of TCER™ bispecific molecules, DNA-sequences coding for various combinations of VH and VL and variable alpha (Valpha) and variable beta (Vbeta), as well as sequences coding for linkers may be obtained by, for instance, gene synthesis. Resulting DNA-sequences may be cloned in frame into expression vectors coding for hinge region, $C_{H2}$ and $C_{H3}$ domain derived from, for example, human IgG4 [Accession #: K01316] and IgG1 [Accession #: P01857], respectively and may be further engineered. Engineering may be performed to incorporate knob-into-hole mutations into $C_{H3}$-domains with and without additional interchain disulfide bond stabilization; to remove an N-glycosylation site in $C_{H2}$ (e.g. N297Q mutation); to introduce $F_c$-silencing mutations or to introduce additional disulfide bond stabilization into $V_L$ and $V_H$, respectively, according to the methods described by Reiter et al. (Stabilization of the Fv Fragments in Recombinant Immunotoxins by Disulfide Bonds Engineered into Conserved Framework Regions. Biochemistry, 1994, 33, 5451-5459); to include stability- or manufacturability-enhancing mutations.

Antigen binding proteins of the invention are suitably separated from the culture medium by immunoglobulin purification procedures such as, for example, protein A-SEPHAROSE, protein L-SEPHAROSE, protein G-SEPHAROSE, hydroxylapatite chromatography, gel electrophoresis, dialysis, or affinity chromatography.

In one embodiment, recovering the expressed antigen binding proteins or polypeptides herein refers to performing a protein A chromatography, a protein L chromatography, a Kappa select chromatography, and/or a size exclusion chromatography, preferably a protein L chromatography and/or a size exclusion chromatography, more preferably a protein L-chromatography and a size exclusion chromatography.

Methods for producing antigen binding proteins of the invention involve recombinant DNA and gene transfection techniques are well known in the art (See Morrison S L. et al. (1984) and patent documents U.S. Pat. Nos. 5,202,238; and 5,204,244).

Furthermore, methods for producing humanized antibodies based on conventional recombinant DNA and gene transfection techniques are well known in the art (See, e.g., Riechmann L. et al. 1988; Neuberger M S. et al. 1985) and can be easily applied to the production of antigen binding proteins of the invention.

In one example, vectors for the expression of the recombinant antigen binding proteins of the invention were designed as mono-cistronic, for instance, controlled by HCMV-derived promoter elements, pUC19-derivatives. Plasmid DNA was amplified, for example, in E. coli according to standard culture methods and subsequently purified using commercial-available kits (Macherey & Nagel). Purified plasmid DNA was used for transient transfection of, for example, CHO-S cells according to instructions of the manufacturer (ExpiCHO™ system; Thermo Fisher Scientific) or utilizing an electroporation systems (MaxCyte STX). Transfected CHO-cells were cultured, for instance, for 6-14 days at, for example, 32° C. to 37° C. and received one to two feeds of ExpiCHO™ Feed or Cellboost 7a and 7b (GE Healthcare™) solution.

Conditioned cell supernatant was cleared by, for example, filtration (0.22 μm) utilizing, for instance, Sartoclear Dynamics® Lab Filter Aid (Sartorius). Bispecific antigen binding proteins were purified using, for example, an AKTA Pure 25 L FPLC system (GE Lifesciences) equipped to perform affinity and size-exclusion chromatography in line. Affinity chromatography was performed on, for example, protein A or L columns (GE Lifesciences) following standard affinity chromatographic protocols. For instance, size exclusion chromatography was performed directly after elution (pH 2.8) from the affinity column to obtain highly pure monomeric protein using, for example, SUPERDEX 200 μg 16/600 columns (GE Lifesciences) following standard protocols. Protein concentrations were determined on, for example, a NANODROP system (Thermo Scientific) using calculated extinction coefficients according to predicted protein sequences. Concentration was adjusted, if needed, by using VIVASPIN devices (Sartorius). Finally, purified molecules were stored in, for example, phosphate-buffered saline at concentrations of about 1 mg/mL at temperatures of 2-8° C.

Quality of purified bispecific antigen binding proteins was determined by, for example, HPLC-SEC on MabPac SEC-1 columns (5 lam, 4×300 mm) running in, for example, 50 mM sodium-phosphate pH 6.8 containing 300 mM NaCl within a Vanquish uHPLC-System.

In one particular embodiment, a T cell, as defined above, is provided in step a) and the antigen binding protein is a TCR or a fragment thereof. Accordingly, the antigen binding protein is expressed on the cell surface of the T cell. The method thus produces a T cell expressing on its surface an antigen binding protein, such as a TCR, which is specific for cancer cells as defined in the context of the invention.

Pharmaceutical Compositions

The invention further refers to a pharmaceutical composition comprising the antigen binding protein of the invention, the nucleic acids of the invention, the vector of the invention, or the host cell of the invention and a pharmaceutically acceptable carrier.

The invention also relates to an antigen binding protein according to the invention, for use as a medicament. The invention also relates to a pharmaceutical composition of the invention for use as a medicament.

The invention also relates to the use of an antigen binding protein according to the invention or/and to a pharmaceutical composition of the invention, in the manufacture of a medicament.

The terms "pharmaceutical composition" or "therapeutic composition" as used herein refer to a compound or composition capable of inducing a desired therapeutic effect when properly administered to a subject.

In some embodiments, the subject may also be referred to as patient.

Such therapeutic or pharmaceutical compositions may comprise a therapeutically effective amount of an antigen binding protein of the invention or an antigen binding protein further comprising a therapeutic agent, in admixture with a pharmaceutically or physiologically acceptable formulation agent selected for suitability with the mode of administration.

The antigen binding protein of the present invention will usually be supplied as part of a sterile, pharmaceutical composition which will normally include a pharmaceutically acceptable carrier.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

A "pharmaceutically-acceptable carrier" may also be referred to as "pharmaceutically acceptable diluent" or "pharmaceutically acceptable vehicles" and may include solvents, bulking agents, stabilizing agents, dispersion media, coatings, antibacterial and antifungal agents, isotonic and absorption delaying agents, and the like which are physiologically compatible. Accordingly, in one embodiment the carrier is an aqueous carrier.

In another aspect, the aqueous carrier is capable of imparting improved properties when combined with an antigen binding protein described herein, for example, improved solubility, efficacy, and/or improved immunotherapy.

The form of the pharmaceutical compositions, the route of administration, the dosage and the regimen naturally depend upon the condition to be treated, the severity of the illness, the age, weight, and gender of the patient, the desired duration of the treatment etc. This pharmaceutical composition may be in any suitable form, (depending upon the desired method of administering it to a patient). It may be provided in a unit dosage form, will generally be provided in a sealed container and may be provided as part of a kit. Such a kit would normally (although not necessarily) include instructions for use. It may include a plurality of said unit dosage forms.

Empirical considerations, such as the biological half-life, generally will contribute to the determination of the dosage. Frequency of administration may be determined and adjusted over the course of therapy and is based on reducing the number of cancer cells, maintaining the reduction of cancer cells, reducing the proliferation of cancer cells, or killing the cancer cells. Alternatively, sustained continuous release formulations of the antigen binding protein may be appropriate. Various formulations and devices for achieving sustained release are known in the art.

In one embodiment, dosages for the antigen binding proteins may be determined empirically in individuals who have been given one or more administration(s). Individuals are given incremental dosages of the antigen binding protein. To assess efficacy of the antigen binding protein, a marker of the cancer cell state can be followed. These include direct measurements of cancer cell proliferation and cell death by FACS, other imaging techniques; an improvement in health as assessed by such measurements, or an increase in quality of life as measured by accepted tests or prolongation of survival. It will be apparent to one of skill in the art that the dosage will vary depending on the individual, the stage of the disease, and the past and concurrent treatments being used.

In particular, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

To prepare pharmaceutical compositions, an effective amount of the antigen binding protein of the invention may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antigen binding protein of the invention can be formulated into a composition in a neutral or salt form using pharmaceutically acceptable salts.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

Therapeutic Methods and Uses

The inventors have shown in example 6 of the experimental section in vitro for several antigen binding proteins of the invention, in particular TCER™ molecules of the invention, such as the soluble TCER™ molecules #114-iso0-UCHT1(17), #114-iso1-UCHT1(17), #114-iso2-UCHT1(17), #114-iso0-BMA031(36), #114-iso1-BMA031(36) and #114-iso2-BMA031(36), the cytotoxic activity of those molecules for MAG-003 positive cancer cell lines such as Hs695T, A375 and U2OS. The inventors have furthermore demonstrated that said cytotoxic activity is highly specific and limited to MAG-003-positive cells since only marginal lysis was induced by the bispecific antigen binding proteins in cell lines expressing HLA-A*02 but not presenting the peptide MAG-003.

Furthermore, the inventors demonstrated the in vivo efficacy of the antigen binding proteins of the invention, such as the TCER™ targeting MAG-003 (SEQ ID NO: 127 and 130, group 3; SEQ ID NO: 135 and 136, group 4), leading in the HS695T tumor in NOG mice to complete remission as described in detail in example 7 and as shown in FIG. 11.

As demonstrated by the inventors, the antigen binding proteins of the present invention are useful for generating an immune response in a subject, preferably a patient, wherein tumor cells can be destroyed by this immune response. The immune response originating from such a therapeutic vaccination can be expected to be highly specific against tumor cells because the peptide KVLEHVVRV (SEQ ID NO: 1) is not presented or over-presented on normal tissues in comparable copy numbers, preventing the risk of undesired autoimmune reactions against normal cells in the patient. Furthermore, as indicated in the introductory part of this specification, the antigen binding proteins of the invention bind specifically to KVLEHVVRV (SEQ ID NO. 1), in particular to the epitope in said peptide MAG-003 as herein defined and thus, do not recognize or cross-react with other related peptide antigens (similar peptides) present on normal tissue through cross-reactivity. The antigen binding proteins of the invention are thus, useful for immunotherapy.

Accordingly, the antigen binding proteins of the present invention, in particular bispecific antigen binding proteins, such as TCER™ molecules, may be used to treat cancer.

The antigen binding proteins of the present invention may be used for therapeutic purposes in humans and/or non-human mammalian animals, in particular in humans.

In one embodiment, the antigen binding proteins of the present invention can bind to tumor cells and reduce the growth of and/or kill the tumor cells presenting the peptide KVLEHVVRV (SEQ ID NO: 1)/MHC complex on their cell surface. It is understood that the antigen binding protein is administered at a concentration that promotes binding at physiological (e.g. in vivo) conditions.

Accordingly, in one embodiment, the antigen binding proteins of the invention can be used for immunotherapy directed against tumor cells of different tissues such as colon, lung, breast, prostate, ovary, pancreas, kidney etc. In another embodiment, the antigen binding proteins of the invention can bind to and reduce the growth of and/or kill tumor cells.

Therefore, the invention relates to a method of treating or preventing a proliferative disease or disorder comprising administering to a subject in need thereof a therapeutically effective amount of the antigen binding protein, the nucleic acid or vector, the host cell or the pharmaceutical composition according to the invention as defined herein above in the section "Antigen binding protein" "Nucleic acids" or "Pharmaceutical compositions".

In a particular embodiment, the invention relates to a method of treating a subject who has a proliferative disease comprising administering to said subject T cells expressing the antigen binding protein of the invention on the cell surface.

In a further embodiment, the invention refers to a method of eliciting an immune response in a subject, who has a proliferative disease, comprising administering to said subject a composition comprising T cells expressing the antigen recognizing construct of the invention on the cell surface.

In one embodiment, the immune response referred to in said method is a cytotoxic T cell response.

The invention further refers to antigen binding proteins of the invention, the nucleic acid of the invention or the vector of the invention, the host cell of the invention or the pharmaceutical composition of the invention for use in the diagnosis, prevention, and/or treatment of a proliferative disease.

The invention further refers to the use of the antigen binding proteins of the invention, the nucleic acid of the invention or the vector of the invention, the host cell of the invention or the pharmaceutical composition of the invention in the manufacture of a medicament for the diagnosis, prevention, and/or treatment of a proliferative disease.

In one embodiment, the invention refers to the use of the antigen binding protein, the nucleic acid or vector, the host cell or the pharmaceutical composition according to the invention for treating or preventing a proliferative disease or disorder in a subject.

In preferred embodiments, the T cells are autologous to the subject or allogeneic to the subject, preferably autologous. Preferably, the T cells are obtained from tumor infiltrating lymphocytes or peripheral blood mononuclear cells. Preferably, the T cells are administered in the form of a composition. In one preferred related embodiment, said composition further comprises an adjuvant, wherein the adjuvant is as defined herein above in the section pharmaceutical composition.

The term "subject" or "individual" are used interchangeably and may be, for example, a human or a non-human mammal, preferably, a human.

In the context of the invention, the term "treating" or "treatment", refers to a therapeutic use (i.e. on a subject having a given disease) and means reversing, alleviating, inhibiting the progress of one or more symptoms of such disorder or condition. Therefore, treatment does not only refer to a treatment that leads to a complete cure of the disease, but also to treatments that slow down the progression of the disease and/or prolong the survival of the subject.

By "preventing" is meant a prophylactic use (i.e. on a subject susceptible of developing a given disease).

In one embodiment, a "disease" or "disorder" is any condition that would benefit from treatment with the antigen binding protein of the invention. In one embodiment, this includes chronic and acute disorders or diseases including those pathological conditions which predisposes the subject to the disorder in question.

The term "in need of treatment" refers to a subject having already the disorder as well as those in which the disorder is to be prevented. Accordingly, in one embodiment, the subject is a patient.

"Proliferative diseases", such as cancer, involve the unregulated and/or inappropriate proliferation of cells.

In one embodiment, the proliferative disorder or disease is, for example, a tumor disease characterized by the expression of MAGEA4 and/or MAGEA8, in a cancer or tumor cell of said tumor disease.

Accordingly, a particularly preferred cancer is a MAGEA4 and/or MAGEA8 positive cancer.

In the context of the present invention, a cancer is considered to be "MAGEA4 and/or MAGEA8 "positive"", if the related peptide, such as, for example the MAG-003 peptide, is presented in >98% of all cancers according to the guidelines by the NCI. In all other indications named here a biopsy can be performed as it is standard in the treatment of these cancers and the peptide can be identified according to the XPresident® and related methods (according to WO 03/100432; WO 2005/076009; WO 2011/128448; WO 2016/107740, U.S. Pat. Nos. 7,811,828, 9,791,444, and US 2016/0187351, the contents of each are hereby incorporated by reference in their entirety). In one embodiment, the cancer is readily assayed (i.e. diagnosed) for instance by using an antigen binding protein of the invention. Methods to identify an antigen expressing cancer using an antigen binding protein are known to the skilled in the art. It is to be understood that the terms "cancer" and "carcinoma" are not used interchangeably herein since a carcinoma is a specific type of cancer emerging in the skin or in tissues that line or cover body organs. However, tissue samples used in Example 11, are derived from tumor patients and samples are allotted to the patient's disease.

In one embodiment, the cancer that is MAGEA4 and/or MAGEA8 "positive", i.e. that presents the target peptide, is selected from the group consisting of lung cancer, such as non-small cell lung cancer, small cell lung cancer, liver cancer, head and neck cancer, skin cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer, osteosarcoma, and esophageal cancer.

In one embodiment, the cancer that is MAGEA4 and/or MAGEA8 "positive", i.e. that presents the target peptide, is selected from the group consisting of lung cancer, such as non-small cell lung cancer, small cell lung cancer, liver cancer, head and neck cancer, skin cancer, gastric cancer, colorectal cancer, hepatocellular cancer, pancreatic cancer, breast cancer, melanoma, ovarian cancer, urinary bladder cancer, uterine cancer, gallbladder and bile duct cancer, and esophageal cancer.

In another embodiment the lung cancer is non-small cell lung cancer (NSCLC), preferably non-small cell lung cancer adenocarcinoma or squamous cell non-small cell lung cancer (SNSCLC); or small cell lung cancer (SCLC). In another embodiment the cancer is skin cancer, preferably melanoma. In another embodiment the cancer is head and neck cancer, preferably is head and neck squamous cell carcinoma (HN-SCC). In another embodiment the cancer is liver cancer, preferably hepatocellular cancer (HCC). In another embodiment the cancer is esophageal cancer, preferably gastroesophageal junction cancer.

Among the texts providing guidance for cancer therapy is Cancer, Principles and Practice of Oncology, 4th Edition, DeVita et al, Eds. J. B. Lippincott Co., Philadelphia, Pa. (1993). An appropriate therapeutic approach is chosen according to the particular type of cancer, and other factors such as the general condition of the patient, as is recognized in the pertinent field. The antigen binding proteins of the present invention can be used by itself or can be added to a therapy regimen using other anti-cancer agents typically used in treating a cancer patient.

Accordingly, in some embodiments, the antigen binding protein of the invention can be administered concurrently with, before, or after a variety of drugs and treatments widely employed in cancer treatment such as, for example, chemotherapeutic agents, non-chemotherapeutic, anti-neoplastic agents, and/or radiation, preferably chemotherapeutic agents.

"Diagnosis" herein refers to a Medical diagnosis and refers to determining which disease or condition explains a person's symptoms and signs.

By a "therapeutically effective amount" of the antigen binding protein or pharmaceutical composition thereof is meant a sufficient amount of the antigen binding protein to treat said proliferative disease, at a reasonable benefit/risk ratio applicable to any medical treatment. It will be understood, however, that the total daily or monthly usage of the antigen binding proteins, the nucleic acid or vector, the host cell or the pharmaceutical composition of the present invention will be decided by the attending physician within the scope of sound medical judgment. The specific therapeutically effective dose level for any particular patient will depend upon a variety of factors including the disorder or disease being treated and the severity of the disorder; activity of the specific antigen binding protein employed; the specific composition employed, the age, body weight, general health, sex and diet of the patient; the time of administration, route of administration, and rate of excretion of the specific polypeptide employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved.

In one embodiment, efficacy of the treatment with an antigen binding protein of the invention is assayed in vivo, for instance in a mouse model of cancer and by measuring, for example, changes in tumor volume between treated and control groups.

Pharmaceutical compositions, vectors, nucleic acids and cells of the invention may be provided in substantially pure form, for example, wherein at least 80%, at least 85%, at least 90%, at least 91%, at least 92%, at least 93%, at least 94%, at least 95%, at least 96%, at least 97%, at least 98%, at least 99% or 100% by weight of the antigen binding protein of the same type are present.

The antigen binding protein of the invention, the nucleic acid of the invention or the vector of the invention, the host cell of the invention or the pharmaceutical composition of the invention can be administered by any feasible method.

As herein disclosed, in some embodiments host cells, preferably lymphocytes, such as T lymphocytes or T lymphocyte progenitor cells, for example a CD4 or CD8 positive T cells, most preferably T cells, are used in the herein described medical uses or treatment methods.

Accordingly, the host cell of the present invention, preferably the T cells, may be used as active ingredients of a therapeutic composition. Thus, the invention also provides a method of killing target cells in a patient the method comprising administering to the patient an effective number of host cells as defined above, preferably T cells. In the context of this method the host cells, once administered to the subject, preferably elicit an immune response.

For purposes of the inventive methods, wherein host cells or populations of cells are administered to the subject, the host cells can be cells that are allogeneic (from another subject) or autologous to the subject. Preferably, the cells are autologous to the subject.

In case the host cells are allogeneic and thus from another subject, said other subject is healthy.

In some embodiments, T cells may be manufactured according to the methods described in US20190175650, U.S. application Ser. No. 16/271,393, and U.S. application Ser. No. 16/361,043, the contents of which are hereby incorporated by reference in their entireties.

By "healthy" it is meant that the subject is generally in good health, preferably has a competent immune system and, more preferably, is not suffering from any disease that can be readily tested for and detected.

In specific example the host cell is a T cell. Accordingly, in the context of the present invention, when a T cell as defined herein above is used as a medicament, usually, T cells are collected from a subject by apheresis. Then the T cells are genetically engineered to express the antigen binding protein of the present invention on their cell surface, the genetically engineered T cells are then expanded and then re-infused into the subject. In this example, the antigen binding protein is preferably a TCR.

In another approach, the host cell may be a stem cell, such as a mesenchymal stem cell and is engineered to express the antigen binding protein of the invention. In this example, the antigen binding protein is a soluble protein such as an antibody, a scTCR or a soluble antigen binding protein as herein defined, more preferably a bispecific, soluble antigen binding protein such as a TCER™ as herein described.

Accordingly, the host cell has been transformed, transduced or transfected with a nucleic acid and/or a vector according to the invention, as described herein above in the section 'nucleic acids, vectors and recombinant host cells'.

When the host cell is transformed, transduced or transfected to express the antigen binding protein of the invention, preferably the cell comprises an expression vector capable of expressing the antigen binding protein. Once the host cell expresses the antigen binding protein of the invention, the host cell may then be referred to as activated host cell.

Protocols for this so-called adoptive transfer of T cells are well known in the art. Reviews can be found in: Gattioni et al. and Morgan et al. (Gattinoni, L. et al., Nat. Rev. Immunol. 6 (2006): 383-393; Morgan, R. A. et al., Science 314 (2006): 126-129).

A number of methods may be used for generating T cells in vitro. For example, autologous tumor-infiltrating lymphocytes can be used in the generation of CTL. Plebanski et al. (Plebanski, M. et al., Eur. J Immunol 25 (1995): 1783-1787) made use of autologous peripheral blood lymphocytes (PLBs) in the preparation of T cells. Also, B cells can be used in the production of autologous T cells.

Allogeneic cells may also be used in the preparation of T cells and a method is described in detail in U.S. Pat. No. 6,805,861, incorporated herein by reference In an aspect, the TCR-elicited immune response or T cell response may refer to the proliferation and activation of effector functions induced by the binding to the MAG-003/MHC complex, in vitro or in vivo. For MHC class I restricted cytotoxic T cells, for example, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, for example, granzymes or perforins induced by peptide, or degranulation.

As described herein above, host cells, such as T cells, expressing the antigen binding protein of the invention specifically binding to the MAG-003/MHC complex are useful in therapy. Thus, a further aspect of the invention provides activated host cells obtainable by the foregoing methods of the invention.

Activated host cells, which are produced by the above method, may selectively recognize a target cell.

A "target cell" herein refers to a MAGE-A/MHC presenting cell as defined herein above in the section "antigen binding proteins".

In one embodiment, a target cell is preferably a cancer cell, wherein the cancer is as defined herein above.

In vivo, the target cells for the CD8-positive T cells according to the present invention can be cells of the tumor (which sometimes express MHC class II) and/or stromal cells surrounding the tumor (tumor cells) (which sometimes also express MHC class II; (Dengjel, J. et al., Clin Cancer Res 12 (2006): 4163-4170).

Kits

Finally, the invention also provides kits comprising at least one antigen binding protein of the invention.

In one embodiment, the kit comprises
a) at least one antigen binding protein of the invention as defined herein above in the section "antigen binding proteins",
b) optionally packaging material, and
c) optionally a label or packaging insert contained within said packaging material indicating that said antigen binding protein is effective for treating cancer or for use for the treatment of cancer.

In a related embodiment, the at least one antigen binding proteins of the invention is contained in a single and/or multi-chambered pre-filled syringe/s (e.g., liquid syringes and lyosyringes).

In one embodiment, the invention encompasses kits for producing a single-dose administration unit.

Accordingly, in one embodiment, the at least one antigen binding proteins of the invention as mentioned in a) of the kit of the invention is a dried antigen binding protein of the invention contained in a first container. The kit then further contains a second container having an aqueous formulation.

Accordingly, in one embodiment, the kit comprises
a) a first container comprising at least one dried antigen binding protein of the invention as defined herein above in the section "Antigen binding proteins",
b) a second container comprising an aqueous formulation;
c) optionally packaging material, and
d) optionally a label or packaging insert contained within said packaging material indicating that said antigen binding protein is effective for treating cancer or for use in the treatment of cancer.

The aqueous formulation is typically an aqueous solution comprising pharmaceutically-acceptable carriers as defined herein above in the section "pharmaceutical compositions".

In a related embodiment, the "first container" and the "second" container refer to the chambers of a multi-chambered pre-filled syringes (e.g., lyo syringes).

The cancer is as defined herein above in the context of the invention.

Throughout the present application, the term "and/or" is a grammatical conjunction that is to be interpreted as encompassing that one or more of the cases it connects may occur. For example, the wording "such native sequence proteins can be prepared using standard recombinant and/or synthetic methods" indicates that native sequence proteins can be prepared using standard recombinant and synthetic methods or native sequence proteins can be prepared using standard recombinant methods or native sequence proteins can be prepared using synthetic methods.

Furthermore, throughout the present application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of").

Furthermore the indefinite article "a" or "an" does not exclude a plurality. The mere fact that certain measures are recited in mutually different dependent claims does not indicate that a combination of these measures cannot be used to advantage.

The invention will now be described in more details with reference to the following figures and examples. All literature and patent documents cited herein are hereby incorporated by reference in their entirety. While the invention has been illustrated and described in detail in the foregoing description, the examples are to be considered illustrative or exemplary and not restrictive.

DESCRIPTION OF THE SEQUENCES

| SEQ ID NO: | Name | Amino Acid Sequence |
|---|---|---|
| 1 | MAG-003 | KVLEHVVRV |
| 2 | R7P1D5 TCR alpha chain - full length | MKTFAGFSFLFLWLQLDCMSRGEDVEQSLFLSV REGDSSVINCTYTDSSSTYLYWYKQEPGAGLQL LTYIFSNMDMKQDQRLTVLLNKKDKHLSLRIAD TQTGDSAIYFCAEYSSASKIIFGSGTRLSIRPNIQN PDPAVYQLRDSKSSDKSVCLFTDFDSQTNVSQS KDSDVYITDKTVLDMRSMDFKSNSAVAWSNKS DFACANAFNNSIIPEDTFFPSPESSCDVKLVEKSF ETDTNLNFQNLSVIGFRILLLKVAGFNLLMTLRL WSS |
| 3 | R7P1D5 TCR alpha leader peptide | MKTFAGFSFLFLWLQLDCMSR |
| 4 | R7P1D5 alpha variable domain | GEDVEQSLFLSVREGDSSVINCTYTDSSSTYLYW YKQEPGAGLQLLTYIFSNMDMKQDQRLTVLLN KKDKHLSLRIADTQTGDSAIYFCAEYSSASKIIFG SGTRLSIRP |
| 5 | R7P1D5 CDRa1 | DSSSTY |
| 6 | R7P1D5 CDRa2 | IFSNMDM |
| 7 | R7P1D5 CDRa3 | CAEYSSASKIIF |
| 8 | R7P1D5 - alpha constant domain | NIQNPDPAVYQLRDSKSSDKSVCLFTDFDSQTN VSQSKDSDVYITDKTVLDMRSMDFKSNSAVAW SNKSDFACANAFNNSIIPEDTFFPSPESSCDVKLV EKSFETDTNLNFQNLSVIGFRILLLKVAGFNLLM TLRLWSS |
| 9 | R7P1D5 TCR beta chain - full length | MGSWTLCCVSLCILVAKHTDAGVIQSPRHEVTE MGQEVTLRCKPISGHDYLFWYRQTMMRGLELLI YFNNNVPIDDSGMPEDRESAKMPNASFSTLKIQP SEPRDSAVYFCASRANTGELFFGEGSRLTVLEDL KNVFPPEVAVFEPSEAEISHTQKATLVCLATGFY PDHVELSWWVNGKEVHSGVSTDPQPLKEQPAL NDSRYCLSSRLRVSATFWQNPRNHFRCQVQFYG LSENDEWTQDRAKPVTQIVSAEAWGRADCGFT SESYQQGVLSATILYEILLGKATLYAVLVSALVL MAMVKRKDSRG |
| 10 | R7P1D5 TCR beta leader peptide | MGSWTLCCVSLCILVAKHT |
| 11 | R7P1D5 beta variable domain | DAGVIQSPRHEVTEMGQEVTLRCKPISGHDYLF WYRQTMMRGLELLIYFNNNVPIDDSGMPEDRFS AKMPNASFSTLKIQPSEPRDSAVYFCASRANTGE LFFGEGSRLTVL |
| 12 | R7P1D5 CDRb1 | SGHDY |
| 13 | R7P1D5 CDRb2 | FNNNVP |
| 14 | R7P1D5 CDRb3 | CASRANTGELFF |
| 15 | R7P1D5 beta constant domain | EDLKNVFPPEVAVFEPSEAEISHTQKATLVCLAT GFYPDHVELSWWVNGKEVHSGVSTDPQPLKEQ PALNDSRYCLSSRLRVSATFWQNPRNHFRCQVQ FYGLSENDEWTQDRAKPVTQIVSAEAWGRADC GFTSESYQQGVLSATILYEILLGKATLYAVLVSA LVLMAMVKRKDSRG |
| 16 | Aga2p fusion protein with scTv R7P1D5 and tags | MQLLRCFSIFSVIASVLAQELTTICEQIPSPTLEST PYSLSTTTILANGKAMQGVFEYYKSVTFVSNCG SHPSTTSKGSPINTQYVFGGGGSDYKDDDDKGG GASGEDVEQSLFLSVREGDSSVINCTYTDSSSTY LYWYKQEPGAGLQLLTYIFSNMDMKQDQRLTV LLNKKDKHLSLRIADTQTGDSAIYFCAEYSSASK IIFGSGTRLSIRPGGGGSGGGGSGGGGSGGGGSG GGGSDAGVIQSPRHEVTEMGQEVTLRCKPISGH DYLFWYRQTMMRGLELLIYFNNNVPIDDSGMPE DRFSAKMPNASFSTLKIQPSEPRDSAVYFCASRA NTGELFFGEGSRLTVLAAAGGSGGEQKLISEEDL |

| SEQ ID NO: | Name | Amino Acid Sequence |
|---|---|---|
| 17 | Leader sequence and Aga2p | MQLLRCFSIFSVIASVLAQELTTICEQIPSPTLEST PYSLSTTTILANGKAMQGVFEYYKSVTFVSNCG SHPSTTSKGSPINTQYVF |
| 18 | FLAG tag plus linkers | GGGGSDYKDDDDKGGGAS |
| 19 | Single chain variable domains of R7P1D5 with linker | GEDVEQSLFLSVREGDSSVINCTYTDSSSTYLYW YKQEPGAGLQLLTYIFSNMDMKQDQRLTVLLN KKDKHLSLRIADTQTGDSAIYFCAEYSSASKIIFG SGTRLSIRPGGGGSGGGGSGGGGSGGGGSGGGG SDAGVIQSPRHEVTEMGQEVTLRCKPISGHDYLF WYRQTMMRGLELLIYFNNNVPIDDSGMPEDRFS AKMPNASFSTLKIQPSEPRDSAVYFCASRANTGE LFFGEGSRLTVL |
| 20 | Linker and Myc tag | AAAGGSGGEQKLISEEDL |
| 21 | CDRa2 mutant 1 (aF57Y) | IYSNMDM |
| 22 | scTv R7P1D5S (stabilized) | GEDVEQSLFLSVREGDSAVINCTYTDSSSTYLY WYKQEPGAGLQLLTYIYSNMDMKQDQRLTVLL NKKDKHLSLRIADTQTGDSAIYFCAEYSSASKIIF GSGTRLSIRPGGGGSGGGGSGGGGSGGGGSGGG GSDAGVIQSPRHEVTEMGQEVTLRCKPISGHDY LFWYRQTMMRGLELLIYFNNNVPIDDSGMPEDR FSAKMPNASFSTLKIQPSEPRDSAVYFCASRANT GELFFGEGSRLTVL |
| 23 | RABGAP1L-001 | FLLETVVRV |
| 24 | AXIN1-001 | ILDEHVQRV |
| 25 | ANO5-001 | IVMEHVVFL |
| 26 | TPX2-001 | KILEDVVGV |
| 27 | SYNE3-001 | KLLDLQVRV |
| 28 | MIA3-001 | KVLDKVFRA |
| 29 | HERC4-001 | KVLEILHRV |
| 30 | PSME2-001 | KVLERVNAV |
| 31 | HEATR5A-001 | KVLETLVTV |
| 32 | CNOT1-003 | KVLGIVVGV |
| 33 | TEP1-003 | AVEEHVVSV |
| 34 | PITPNM3-001 | SVLEKVTRA |
| 35 | CDRa3 mutant 1 | CAEMTSESKIIF |
| 36 | CDRa3 mutant 2 | CAEFTSESKIIF |
| 37 | CDRa3 mutant 3 | CAEFNSESKIIF |
| 38 | CDRa3 mutant 4 | CAEFSSASKIIF |
| 39 | CDRa3 mutant 5 | CAEATSESKIIF |
| 40 | R7P1D5_aMTSE (R7P1D5 - alpha chain variant 1) | MKTFAGFSFLFLWLQLDCMSRGEDVEQSLFLSV REGDSSVINCTYTDSSSTYLYWKQEPGAGLQL LTYIFSNMDMKQDQRLTVLLNKKDKHLSLRIAD TQTGDSAIYFCAEMTSESKIIFGSGTRLSIRPNIQN PDPAVYQLRDSKSSDKSVCLFTDFDSQTNVSQS KDSDVYITDKTVLDMRSMDFKSNSAVAWSNKS DFACANAFNNSIIPEDTFFPSPESSCDVKLVEKSF ETDTNLNFQNLSVIGFRILLLKVAGFNLLMTRL WSS |

-continued

| SEQ ID NO: | Name | Amino Acid Sequence |
|---|---|---|
| 41 | R7P1D5_aFTSE (R7P1D5 - alpha chain variant 2) | MKTFAGFSLFLFLWLQLDCMSRGEDVEQSLFLSV REGDSSVINCTYTDSSSTYLYWYKQEPGAGLQL LTYIFSNMDMKQDQRLTVLLNKKDKHLSLRIAD TQTGDSAIYFCAEFTSESKIIFGSGTRLSIRPNIQN PDPAVYQLRDSKSSDKSVCLFTDFDSQTNVSQS KDSDVYITDKTVLDMRSMDFKSNSAVAWSNKS DFACANAFNNSIIPEDTFFPSPESSCDVKLVEKSF ETDTNLNFQNLSVIGFRILLLKVAGFNLLMTLRL WSS |
| 42 | R7P1D5_aFNSE ((R7P1D5 - alpha chain variant 3) | MKTFAGFSLFLFLWLQLDCMSRGEDVEQSLFLSV REGDSSVINCTYTDSSSTYLYWYKQEPGAGLQL LTYIFSNMDMKQDQRLTVLLNKKDKHLSLRIAD TQTGDSAIYFCAEFNSESKIIFGSGTRLSIRPNIQN PDPAVYQLRDSKSSDKSVCLFTDFDSQTNVSQS KDSDVYITDKTVLDMRSMDFKSNSAVAWSNKS DFACANAFNNSIIPEDTFFPSPESSCDVKLVEKSF ETDTNLNFQNLSVIGFRILLLKVAGFNLLMTLRL WSS |
| 43 | R7P1D5_aFSSA (R7P1D5 - alpha chain variant 4) | MKTFAGFSLFLFLWLQLDCMSRGEDVEQSLFLSV REGDSSVINCTYTDSSSTYLYWYKQEPGAGLQL LTYIFSNMDMKQDQRLTVLLNKKDKHLSLRIAD TQTGDSAIYFCAEFSSASKIIFGSGTRLSIRPNIQN PDPAVYQLRDSKSSDKSVCLFTDFDSQTNVSQS KDSDVYITDKTVLDMRSMDFKSNSAVAWSNKS DFACANAFNNSIIPEDTFFPSPESSCDVKLVEKSF ETDTNLNFQNLSVIGFRILLLKVAGFNLLMTLRL WSS |
| 44 | R7P1D5_aATSE (R7P1D5 - alpha chain variant 5) | MKTFAGFSLFLFLWLQLDCMSRGEDVEQSLFLSV REGDSSVINCTYTDSSSTYLYWYKQEPGAGLQL LTYIFSNMDMKQDQRLTVLLNKKDKHLSLRIAD TQTGDSAIYFCAEATSESKIIFGSGTRLSIRPNIQN PDPAVYQLRDSKSSDKSVCLFTDFDSQTNVSQS KDSDVYITDKTVLDMRSMDFKSNSAVAWSNKS DFACANAFNNSIIPEDTFFPSPESSCDVKLVEKSF ETDTNLNFQNLSVIGFRILLLKVAGFNLLMTLRL WSS |
| 45 | NYESO1-001 | SLLMWITQV |
| 46 | MAG-003_A1 | AVLEHVVRV |
| 47 | MAG-003_A2 | KALEHVVRV |
| 48 | MAG-003_A3 | KVAEHVVRV |
| 49 | MAG-003_A4 | KVLAHVVRV |
| 50 | MAG-003_A5 | KVLEAVVRV |
| 51 | MAG-003_A6 | KVLEHAVRV |
| 52 | MAG-003_A7 | KVLEHVARV |
| 53 | MAG-003_A8 | KVLEHVVAV |
| 54 | MAG-003_A9 | KVLEHVVRA |
| 55 | CDRa1 mutant 1 | ESSSTY |
| 56 | CDRa2 mutant 2 | IYSSQDQ |
| 57 | CDRa2 mutant 3 | IYSSQDV |
| 58 | 75-NU(17)-R7P1D5#1 (HC) | EVQLVQSGAEVKKPGASVKVSCKASGYSFTGYT MNWVRQAPGQGLEWMGLINPYKGVSTYAQKF QDRVTLTVDKSTSTAYMELSSLRSEDTAVYYCA RSGYYGDSDWYFDVWGQGTLVTVSSASTKGPS VFPLAPSSKSTSGGTAALGCLVKDYFPEPVTVS WNSGALTSGVHTFPAVLQSSGLYSLSSVVTVPSS SLGTQTYICNVNHKPSNTKVDKKVEPKSCDKTH TSPPSPAPPVAGGEDVEQSLFLSVREGDSAVINC TYTDSSSTYLYWYKQEPGAGLQLLTYIYSSQDQ KQDQRLTVLLNKKDKHLSLRIADTQTGDSAIYF |

-continued

| SEQ ID NO: | Name | Amino Acid Sequence |
|---|---|---|
| | | CAEMTSESKIIFGSGTRLSIRPGGGSGGGGSGG<br>GGSGGGGSGGGGSDAGVIQSPRHEVTEMGQEV<br>TLRCKPIPGHDYLFWYRQTMMRGLELLIYFNNN<br>VPIDDSGMPEDRFSAKMPNASFSTLKIQPSEPRD<br>SAVYFCASRANTGELFFGEGSRLTVL |
| 59 | CDRa2 mutant 4 | IYSSQDS |
| 60 | 75-NU(17)-R7P1D5#20 (HC) | EVQLVQSGAEVKKPGASVKVSCKASGYSFTGYT<br>MNWVRQAPGQGLEWMGLINPYKGVSTYAQKF<br>QDRVTLTVDKSTSTAYMELSSLRSEDTAVYYCA<br>RSGYYGDSDWYFDVWGQGTLVTVSSASTKGPS<br>VFPLAPSSKSTSGGTAALGCLVKDYFPEPVTVS<br>WNSGALTSGVHTFPAVLQSSGLYSLSSVVTVPSS<br>SLGTQTYICNVNHKPSNTKVDKKVEPKSCDKTH<br>TSPPSPAPPVAGGEDVEQSLFLSVREGDSAVINC<br>TYTDSSSTYLYWYKQEPGAGLQLLTYIYSSQDS<br>KQDQRLTVLLNKKDKHLSLRIADTQTGDSAIYF<br>CAEMTSESKIIFGSGTRLSIRPGGGGSGGGGSGG<br>GGSGGGGSGGGGSDAGVIQSPRHEVTEMGQEV<br>TLRCKPIPGHDYLFWYRQTMMRGLELLIYFCYG<br>TPCDDSGMPEDRFSAKMPNASFSTLKIQPSEPRD<br>SAVYFCASRADTGELFFGEGSRLTVL |
| 61 | 75-NU(17)-R7P1D5#21 (HC) | EVQLVQSGAEVKKPGASVKVSCKASGYSFTGYT<br>MNWVRQAPGQGLEWMGLINPYKGVSTYAQKF<br>QDRVTLTVDKSTSTAYMELSSLRSEDTAVYYCA<br>RSGYYGDSDWYFDVWGQGTLVTVSSASTKGPS<br>VFPLAPSSKSTSGGTAALGCLVKDYFPEPVTVS<br>WNSGALTSGVHTFPAVLQSSGLYSLSSVVTVPSS<br>SLGTQTYICNVNHKPSNTKVDKKVEPKSCDKTH<br>TSPPSPAPPVAGGEDVEQSLFLSVREGDSAVINC<br>TYTDSSSTYLYWYKQEPGAGLQLLTYIYSSQDS<br>KQDQRLTVLLNKKDKHLSLRIADTQTGDSAIYF<br>CAEMTSESKIIFGSGTRLSIRPGGGGSGGGGSGG<br>GGSGGGGSGGGGSDAGVIQSPRHEVTEMGQEV<br>TLRCKPIPGHDYLFWYRQTMMRGLELLFYFCYG<br>TPCDDSGMPEDRFSAKMPNASFSTLKIQPSEPRD<br>SAVYFCASRADTGELFFGEGSRLTVL |
| 62 | CDRb1 mutant 1 | PGHDY |
| 63 | CDRb2 mutant 1 | FCYGHP |
| 64 | CDRb2 mutant 2 | FCYGVP |
| 65 | CDRb2 mutant 3 | FCYGTP |
| 66 | CDRb2 mutant 4 | FCYGAP |
| 67 | 75-NU(17)-R7P1D5#29 (HC) | EVQLVQSGAEVKKPGASVKVSCKASGYSFTGYT<br>MNWVRQAPGQGLEWMGLINPYKGVSTYAQKF<br>QDRVTLTVDKSTSTAYMELSSLRSEDTAVYYCA<br>RSGYYGDSDWYFDVWGQGTLVTVSSASTKGPS<br>VFPLAPSSKSTSGGTAALGCLVKDYFPEPVTVS<br>WNSGALTSGVHTFPAVLQSSGLYSLSSVVTVPSS<br>SLGTQTYICNVNHKPSNTKVDKKVEPKSCDKTH<br>TSPPSPAPPVAGGEDVEQSLFLSVREGDSSVINCT<br>YTDSSSTYLYWYKQEPGAGPQLLTYIYSSQDQK<br>QDQRLTVLLNKKDKHLSLRIADTQTGDSAIYFC<br>AEMTSESKIIFGSGTRLSIRPGGGSGGGGSGGG<br>GSGGGGSGGGGSDAGVIQSPRHEVTEMGQEVTL<br>RCKPIPGHDYLFWYRQTPGRGLELLIYFNNNVPI<br>DDSGMPEDRFSAKMPNASFSTLKIQPSEPRDSAV<br>YFCASRANTGELFFGEGSRLTVL |
| 68 | 75-NU(17)-R7P1D5#30 (HC) | EVQLVQSGAEVKKPGASVKVSCKASGYSFTGYT<br>MNWVRQAPGQGLEWMGLINPYKGVSTYAQKF<br>QDRVTLTVDKSTSTAYMELSSLRSEDTAVYYCA<br>RSGYYGDSDWYFDVWGQGTLVTVSSASTKGPS<br>VFPLAPSSKSTSGGTAALGCLVKDYFPEPVTVS<br>WNSGALTSGVHTFPAVLQSSGLYSLSSVVTVPSS<br>SLGTQTYICNVNHKPSNTKVDKKVEPKSCDKTH<br>TSPPSPAPPVAGGEDVEQSLFLSVREGDSAVINC<br>TYTDSSSTYLYWYKQEPGAGPQLLTYIYSSQDQ<br>KQDQRLTVLLNKKDKHLSLRIADTQTGDSAIYF |

| SEQ ID NO: | Name | Amino Acid Sequence |
|---|---|---|
| | | CAEMTSESKIIFGSGTRLSIRPGGGSGGGGSGG GGSGGGGSGGGGSDAGVIQSPRHEVTEMGQEV TLRCKPIPGHDYLFWYRQTPGRGLELLIYFNNNV PIDDSGMPEDRFSAKMPNASFSTLKIQPSEPRDS AVYFCASRANTGELFFGEGSRLTVL |
| 69 | 75-NU(17)-R7P1D5#31 (HC) | EVQLVQSGAEVKKPGASVKVSCKASGYSFTGYT MNWVRQAPGQGLEWMGLINPYKGVSTYAQKF QDRVTLTVDKSTSTAYMELSSLRSEDTAVYYCA RSGYYGDSDWYFDVWGQGTLVTVSSASTKGPS VFPLAPSSKSTSGGTAALGCLVKDYFPEPVTVS WNSGALTSGVHTFPAVLQSSGLYSLSSVVTVPSS SLGTQTYICNVNHKPSNTKVDKKVEPKSCDKTH TSPPSPAPPVAGGEDVEQSLFLSVREGDSSVINCT YTDSSSTYLYWYKQEPGKGPQLLTYIYSSQDQK QDQRLTVLLNKKDKHLSRIADTQTGDSAIYFC AEMTSESKIIFGSGTRLSIRPGGGSGGGGSGGG GSGGGGSGGGGSDAGVIQSPRHEVTEMGQEVTL RCKPIPGHDYLFWYRQTPGRGLELLIYFNNNVPI DDSGMPEDRFSAKMPNASFSTLKIQPSEPRDSAV YFCASRANTGELFFGEGSRLTVL |
| 70 | CDRb2 mutant 5 | FCYGMP |
| 71 | CDRb3 mutant 1 (bN109D) | CASRADTGELFF |
| 72 | CDRa1 consensus-ACT + TCER | $X_1$SSSTY |
| 73 | CDRa2 consensus-ACT + TCER | I$X_1$S$X_2$$X_3$D$X_4$ |
| 74 | CDRa2 consensus p1-TCER | IYSSQDX1 |
| 75 | 75-NU(17)-R7P1D5#32 (HC) | EVQLVQSGAEVKKPGASVKVSCKASGYSFTGYT MNWVRQAPGQGLEWMGLINPYKGVSTYAQKF QDRVTLTVDKSTSTAYMELSSLRSEDTAVYYCA RSGYYGDSDWYFDVWGQGTLVTVSSASTKGPS VFPLAPSSKSTSGGTAALGCLVKDYFPEPVTVS WNSGALTSGVHTFPAVLQSSGLYSLSSVVTVPSS SLGTQTYICNVNHKPSNTKVDKKVEPKSCDKTH TSPPSPAPPVAGGEDVEQSLFLSVREGDSVVINC TYTDSSSTYLYWYKQEPGAGPQLLTYIYSSQDQ KQDQRLTVLLNKKDKHLSRIADTQTGDSAIYF CAEMTSESKIIFGSGTRLSIRPGGGSGGGGSGG GGSGGGGSGGGGSDAGVIQSPRHEVTEMGQEV TLRCKPIPGHDYLFWYRQTPGRGLELLIYFNNNV PIDDSGMPEDRFSAKMPNASFSTLKIQPSEPRDS AVYFCASRANTGELFFGEGSRLTVL |
| 76 | 75-NU(17)-R7P1D5#2 (HC) | EVQLVQSGAEVKKPGASVKVSCKASGYSFTGYT MNWVRQAPGQGLEWMGLINPYKGVSTYAQKF QDRVTLTVDKSTSTAYMELSSLRSEDTAVYYCA RSGYYGDSDWYFDVWGQGTLVTVSSASTKGPS VFPLAPSSKSTSGGTAALGCLVKDYFPEPVTVS WNSGALTSGVHTFPAVLQSSGLYSLSSVVTVPSS SLGTQTYICNVNHKPSNTKVDKKVEPKSCDKTH TSPPSPAPPVAGGEDVEQSLFLSVREGDSAVINC TYTDSSSTYLYWYKQEPGAGLQLLTYIYSSQDS KQDQRLTVLLNKKDKHLSRIADTQTGDSAIYF CAEMTSESKIIFGSGTRLSIRPGGGSGGGGSGG GGSGGGGSGGGGSDAGVIQSPRHEVTEMGQEV TLRCKPIPGHDYLFWYRQTMMRGLELLIYFNNN VPIDDSGMPEDRFSAKMPNASFSTLKIQPSEPRD SAVYFCASRANTGELFFGEGSRLTVL |
| 77 | CDRa3 consensus ACT + TCER | CAE$X_1$$X_2$S$X_3$SKIIF |
| 78 | CDRb1 consensus-ACT + TCER | $X_1$GHDY |
| 79 | CDRb2 consensus-ACT + TCER | F$X_1$$X_2$$X_3$$X_4$P |

-continued

| SEQ ID NO: | Name | Amino Acid Sequence |
|---|---|---|
| 80 | 75-NU(17)-R7P1D5x (common LC) | DIQMTQSPSSLSASVGDRVTITCRASQDIRNYLN WYQQKPGKAPKLLIYYTSRLHSGVPSRFSGSGS GTDYTLTISSLQPEDIATYFCQQGQTLPWTFGQG TKVEIKRTVAAPSVFIFPPSDEQLKSGTASVVCLL NNFYPREAKVQWKVDNALQSGNSQESVTEQDS KDSTYSLSSTLTLSKADYEKHKVYACEVTHQGL SSPVTKSFNRGEC |
| 81 | CDRb2 consensus p3-TCER | FCYGX$_1$P |
| 82 | CDRb3 consensus ACT + TCER | CASRAX$_1$TGELFF |
| 83 | FR1-a | EDVEQSLFLSVREGDSSVINCTYT |
| 84 | FR2-a | LYWYKQEPGAGLQLLTY |
| 85 | FR3-a | KQDQRLTVLLNKKDKHLSLRIADTQTGDSAIYF |
| 86 | FR4-a | GSGTRLSIRP |
| 87 | FR1-b | DAGVIQSPRHEVTEMGQEVTLRCKPI |
| 88 | FR2-b | LFWYRQTMMRGLELLIY |
| 89 | FR3-b | IDDSGMPEDRFSAKMPNASFSTLKIQPSEPRDSA VYF |
| 90 | FR4-b | GEGSRLTVL |
| 91 | FR1-a (19V) | EDVEQSLFLSVREGDSVVINCTYT |
| 92 | FR2-a (48K) | LYWYKQEPGKGLQLLTY |
| 93 | FR2-b (54F) | LFWYRQTMMRGLELLFY |
| 94 | FR3-b (66C) | CDDSGMPEDRFSAKMPNASFSTLKIQPSEPRDSA VYF |
| 95 | MUM-001 | KLVEYIVKA |
| 96 | preferred linker | GGGSGGGG |
| 97 | MAGEA4 as accessible under Uniprot accession number P43358 | MSSEQKSQHCKPEEGVEAQEEALGLVGAQAPTT EEQEAAVSSSSPLVPGTLEEVPAAESA GPPQSPQGASALPTTISFTCWRQPNEGSSSQEEE GPSTSPDAESLFREALSNKVDELAHF LLRKYRAKELVTKAEMLERVIKNYKRCFPVIFG KASESLKMIFGIDVKEVDPASNTYTLV TCLGLSYDGLLGNNQIFPKTGLLIIVLGTIAMEG DSASEEEIWEELGVMGVYDGREHTVY GEPRKLLTQDWVQENYLEYRQVPGSNPARYEFL WGPRALAETSYVKVLEHVVRVNARVRI AYPSLREAALLEEEEGV |
| 98 | MAGEA8 as accessible under Uniprot accession number P43361 | MLLGQKSQRYKAEEGLQAQGEAPGLMDVQIPT AEEQKAASSSSTLIMGTLEEVTDSGSPS PPQSPEGASSSLTVTDSTLWSQSDEGSSSNEEEGP STSPDPAHLESLFREALDEKVAELV RFLLRKYQIKEPVTKAEMLESVIKNYKNHFPDIF SKASECMQVIFGIDVKEVDPAGHSYI LVTCLGLSYDGLLGDDQSTPKTGLLIIVLGMILM EGSRAPEEAIWEALSVMGLYDGREHS VYWKLRKLLTQEWVQENYLEYRQAPGSDPVRY EFLWGPRALAETSYVKVLEHVVRVNARV RISYPSLHEEALGEEKGV |
| 99 | Linker | TVAAP |
| 100 | Linker | GGGS |
| 101 | Linker | GGGGS |
| 102 | Linker | TVLRT |

| SEQ ID NO: | Name | Amino Acid Sequence |
|---|---|---|
| 103 | Linker | TVSSAS |
| 104 | Linker | GGGGSGGGGS |
| 105 | Linker | GGGGSAAA |
| 106 | Linker | GGGGSGGGGSGGGGS |
| 107 | Linker | GGGGSGGGGSGGGGSGGGGSGGGGSGS |
| 108 | Linker | GGGGSGGGGSGGGGSGGGGSGGGGS |
| 109 | Linker | TVLSSAS |
| 110 | Linker | GGGGSGGGGSGGGGSGGGGS |
| 111 | native Fc amino acid sequence of IGHG1*01 | EPKSCDKTHTCPPCPAPELLGGPSVFLFPPKPKDT LMISRTPEVTCVVVDVSHEDPEVKFNWYVDGVE EVHNAKTKPREEQYNSTYRVVSVLTVLHQDWL NGKEYKCKVSNKALPAPIEKTISKAKGQPREPQ VYTLPPSRDELTKNQVSLTCLVKGFYPSDIAVE WESNGQPENNYKTTPPVLDSDGSFFLYSKLTVD KSRWQQGNVFSCSVMHEALHNHYTQKSLSLSP GK |
| 112 | Fc with knob mutation [S354C and T366W] | EPKSSDKTHTCPPCPAPPVAGPSVFLFPPKPKDTL MISRTPEVTCVVVDVSHEDPEVKFNWYVDGVE VHNAKTKPREEQYQSTYRVVSVLTVLHQDWLN GKEYKCKVSNKALPASIEKTISKAKGQPREPQV YTLPPCRDELTKNQVSLWCLVKGFYPSDIAVEW ESNGQPENNYKTTPPVLDSDGSFFLYSKLTVDKS RWQQGNVFSCSVMHEALHNHYTQKSLSLSP |
| 113 | Fc with hole mutation [(Y349C, T366S, L368A and Y407V + | EPKSSDKTHTCPPCPAPPVAGPSVFLFPPKPKDTL MISRTPEVTCVVVDVSHEDPEVKFNWYVDGVE VHNAKTKPREEQYQSTYRVVSVLTVLHQDWLN GKEYKCKVSNKALPASIEKTISKAKGQPREPQVC TLPPSRDELTKNQVSLSCAVKGFYPSDIAVEWES NGQPENNYKTTPPVLDSDGSFFLVSKLTVDKSR WQQGNVFSCSVMHEALHNHYTQKSLSLSP |
| 114 | IgG1- hinge | EPKSCDKTHTCPPCPAPELLG |
| 115 | IgG2-hinge | ERKCCVECPPCPAPPVAGP |
| 116 | IgG3-hinge | ELKTPLGDTT HTCPRCPEPK SCDTPPPCPR CPEPKSCDTP PPCPRCPAPE LLG |
| 117 | IgG4-hinge | ESKYGPPCPSCPAPEFLG |
| 118 | R7P1D5_aMTSE (R7P1D5 - alpha variable domain var. 1) | EDVEQSLFLSVREGDSSVINCTYTDSSSTYLYWY KQEPGAGLQLLTYIFSNMDMKQDQRLTVLLNK KDKHLSLRIADTQTGDSAIYFCAEMTSESKIIFGS GTRLSIRP |
| 119 | R7P1D5_aFTSE (R7P1D5 - alpha variable domain var. 2) | EDVEQSLFLSVREGDSSVINCTYTDSSSTYLYWY KQEPGAGLQLLTYIFSNMDMKQDQRLTVLLNK KDKHLSLRIADTQTGDSAIYFCAEFTSESKIIFGS GTRLSIRP |
| 120 | R7P1D5_aFNSE ((R7P1D5 - alpha variable domain var. 3) | EDVEQSLFLSVREGDSSVINCTYTDSSSTYLYWY KQEPGAGLQLLTYIFSNMDMKQDQRLTVLLNK KDKHLSLRIADTQTGDSAIYFCAEFNSESKIIFGS GTRLSIRP |
| 121 | R7P1D5_aFSSA (R7P1D5 - alpha variable domain var. 4) | EDVEQSLFLSVREGDSSVINCTYTDSSSTYLYWY KQEPGAGLQLLTYIFSNMDMKQDQRLTVLLNK KDKHLSLRIADTQTGDSAIYFCAEFSSASKIIFGS GTRLSIRP |
| 122 | R7P1D5_aATSE (R7P1D5 - alpha variable domain var. 5) | EDVEQSLFLSVREGDSSVINCTYTDSSSTYLYWY KQEPGAGLQLLTYIFSNMDMKQDQRLTVLLNK KDKHLSLRIADTQTGDSAIYFCAEATSESKIIFGS GTRLSIRP |

| SEQ ID NO: | Name | Amino Acid Sequence |
|---|---|---|
| 123 | 75-NU (V9) light chain for CR7P1D5S-common LC | DIQMTQSPSSLSASVGDRVTITCRASQDIRNYLN WYQQKPGKAPKLLIYYTSRLESGVPSRFSGSGSG TDYTLTISSLQPEDFATYYCQQGNTLPWTFGQG TKVEIKRTVAAPSVFIFPPSDEQLKSGTASVVCLL NNFYPREAKVQWKVDNALQSGNSQESVTEQDS KDSTYSLSNTLTLSKADYEKHKVYACEVTHQGL SSPVTKSFNRGEC |
| 124 | 75-NU(V9)-CR7P1D5S (HC) | EVQLVESGGGLVQPGGSLRLSCAASGYSFTGYT MNWVRQAPGKGLEWVALINPYKGVSTYNQKF KDRFTISVDKSKNTAYLQMNSLRAEDTAVYYC ARSGYYGDSDWYFDVWGQGTLVTVSSASTKGP SVFPLAPSSKSTSGGTAALGCLVKDYFPEPVTVS WNSGALTSGVHTFPAVLQSSGLYSLSSVVTVPSS SLGTQTYICNVNHKPSNTKVDKKVEPKSCDKTH TSPPSPAPPVAGEDVEQSLFLSVREGDSAVINCT YTDSSSTYLYWYKQEPGAGLQLLTYIYSNMDM KQDQRLTVLLNKKDKHLSRIADTQTGDSAIYF CAEYSSASKIIFGSGTRLSIRPGGGGSGGGGSG GGSGGGGSGGGGSDAGVIQSPRHEVTEMGQEV TLRCKPISGHDYLFWYRQTMMRGLELLIYFNNN VPIDDSGMPEDRFSAKMPNASFSTLKIQPSEPRD SAVYFCASRANTGELFFGEGSRLTVL |
| 125 | 75-NU(Var17)-CR7P1D5#19 (HC) | EVQLVQSGAEVKKPGASVKVSCKASGYSFTGYT MNWVRQAPGQGLEWMGLINPYKGVSTYAQKF QDRVTLTVDKSTSTAYMELSSLRSEDTAVYYCA RSGYYGDSDWYFDVWGQGTLVTVSSASTKGPS VFPLAPSSKSTSGGTAALGCLVKDYFPEPVTVS WNSGALTSGVHTFPAVLQSSGLYSLSSVVTVPSS SLGTQTYICNVNHKPSNTKVDKKVEPKSCDKTH TSPPSPAPPVAGGEDVEQSLFLSVREGDSAVINC TYTDSSSTYLYWYKQEPGAGLQLLTYIYSSQDS KQDQRLTVLLNKKDKHLSRIADTQTGDSAIYF CAEMTSESKIIFGSGTRLSIRPGGGGSGGGGSGG GGSGGGGSGGGGSDAGVIQSPRHEVTEMGQEV TLRCKPIPGHDYLFWYRQTMMRGLELLFYFCYG TPCDDSGMPEDRFSAKMPNASFSTLKIQPSEPRD SAVYFCASRANTGELFFGEGSRLTVL |
| 126 | 75-NU(Var17)-CR7P1D5I (HC) | EVQLVQSGAEVKKPGASVKVSCKASGYSFTGYT MNWVRQAPGQGLEWMGLINPYKGVSTYAQKF QDRVTLTVDKSTSTAYMELSSLRSEDTAVYYCA RSGYYGDSDWYFDVWGQGTLVTVSSASTKGPS VFPLAPSSKSTSGGTAALGCLVKDYFPEPVTVS WNSGALTSGVHTFPAVLQSSGLYSLSSVVTVPSS SLGTQTYICNVNHKPSNTKVDKKVEPKSCDKTH TSPPSPAPPVAGGEDVEQSLFLSVREGDSAVINC TYTDSSSTYLYWYKQEPGAGLQLLTYIYSSQDS KQDQRLTVLLNKKDKHLSRIADTQTGDSAIYF CAEMTSESKIIFGSGTRLSIRPGGGGSGGGGSGG GGSGGGGSGGGGSDAGVIQSPRHEVTEMGQEV TLRCKPIPGHDYLFWYRQTMMRGLELLIYFCYG TPCDDSGMPEDRFSAKMPNASFSTLKIQPSEPRD SAVYFCASRANTGELFFGEGSRLTVL |
| 127 | 100(A)-NU(V17)-R7P1D5#114-iso0-dsFcKO-GK (alpha-VL) | EDVEQSLFLSVREGDSVVINCTYTDSSSTYLYW YKQEPGKGLQLLTYIYSSQDSKQDQRLTVLLNK KDKHLSRIADTQTGDSAIYFCAEMTSESKIIFGS GTRLSIRPGGGSGGGGDIQMTQSPSSLSASVGDR VTITCRASQDIRNYLNWYQQKPGKAPKLLIYYT SRLHSGVPSRFSGSGSGTDYTLTISSLQPEDIATY FCQQGQTLPWTFGQGTKVEIKEPKSSDKTHTCPP CPAPPVAGPSVFLFPPKPKDTLMISRTPEVTCVV VDVSHEDPEVKFNWYVDGVEVHNAKTKPREEQ YQSTYRVVSVLTVLHQDWLNGKEYKCKVSNKA LPASIEKTISKAKGQPREPQVYTLPPCRDELTKN QVSLWCLVKGFYPSDIAVEWESNGQPENNYKTT PPVLDSDGSFFLYSKLTVDKSRWQQGNVFSCSV MHEALHNHYTQKSLSLSP |
| 128 | 100(A)-NU(V17)-R7P1D5#112-dsFcKO-GK (VH-beta) | EVQLVQSGAEVKKPGASVKVSCKASGYSFTGYT MNWVRQAPGQGLEWMGLINPYKGVSTYAQKF QDRVTLTVDKSTSTAYMELSSLRSEDTAVYYCA RSGYYGDSDWYFDVWGQGTLVTVSSGGGSGG GGDAGVIQSPRHEVTEMGQEVTLRCKPIPGHDY |

-continued

| SEQ ID NO: | Name | Amino Acid Sequence |
|---|---|---|
| | | LFWYRQTMMRGLELLFYFCYGTPCDDSGMPED RFSAKMPNASFSTLKIQPSEPRDSAVYFCASRAN TGELFFGEGSRLTVLEPKSSDKTHTCPPCPAPPV AGPSVFLFPPKPKDTLMISRTPEVTCVVVDVSHE DPEVKFNWYVDGVEVHNAKTKPREEQYQSTYR VVSVLTVLHQDWLNGKEYKCKVSNKALPASIE KTISKAKGQPREPQVCTLPPSRDELTKNQVSLSC AVKGFYPSDIAVEWESNGQPENNYKTTPPVLDS DGSFFLVSKLTVDKSRWQQGNVFSCSVMHEAL HNHYTQKSLSLSP |
| 129 | ZFC-001 | KLQEQIHRV |
| 130 | 100(A)-NU(V17)-R7P1D5#114-dsFcKO-GK (VH-beta) | EVQLVQSGAEVKKPGASVKVSCKASGYSFTGYT MNWVRQAPGQGLEWMGLINPYKGVSTYAQKF QDRVTLTVDKSTSTAYMELSSLRSEDTAVYYCA RSGYYGDSDWYFDVWGQGTLVTVSSGGGSGG GGDAGVIQSPRHEVTEMGQEVTLRCKPIPGHDY LFWYRQTMMRGLELLFYFCYGTPCDDSGMPED RFSAKMPNASFSTLKIQPSEPRDSAVYFCASRAD TGELFFGEGSRLTVLEPKSSDKTHTCPPCPAPPV AGPSVFLFPPKPKDTLMISRTPEVTCVVVDVSHE DPEVKFNWYVDGVEVHNAKTKPREEQYQSTYR VVSVLTVLHQDWLNGKEYKCKVSNKALPASIE KTISKAKGQPREPQVCTLPPSRDELTKNQVSLSC AVKGFYPSDIAVEWESNGQPENNYKTTPPVLDS DGSFFLVSKLTVDKSRWQQGNVFSCSVMHEAL HNHYTQKSLSLSP |
| 131 | 100(A)-NU(V17)-R7P1D5#114-iso1-dsFcKO-GK (alpha-VL) | EDVEQSLFLSVREGDSVVINCTYTDSSSTYLYW YKQEPGKGLQLLTYIYSSQDQKQDQRLTVLLNK KDKHLSLRIADTQTGDSAIYFCAEMTSESKIIFGS GTRLSIRPGGGSGGGGDIQMTQSPSSLSASVGDR VTITCRASQDIRNYLNWYQQKPGKAPKLLIYYT SRLHSGVPSRFSGSGSGTDYTLTISSLQPEDIATY FCQQGQTLPWTFGQGTKVEIKEPKSSDKTHTCPP CPAPPVAGPSVFLFPPKPKDTLMISRTPEVTCVV VDVSHEDPEVKFNWYVDGVEVHNAKTKPREEQ YQSTYRVVSVLTVLHQDWLNGKEYKCKVSNKA LPASIEKTISKAKGQPREPQVYTLPPCRDELTKN QVSLWCLVKGFYPSDIAVEWESNGQPENNYKTT PPVLDSDGSFFLYSKLTVDKSRWQQGNVFSCSV MHEALHNHYTQKSLSLSP |
| 132 | 1G4 alpha chain | METLLGLLILWLQLQWVSSKQEVTQIPAALSVP EGENLVLNCSFTDSAIYNLQWFRQDPGKGLTSL LLIQSSQREQTSGRLNASLDKSSGRSTLYIAASQP GDSATYLCAVRPTSGGSYIPTFGRGTSLIVHPYIQ NPDPAVYQLRDSKSSDKSVCLFTDFDSQTNVSQ SKDSDVYITDKTVLDMRSMDFKSNSAVAWSNK SDFACANAFNNSIIPEDTFFPSPESSCDVKLVEKS FETDTNLNFQNLSVIGFRILLLKVAGFNLLMTLR LWSS |
| 133 | 100(A)-NU(V17)-R7P1D5#114-iso2-dsFcKO-GK (alpha-VL) | EDVEQSLFLSVREGDSVVINCTYTESSSTYLYWY KQEPGKGLQLLTYIYSSQDQKQDQRLTVLLNKK DKHLSLRIADTQTGDSAIYFCAEMTSESKIIFGSG TRLSIRPGGGSGGGGDIQMTQSPSSLSASVGDRV TITCRASQDIRNYLNWYQQKPGKAPKLLIYYTSR LHSGVPSRFSGSGSGTDYTLTISSLQPEDIATYFC QQGQTLPWTFGQGTKVEIKEPKSSDKTHTCPPCP APPVAGPSVFLFPPKPKDTLMISRTPEVTCVVVD VSHEDPEVKFNWYVDGVEVHNAKTKPREEQYQ STYRVVSVLTVLHQDWLNGKEYKCKVSNKALP ASIEKTISKAKGQPREPQVYTLPPCRDELTKNQV SLWCLVKGFYPSDIAVEWESNGQPENNYKTTPP VLDSDGSFFLYSKLTVDKSRWQQGNVFSCSVM HEALHNHYTQKSLSLSP |
| 134 | 1G4 beta chain | MSIGLLCCAALSLLWAGPVNAGVTQTPKFQVLK TGQSMTLQCAQDMNHEYMSWYRQDPGMGLRL IHYSVGAGITDQGEVPNGYNVSRSTTEDFPLRLL SAAPSQTSVYFCASSYVGNTGELFFGEGSRLTVL EDLKNVFPPEVAVFEPSEAEISHTQKATLVCLAT GFYPDHVELSWWVNGKEVHSGVSTDPQPLKEQ PALNDSRYCLSSRLRVSATFWQNPRNHFRCQVQ |

-continued

| SEQ ID NO: | Name | Amino Acid Sequence |
|---|---|---|
| | | FYGLSENDEWTQDRAKPVTQIVSAEAWGRADC GFTSESYQQGVLSATILYEILLGKATLYAVLVSA LVLMAMVKRKDSRG |
| 135 | 100(D)-NB(V36)-R7P1D5#114-iso0-dsFcKO-GK (alpha-VH) | EDVEQSLFLSVREGDSVVINCTYTDSSSTYLYW YKQEPGKGLQLLTYIYSSQDSKQDQRLTVLLNK KDKHLSLRIADTQTGDSAIYFCAEMTSESKIIFGS GTRLSIRPGGGSGGGGEVQLVQSGAEVKKPGAS VKVSCKASGYKFTSYVMHWVRQAPGQGLEWM GYINPYNDVTKYAEKFQGRVTLTSDTSTSTAYM ELSSLRSEDTAVHYCARGSYYDYEGFVYWGQG TLVTVSSEPKSSDKTHTCPPCPAPPVAGPSVFLFP PKPKDTLMISRTPEVTCVVVDVSHEDPEVKFNW YVDGVEVHNAKTKPREEQYQSTYRVVSVLTVL HQDWLNGKEYKCKVSNKALPASIEKTISKAKGQ PREPQVCTLPPSRDELTKNQVSLSCAVKGFYPSD IAVEWESNGQPENNYKTTPPVLDSDGSFFLVSKL TVDKSRWQQGNVFSCSVMHEALHNHYTQKSLS LSP |
| 136 | 100(D)-NB(V36)-R7P1D5#114-dsFcKO-GK (VL-beta) | QIQMTQSPSSLSASVGDRVTITCSATSSVSYMHW YQQKPGKAPKRWIYDTSKLASGVPSRFSGSGSG TDYTLTISSLQPEDAATYYCQQWSSNPLTFGGGT KVEIKGGGSGGGGDAGVIQSPRHEVTEMGQEVT LRCKPIPGHDYLFWYRQTMMRGLELLFYFCYGT PCDDSGMPEDRFSAKMPNASFSTLKIQPSEPRDS AVYFCASRADTGELFFGEGSRLTVLEPKSSDKTH TCPPCPAPPVAGPSVFLFPPKPKDTLMISRTPEVT CVVVDVSHEDPEVKFNWYVDGVEVHNAKTKP REEQYQSTYRVVSVLTVLHQDWLNGKEYKCKV SNKALPASIEKTISKAKGQPREPQVYTLPPCRDE LTKNQVSLWCLVKGFYPSDIAVEWESNGQPENN YKTTPPVLDSDGSFFLYSKLTVDKSRWQQGNVF SCSVMHEALHNHYTQKSLSLSP |
| 137 | 100(D)-NB(V36)-R7P1D5#114-iso1-dsFcKO-GK (alpha-VH) | EDVEQSLFLSVREGDSVVINCTYTDSSSTYLYW YKQEPGKGLQLLTYIYSSQDKQDQRLTVLLNK KDKHLSLRIADTQTGDSAIYFCAEMTSESKIIFGS GTRLSIRPGGGSGGGGEVQLVQSGAEVKKPGAS VKVSCKASGYKFTSYVMHWVRQAPGQGLEWM GYINPYNDVTKYAEKFQGRVTLTSDTSTSTAYM ELSSLRSEDTAVHYCARGSYYDYEGFVYWGQG TLVTVSSEPKSSDKTHTCPPCPAPPVAGPSVFLFP PKPKDTLMISRTPEVTCVVVDVSHEDPEVKFNW YVDGVEVHNAKTKPREEQYQSTYRVVSVLTVL HQDWLNGKEYKCKVSNKALPASIEKTISKAKGQ PREPQVCTLPPSRDELTKNQVSLSCAVKGFYPSD IAVEWESNGQPENNYKTTPPVLDSDGSFFLVSKL TVDKSRWQQGNVFSCSVMHEALHNHYTQKSLS LSP |
| 138 | R7P1D5#114-iso0-Valpha | EDVEQSLFLSVREGDSVVINCTYTDSSSTYLYW YKQEPGKGLQLLTYIYSSQDSKQDQRLTVLLNK KDKHLSLRIADTQTGDSAIYFCAEMTSESKIIFGS GTRLSIRP |
| 139 | 100(D)-NB(V36)-R7P1D5#114-iso2-dsFcKO-GK (alpha-VH) | EDVEQSLFLSVREGDSVVINCTYTESSSTYLYWY KQEPGKGLQLLTYIYSSQDKQDQRLTVLLNKK DKHLSLRIADTQTGDSAIYFCAEMTSESKIIFGSG TRLSIRPGGGSGGGGEVQLVQSGAEVKKPGASV KVSCKASGYKFTSYVMHWVRQAPGQGLEWMG YINPYNDVTKYAEKFQGRVTLTSDTSTSTAYME LSSLRSEDTAVHYCARGSYYDYEGFVYWGQGT LVTVSSEPKSSDKTHTCPPCPAPPVAGPSVFLFPP KPKDTLMISRTPEVTCVVVDVSHEDPEVKFNWY VDGVEVHNAKTKPREEQYQSTYRVVSVLTVLH QDWLNGKEYKCKVSNKALPASIEKTISKAKGQP REPQVCTLPPSRDELTKNQVSLSCAVKGFYPSDI AVEWESNGQPENNYKTTPPVLDSDGSFFLVSKL TVDKSRWQQGNVFSCSVMHEALHNHYTQKSLS LSP |
| 140 | Linker | GGSGG |
| 141 | Linker | GGSGGGGSGG |

| SEQ ID NO: | Name | Amino Acid Sequence |
|---|---|---|
| 142 | 100(A)-NU(V23)-R7P1D5#114-dsFcKO-GK (VH-beta) | EVQLVQSGAEVKKPGASVKVSCKASGYSFTEYT MNWVRQAPGQGLEWMGLINPQKGVSTYAQKF QDRVTLTVDKSTSTAYMELSSLRSEDTAVYYCA RSGYYGDSDWYFDVWGQGTLVTVSSGGGSGG GGDAGVIQSPRHEVTEMGQEVTLRCKPIPGHDY LFWYRQTMMRGLELLFYFCYGTPCDDSGMPED RFSAKMPNASFSTLKIQPSEPRDSAVYFCASRAD TGELFFGEGSRLTVLEPKSSDKTHTCPPCPAPPV AGPSVFLFPPKPKDTLMISRTPEVTCVVVDVSHE DPEVKFNWYVDGVEVHNAKTKPREEQYQSTYR VVSVLTVLHQDWLNGKEYKCKVSNKALPASIE KTISKAKGQPREPQVCTLPPSRDELTKNQVSLSC AVKGFYPSDIAVEWESNGQPENNYKTTPPVLDS DGSFFLVSKLTVDKSRWQQGNVFSCSVMHEAL HNHYTQKSLSLSP |
| 143 | Linker | GGSGGGGSGGGGSGG |
| 144 | Linker | GGSGGGGSGGGGSGGGGSGG |
| 145 | Linker | GGSGGGGSGGGGSGGGGSGGGGSGG |
| 146 | Linker | GSADDAKKDAAKKDGKS |
| 147 | Linker | GGQGSGGTGSGGQGSGGTGSGGQGS |
| 148 | Linker | GGGGSGT |
| 149 | R7P1D5#112-Vbeta | DAGVIQSPRHEVTEMGQEVTLRCKPIPGHDYLF WYRQTMMRGLELLFYFCYGTPCDDSGMPEDRF SAKMPNASFSTLKIQPSEPRDSAVYFCASRANTG ELFFGEGSRLTVL |
| 150 | R7P1D5#114-Vbeta | DAGVIQSPRHEVTEMGQEVTLRCKPIPGHDYLF WYRQTMMRGLELLFYFCYGTPCDDSGMPEDRF SAKMPNASFSTLKIQPSEPRDSAVYFCASRADTG ELFFGEGSRLTVL |
| 151 | R7P1D5#114-iso1-Valpha | EDVEQSLFLSVREGDSVVINCTYTDSSSTYLYW YKQEPGKGLQLLTYIYSSQDQKQDQRLTVLLNK KDKHLSLRIADTQTGDSAIYFCAEMTSESKIIFGS GTRLSIRP |
| 152 | R7P1D5#114-iso2-Valpha | EDVEQSLFLSVREGDSVVINCTYTESSSTYLYWY KQEPGKGLQLLTYIYSSQDQKQDQRLTVLLNKK DKHLSLRIADTQTGDSAIYFCAEMTSESKIIFGSG TRLSIRP |
| 153 | UCHT1(17) VL | DIQMTQSPSSLSASVGDRVTITCRASQDIRNYLN WYQQKPGKAPKLLIYYTSRLHSGVPSRFSGSGS GTDYTLTISSLQPEDIATYFCQQGQTLPWTFGQG TKVEIK |
| 154 | UCHT1(17) VH | EVQLVQSGAEVKKPGASVKVSCKASGYSFTGYT MNWVRQAPGQGLEWMGLINPYKGVSTYAQKF QDRVTLTVDKSTSTAYMELSSLRSEDTAVYYCA RSGYYGDSDWYFDVWGQGTLVTVSS |
| 155 | Linker | GGGGSGGGGSGT |
| 156 | UCHT1(23) VH | EVQLVQSGAEVKKPGASVKVSCKASGYSFTEYT MNWVRQAPGQGLEWMGLINPQKGVSTYAQKF QDRVTLTVDKSTSTAYMELSSLRSEDTAVYYCA RSGYYGDSDWYFDVWGQGTLVTVSS |
| 157 | BMA(10) VL | QIQMTQSPSSLSASVGDRVTITCSATSSVSYMHW YQQKPGKAPKRWIYDTSKLASGVPSRFSGSGSG TDYTLTISSLQPEDAATYYCQQWSSNPLTFGGGT KVEIK |
| 158 | BMA(10) VH | EVQLVQSGAEVKKPGASVKVSCKASGYKFTSY VMHWVRQAPGQGLEWMGYINPYNDVTKYAEK FQGRVTLTSDTSTSTAYMELSSLRSEDTAVHYC ARGSYYDYDGFVYWGQGTLVTVSS |

-continued

| SEQ ID NO: | Name | Amino Acid Sequence |
|---|---|---|
| 159 | BMA(36) VL | QIQMTQSPSSLSASVGDRVTITCSATSSVSYMHW YQQKPGKAPKRWIYDTSKLASGVPSRFSGSGSG TDYTLTISSLQPEDAATYYCQQWSSNPLTFGGGT KVEIK |
| 160 | BMA(36) VH | EVQLVQSGAEVKKPGASVKVSCKASGYKFTSY VMHWVRQAPGQGLEWMGYINPYNDVTKYAEK FQGRVTLTSDTSTSTAYMELSSLRSEDTAVHYC ARGSYYDYEGFVYWGQGTLVTVSS |
| 161 | Linker | GGGGSGGGGSGGGGSGT |
| 162 | UCHT1(17opt) VH | EVQLVQSGAEVKKPGASVKVSCKASGYSFTGYT MNWVRQAPGQGLEWMGLINPYKGVSTYAQKF QDRVTLTVDKSTSTAYMELSSLRSEDTAVYYCA RSGYYGESDWYFDVWGQGTLVTVSS |
| 163 | Linker | GGGGSGGGGSGGGGSGGGGSGT |
| 164 | UCHT1(21) VH | EVQLVQSGAEVKKPGASVKVSCKASGYSFTGYT MNWVRQAPGQGLEWMGLINPQKGVSTYAQKF QDRVTLTVDKSTSTAYMELSSLRSEDTAVYYCA RSGYYGDSDWYFDVWGQGTLVTVSS |
| 165 | Linker | GGGGSGGGGSGGGGSGGGGSGGGGSGT |
| 166 | 100(A)-NU(V21)-R7P1D5#114-dsFcKO-GK (VH-beta) | EVQLVQSGAEVKKPGASVKVSCKASGYSFTGYT MNWVRQAPGQGLEWMGLINPQKGVSTYAQKF QDRVTLTVDKSTSTAYMELSSLRSEDTAVYYCA RSGYYGDSDWYFDVWGQGTLVTVSSGGGSGG GGDAGVIQSPRHEVTEMGQEVTLRCKPIPGHDY LFWYRQTMMRGLELLFYCYGTPCDDSGMPED RFSAKMPNASFSTLKIQPSEPRDSAVYFCASRAD TGELFFGEGSRLTVLEPKSSDKTHTCPPCPAPPV AGPSVFLFPPKPKDTLMISRTPEVTCVVVDVSHE DPEVKFNWYVDGVEVHNAKTKPREEQYQSTYR VVSVLTVLHQDWLNGKEYKCKVSNKALPASIE KTISKAKGQPREPQVCTLPPSRDELTKNQVSLSC AVKGFYPSDIAVEWESNGQPENNYKTTPPVLDS DGSFFLVSKLTVDKSRWQQGNVFSCSVMHEAL HNHYTQKSLSLSP |
| 167 | 100(A)-NU(V17opt)-R7P1D5#114-dsFcKO-GK (VH-beta) | EVQLVQSGAEVKKPGASVKVSCKASGYSFTGYT MNWVRQAPGQGLEWMGLINPYKGVSTYAQKF QDRVTLTVDKSTSTAYMELSSLRSEDTAVYYCA RSGYYGESDWYFDVWGQGTLVTVSSGGGSGGG GDAGVIQSPRHEVTEMGQEVTLRCKPIPGHDYL FWYRQTMMRGLELLFYCYGTPCDDSGMPEDR FSAKMPNASFSTLKIQPSEPRDSAVYFCASRADT GELFFGEGSRLTVLEPKSSDKTHTCPPCPAPPVA GPSVFLFPPKPKDTLMISRTPEVTCVVVDVSHED PEVKFNWYVDGVEVHNAKTKPREEQYQSTYRV VSVLTVLHQDWLNGKEYKCKVSNKALPASIEKT ISKAKGQPREPQVCTLPPSRDELTKNQVSLSCAV KGFYPSDIAVEWESNGQPENNYKTTPPVLDSDG SFFLVSKLTVDKSRWQQGNVFSCSVMHEALHN HYTQKSLSLSP |
| 168 | PRAME-004 | SLLQHLIGL |
| 169 | 100(A)-NU(17)-PRAME-dsFcKO-GK (alpha-VL) | QKEVEQNSGPLSVPEGAIASLNCTYSDRGSQSFF WYRQYSGKSPELIMSIYQEGDKEDGRFTAQLNK ASQYVSLLIRDSQPSDSATYLCAAVIDNDQGGIL TFGTGTRLTIIPNIQNGGGSGGGGDIQMTQSPSSL SASVGDRVTITCRASQDIRNYLNWYQQKPGKAP KLLIYYTSRLHSGVPSRFSGSGSGTDYTLTISSLQ PEDIATYFCQQGQTLPWTFGQGTKVEIKEPKSSD KTHTCPPCPAPPVAGPSVFLFPPKPKDTLMISRTP EVTCVVVDVSHEDPEVKFNWYVDGVEVHNAK TKPREEQYQSTYRVVSVLTVLHQDWLNGKEYK CKVSNKALPASIEKTISKAKGQPREPQVYTLPPC RDELTKNQVSLWCLVKGFYPSDIAVEWESNGQP ENNYKTTPPVLDSDGSFFLYSKLTVDKSRWQQG NVFSCSVMHEALHNHYTQKSLSLSP |

| SEQ ID NO: | Name | Amino Acid Sequence |
|---|---|---|
| 170 | 100(A)-NU(17)-PRAME-dsFcKO-GK (VH-beta) | EVQLVQSGAEVKKPGASVKVSCKASGYSFTGYT MNWVRQAPGQGLEWMGLINPYKGVSTYAQKF QDRVTLTVDKSTSTAYMELSSLRSEDTAVYYCA RSGYYGDSDWYFDVWGQGTLVTVSSGGGSGG GGKAGVTQTPRYLIKTRGQQVTLSCSPIPGHRAV SWYQQTPGQGLQFLFEYVHGEERNKGNFPGRFS GRQFSNSSSEMNISNLELGDSALYLCASSPWDSP NVQYFGPGTRLTVTEDLKNEPKSSDKTHTCPPCP APPVAGPSVFLFPPKPKDTLMISRTPEVTCVVVD VSHEDPEVKFNWYVDGVEVHNAKTKPREEQYQ STYRVVSVLTVLHQDWLNGKEYKCKVSNKALP ASIEKTISKAKGQPREPQVCTLPPSRDELTKNQV SLSCAVKGFYPSDIAVEWESNGQPENNYKTTPP VLDSDGSFFLVSKLTVDKSRWQQGNVFSCSVM HEALHNHYTQKSLSLSP |
| 171 | INTS4-002 | KLLDLMPRL |
| 172 | SAMH-001 | KLLSYIQRL |
| 173 | PPP1CA-006 | SIIGRLLEV |
| 174 | RPL-007 | KIYEGQVEV |
| 175 | SETD1A-001 | ILLEHNYAL |
| 176 | NOMAP-1-0320 | ALSNLEVKL |
| 177 | NOMAP-1-1223 | LLDVPTAAV |
| 178 | ODC-001 | ILDQKINEV |
| 179 | COL6A3-010 | KLLPYIVGV |
| 180 | FAM115A-001 | KLGSVPVTV |
| 181 | PHTF2-001 | KLFGHLTSA |
| 182 | RPP1-001 | KTLSAILRI |

DETAILED DESCRIPTION OF A PREFERRED EMBODIMENT

Figure 1:
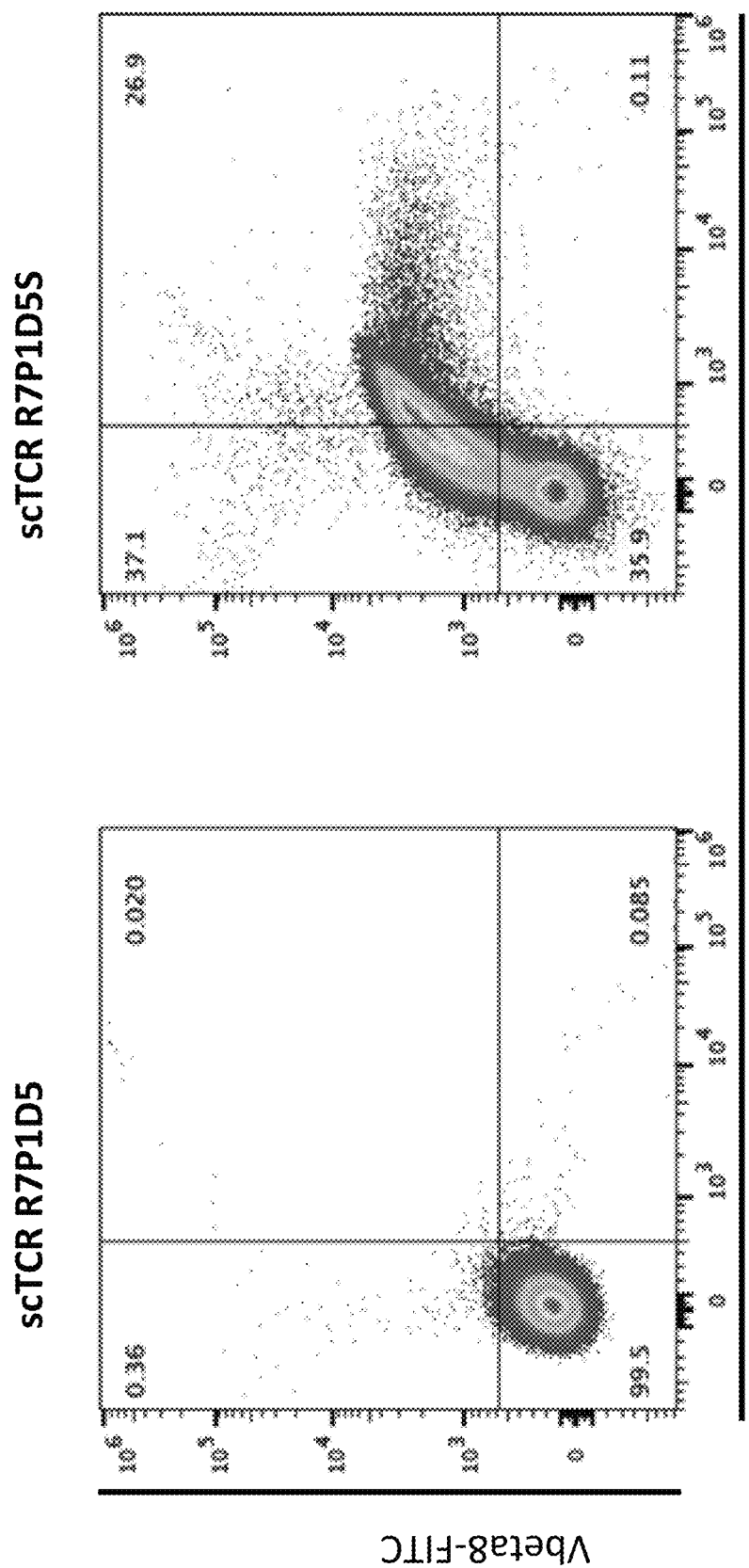
FIGS. 1-18 depict embodiments as described herein.

FIG. 1 shows results from conversion of a TCR into stabilized scTCR via yeast surface display. ScTCR molecules displayed on the surface of transformed *Saccharomyces cerevisiae* EBY100 were stained with FITC-labeled anti-Vbeta8 antibody and PE-labeled HLA-A*02/MAG-003 tetramer. The non-modified scTCR R7P1D5 (left panel, SEQ ID NO: 19) is compared to a scTCR variant bearing two stabilizing single point mutations (right panel, SEQ ID NO: 22), which was derived from the selection of a random mutation scTCR library. It can be seen that the scTCR variant bearing two stabilizing single point mutations shows an increased HLA-A*02/MAG-003 tetramer staining.

Figure 2A:
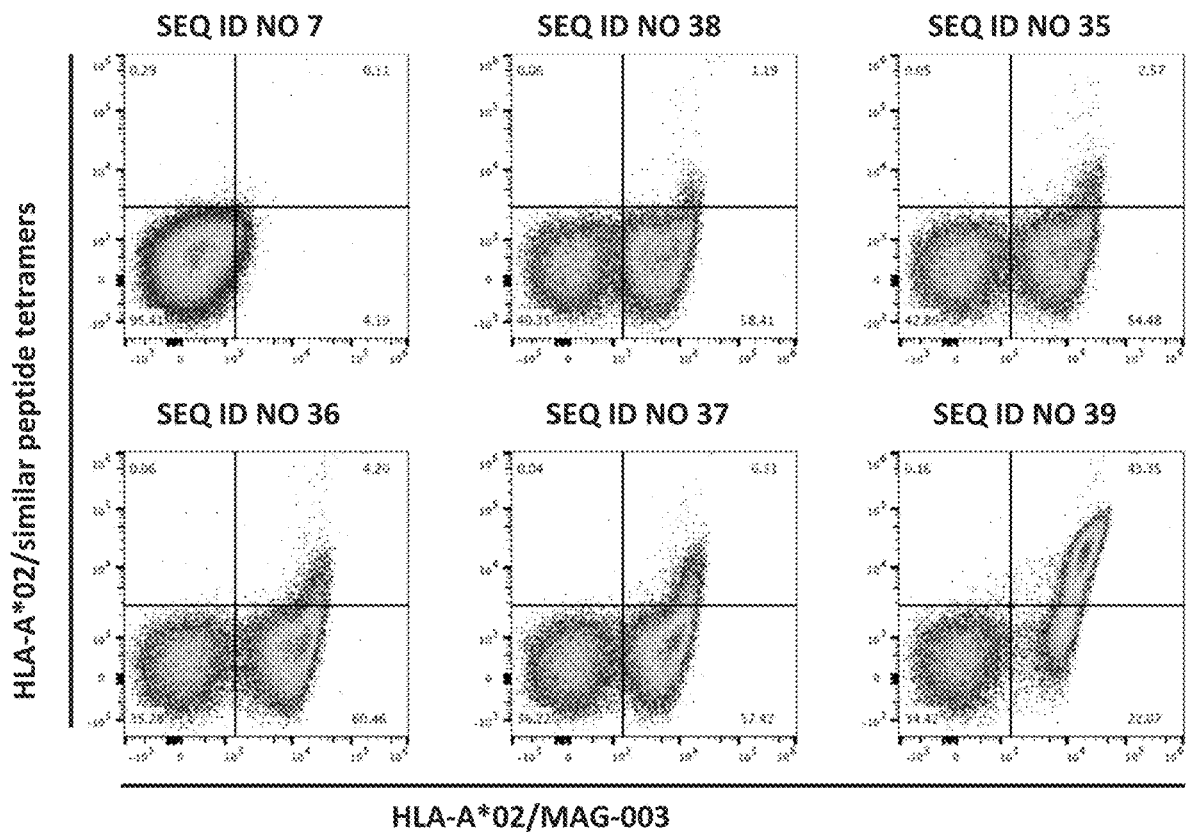

FIG. 2A shows results from yeast surface display for scTCR affinity maturation of CDR3 alpha. Stabilized scTCR comprising non-modified and maturated CDR3 alpha were stained with HLA-A*02/MAG-003 monomers at a concentration of 15 nM. Counterstaining with a mix of 10 HLA-A*02 tetramers, each applied at a concentration of 10 nM, containing peptides (SEQ ID NO: 23 to 32) with high sequence similarity to MAG-003 (SEQ ID NO: 1). Stabilized scTCR (SEQ ID NO: 22) with non-modified alpha chain CDR3 sequence CAEYSSASKIIF (SEQ ID NO: 7) is compared with scTCR variants comprising the affinity maturated alpha chain CDR3 sequences CAEFSSASKIIF (SEQ ID NO: 38), CAEMTSESKIIF (SEQ ID NO: 35), CAEFTSESKIIF (SEQ ID NO: 36), CAEFNSESKIIF (SEQ ID NO: 37) and CAEATSESKIIF (SEQ ID NO: 39), respectively. It can be seen, that the yeast clones with mutated CDRs alpha 2 (SEQ ID NOs 56, 57, 59), beta 1 (SEQ ID NO 62) or beta 2 (SEQ ID NOs 63, 64, 65, 66, 70) also revealed strongly improved binding while specificity for HLA-A*02/MAG-003 was mainly retained.

Figure 2B:
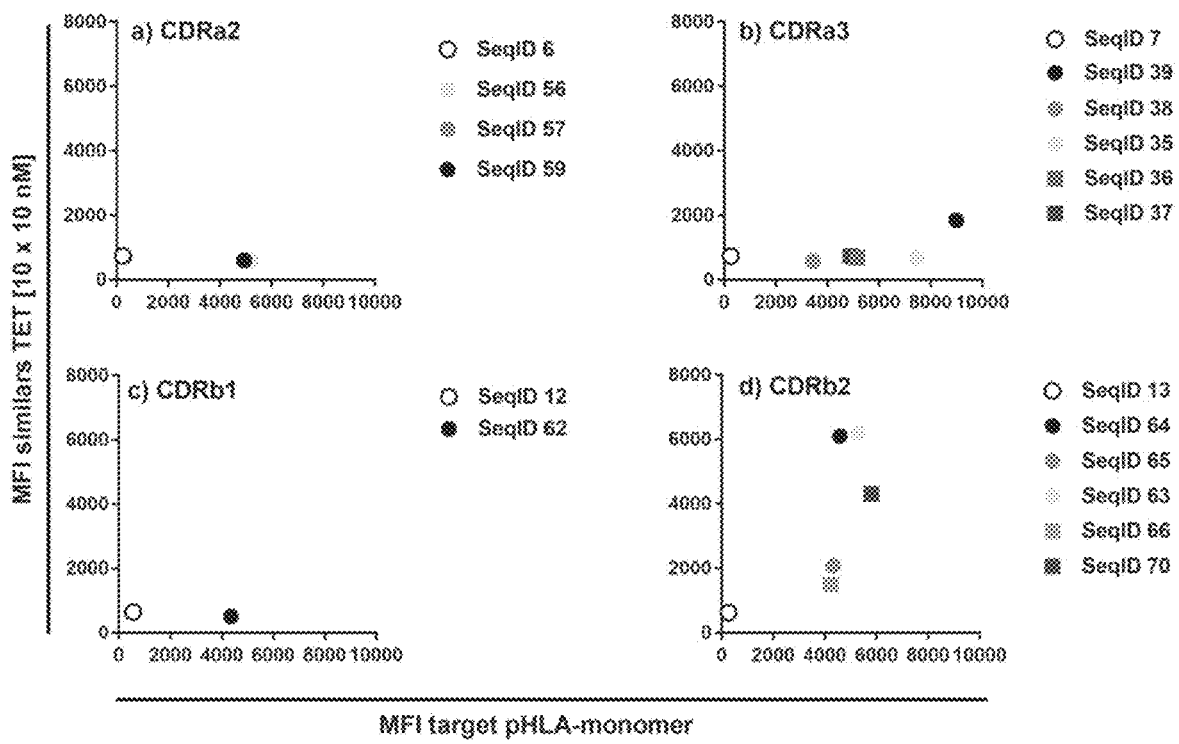

FIG. 2B shows results from yeast surface display for scTCR affinity maturation of CDR2 alpha, CDR3 alpha, CDR1 beta and CDR2 beta, respectively. Stabilized scTCR comprising non-modified and maturated CDRs were stained with HLA-A*02/MAG-003 monomer (target pHLA monomer) and counterstained with a mix of 10 HLA-A*02 tetramers, each applied at a concentration of 10 nM, containing peptides (SEQ ID NO: 23 to 32) with high sequence similarity to MAG-003 (SEQ ID NO: 1). (a) Comparison of scTCR variants with non-modified (SEQ ID NO: 6) and maturated alpha chain CDR2 sequences IYSSQDQ (SEQ ID 56), IYSSQDV (SEQ ID 57) and IYSSQDS (SEQ ID 59), each stained with 40 nM HLA-A*02/MAG-003 monomer. (b) Comparison of scTCR variants with non-modified (SEQ ID NO: 7) and maturated alpha chain CDR3 sequences CAEFSSASKIIF (SEQ ID NO: 38), CAEMTSESKIIF (SEQ ID NO: 35), CAEFTSESKIIF (SEQ ID NO: 36), CAEFNSESKIIF (SEQ ID NO: 37) and CAEATSESKIIF (SEQ ID NO: 39), each stained with 15 nM HLA-A*02/

MAG-003 monomer. (c) Comparison of scTCR variants with non-modified (SEQ ID NO: 12) and maturated beta chain CDR1 sequence PGHDY (SEQ ID NO: 62), each stained with 40 nM HLA-A*02/MAG-003 monomer. (d) Comparison of scTCR variants with non-modified (SEQ ID NO: 13) and maturated beta chain CDR2 sequences FCYGHP (SEQ ID NO: 63), FCYGVP (SEQ ID NO: 64), FCYGTP (SEQ ID NO: 65), FCYGAP (SEQ ID NO: 66), FCYGMP (SEQ ID NO: 70), each stained with 5 nM HLA-A*02/MAG-003 monomer. Staining with HLA-A*02/MAG-003 tetramers was significantly increased for all R7P1D5 CDRa3 mutants when compared to the parental TCR R7P1D5, indicating an improved peptide-HLA binding of the mutant variants.

Figure 3:
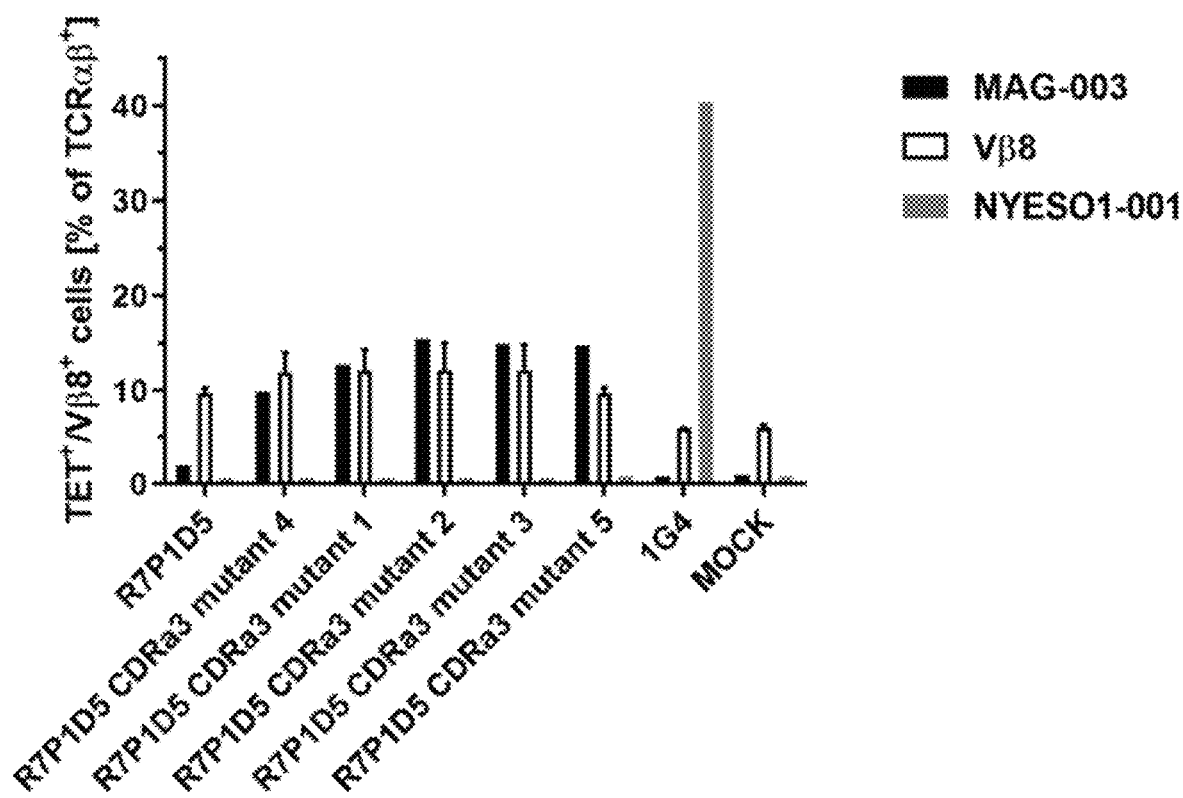

FIG. 3 shows staining of maturated R7P1D5 TCR variant expressing human CD8+ T cells with PE-labeled HLA-A*02/MAG-003 tetramers and FITC-labeled anti-Vbeta 8 antibody. For control purpose, no TCR (MOCK) or the 1G4 TCR specific for NYESO1-001 were expressed and staining with PE-labeled HLA-A*02/NYESO1-001 tetramers was used.

Figure 4:
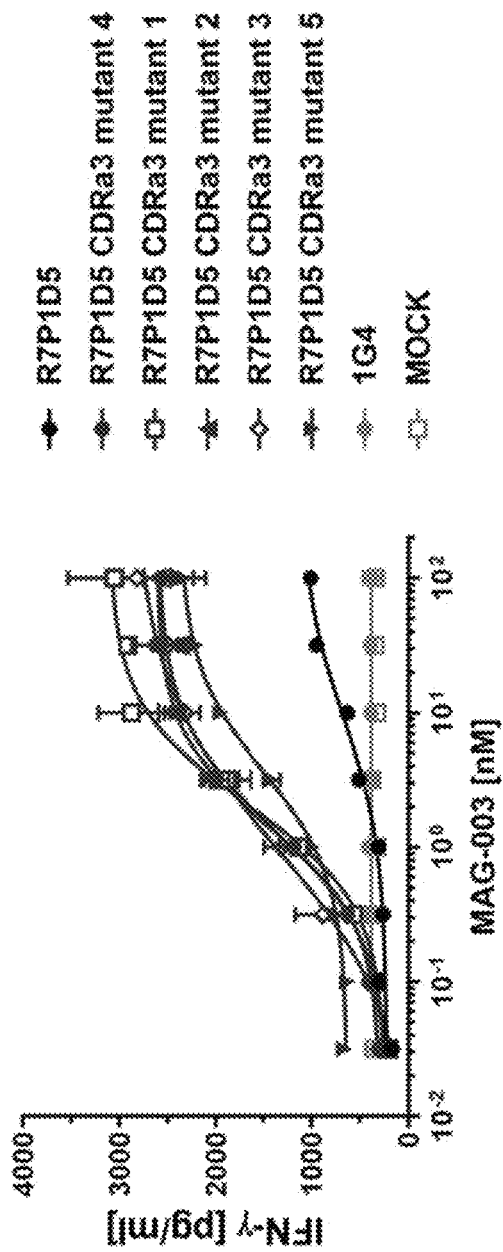

FIG. 4 shows IFN-gamma release of maturated R7P1D5 TCR variant expressing human CD8+ T cells in response to MAG-003. For control purpose, no TCR (MOCK) or the 1G4 TCR specific for NYESO1-001 were expressed. IFN-gamma release was determined by ELISA after co-culture of electroporated CD8+ T cells with T2 cells loaded with a serial dilution of MAG-003. Baseline levels of IFN-gamma (released by MOCK electroporated CD8+ T cells upon coculture with respectively loaded T2 cells) were subtracted. Compared to the parental TCR R7P1D5, maturated R7P1D5 CDRa3 mutants 1-5 showed an increased IFN-gamma release in response to MAG-003.

Figure 5:
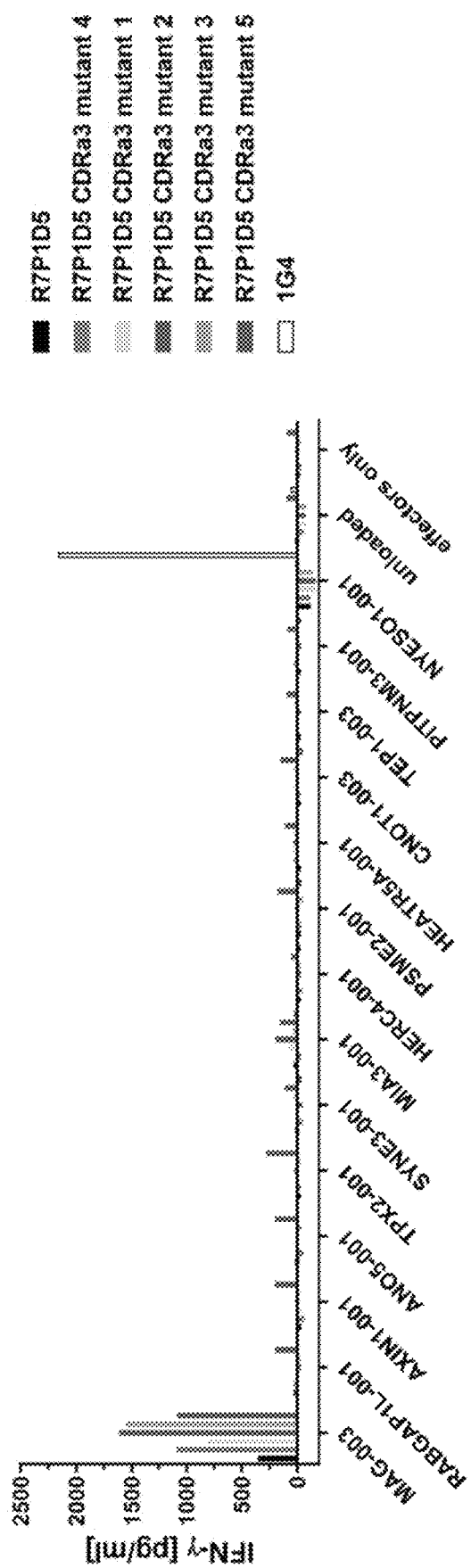

FIG. 5 shows IFN-gamma release of maturated R7P1D5 TCR variant expressing human CD8+ T cells in response to MAG-003 and different similar peptides. For control purpose, no TCR (MOCK) or the 1G4 TCR specific for NYESO1-001 were expressed. IFN-gamma release was determined by ELISA after co-culture of electroporated CD8+ T cells with T2 cells loaded with 10 µM peptide. Baseline levels of IFN-gamma (released by MOCK electroporated CD8+ T cells upon coculture with respectively loaded T2 cells) were subtracted. Compared to the parental TCR R7P1D5, maturated R7P1D5 CDRa3 mutants 1-5 showed an increased IFN-gamma release in response to MAG-003 and no IFN-gamma release for the tested similar peptides.

Figure 6:
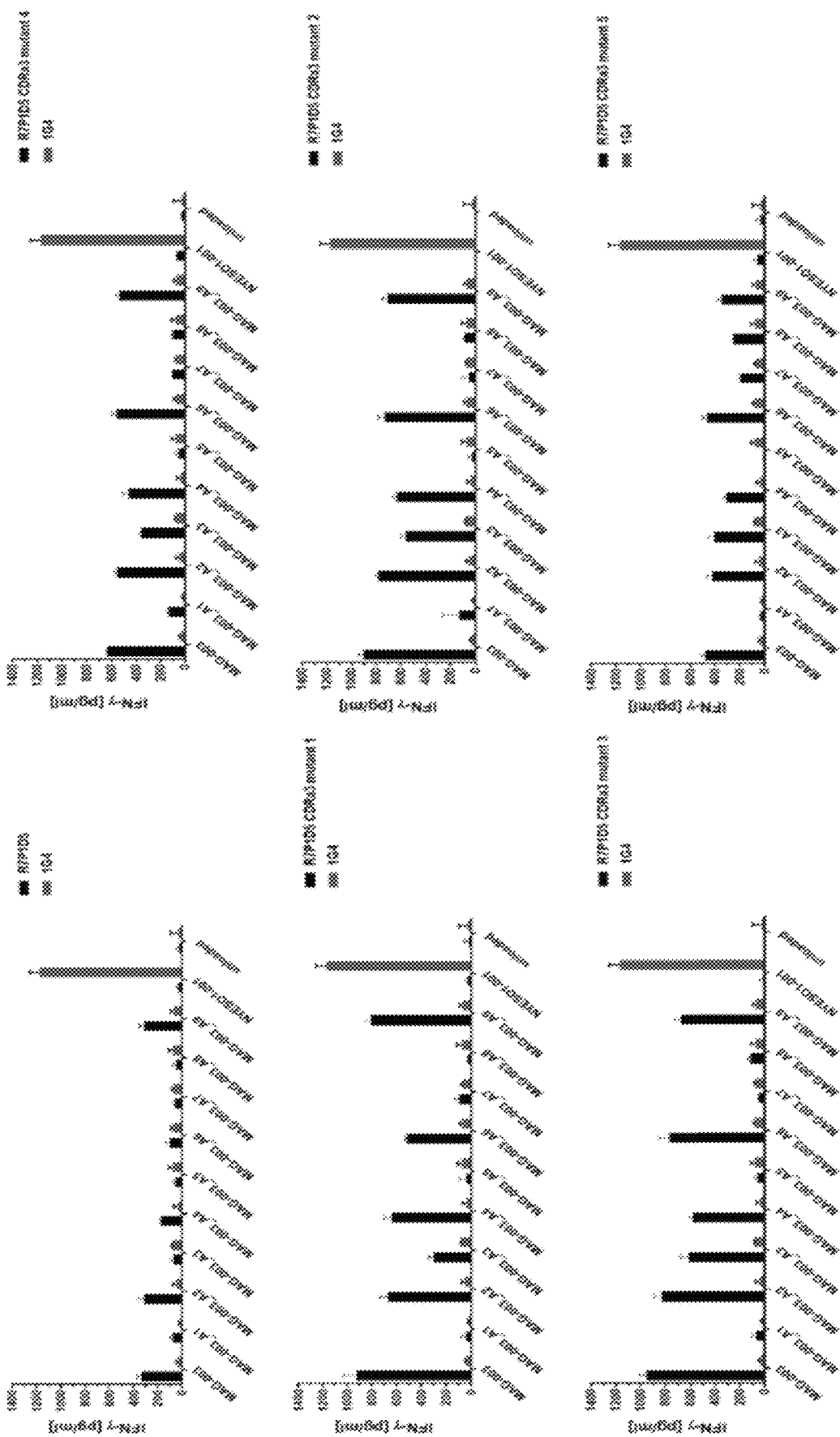

FIG. 6 shows IFN-gamma release of maturated R7P1D5 TCR variant expressing human CD8+ T cells in response to MAG-003 and the respective alanine-substitution peptides. For control purpose, no TCR (MOCK) or the 1G4 TCR specific for NYESO1-001 were expressed. IFN-gamma release was determined by ELISA after co-culture of electroporated CD8+ T cells with T2 cells loaded with 10 µM peptide. Baseline levels of IFN-gamma (released by MOCK electroporated CD8+ T cells upon coculture with respectively loaded T2 cells) were subtracted.

Figure 7A:
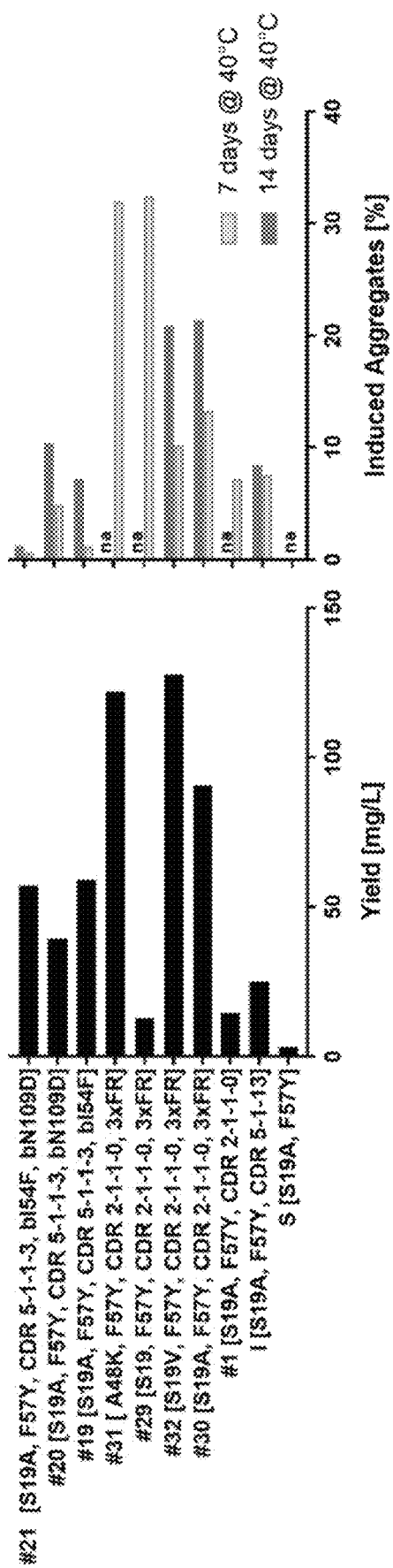

FIG. 7A shows production yields and heat-stress stability data of soluble scTCR-Fab antigen binding proteins comprising TCR variable domains with different affinity-maturated CDRs and/or framework mutations.

Figure 7B:
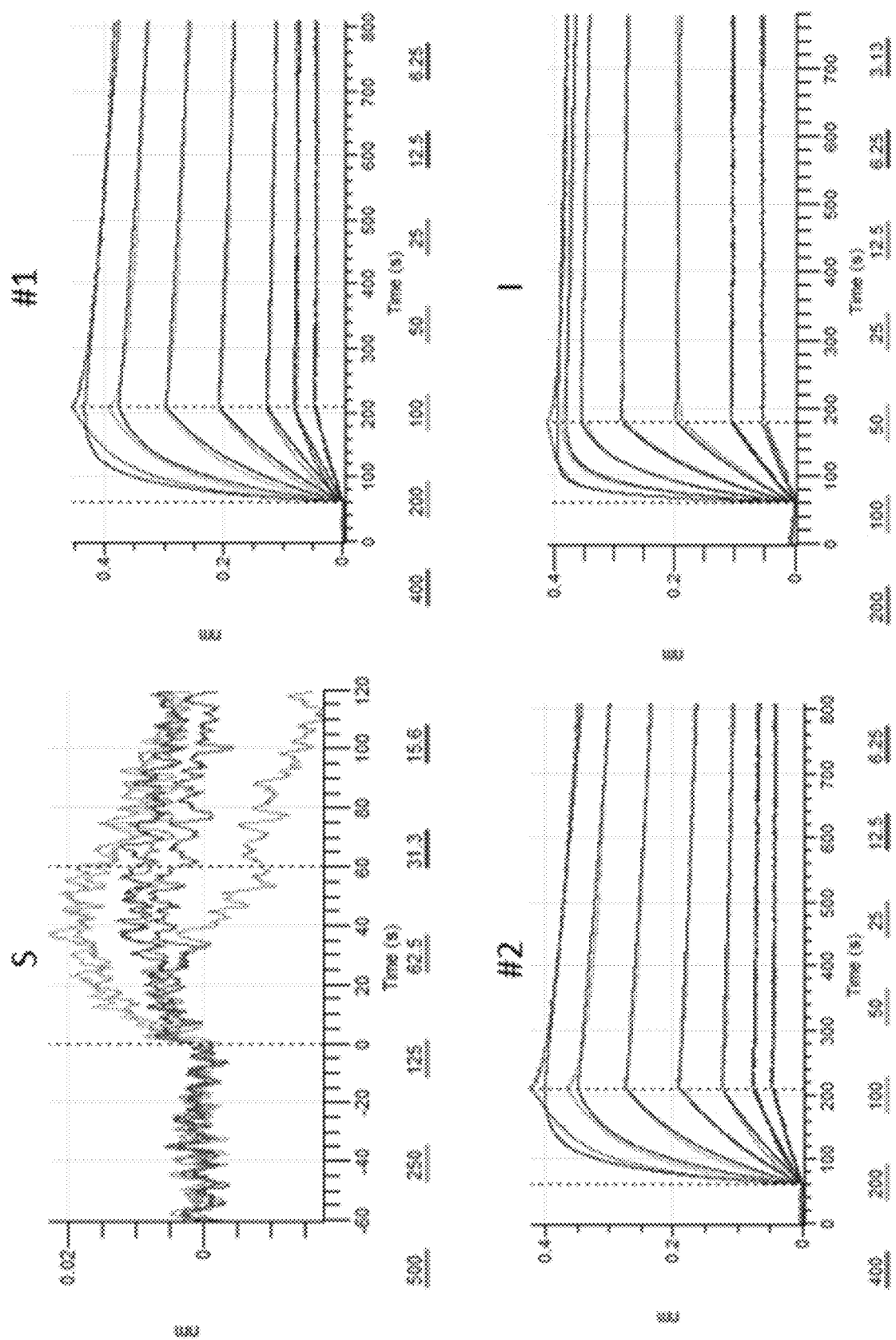

FIG. 7B shows binding curves of soluble scTCR-Fab antigen binding proteins S, #1, #2 and I to MAG-003 in complex with HLA-A*02 as measured by biolayer interferometry. Increasing concentrations of HLA-A*02/MAG-003 monomers in solution were used for each interaction measurement and are given in nM.

Figure 7C:
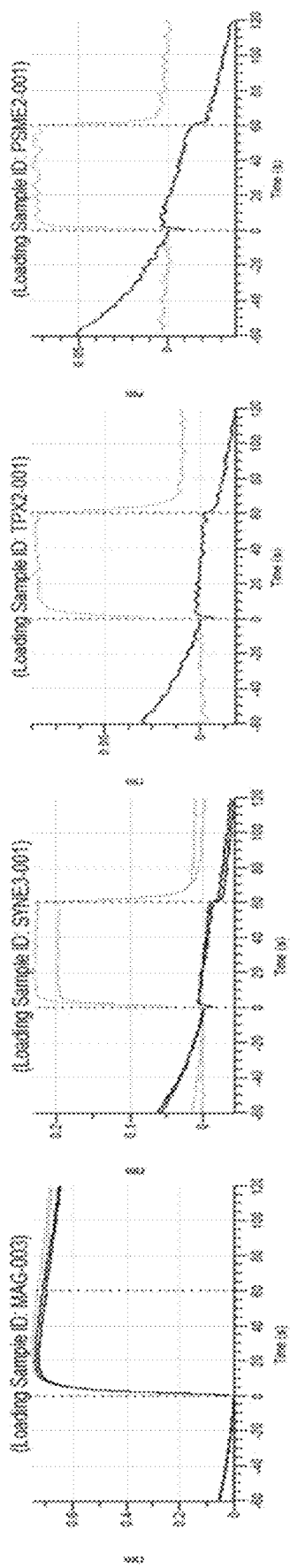

FIG. 7C shows binding curves of soluble scTCR-Fab antigen binding proteins I (grey curves) and #19 (black curves) for MAG-003 and the normal tissue-derived off-target peptides SYNE3-001, TPX2-001, PSME2-001, respectively, in complex with HLA-A*02. Biolayer interferometry was used for the measurement and a concentration of 1 µM scTCR-Fab in solution was applied.

Figure 8A:
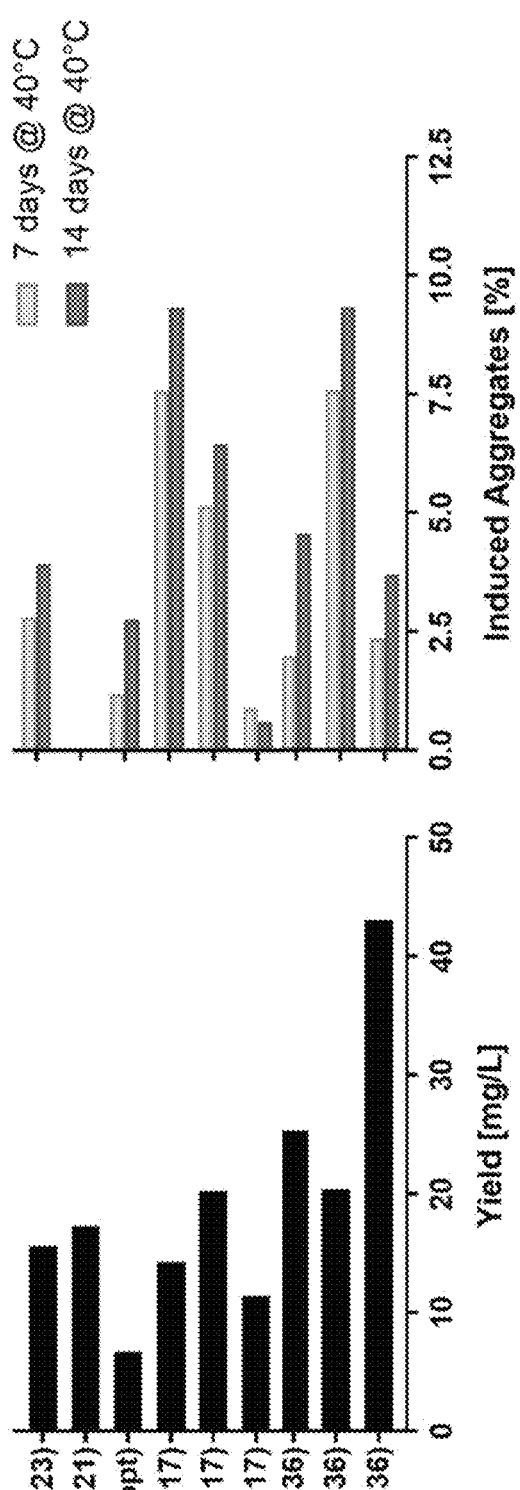

FIG. 8A shows production yields and heat-stress stability data of soluble TCER™ antigen binding proteins comprising TCR variable domains with selected affinity-maturated CDRs combined with different VH/VL sequences of the humanized T cell-recruiting antibody BMA031(36) as well as different variants 17, 17opt, 21, 23 of the humanized T cell-recruiting antibody UCHT1.

Figure 8B:
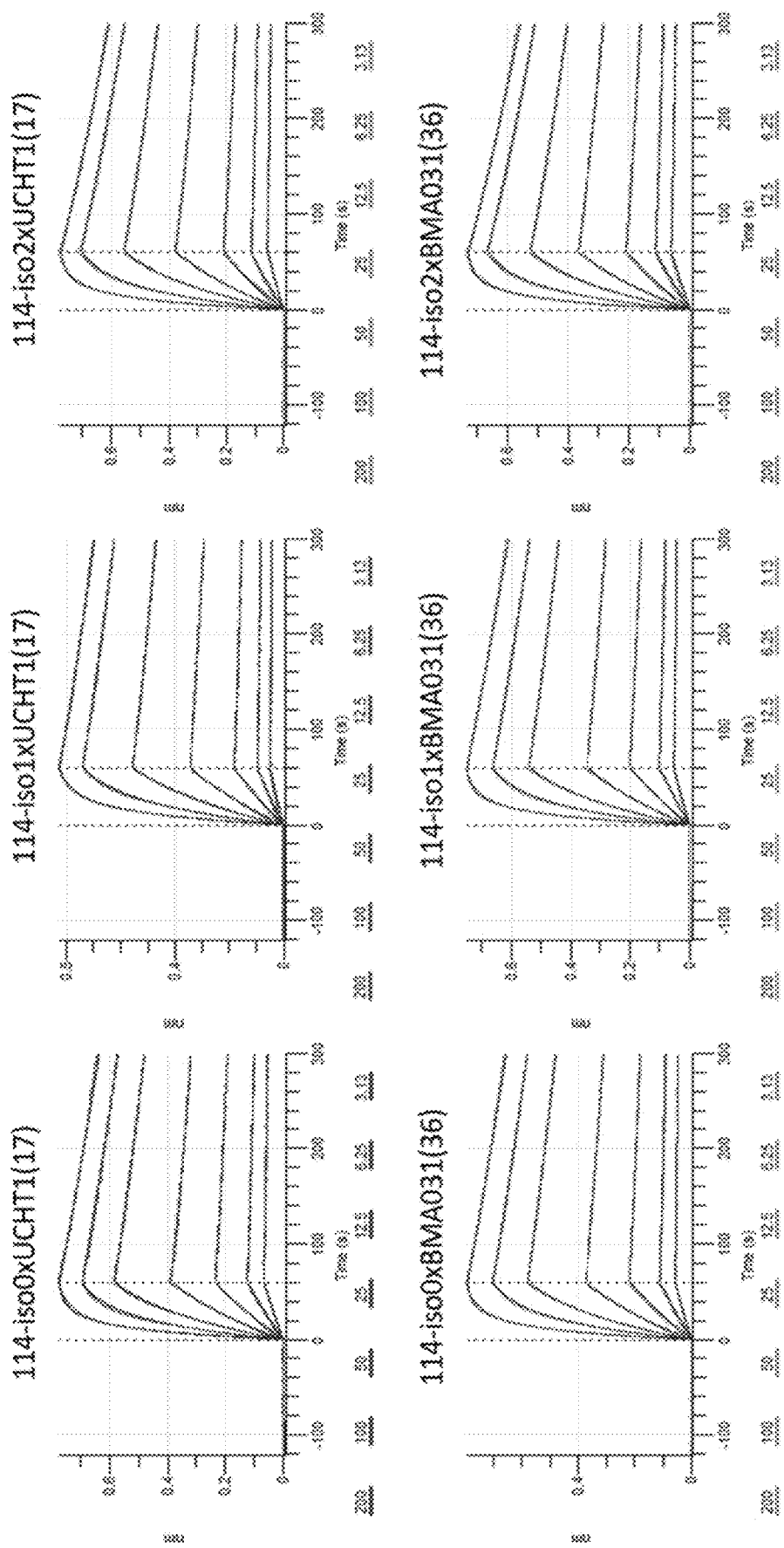

FIG. 8B shows binding curves of TCER™ antigen binding proteins comprising the TCR variable domain variants 114-iso0, 114-iso1 and 114-iso2 in combination with UCHT1(17) and BMA031(36) for MAG-003 in complex with HLA-A*02. Biolayer interferometry was used for the measurement and increasing concentrations of TCER™ molecules in solution were applied and are given in nM.

Figure 8C:
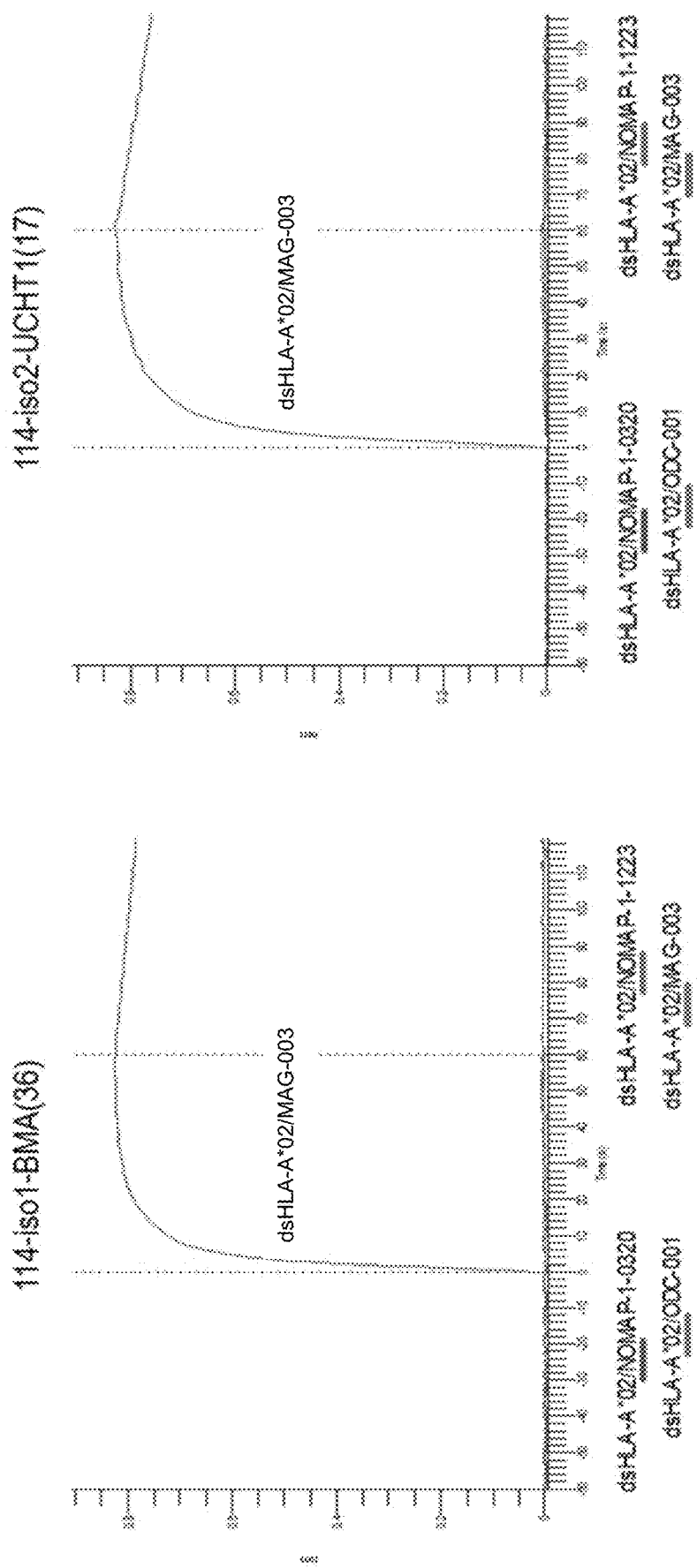

FIG. 8C shows binding curves of 114-iso1-BMA(36) and 114-iso2-UCHT1(17) TCER™ molecules for MAG-003 and normal tissue-derived off-target peptides NOMAP-1-0320, NOMAP-1-1223, ODC-001, respectively, in complex with disulfide-stabilized HLA-A*02. Biolayer interferometry was used for the measurement and a concentration of 1 µM TCER™ in solution was applied.

Figure 9:
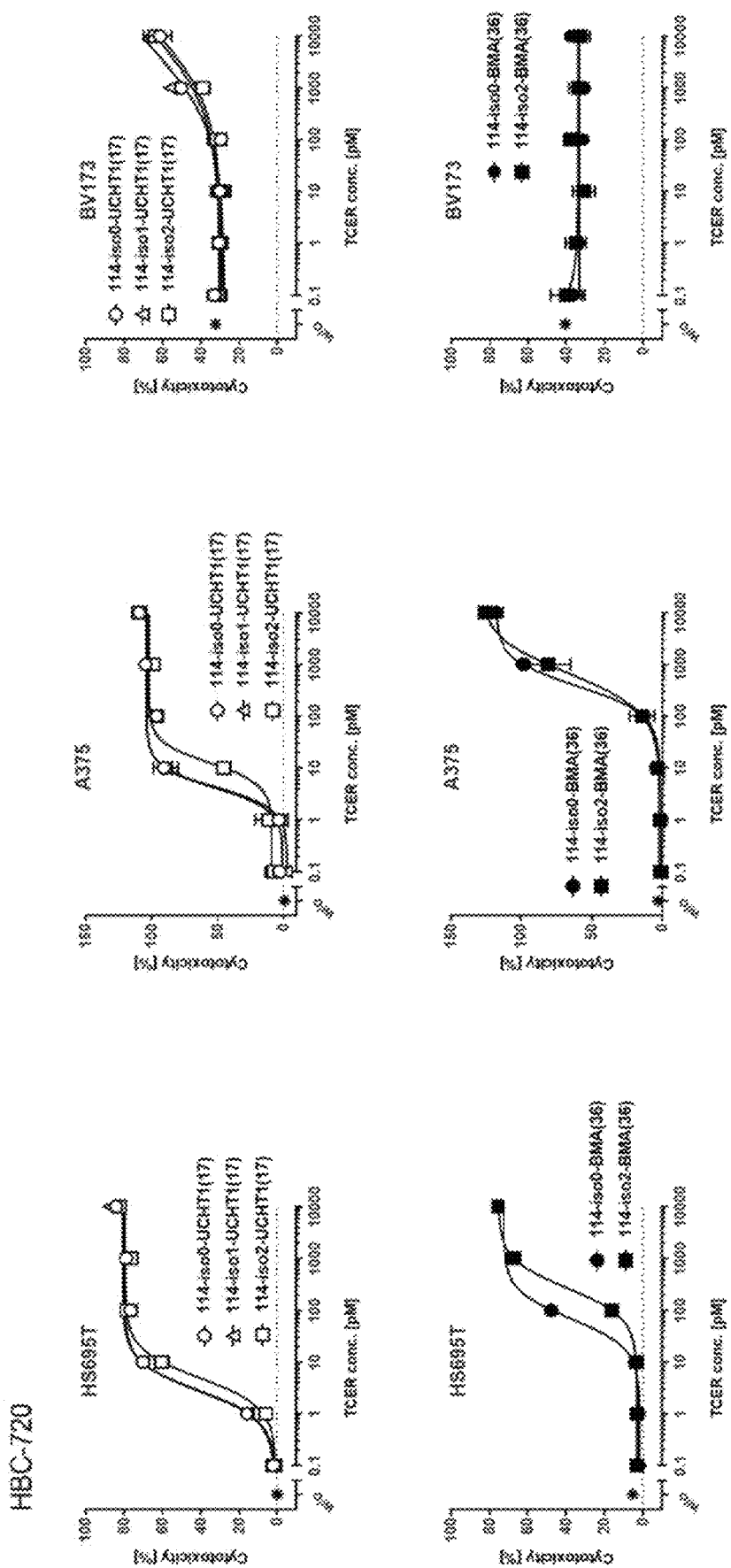

FIG. 9 shows in vitro efficiency data of TCER™-mediated killing of HLA-A*02-positive tumor cell lines with detectable MAG-003 expression (Hs695T and A375) and without detectable MAG-003 expression (BV173). TCER™ molecules comprising UCHT1 (17) antibody variable domains with variable domains of the TCR variants #114-iso0 (SEQ ID NO: 127 and 130), #114-iso1 (SEQ ID NO: 131 and 130) and #114-iso2 (SEQ ID NO: 133 and 130) were tested (upper panel). Furthermore, TCER™ molecules comprising BMA031 (36) antibody variable domains with variable domains of the TCR variants #114-iso0 (SEQ ID NO: 135 and 136) and #114-iso2 (SEQ ID NO: 139 and 136) were tested (lower panel). The tumor cells were co-incubated with human PBMC from a healthy HLA-A*02+donor (HBC-720) at a ratio of 1:10 and the cytotoxic activity in presence of increasing concentrations of TCER™ molecules was analyzed by LDH-release assay. After 48 hours, lysis of target cell lines was measured utilizing CYTOTOX 96 Non-Radioactive Cytotoxicity Assay Kits (PROMEGA). Efficient cell lysis is shown for TCER™ molecules comprising UCHT1 (17) and BMA031 (36) antibodies.

Figure 10:
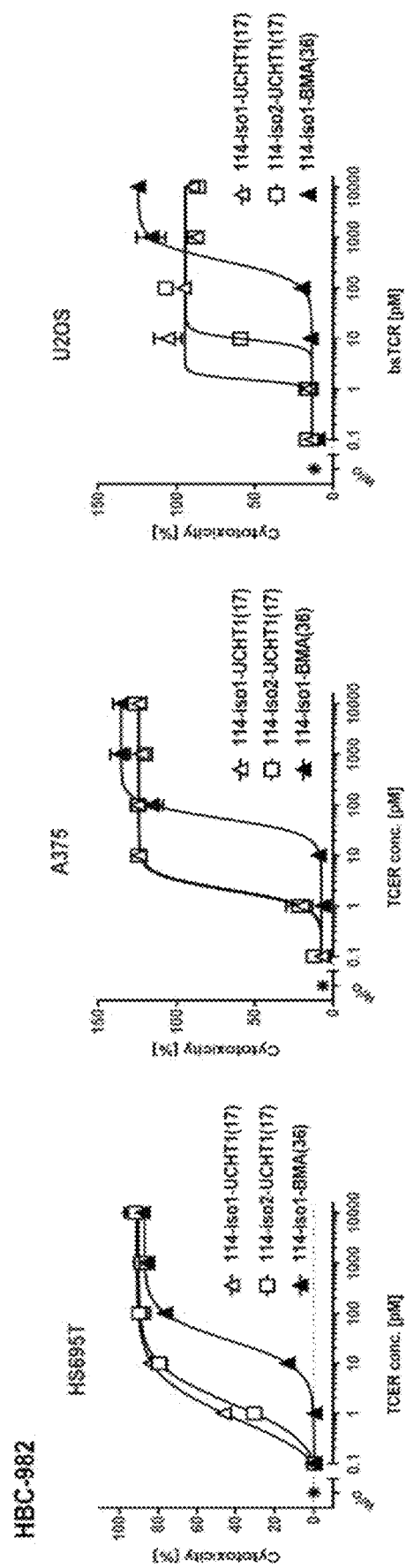

FIG. 10 shows TCER™-mediated in vitro killing of HLA-A*02-positive tumor cell lines with detectable MAG-003 expression (Hs695T, A375 and U2OS). TCER™ molecules comprising UCHT1(17) antibody variable domains with variable domains of the TCR variants #114-iso1 (SEQ ID NO: 131 and 130) and #114-iso2 (SEQ ID NO: 133 and 130) as well as TCER™ molecules comprising BMA031 (36) antibody variable domains with variable domains of the TCR variant #114-iso1 (SEQ ID NO: 137 and 136) were tested. The tumor cells were co-incubated with human PBMC from a healthy HLA-A*02+ donor (HBC-982) at a ratio of 1:10 and the cytotoxic activity in presence of increasing concentrations of TCER™ molecules was analyzed by LDH-release assay. After 48 hours, lysis of tumor cell lines was measured utilizing CytoTox 96 Non-Radioactive Cytotoxicity Assay Kits (PROMEGA). Efficient tumor cell lysis is shown for TCER™ molecules comprising UCHT1(17) and BMA031(36) antibodies.

Figure 11:
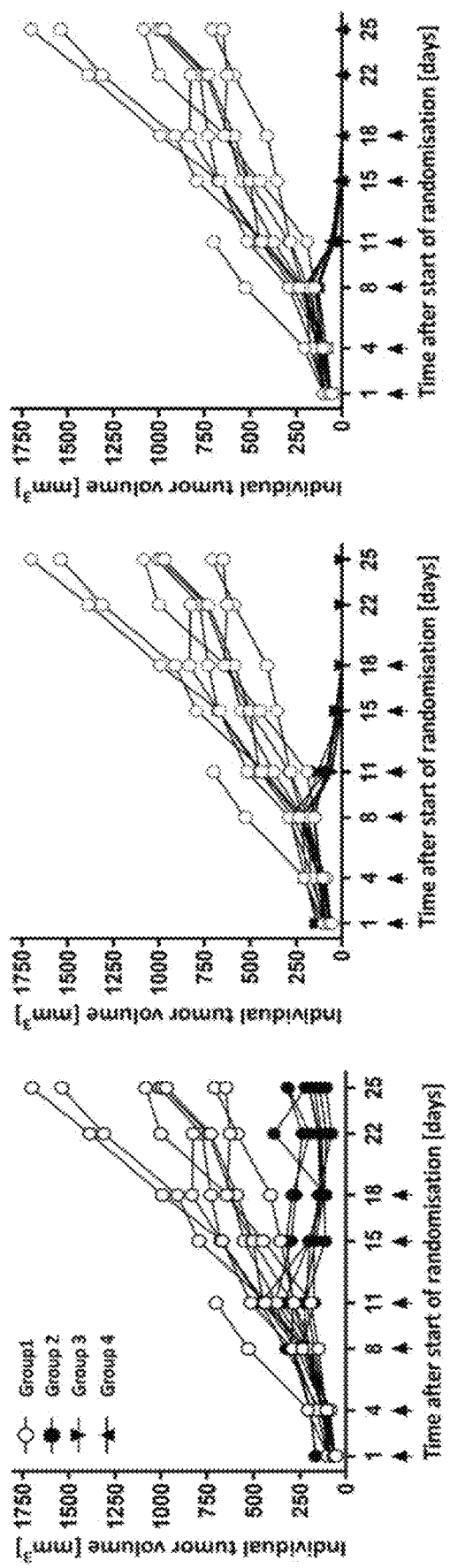

FIG. 11 shows TCER™-mediated in vivo efficacy in human PBMC-engrafted, immunodeficient NOG mice against tumor xenografts of Hs695T cells, an HLA-A*02-positive tumor cell line with detectable presentation of MAG-003 (SEQ ID NO: 1) and PRAME-004 (SEQ ID NO: 168). TCER™ comprising UCHT1(17) antibody variable domains with variable domains of the TCR variant #114-iso0 (SEQ ID NO: 127 and 130, group 3) were compared to TCER™ comprising BMA031(36) antibody variable domains with variable domains of the TCR variant #114-iso0 (SEQ ID NO: 135 and 136, group 4). As a control, a PRAME-004-targeting TCER (SEQ ID NO 169 and 170, group 2) was used. Group 1 represent the vehicle-treated control group in which one animal was sacrificed due to tumor ulceration at day 11. Each symbol connected by a line represents an individual animal and treatment days are indicated with an arrow. Complete remission is shown for the TCER™ comprising UCHT1(17) antibody and BMA031(36) antibody for T cell recruitment.

Figure 12:
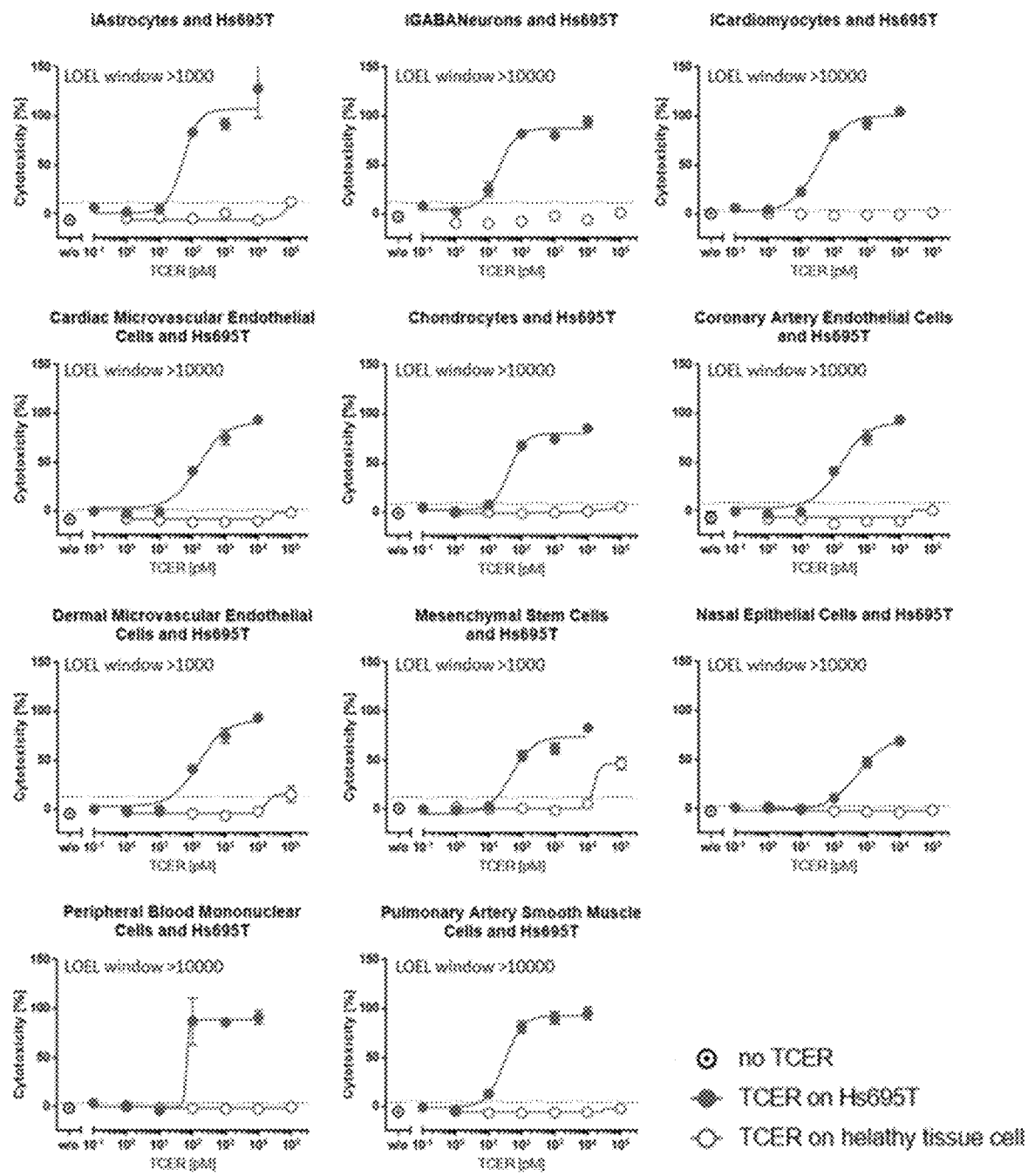

FIG. 12 shows in vitro safety data for TCER™ molecule 114-iso1-BMA(36) (SEQ ID NO: 137 and 136) as assessed in LDH-killing experiments with 11 human HLA-A*02-positive normal tissue primary cells from different organs. The different cells were co-cultured with PBMC effector cells from healthy HLA-A*02+ donors at a ratio of 1:10 and increasing TCER™ concentrations. Cells were co-incubated in a 50% mixture of primary tissue cell-were co-incubated in an identical setup with the MAG-003-positive tumor cell line Hs695T. The safety window was defined based on the lowest observed effect level (LOEL) determined as the first TCER™ concentration exhibiting a response over the cut-off value. The cut-off was defined as ([standard deviation from all triplicates×3]+control normal tissue sample w/o TCER) and is indicated as dotted line in each cytotoxicity plot. For each normal tissue cell type, the safety window determined based on LOEL was larger than 1,000-fold or 10,000-fold indicating a favorable safety profile of the 114-iso1-BMA(36) TCER™ molecule.

Figure 13:
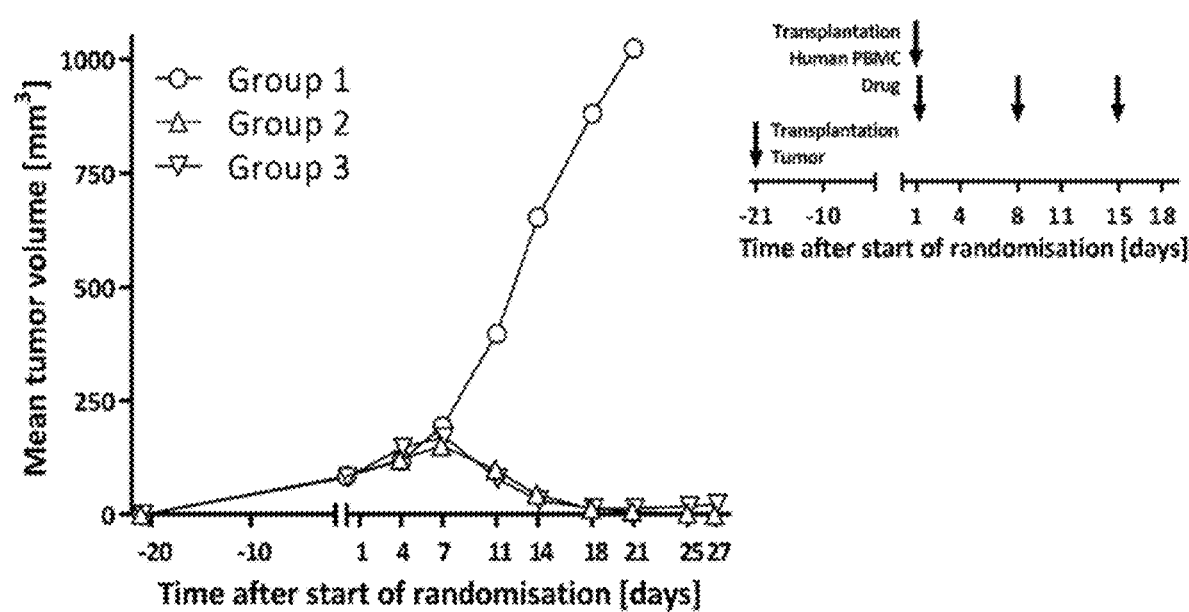

FIG. 13 shows TCER™-mediated in vivo efficacy in human PBMC-engrafted, immunodeficient NOG mice against tumor xenografts of Hs695T cells, an HLA-A*02-positive tumor cell line with detectable presentation of MAG-003 (SEQ ID NO: 1). TCER™ molecules comprising UCHT1($V_{17}$opt) antibody variable domains and variable domains of the TCR variant 114-iso1 (SEQ ID NO: 131 and 167, group 3) were compared to TCER™ comprising BMA031(36) antibody variable domains with variable domains of the TCR variant 114-iso1 (SEQ ID NO: 137 and 136, group 2). Group 1 represent the vehicle-treated control group. The graphs show the mean tumor volume derived from six (group 2 and 3) to ten (vehicle) mice per group. Complete remission is shown for the TCER™ molecules comprising UCHT1(17opt) antibody and BMA031(36) antibody for T cell recruitment upon once weekly i.v. dosing of 0.01 mg/kg body weight.

Figure 14:
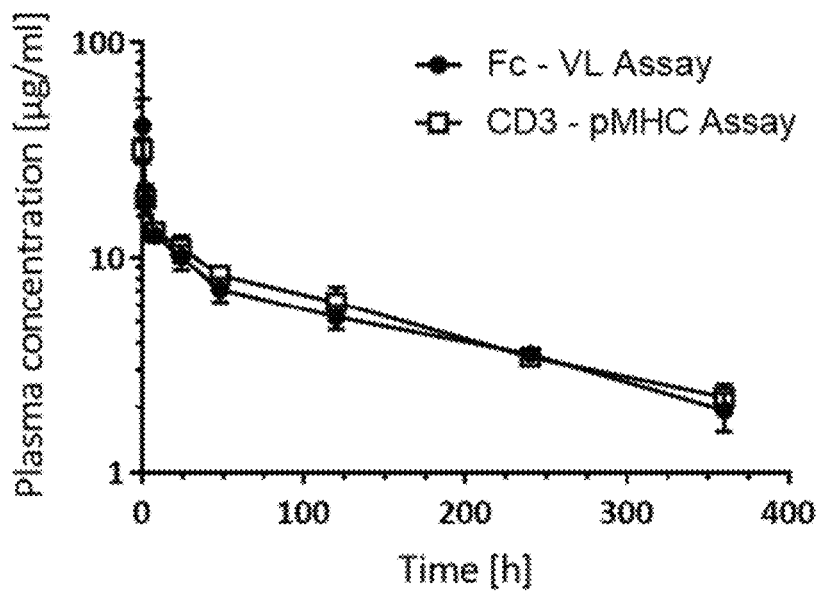
Figure 14:
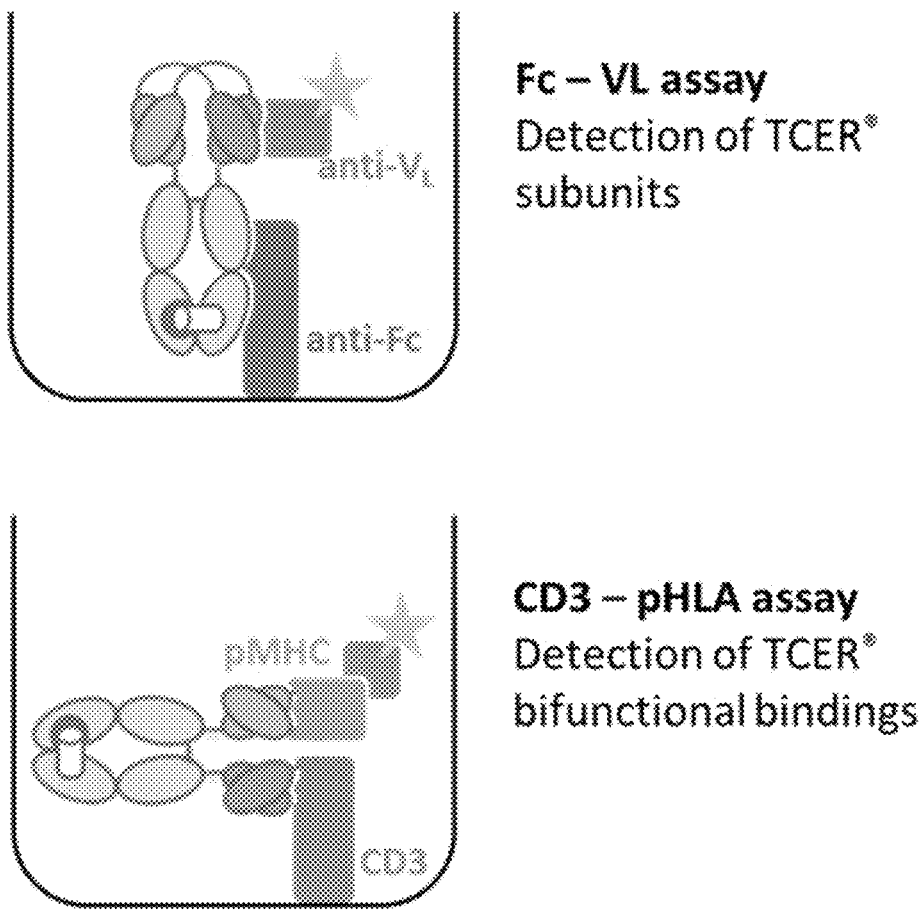

FIG. 14 shows the pharmacokinetic profile of 114-iso1-UCHT1(17) TCER™ molecule in NOG mice. Mice received a single intravenous injection of 2 mg/kg body weight. TCER™ plasma concentrations of samples collected at different time points were determined by ELISA detecting either the presence of specific protein domains ($F_c$-$V_L$ assay) or bispecific binding activity (CD3—pMHC assay).

Figure 15:
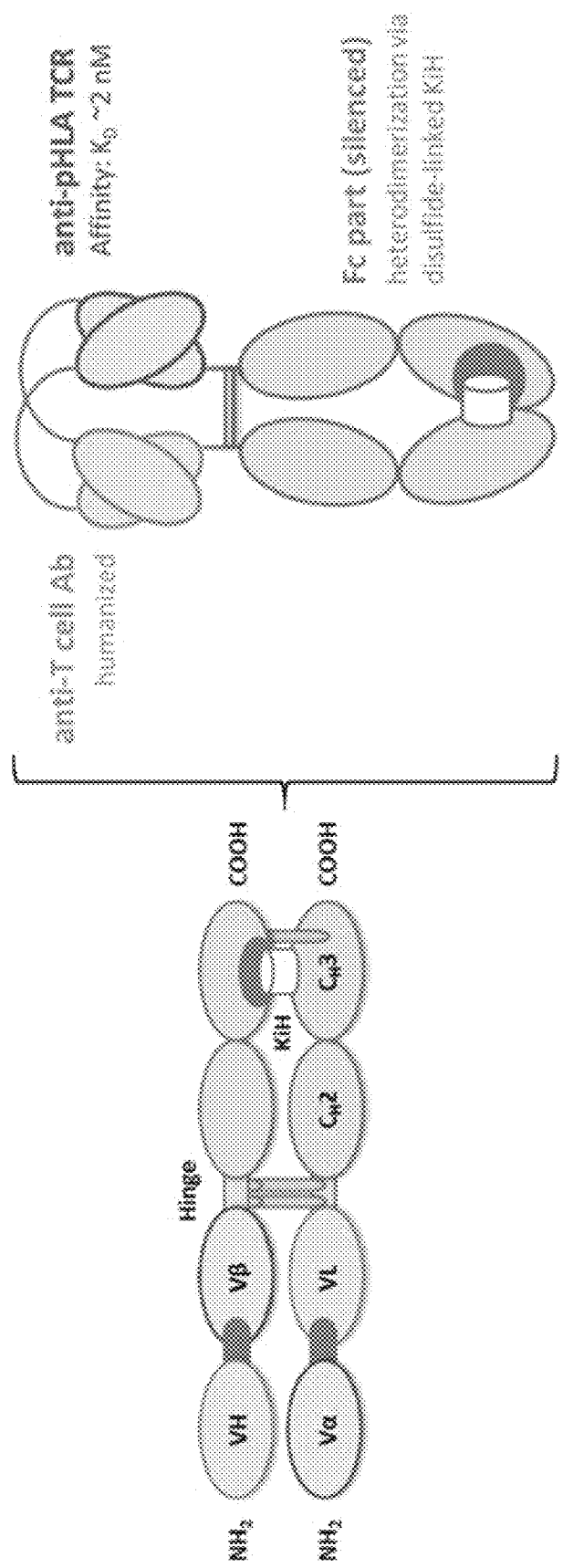

FIG. 15 shows design of TCER™ molecules. Bispecific T cell-engaging receptors (TCER™) are fusion proteins containing the variable domains (V□, V□) of an affinity-matured TCR and the variable domains (VH, VL) of a humanized T cell-recruiting antibody. The molecules use an effector function-silenced $F_c$ part, which confers extended half-life and also improved stability/manufacturability characteristics.

Figure 16:
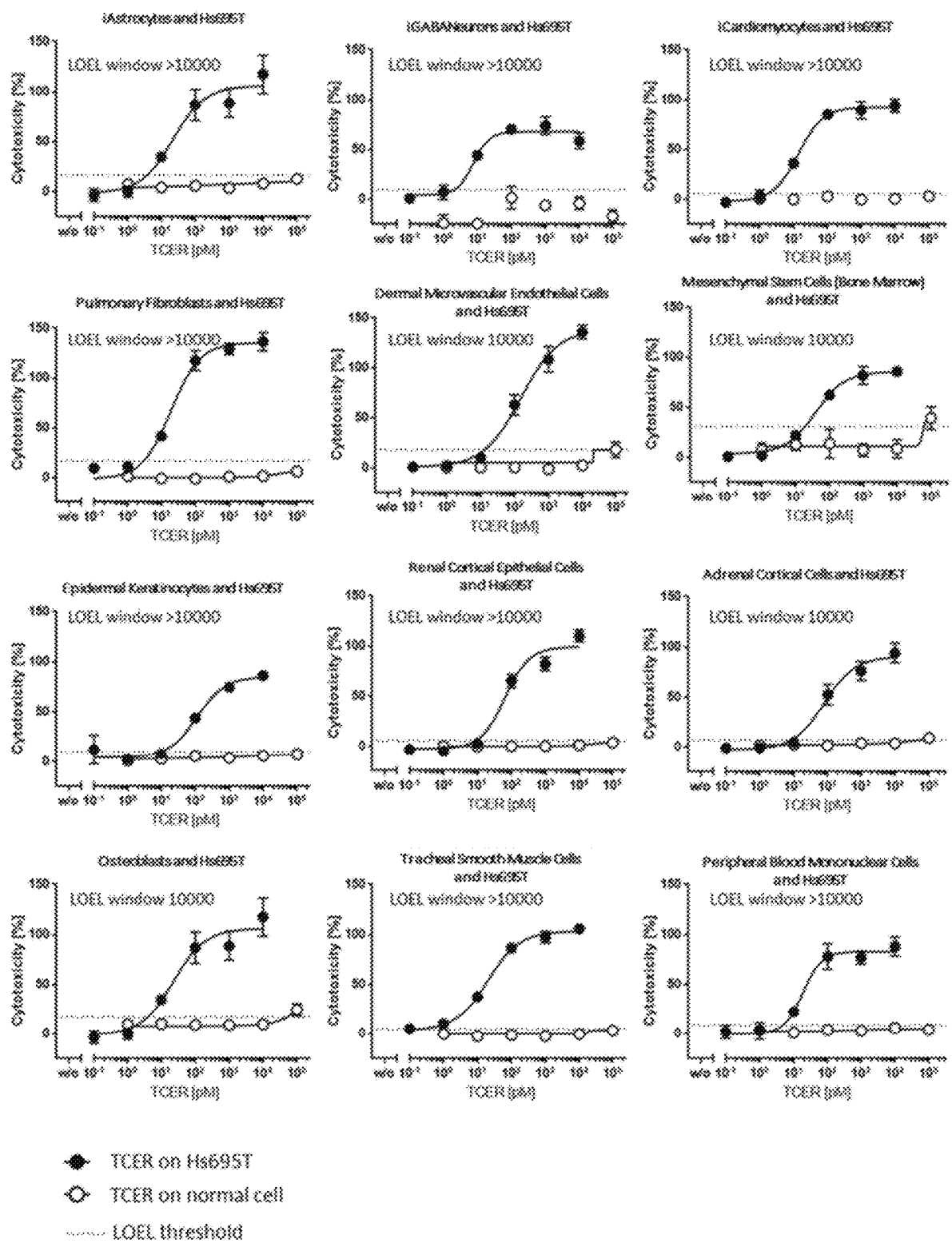

FIG. 16 shows in vitro safety data for TCER™ molecule 114-iso1-BMA(36) (SEQ ID NO: 137 and 136) as assessed in LDH-killing experiments with 12 human HLA-A*02-positive normal tissue primary cells from different organs. The different cells were co-cultured with PBMC effector cells from healthy HLA-A*02+ donors at a ratio of 1:10 and increasing TCER™ concentrations. Cells were co-incubated in a 50% mixture of primary tissue cell-were co-incubated in an identical setup with the MAG-003-positive tumor cell line Hs695T. The safety window was defined based on the lowest observed effect level (LOEL) determined as the first TCER™ concentration exhibiting a response over the cut-off value. The cut-off was defined as ([standard deviation from all triplicates×3]+control normal tissue sample w/o TCER) and is indicated as dotted line in each cytotoxicity plot. For each normal tissue cell type, the safety window determined based on LOEL was larger than 1,000-fold or 10,000-fold indicating a favorable safety profile of the 114-iso1-BMA(36) TCER™ molecule.

Figure 17A:
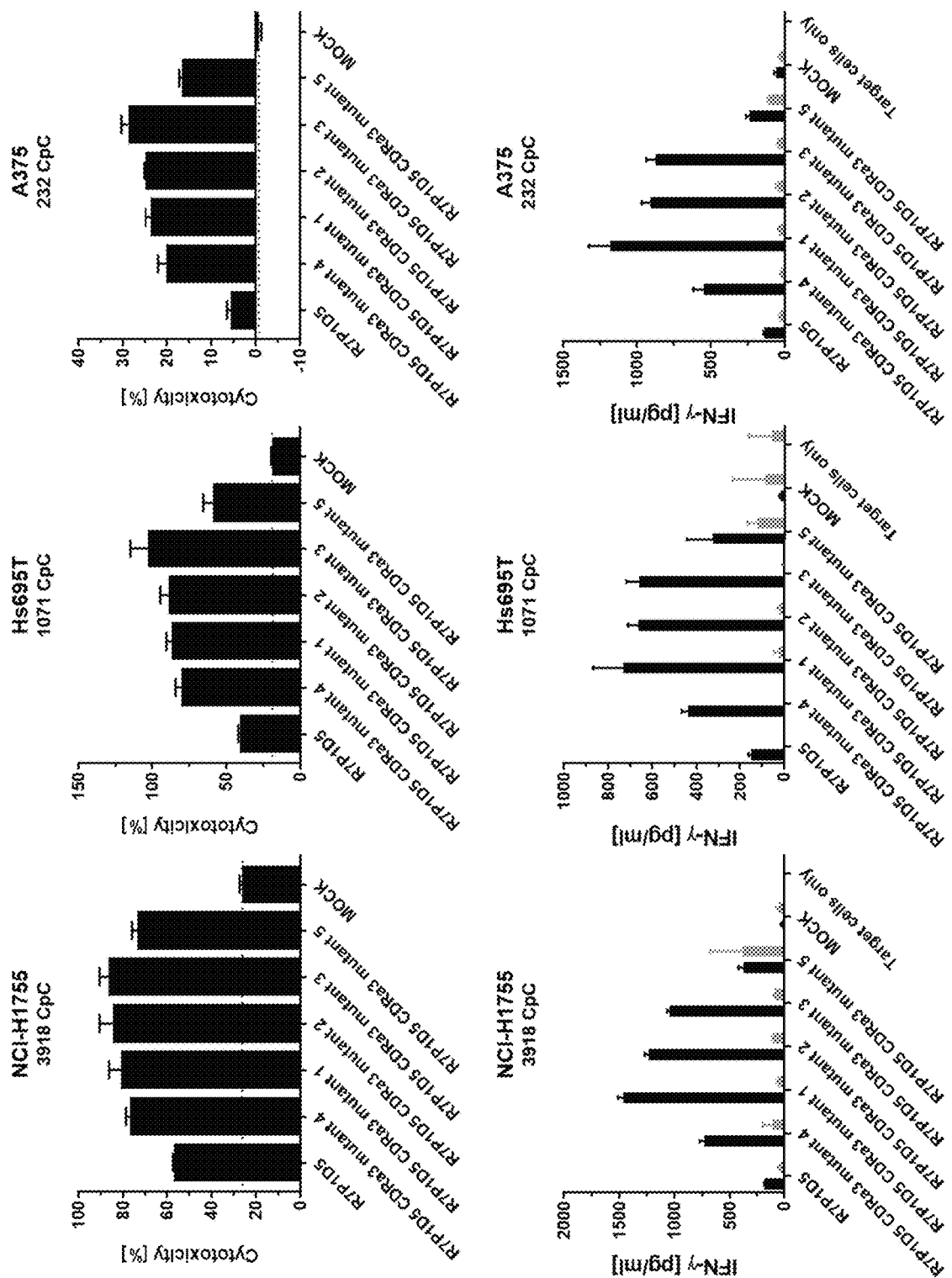
Figure 17B:
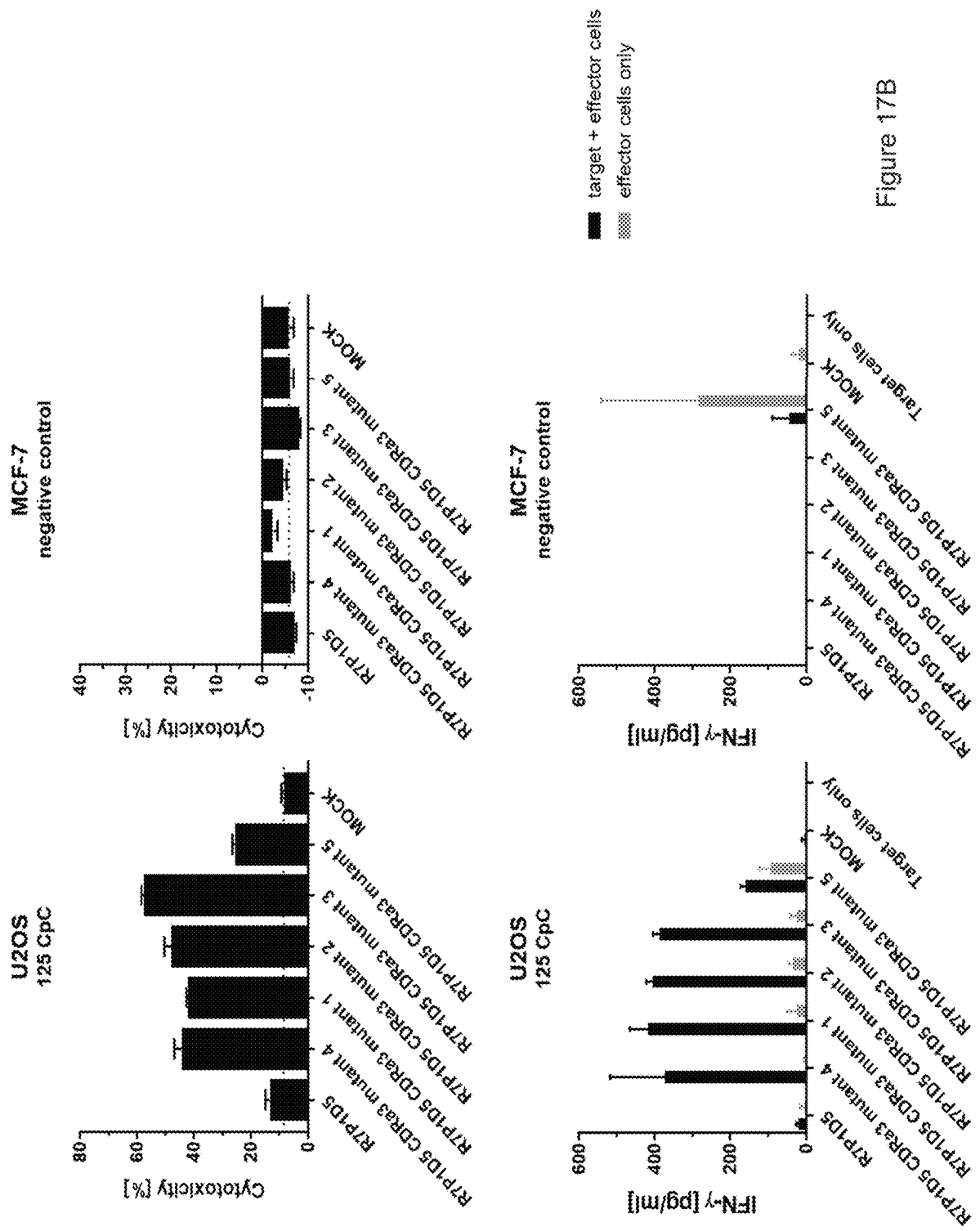

FIGS. 17A & 17B show cytotoxicity and IFN-gamma release of maturated R7P1D5 TCR variant expressing human CD8+ T cells in response to tumor cell lines presenting different copy numbers of HLA-A*02/MAG-003. For control purpose, no TCR (MOCK) or the 1G4 TCR specific for NYESO1-001 were expressed. LDH and IFN-gamma levels in the supernatants were determined after co-culture of electroporated CD8+ T cells with the tumor cell lines.

Figure 18:
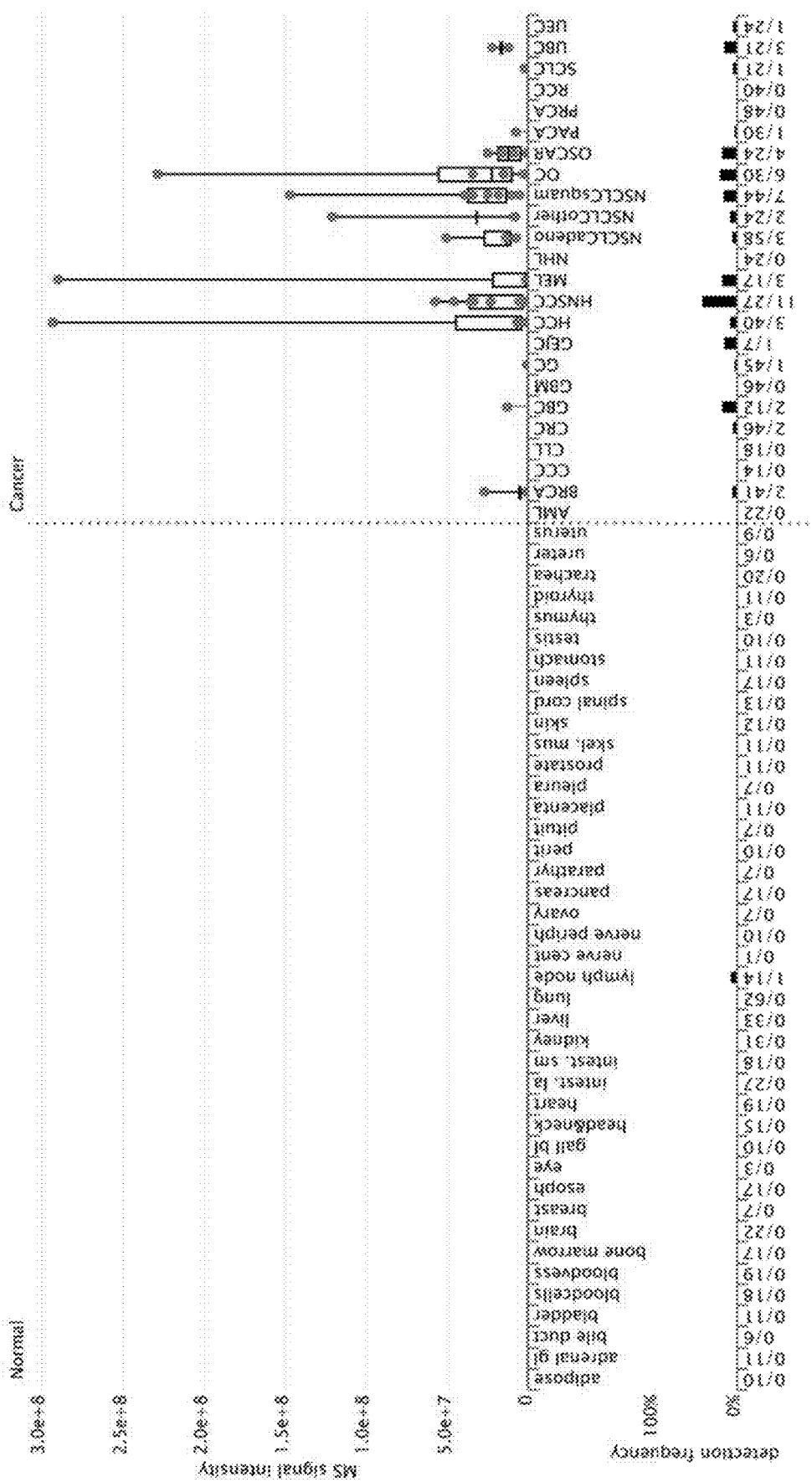

FIG. 18: Normal tissues and tumor samples analyzed for peptide presentation have been grouped according to their organ of origin. Upper part: Median MS signal intensities from technical replicate measurements and aliquot measurements are plotted as dots for single HLA-A*02 positive normal (left part of figure) and tumor samples (right part of figure) on which the peptide was detected. Box-and-whisker plots represent normalized signal intensities over multiple samples and have been defined in log space. Boxes display median, 25th and 75th percentile. Whiskers extend to the lowest data point still within 1.5 interquartile range (IQR) of the lower quartile, and the highest data point still within 1.5 IQR of the upper quartile. Lower part: The relative peptide detection frequency in every organ is shown as spine plot. Numbers below the panel indicate number of samples on which the peptide was detected out of the total number of samples evaluable for this analysis for each organ (N=581 for normal samples, N=771 for tumor samples). If the peptide has been detected on a sample but could not be quantified for technical reasons, the sample is included in this representation of detection frequency, but no dot is shown in the upper part of the figure.

Abbreviations used: adipose: adipose tissue; adrenal gl: adrenal gland; bladder: urinary bladder; bloodvess: blood vessel; esoph: esophagus; gall bl: gallbladder; intest. la: large intestine; intest. sm: small intestine; nerve cent: central nerve; nerve perith: peritheral nerve; parathyr: parathyroid gland; perit: peritoneum; pituit: pituitary; skel. mus: skeletal muscle; AML: acute myeloid leukemia; BRCA: breast cancer; CCC: cholangiocellular carcinoma; CLL: chronic lymphocytic leukemia; CRC: colorectal cancer; GBC: gallbladder cancer; GBM: glioblastoma; GC: gastric cancer; GEJC: gastro-esophageal junction cancer; HCC: hepatocellular carcinoma; HNSCC: head and neck squamous cell carcinoma; MEL: melanoma; NHL: Non-Hodgkin lymphoma; NSCL- Cadeno: non-small cell lung cancer adenocarcinoma; NSCLCother: NSCLC samples that could not unambiguously be assigned to NSCLCadeno or NSCLCsquam; NSCLCsquam: squamous cell non-small cell lung cancer; OC: ovarian cancer; OSCAR: esophageal cancer; PACA: pancreatic cancer; PRCA: prostate cancer; RCC: renal cell carcinoma; SCLC: small cell lung cancer; UBC: urinary bladder carcinoma; UEC: uterine and endometrial cancer.

EXAMPLES

T cell receptors (TCRs) against cancer antigens are often of lower affinity when compared to TCRs targeting viral antigens, and this may be one possible explanation for tumor immune escape (Aleksic et al. 2012, Eur J Immunol. 2012 December; 42(12):3174-9). Therefore, it is desirable to generate TCR variants with higher affinity for the use as cancer antigen-targeting constructs in an adoptive cell therapy, or as recognition module of a soluble therapeutic drug, i.e. bispecific molecules (Hickman et al. 2016, J Biomol Screen. 2016 September; 21(8):769-85). This invention thus relates to the modification and optimization of the T cell receptor R7P1D5, which was identified from the human natural TCR repertoire based on high avidity and selectivity for the tumor associated peptide MAG-003 (SEQ ID NO: 1). TCR R7P1D5 comprises an alpha variable domain with the amino acid sequence of SEQ ID NO: 4 and a beta variable domain with the amino acid sequence of SEQ ID NO: 11, which are disclosed in WO 2017/158103.

Example 1: Generation of Stable scTCR

For the present invention, the TCR R7P1D5 (SEQ ID NOs: 2 and 9, full length) was converted into a single chain TCR construct (scTCR R7P1D5, SEQ ID NO: 19) using the variable alpha (SEQ ID NO: 4) and beta (SEQ ID NO: 11) domains and an appropriate glycine-serine linker sequence. For TCR maturation via yeast surface display, the DNA of the corresponding sequence was synthesized and transformed into *Saccharomyces cerevisiae* EBY100 (MATa AGA1::GAL1¬1AGA1::URA3 ura3¬52 trp1 leu2¬idelta200 his3¬delta200 pep4::HIS3 prbd1.6R can1 GAL) (ATCC® MYA¬4941™) together with a yeast display vector containing a leader sequence and the Aga2p yeast mating protein (SEQ ID NO: 19), based on pCT302 (Boder and Wittrup, Methods Enzymol. 2000; 328:430-44). The resulting fusion protein after homologous recombination in the yeast (SEQ ID NO: 16) contains a leader peptide at the N-terminus of the Aga2p protein, responsible for the display of the protein of interest (Boder and Wittrup, Nat Biotechnol. 1997 June; 15(6):553-7), short peptide tags including linker sequences (SEQ ID NOs: 18 and 20) for expression controls and the protein of interest, namely the scTCR R7P1D5 (SEQ ID NO: 19) or its variants. Libraries of scTCR variants were generated via a random mutation PCR approach spanning the whole gene sequence of the scTCR R7P1D5. The transformation of yeast cells was performed as described in WO 2018/091396 and resulted in up to 109 yeast clones per library. The selection process for the yeast clones bearing mutant scTCR variants with improved binding to MAG-003 in the context of HLA-A*02 was essentially performed as described in Smith et al. (Methods Mol Biol. 2015; 1319:95-141). To ascertain high expression and correct conformation of yeast surface-displayed R7P1D5 scTCR variants, staining with an anti-Vbeta8 (Life technologies, clone 1C1) antibody was used, together with HLA-A*02/MAG-003 tetramer staining (FIG. 1). The scTCR conversion by yeast surface display revealed two crucial stabilizing mutations for the proper presentation of the scTCR on the cell surface, one in the framework region FR1-a (SEQ ID NO: 83) of the scTCR alpha chain and one in the CDR2 of the alpha chain (SEQ ID NO: 6), which resulted in the stabilized version scTCR R7P1D5S (SEQ ID NO: 22) showing improved HLA-A*02/MAG-003 tetramer binding.

Example 2: Affinity Maturation of Stabilized scTCR

To generate scTCR molecules with higher binding affinity towards HLA-A*02/MAG-003, all CDRs were maturated individually, using the previously identified stabilized scTCR R7P1D5S (SEQ ID NO: 22). The CDR residues were randomized by using degenerate DNA oligo primers essentially as described previously (Smith et al., Methods Mol Biol. 2015; 1319:95-141). The resulting DNA libraries were transformed as described in example 1. For preservation of binding specificity, negative selection was employed against a mix of HLA A*02 tetramers comprising normal tissue-derived peptides (SEQ ID NOs: 23 to 32) showing high degree of sequence similarity to MAG-003 peptide (SEQ ID NO 1).

For the selection of affinity enhanced and selective R7P1D5S scTCR variants, a decreasing concentration of HLA-A*02/MAG-003 tetramer or monomer was used for each selection round. After three selection rounds, single scTCR clones were isolated and sequenced, resulting in different affinity maturated CDR sequences. As exemplarily shown for scTCR with maturated CDRa3 sequences (SEQ ID NOs: 35 to 39), a strong improvement in HLA-A*02/MAG-003 monomer binding could be demonstrated. The selectivity of HLA-A*02/MAG-003 binding was retained as confirmed by the low binding to the mix of 10 HLA-A*02 tetramers containing normal tissue-derived peptides with high degree of sequence similarity to MAG-003 peptide (SEQ ID NO 1). CDRa3 mutant 5 (SEQ ID NO: 39) showed slightly increased cross-binding of tetrameric HLA-A*02/similar peptides (FIG. 2A). Additionally, the yeast clones with mutated CDRs alpha 2 (SEQ ID NOs 56, 57, 59), beta 1 (SEQ ID NO 62) or beta 2 (SEQ ID NOs 63, 64, 65, 66, 70) revealed strongly improved binding while specificity for HLA-A*02/MAG-003 was mainly retained (FIG. 2B).

Example 3: Use of Maturated TCRs for Cellular Expression

Modification of T cells to express TCRs recognizing a tumor-specific peptide-MHC is a promising strategy of redirecting T cells to cancer cells. The usage of maturated CDR3 sequences could improve reactivity of cell-bound TCRs against HLA-A*02/MAG-003 and the identified CDRa3 mutant sequences (SEQ ID NOs: 35 to 39) were grafted onto the parental TCR R7P1D5 alpha chain (SEQ ID NO: 2) and combined with the parental TCR R7P1D5 beta chain (SEQ ID NO: 9). The resulting mutant TCR variants (R7P1D5 CDRa3 mutant 1-5 comprising the alpha chain variant sequences SEQ ID NOs: 40 to 44, respectively) were expressed in human CD8+ T cells after electroporation of respective mRNA generated by in vitro transcription of PCR-amplified DNA constructs. For control purpose, the 1G4 TCR (SEQ ID NOs: 132 and 134) was expressed, which is directed against NYESO1-001 peptide (SEQ ID NO: 45) in complex with HLA-A*02. After overnight incubation of RNA-electroporated CD8+ T cells, expression of introduced TCR variants was analyzed by staining with PE-labeled peptide-HLA-A*02 tetramers and FITC-labeled anti-Vbeta 8 antibody. The parental TCR R7P1D5 and all variants derived thereof showed similar anti-Vbeta 8 staining when compared to the background levels from mock-electroporated sample and the Vbeta 8-negative NYESO1 TCR control, which argues for similar expression efficiency. In contrast, staining with HLA-A*02/MAG-003 tetramers was significantly increased for all R7P1D5 CDRa3 mutants when compared to the parental TCR R7P1D5 (FIG. 3), indicating an improved peptide-HLA binding of the mutant variants. Functional activation of CD8+ T cells (20,000 cells/well) expressing the different R7P1D5 TCR variants was investigated by measuring T cell-mediated IFN-gamma release in response to T2 target cells (20,000 cells/well) loaded with either a dilution series of MAG-003 (FIG. 4) or 10 µM of MAG-003 and potential off-target peptides (FIG. 5). Potential off-target peptides were selected from a database of normal tissue-presented HLA-A*02 bound peptides (XPRESIDENT database) based on high sequence similarity (similarity BLAST search) to MAG-003. Compared to the parental TCR R7P1D5, maturated R7P1D5 CDRa3 mutants 1-5 showed increased reactivity (FIG. 4) as indicated by the 3- to 9-fold lower concentration ($EC_{50}$ values, Table 3) required to induced half-maximal IFN-gamma release. As expected, only background IFN-gamma release was observed with T cells expressing no additional TCR (MOCK) or the 1G4 control TCR specific for NYESO1-001. To analyze the selectivity of MAG-003 recognition of the maturated R7P1D5 TCR variants, the IFN-gamma release in response to T2 cells loaded with different similar peptides (SEQ ID NOs: 23 to 34) was analyzed. Data were corrected for background IFN-gamma release by subtracting IFN-gamma levels released by mock-electroporated CD8+ T cells upon coculture with respectively loaded T2 cells. Except for R7P1D5 CDRa3 mutant 5 that showed slightly increased signals for several similar peptides and a low signal of R7P1D5 CDRa3 mutant 2 against MIA3-001, all other maturated R7P1D5 TCR variants were highly selective with no cross-reactivity towards the tested similar peptides (FIG. 5). As all TCR mutant variants induced considerably higher MAG-003-specific IFN-gamma release compared to the parental TCR, the R7P1D5 CDRa3 mutants 4, 1 and 3 (and potentially 2) are most promising candidates for cellular TCR-based tumor targeting. R7P1D5 CDRa3 mutants 1-5 were further characterized with respect to their binding epitope by mutational analysis. R7P1D5 CDRa3 mutants 1-4 showed a broad binding epitope with stringent recognition of positions 1, 5, 7, and 8 as alanine substitutions at these positions abrogated the response. For some R7P1D5 variants, such as mutant 1, a slight effect was also observed for alanine substitution at position 3. In accordance with its lower specificity shown with the similar peptides, the R7P1D5 CDRa3 mutant 5 TCR recognized positions 7 and 8 with reduced stringency when compared to mutant variants 1-4 (FIG. 6). The functional activity of the CDRa3 mutant TCR variants was further evaluated on tumor cell lines presenting different copy numbers of HLA-A*02/MAG-003. RNA-electroporated CD8+ T cells were cocultured with the tumor cell lines at an effector-to-target ratio of 3:1 (NCI-H1755, MCF-7: 25,000 cells/well; Hs695T, A375, U20: 12,500 cells/well). Expression of the introduced TCR variants in CD8+ T cells was verified as described above. After coculturing effector and target cells for 24 h, levels of LDH and IFN-gamma released into the supernatants were quantified. LDH levels were determined with CytoTox 96 Non-Radioactive Cytotoxicity Assay Kits (PROMEGA) and cytotoxicity was calculated as percentage of the total lysis control after subtracting spontaneous LDH release of effector and target cells. All CDRa3 mutant TCR variants induced stronger killing of all analyzed tumor cell lines compared to the parental TCR, while no killing was observed for target-negative MCF-7 cells. For tumor cell lines presenting lower target copy numbers (A375, U205), only minimal cytotoxicity was found for the wildtype TCR, whereas especially the maturated variants 1-4 were able to induce substantial killing, which indicates that these variants will allow treatment of patient populations with low target copy numbers. In line with the cytotoxicity data, also enhanced IFN-gamma release was observed for T cells expressing the maturated TCR variants compared to the wildtype.

TABLE 3

Concentrations of half-maximal IFN-gamma release [nM] of parental R7P1D5 and CDRa3 mutant variants 1-5. The parental TCR R7P1D5 is based on SEQ ID NOs 2 and 11 and the mutant variant TCRs 1-5 are based on SEQ ID NOs: 40 to 44, respectively, and SEQ ID NO: 11.

| Variant | $EC_{50}$ [nM] |
| --- | --- |
| R7P1D5 | 9.5 |
| R7P1D5 CDRa3 mutant 4 | 1.4 |
| R7P1D5 CDRa3 mutant 1 | 2.1 |
| R7P1D5 CDRa3 mutant 2 | 1.4 |
| R7P1D5 CDRa3 mutant 3 | 1.1 |
| R7P1D5 CDRa3 mutant 5 | 3.7 |

Example 4: Production, Purification and Characterization of scTCR Variants

TCRs consisting of Valpha and Vbeta domains were designed, produced and tested in a single-chain (scTCR) format in conjunction with a Fab fragment derived from humanized CD3-specific T cell-recruiting antibody UCHT1. Therefore, plasmids containing either the light chains of humanized UCHT1 antibodies (SEQ ID No: 123 for variant S and SEQ ID No: 80 for other variants except S) or the respective scTCR sequences coupled to the C-terminus of $V_H$-$C_{H1}$ of the humanized UCHT1 antibody, controlled by HCMV-derived promoter elements, were generated.

TABLE 4

Combinations of sequences for the generation of scTCR variants expressed in conjunction with a Fab fragment. For transfections plasmids containing the light chain sequence were mixed with plasmids containing respective Fab heavy chain sequence.

| Variant | Light Chain (SEQ ID No:) | Heavy chain (SEQ ID No:) |
| --- | --- | --- |
| S | 123 | 124 |
| I | 80 | 126 |
| #1 | 80 | 58 |
| #2 | 80 | 76 |
| #19 | 80 | 125 |
| #20 | 80 | 60 |
| #21 | 80 | 61 |
| #29 | 80 | 67 |
| #30 | 80 | 68 |
| #31 | 80 | 69 |
| #32 | 80 | 75 |

Plasmid DNA was amplified in *E. coli* according to standard culture methods and subsequently purified using commercial-available kits (Macherey & Nagel). Purified plasmid DNA was used for transient transfection of CHO-S cells according to instructions of the manufacturer (ExpiCHO™ system; Thermo Fisher Scientific). Transfected CHO-cells were cultured 10-12 days at 32° C. to 37° C. and received one feeds of ExpiCHO™ Feed. Conditioned cell supernatant was cleared by filtration (0.22 μm) utilizing Sartoclear Dynamics® Lab Filter Aid (Sartorius). Bispecific antigen binding proteins were purified using an Akta Pure 25 L FPLC system (GE Lifesciences) equipped to perform affinity and size-exclusion chromatography in line. Affinity chromatography was performed on protein L columns (GE Lifesciences) following standard affinity chromatographic protocols. Size exclusion chromatography was performed directly after acidic elution (pH 2.8) from the affinity column to obtain highly pure monomeric protein using, Superdex 200 pg 16/600 columns (GE Lifesciences) following standard protocols. Protein concentrations were determined on a NanoDrop system (Thermo Scientific) using calculated extinction coefficients according to predicted protein sequences. Concentration was adjusted, if needed, by using Vivaspin devices (Sartorius). Finally, purified molecules were stored in phosphate-buffered saline (DPBS, pH 7.2) at concentrations of about 1 mg/mL at temperatures of 2-8° C. Productivity of each molecule was assessed by calculating the yield as [milligram protein purified/liter cell supernatant].

Quality of purified scTCR-Fab antigen binding proteins was determined by HPLC-SEC on MabPac SEC-1 columns (5 lam, 7.8×300 mm) running in 50 mM sodium-phosphate pH 6.8 containing 300 mM NaCl within a Vanquish uHPLC-System. Detector wavelength was set to 214 nm. Using the same methodology heat-stressed samples of the respective molecules (after storage for 7 or 14 days at 40° C. in DPBS at 1 mg/mL) were analyzed. Induced aggregates were calculated as [% aggregates (after stress)]–[% aggregates (start)]. Monomer recovery was calculated as [monomer peak area (after stress)]/[monomer peak area (start)]×100%. As shown in FIG. 7A, pronounced differences in production yield (left panel) and heat stress stability were observed among the different scTCR variants. The stabilized scTCR variant S (SEQ ID No: 124) containing wild-type CDR-sequences combined with two framework mutations (aS19A, aF57Y) could only be expressed at low levels. Increased expression levels and increased heat-stress stability could be achieved after the incorporation of affinity-maturated CDRa2, CDRa3 and CDRb1 sequences (variant #1) and affinity-maturated CDRa2, CDRa3 and CDRb1 sequences together with an affinity-maturated CDRb2 sequence in conjunction with the adjacent framework mutation bI66C (variant I). Using both CDR-maturated scTCR variants, I and #1, further modifications of the framework regions were tested to improve expression yield and heat-stress stability. Incorporation of 3 framework mutations (aL50P, bM46P and bM47G) into variant #1 generated variant #30 with increased production yield, which could be further improved by replacing the framework mutation aS19A to aS19V (variant #32). The impact of the aS19A or aS19V mutation is highlighted by variant #29 representing variant #32 with a aS19 backmutation, which resulted in strongly reduced productivity and elevated aggregation levels. Notably, the latter negative effect of the aS19 backmutation on production yield could be reversed by the introduction of the framework mutation aA48K (variant #31). In the context of the CDR-maturated scTCR variant I, an additional framework mutation bI54F (variant #19) and a bN109D mutation in the beta chain CDR3 (variant #20) was tested alone or in combination (variant #21). The mutation bN109D in CDRb3 converted a NT-motif, which is potentially prone to deamidiation of the Asn-residue, into a DT motif, which could be of advantage in terms of design approaches to remove sequence liabilities within the CDR sequences. Introduction of a bI54F framework mutation into variant I (variant #19) resulted in improved yield and improved heat-stress stability of the scTCR. The additional introduction of the CDRb3 mutation bN109D into variant #19 generated the scTCR variant #21 with further strongly improved heat stress-stability albeit the bN109D mutation alone (variant #20) showed only slightly improved productivity and similar stability when compared to variant I.

The scTCR-Fab antigen binding proteins were analyzed for their binding affinity towards the MAGE-A antigenic peptide of SEQ ID NO: 1 in complex with HLA-A*02 via biolayer interferometry. Measurements were performed on an Octet RED384 system using settings recommended by the manufacturer. Briefly, binding kinetics were measured at 30° C. and 1000 rpm shake speed using PBS, 0.05% TWEEN® 20 (polysorbate 20), 0.1% BSA as buffer. Bispecific molecules were loaded onto biosensors (FAB2G) prior to analyzing serial dilutions of the peptide-HLA-A*02 complex. The bispecific antigen binding protein comprising a stabilized scTCR variant S (SEQ ID NOs: 123 and 124) showed only very weak binding signals up to a concentration of 500 nM (FIG. 7B, Table 5). Introducing affinity-maturated CDRa2, CDRa3 and CDRb1 sequences (variant #1 and variant #2) strongly improved binding towards target peptide-MHC. $K_D$ values of 2-3 nM were determined for variants #1 (SEQ ID NOs: 80, 58) and #2 (SEQ ID NOs: 80, 76). The additional inclusion of a maturated CDRb2 sequence together with the framework mutation bI66C into the scTCR variant #2 led to a further improvement in binding affinity with a measured $K_D$ of 150 pM for variant I (SEQ ID NOs: 80, 126).

TABLE 5

Framework mutations, CDR combinations and $K_D$ values of variants S (SEQ ID NOs: 123, 124), #1, #2 and I (SEQ ID NOs: 80 combined with 58, 76 or 126, respectively). $K_D$ values were measured by biolayer interferometry.

| TCR variant | CDRa1 | CDRa2 | CDRa3 | CDRb1 | CDRb2 | CDRb3 | $K_D$ [M] |
|---|---|---|---|---|---|---|---|
| S aS19A | DSSSTY SEQ ID NO 5 | IYSNMDM SEQ ID NO 21 | CAEYSSASKIIF SEQ ID NO 7 | SGHDY SEQ ID NO 12 | FNNNVP SEQ ID NO 13 | CASRANTGELFF SEQ ID NO 14 | —* |
| #1 aS19A | DSSSTY SEQ ID NO 5 | IYSSQDQ SEQ ID NO 56 | CAEMTSESKIIF SEQ ID NO 35 | PGHDY SEQ ID NO 62 | FNNNVP SEQ ID NO 13 | CASRANTGELFF SEQ ID NO 14 | 2.35E-09 |

TABLE 5-continued

Framework mutations, CDR combinations and $K_D$ values of variants S (SEQ ID NOs: 123, 124), #1, #2 and I (SEQ ID NOs: 80 combined with 58, 76 or 126, respectively). $K_D$ values were measured by biolayer interferometry.

| TCR variant | CDRa1 | CDRa2 | CDRa3 | CDRb1 | CDRb2 | CDRb3 | $K_D$ [M] |
|---|---|---|---|---|---|---|---|
| #2 aS19A | DSSSTY SEQ ID NO 5 | IYSSQDS SEQ ID NO 59 | CAEMTSESKIIF SEQ ID NO 35 | PGHDY SEQ ID NO 62 | FNNNVP SEQ ID NO 13 | CASRANTGELFF SEQ ID NO 14 | 2.69E-09 |
| I aS19A bI66C | DSSSTY SEQ ID NO 5 | IYSSQDS SEQ ID NO 59 | CAEMTSESKIIF SEQ ID NO 35 | PGHDY SEQ ID NO 62 | FCYGTP SEQ ID NO 65 | CASRANTGELFF SEQ ID NO 14 | 1.53E-10 |

*no relevant binding signals up to 500 nM

The scTCR-Fab antigen binding proteins were further characterized with respect to their specificity by analyzing binding to potential off-target peptides in complex with HLA-A*02. Potential off-target peptides were selected from a database of normal tissue-presented HLA-A*02 bound peptides (XPRESIDENT database) based on sequence similarity as determined by similarity BLAST search. Binding was analyzed via biolayer interferometry essentially as described above. Binding signals of all interactions were determined at a concentration of 1 µM bispecific scTCR-Fab using HIS1K biosensors to load peptide-HLA-A*02 complexes. Potential off-target peptides were analyzed with respect to their binding response at the end of the association phase. In comparison to the scTCR variant I (SEQ ID NO: 80, 126), the variant #19 (SEQ ID NO: 80, 125) comprising the additional framework mutation bI54F showed an improved binding specificity (FIG. 7C, Table 6) besides the improved production yield and stability as shown above. While binding curves for MAG-003 (SEQ ID NO: 1) were similar for both variants (FIG. 7C), variant #19 showed abrogated binding to the off-target peptides SYNE3-001 (SEQ ID NO: 27), TPX2-001 (SEQ ID NO: 26) and PSME2-001 (SEQ ID NO: 30) as shown by lack of binding signals (Table 6).

TABLE 6

Specificity of scTCR-Fab antigen binding proteins with scTCR variant I (SEQ ID NO: 80, 126) and variant #19 (SEQ ID NO: 80, 125). Binding kinetics of 1 µM bispecific was measured via biolayer interferometry. Responses at the end of the association phase (in nm or as % of MAG-003 signal) are shown.

| Loading Sample ID | I Response | I Response (% of MAG-003) | #19 Response | #19 Response (% of MAG-003) |
|---|---|---|---|---|
| MAG-003 | 0.738 | 100.0 | 0.719 | 100.0 |
| SYNE3-001 | 0.226 | 30.6 | -0.006 | -0.9 |
| TPX2-001 | 0.136 | 18.4 | -0.003 | -0.3 |
| PSME2-001 | 0.074 | 10.0 | -0.010 | -1.4 |

Example 5: Production, Purification and Characterization of Bispecific TCER™ Molecules FIG. 15 shows a bispecific TCER™ molecule in accordance with one embodiment of the present disclosure. Bispecific T cell-engaging receptors (TCER™) are fusion proteins containing the variable domains (Vα, Vβ) of an affinity-matured TCR and the variable domains (VH, VL) of a humanized T cell-recruiting antibody. The molecules use an effector function-silenced Fc part, which confers extended half-life and also improved stability/manufacturability characteristics.

Bispecific TCER™ molecules were designed based on selected TCR alpha and beta chain variable domains with preferred CDR and framework mutations, as described in example 4. The respective TCR variable domains of scTCR variant #21 were combined with the beneficial framework mutations aS19V and aA48K resulting in TCR variant #114-iso0 (SEQ ID NO: 138 and SEQ ID No: 150). To further optimize the variable domain sequence of TCR #114-iso0, two potential isomerization sites (DS-motives) located within the CDRa1 (aD27E) and CDRa2 (aS65Q), respectively, were substituted resulting in TCR variants #114-iso1 (SEQ ID NO: 151 and SEQ ID No: 150) and 114-iso2 (SEQ ID NO: 152 and SEQ ID NO: 150) having one or none, respectively, post-translational modification consensus sequences within the CDRs. The above described variable domains of TCR variants #114-iso0, #114-iso1 and #114-iso2 were combined with VL- and VH-domains derived from variants derived from two newly humanized T cell-recruiting antibodies BMA031(36) (SEQ ID NO: 159 and 160), UCHT1(17) (SEQ ID NO: 153 and 154) and different UCHT1(17) variants UCHT1(17opt) (SEQ ID No: 153 and 162), UCHT1(21) (SEQ ID No: 153 and 164) and UCHT1(23) (SEQ ID No: 153 and 156), respectively.

Using a TCR/antibody diabody-$F_c$ format we designed TCER™ molecules (exemplary full-lengths sequences shown in Table 7) and respective vectors with mono-cistronic, controlled by HCMV-derived promoter elements, pUC19-derivatives. Plasmid DNA was amplified in E. coli according to standard culture methods and subsequently purified using commercial-available kits (Macherey & Nagel). Purified plasmid DNA was used for transient transfection of CHO-S cells utilizing an electroporation systems (MaxCyte STX). Transfected CHO-cells were cultured 10-12 days at 32° C. to 37° C. and received one to three feeds of Cellboost 7a and 7b (GE Healthcare™) solution.

TABLE 7

Combination of TCR variable domain sequences and T cell-recruiting antibody variable domain sequences for the generation of the respective variants of TCER ™ molecules. For transfections plasmids containing chain A and plasmids containing chain B were mixed.

| TCER ™ molecule | Chain A SEQ ID No: | Chain B SEQ ID No: |
|---|---|---|
| 114-iso0-UCHT1(17) | 127 | 130 |
| 114-iso1-UCHT1(17) | 131 | 130 |

TABLE 7-continued

Combination of TCR variable domain sequences and T cell-recruiting antibody variable domain sequences for the generation of the respective variants of TCER ™ molecules. For transfections plasmids containing chain A and plasmids containing chain B were mixed.

| TCER ™ molecule | Chain A SEQ ID No: | Chain B SEQ ID No: |
|---|---|---|
| 114-iso2-UCHT1(17) | 133 | 130 |
| 114-iso0-BMA(36) | 135 | 136 |
| 114-iso1-BMA(36) | 137 | 136 |
| 114-iso2-BMA(36) | 139 | 136 |

Conditioned cell supernatant was cleared by filtration (0.22 μm) utilizing Sartoclear Dynamics® Lab Filter Aid (Sartorius). Bispecific antigen binding proteins were purified using an AKTA Pure 25 L FPLC system (GE Lifesciences) equipped to perform affinity and size-exclusion chromatography in line. Affinity chromatography was performed on MAB SELECT SURE or protein L columns (GE Lifesciences) following standard affinity chromatographic protocols. Size exclusion chromatography was performed directly after elution (pH 2.8) from the affinity column to obtain highly pure monomeric protein using, Superdex SUPERDEX 200 μg 26/600 columns (GE Lifesciences) following standard protocols. Protein concentrations were determined on a NANODROP system (Thermo Scientific) using calculated extinction coefficients according to predicted protein sequences. Concentration was adjusted, if needed, by using VIVASPIN devices (Sartorius). Finally, purified molecules were stored in phosphate-buffered saline at concentrations of about 1 mg/mL at temperatures of 2-8° C.

Quality of purified bispecific antigen binding proteins was determined by HPLC-SEC on MABPAC SEC-1 columns (5 μm, 4×300 mm) running in 50 mM sodium-phosphate pH 6.8 containing 300 mM NaCl within a Vanquish uHPLC-System. Detector wavelength was set to 214 nm. Induced aggregates were calculated as [% aggregates (after stress)]−[% aggregates (start)]. Monomer recovery was calculated as [monomer peak area (after stress)]/[monomer peak area (start)]×100%.

Productivity and stress stability data of different TCER™ molecules are shown in FIG. 8A. All variants, except for variant 114-iso1-UCHT1(17opt), showed a production yield of more than 10 mg/l (FIG. 8, left panel). Heat-stress testing of the molecules at 40° C. revealed very good to acceptable stabilities for all produced TCER™ molecules showing less than 10% aggregate formation upon 14 days of heat-stress (FIG. 8A, right panel).

Using biolayer interferometry, bispecific TCER™ antigen binding proteins comprising TCR variants 114-iso0, 114-iso1 and 114-iso2 in combination with UCHT1(17) and BMA031(36), respectively (as shown in Table 7), were characterized for their binding affinity towards the MAGE-A antigenic peptide (SEQ ID NO: 1) in complex with HLA-A*02 (FIG. 8A, Table 8). Measurements were performed on an Octet RED384 system using settings recommended by the manufacturer. Briefly, binding kinetics were measured at 30° C. and 1000 rpm shake speed using PBS, 0.05% TWEEN® 20 (polysorbate 20), 0.1% BSA as buffer. Peptide-HLA-A*02 complexes were loaded onto biosensors (HIS1K) prior to analyzing serial dilutions of the bispecific TCER™ molecules. TCER™ variants 114-iso0, 114-iso1 and 114-iso2 bound strongly to MAG-003 in complex with HLA-A*02 with comparable $K_D$ values of 1.8 nM, 2.0 nM and 2.3 nM, respectively, indicating that HLA-A*02/MAG-003 binding is not affected by the removal of the two isomerization sites in the CDRa1 (aD27E) and CDRa2 (aS65Q) of the TCR variable alpha domain.

TABLE 8

Affinity analysis of TCER ™ variants 114-iso0, 114-iso1 and 114-iso2 in combination with UCHT1(17) and BMA031(36) as shown in Table 7. $K_D$ values were measured by biolayer interferometry.

| | UCHT1(17) | | | BMA031(36) | | |
|---|---|---|---|---|---|---|
| | 114-iso0 | 114-iso1 | 114-iso2 | 114-iso0 | 114-iso1 | 114-iso2 |
| $K_D$(MAG-003) [M] | 1.79E−09 | 1.97E−09 | 2.32E−09 | 1.79E−09 | 1.97E−09 | 2.42E−09 |

TCR variants 114-iso0, 114-iso1 and 114-iso2 were furthermore characterized with respect to their specificity by analyzing binding to normal tissue-derived off-target peptides using biolayer interferometry. Measurements were performed as described above. Binding affinities of 114-iso0-UCHT1(17) for MAG-003 (SEQ ID NO: 1) and off-target peptides CNOT1-003 (SEQ ID NO: 32), COL6A3-010 (SEQ ID NO: 179), FAM115A-001 (SEQ ID NO: 180), HEATR5A-001 (SEQ ID NO: 31), HERC4-001 (SEQ ID NO: 29), INTS4-002 (SEQ ID NO: 171), PHTF2-001 (SEQ ID NO: 181), PPP1CA-006 (SEQ ID NO: 173), RPL-007 (SEQ ID NO: 174), RPP1-001 (SEQ ID NO: 182), SAMH-001 (SEQ ID NO: 172), SETD1A-001 (SEQ ID NO: 175) in complex with HLA-A*02 were determined and affinity windows were calculated. Affinity windows ranged from more than 200-fold to no off-target binding at all (Table 9). Specificities of 114-iso1-BMA(36) and 114-iso2-UCHT1 (17) were analyzed by measuring binding signals for MAG-003 (SEQ ID NO: 1) and off-target peptides ODC-001 (SEQ ID NO: 178), NOMAP-1-0320 (SEQ ID NO: 176) and NOMAP-1-1223 (SEQ ID NO: 177) in complex with HLA-A*02 at a concentration of 1 μM TCER™ (FIG. 8C, Table 10). Binding responses of 1% of the MAG-003 signal or lower were detected demonstrating high specificity of the TCR variants for MAG-003.

TABLE 9

Specificity of TCER ™ molecule 114-iso0-UCHT1(17). $K_D$ values were measured by biolayer interferometry analyzing a serial dilution of 114-iso0-UCHT1(17) (500 nM, 250 nM, 125 nM, 62.5 nM). Affinity windows were calculated as $K_D$(similar peptide)/$K_D$(MAG-003).

| | $K_D$ [M] | $K_D$(similar peptide)/$K_D$(MAG-003) |
|---|---|---|
| MAG-003 | 1.56E−09 | — |
| CNOT1-003 | 1.64E−06 | 1050 |
| COL6A3-010 | 9.03E−07 | 579 |

TABLE 9-continued

Specificity of TCER ™ molecule 114-iso0-UCHT1(17).
$K_D$ values were measured by biolayer interferometry
analyzing a serial dilution of 114-iso0-UCHT1(17) (500 nM, 250 nM,
125 nM, 62.5 nM). Affinity windows were calculated as $K_D$(similar
peptide)/$K_D$(MAG-003).

| | $K_D$ [M] | $K_D$(similar peptide)/$K_D$(MAG-003) |
|---|---|---|
| FAM115A-001 | 7.84E-07 | 503 |
| HEATR5A-001 | 3.70E-07 | 238 |
| HERC4-001 | 4.91E-07 | 315 |
| INTS4-002 | 1.98E-06 | 1273 |
| PHTF2-001 | 1.02E-06 | 656 |
| PPP1CA-006 | no binding | no binding |
| RPL-007 | no binding | no binding |
| RPP1-001 | 8.97E-07 | 576 |
| SAMH-001 | 2.11E-06 | 1356 |
| SETD1A-001 | no binding | no binding |

TABLE 10

Specificity of TCER ™ molecules 114-iso1-BMA(36) and
114-iso2-UCHT1(17). Binding kinetics of 1 µM TCER ™ was
measured via biolayer interferometry. Responses at the end
of the association phase (in nm or as % of MAG-003 signal) are shown.

| | 114-iso1-BMA(36) | | 114-iso2-UCHT1(17) | |
|---|---|---|---|---|
| Loading Sample ID | Response | Response (% of MAG-003) | Response | Response (% of MAG-003) |
| MAG-003 | 0.8246 | 100.0 | 0.8233 | 100.0 |
| ODC-001 | 0.0061 | 0.7 | 0.0104 | 1.3 |
| NOMAP-1-0320 | 0.0025 | 0.3 | 0.0025 | 0.3 |
| NOMAP-1-1223 | 0.0005 | 0.1 | 0.0057 | 0.7 |

Example 6: TCER™-Mediated Killing of MAG-003-Positive and Tumor Cell Lines

Maturated TCR variants were expressed as soluble TCER™ molecules #114-iso0-UCHT1(17), #114-iso1-UCHT1(17), #114-iso2-UCHT1(17), #114-iso0-BMA031(36), #114-iso1-BMA031(36) and #114-iso2-BMA031(36) employing a TCR/antiCD3 diabody-Fc format (see also Table 7). The cytotoxic activity of the bispecific TCER™ molecules against MAG-003-positive and MAG-003-negative tumor cell lines, respectively, was analyzed by LDH-release assay. Therefore, tumor cell lines presenting different amounts of HLA-A*02/MAG-003 molecules on the cell surface were co-incubated with PBMC from healthy HLA-A*02+ donors in presence of increasing concentrations of TCER™ molecules. After 48 hours, lysis of target cell lines was measured utilizing CytoTox 96 Non-Radioactive Cytotoxicity Assay Kits (PROMEGA). As shown in FIG. 9 and FIG. 10, TCER™ molecules exhibited efficient lysis of MAG-003-positive tumor cell lines Hs695T, A375 and U2OS displaying 1100, 230 and 120 copies per tumor cell, respectively, as determined by mass-spectrometry-based quantification of HLA-A*02/MAG-003 complexes. For killing assays, PBMC from two healthy donors (HBC-720 in FIG. 9 and HBC-982 in FIG. 10) were used. Within the same experiments the cell line BV-173 expressing HLA-A*02 but not presenting the peptide MAG-003 at detectable levels, no or only marginal lysis of cells was induced by the bispecific TCER™ molecules indicating the specificity of the TCR domains.

Example 7: In Vivo Efficacy in Tumor Xenograft Bearing NOG Mice

A pharmacodynamic study was performed in the hyper immune-deficient NOG mouse strain to test the ability of TCER™ molecules in recruiting the activity of human immune T cells by specific binding to a T cell antigen and by specific binding to a human tumor-specific HLA-peptide complex on human cancer cells. The NOG mouse strain hosting the subcutaneously injected human tumor cell line HS695T were intravenously injected with human peripheral blood mononuclear (PBMC) cell xenografts. The human PBMC ($1\times10^7$ cells/mouse) were transplanted within 24 hours when individual Hs695T tumor volume reached 50 mm$^3$ as calculated after caliper measurements. Treatment was initiated within one hour after transplantation of human blood cells. Eight to ten female mice per group (randomized according to tumor size) received intravenous bolus injections (5 mL/kg body weight, twice weekly dosing, six doses) into the tail vein. The injected dose of TCER™ molecules was 0.5 (group 2) and 0.05 (group 3 and 4) mg/kg body weight×injection, PBS was used in the vehicle control group (group 1). As shown in FIG. 11 for individual mice, the treatment with TCER™ molecules induced pronounced anti-tumor responses. Treatment with a TCER™ (SEQ ID NO: 169 and 170) targeting PRAME-004 (SEQ ID NO: 168, group 2) strongly inhibited tumor growth as indicated by reduced increase of mean tumor volume from basal levels (start of randomization) of 90 mm$^3$ to 209 mm$^3$ at day 25 in comparison to the increase observed in the vehicle control group 1 from basal levels of 74 mm$^3$ to 1081 mm$^3$ at day 25. Treatment with TCER™ targeting MAG-003 (SEQ ID NO: 127 and 130, group 3; SEQ ID NO: 135 and 136, group 4) induced complete remission of the Hs695T tumor in all mice at Day 18 until the end of the study at Day 25 compared to basal levels of 86 mm$^3$ (group 3) and 80 mm$^3$ (group 4) at the day of randomization.

Example 8: In-Vitro Safety on Primary Healthy Cells

The safety profile of TCER™ molecule 114-iso1-BMA(36) was assessed in LDH-killing experiments with human normal tissue primary cells of different organs. FIG. 12 shows the results of co-cultures of 11 different primary healthy tissue cells (HLA-A*02+) with PBMC effector cells from healthy HLA-A*02+ donors at a ratio of 1:10 in presence of increasing TCER™ concentrations. The cells were co-incubated in a 1:1 mixture of normal tissue primary cell-specific medium and T cell medium. To determine a safety window, the TCER™ molecules were co-incubated in an identical setup with the MAG-003-positive tumor cell line Hs695T in the respective medium combination of the normal tissue primary cells. After 48 h of co-culture, supernatants were harvested and tumor cell lysis was analyzed by measuring LDH-release using the LDH-Glo™ Kit (Promega).

In FIG. 12, each cytotoxicity plot shows LDH-release of a normal tissue primary cell type (empty circles) in comparison to the control tumor cell line Hs695T (filled circles) in the same medium combination after co-incubation with PBMCs and increasing concentrations of the TCER molecule. In all cases the response against normal tissue primary cells was too low to calculate an EC$_{50}$. Instead, we defined the safety window based on the lowest observed effect level (LOEL) determined as the first TCER™ concentration with a response over cut-off value. The cut-off was defined as ([standard deviation from all triplicates×3]+control normal tissue sample w/o TCER™) and is indicated as dotted line in each cytotoxicity plot. For each normal tissue cell type, the LOEL-based safety window was determined to be larger than 1,000-fold.

The safety profile of TCER™ molecule 114-iso1-BMA (36) was assessed in second LDH-killing experiment with 12 different primary healthy tissue cells (HLA-A*02+) of which some were overlapping with the first experiment. Experimental conditions were used as described above.

In FIG. 16, each cytotoxicity plot shows LDH-release of a normal tissue primary cell type (empty circles) in comparison to the control tumor cell line Hs695T (filled circles) in the same medium combination after co-incubation with PBMCs and increasing concentrations of the TCER™ molecule. In all cases the response against normal tissue primary cells was too low to calculate an $EC_{50}$. Instead, we defined the safety window based on the lowest observed effect level (LOEL) determined as the first TCER™ concentration with a response over cut-off value. The cut-off was defined as ([standard deviation from all triplicates×3]+control normal tissue sample w/o TCER™) and is indicated as dotted line in each cytotoxicity plot. For each normal tissue cell type, the LOEL-based safety window was determined to be larger than 1,000-fold.

Example 9: In Vivo Efficacy with a Once Weekly Treatment in Tumor Xenograft Bearing NOG Mice A pharmacodynamic study was performed in the hyper immune-deficient NOG mouse strain to test the ability of TCER™ molecules in recruiting the activity of human immune T cells by specific binding to a T cell antigen and by specific binding to a human tumor-specific HLA-peptide complex on human cancer cells. The NOG mouse strain hosting the subcutaneously injected human tumor cell line Hs695T were intravenously injected with human peripheral blood mononuclear (PBMC) cell xenografts. The human PBMC ($1×10^7$ cells/mouse) were transplanted within 24 hours when individual Hs695T tumor volume reached 50 $mm^3$ as calculated after caliper measurements. Treatment was initiated within one hour after transplantation of human blood cells. Six to ten female mice per group (randomized according to tumor size) received intravenous bolus injections (5 mL/kg body weight, once weekly dosing, three doses) into the tail vein. The injected dose of TCER™ molecules was 0.01 mg/kg body weight×injection (group 2 and 3), PBS was used in the vehicle control group (group 1). As shown in FIG. 13, the treatment with TCER™ molecules induced pronounced anti-tumor responses. Treatment with MAG-003 TCER™ molecules 114-iso1-BMA(36) (SEQ ID NO: 137 and 136, group 2) and 114-iso1-UCHT1($V_{17}$opt) (SEQ ID NO: 131 and 167, group 3) induced remission of the Hs695T tumor in all mice at day 21. Tumor growth was strongly inhibited as indicated by reduced increase of mean tumor volume from basal levels (start of randomization) of 84 $mm^3$ to 8 $mm^3$ (group 2) and of 83 $mm^3$ to 14 $mm^3$ (group 3) at day 21 in comparison to the increase observed within the vehicle control (group 1) from basal levels of 85 $mm^3$ to 1024 $mm^3$ at day 21. Complete remission was observed in 2 mice of group 2 and 2 mice of group 3.

Example 10: In Vivo Pharmacokinetics in NOG Mice

Pharmacokinetic properties of TCER™ 114-iso1-UCHT1 (17) (SEQ ID NOs: 130 and 131) were analyzed in hyper immune-deficient NOG mice receiving a single intravenous injection of 2 mg/kg body weight. Plasma samples were collected from the retro-bulbar plexus at time points 0 h, 0.1 h, 2 h, 8 h, 24 h, 48 h, 120 h, 240 h and 360 h. Plasma levels of 114-iso1-UCHT1(17) were determined by ELISA using two different assay set-ups ($F_c$-$V_L$ assay and CD3—pMHC assay). Using the $F_c$-$V_L$ assay set-up, TCER™ plasma level were quantified by detecting the respective protein subunits. Briefly, goat anti-human IgG $F_c$ was coated at a concentration of 2 µg/ml in PBS at 4° C. overnight. Remaining binding sites were blocked using PBS containing 2% BSA. Samples diluted in blocking buffer were incubated for 1 h at room temperature prior to detection with Protein L-HRP and TMB substrate solution. Using the CD3— pMHC assay, plasma levels of TCER™ 114-iso1-UCHT1(17) were determined via its bispecific binding activity measuring only molecules capable of simultaneously binding to both target molecules. CD3δε-$F_c$ was generated by fusing the extracellular domains of human CD3δ and CD3ε to the N-terminus of Fc-domains as utilized within the TCER™-constructs (containing Knob-into-hole mutations and an additional C-terminal His-Tag). CD3δε-$F_c$ molecules were expressed in ExpiCHO cells and purified using Protein A affinity chromatography followed by size exclusion chromatography as described above. CD3δ6-$F_c$ was coated at a concentration of 1 pg/ml in PBS at 4° C. overnight. Blocking and sample incubation were performed as described above followed by a two-step detection using HLA-A*02/MAG-003 and anti-b2m-HRP. Plasma concentrations of the samples were obtained by interpolation from the respective standard curves. Both assay set-ups lead to the determination of similar TCER™ plasma concentrations showing that protein integrity as well as binding activity of the molecule are retained in plasma (FIG. 14). Linear regression of time points 24 h, 48 h, 120 h, 240 h and 360 h revealed a terminal plasma half-life of 150 h. The results show that the half-life ($T_{1/2}$) of 114-iso1-UCHT1(17) is about 6-7 days.

Example 11: Detection of MAG-003 Peptide on Primary Tissues by Mass Spectrometry HLA molecules from shock-frozen tissue samples were purified, and HLA-associated peptides were isolated. The isolated peptides were separated, and sequences were identified by online nano-electrospray-ionization (nanoESI) liquid chromatography-mass spectrometry (LC-MS) experiments. MAG-003 identified on multiple tissue samples was quantified using ion-counting of label-free LC-MS data. The method assumes that LC-MS signal areas of a peptide correlate with its abundance in the sample. All quantitative signals of a peptide in various LC-MS experiments were normalized based on central tendency, averaged per sample and merged into a plot called presentation profile. The presentation profile consolidates different analysis methods like protein database search, spectral clustering, charge state deconvolution (decharging) and retention time alignment. All automatically derived quantitative and qualitative data were manually inspected (see FIG. 18).

SEQUENCE LISTING

```
Sequence total quantity: 182
SEQ ID NO: 1                moltype = AA   length = 9
FEATURE                     Location/Qualifiers
REGION                      1..9
                            note = MAG-003 peptide
source                      1..9
                            mol_type = protein
                            organism = synthetic construct
SEQUENCE: 1
KVLEHVVRV                                                                     9

SEQ ID NO: 2                moltype = AA   length = 272
FEATURE                     Location/Qualifiers
REGION                      1..272
                            note = R7P1D5 TCR alpha chain full length
source                      1..272
                            mol_type = protein
                            organism = synthetic construct
SEQUENCE: 2
MKTFAGFSFL FLWLQLDCMS RGEDVEQSLF LSVREGDSSV INCTYTDSSS TYLYWYKQEP             60
GAGLQLLTYI FSNMDMKQDQ RLTVLLNKKD KHLSLRIADT QTGDSAIYFC AEYSSASKII            120
FGSGTRLSIR PNIQNPDPAV YQLRDSKSSD KSVCLFTDFD SQTNVSQSKD SDVYITDKTV            180
LDMRSMDFKS NSAVAWSNKS DFACANAFNN SIIPEDTFFP SPESSCDVKL VEKSFETDTN            240
LNFQNLSVIG FRILLLKVAG FNLLMTLRLW SS                                          272

SEQ ID NO: 3                moltype = AA   length = 21
FEATURE                     Location/Qualifiers
REGION                      1..21
                            note = R7P1D5 alpha leader
source                      1..21
                            mol_type = protein
                            organism = synthetic construct
SEQUENCE: 3
MKTFAGFSFL FLWLQLDCMS R                                                      21

SEQ ID NO: 4                moltype = AA   length = 110
FEATURE                     Location/Qualifiers
REGION                      1..110
                            note = R7P1D5 alpha variable
source                      1..110
                            mol_type = protein
                            organism = synthetic construct
SEQUENCE: 4
GEDVEQSLFL SVREGDSSVI NCTYTDSSST YLYWYKQEPG AGLQLLTYIF SNMDMKQDQR             60
LTVLLNKKDK HLSRIADTQ TGDSAIYFCA EYSSASKIIF GSGTRLSIRP                       110

SEQ ID NO: 5                moltype = AA   length = 6
FEATURE                     Location/Qualifiers
REGION                      1..6
                            note = R7P1D5 CDRa1
source                      1..6
                            mol_type = protein
                            organism = synthetic construct
SEQUENCE: 5
DSSSTY                                                                        6

SEQ ID NO: 6                moltype = AA   length = 7
FEATURE                     Location/Qualifiers
REGION                      1..7
                            note = R7P1D5 CDRa2
source                      1..7
                            mol_type = protein
                            organism = synthetic construct
SEQUENCE: 6
IFSNMDM                                                                       7

SEQ ID NO: 7                moltype = AA   length = 12
FEATURE                     Location/Qualifiers
REGION                      1..12
                            note = R7P1D5 CDRa3
source                      1..12
                            mol_type = protein
                            organism = synthetic construct
SEQUENCE: 7
CAEYSSASKI IF                                                                12

SEQ ID NO: 8                moltype = AA   length = 141
FEATURE                     Location/Qualifiers
```

```
REGION                  1..141
                        note = R7P1D5 alpha constant
source                  1..141
                        mol_type = protein
                        organism = synthetic construct
SEQUENCE: 8
NIQNPDDPAVY QLRDSKSSDK SVCLFTDFDS QTNVSQSKDS DVYITDKTVL DMRSMDFKSN    60
SAVAWSNKSD FACANAFNNS IIPEDTFFPS PESSCDVKLV EKSFETDTNL NFQNLSVIGF   120
RILLLKVAGF NLLMTLRLWS S                                             141

SEQ ID NO: 9            moltype = AA  length = 310
FEATURE                 Location/Qualifiers
REGION                  1..310
                        note = R7P1D5 TCR beta chain full length
source                  1..310
                        mol_type = protein
                        organism = synthetic construct
SEQUENCE: 9
MGSWTLCCVS LCILVAKHTD AGVIQSPRHE VTEMGQEVTL RCKPISGHDY LFWYRQTMMR    60
GLELLIYFNN NVPIDDSGMP EDRFSAKMPN ASFSTLKIQP SEPRDSAVYF CASRANTGEL   120
FFGEGSRLTV LEDLKNVFPP EVAVFEPSEA EISHTQKATL VCLATGFYPD HVELSWWVNG   180
KEVHSGVSTD PQPLKEQPAL NDSRYCLSSR LRVSATFWQN PRNHFRCQVQ FYGLSENDEW   240
TQDRAKPVTQ IVSAEAWGRA DCGFTSESYQ QGVLSATILY EILLGKATLY AVLVSALVLM   300
AMVKRKDSRG                                                          310

SEQ ID NO: 10           moltype = AA  length = 19
FEATURE                 Location/Qualifiers
REGION                  1..19
                        note = R7P1D5 beta leader
source                  1..19
                        mol_type = protein
                        organism = synthetic construct
SEQUENCE: 10
MGSWTLCCVS LCILVAKHT                                                 19

SEQ ID NO: 11           moltype = AA  length = 112
FEATURE                 Location/Qualifiers
REGION                  1..112
                        note = R7P1D5 beta variabl
source                  1..112
                        mol_type = protein
                        organism = synthetic construct
SEQUENCE: 11
DAGVIQSPRH EVTEMGQEVT LRCKPISGHD YLFWYRQTMM RGLELLIYFN NNVPIDDSGM    60
PEDRFSAKMP NASFSTLKIQ PSEPRDSAVY FCASRANTGE LFFGEGSRLT VL           112

SEQ ID NO: 12           moltype = AA  length = 5
FEATURE                 Location/Qualifiers
REGION                  1..5
                        note = R7P1D5 CDRb1
source                  1..5
                        mol_type = protein
                        organism = synthetic construct
SEQUENCE: 12
SGHDY                                                                 5

SEQ ID NO: 13           moltype = AA  length = 6
FEATURE                 Location/Qualifiers
REGION                  1..6
                        note = R7P1D5 CDRb2
source                  1..6
                        mol_type = protein
                        organism = synthetic construct
SEQUENCE: 13
FNNNVP                                                                6

SEQ ID NO: 14           moltype = AA  length = 12
FEATURE                 Location/Qualifiers
REGION                  1..12
                        note = R7P1D5 CDRb3
source                  1..12
                        mol_type = protein
                        organism = synthetic construct
SEQUENCE: 14
CASRANTGEL FF                                                        12

SEQ ID NO: 15           moltype = AA  length = 179
FEATURE                 Location/Qualifiers
REGION                  1..179
```

```
                        note = R7P1D5 beta constant
source                  1..179
                        mol_type = protein
                        organism = synthetic construct
SEQUENCE: 15
EDLKNVFPPE VAVFEPSEAE ISHTQKATLV CLATGFYPDH VELSWWVNGK EVHSGVSTDP    60
QPLKEQPALN DSRYCLSSRL RVSATFWQNP RNHFRCQVQF YGLSENDEWT QDRAKPVTQI   120
VSAEAWGRAD CGFTSESYQQ GVLSATILYE ILLGKATLYA VLVSALVLMA MVKRKDSRG    179

SEQ ID NO: 16           moltype = AA   length = 370
FEATURE                 Location/Qualifiers
REGION                  1..370
                        note = Aga2p-R7P1D5
source                  1..370
                        mol_type = protein
                        organism = synthetic construct
SEQUENCE: 16
MQLLRCFSIF SVIASVLAQE LTTICEQIPS PTLESTPYSL STTTILANGK AMQGVFEYYK    60
SVTFVSNCGS HPSTTSKGSP INTQYVFGGG GSDYKDDDDK GGGASGEDVE QSLFLSVREG   120
DSSVINCTYT DSSSTYLYWY KQEPGAGLQL LTYIFSNMDM KQDQRLTVLL NKKDKHLSLR   180
IADTQTGDSA IYFCAEYSSA SKIIFGSGTR LSIRPGGGGS GGGGSGGGGS GGGGSGGGGS   240
DAGVIQSPRH EVTEMGQEVT LRCKPISGHD YLFWYRQTMM RGLELLIYFN NNVPIDDSGM   300
PEDRFSAKMP NASFSTLKIQ PSEPRDSAVY FCASRANTGE LFFGEGSRLT VLAAAGGSGG   360
EQKLISEEDL                                                          370

SEQ ID NO: 17           moltype = AA   length = 87
FEATURE                 Location/Qualifiers
REGION                  1..87
                        note = Leader sequence and Aga2p
source                  1..87
                        mol_type = protein
                        organism = synthetic construct
SEQUENCE: 17
MQLLRCFSIF SVIASVLAQE LTTICEQIPS PTLESTPYSL STTTILANGK AMQGVFEYYK    60
SVTFVSNCGS HPSTTSKGSP INTQYVF                                        87

SEQ ID NO: 18           moltype = AA   length = 18
FEATURE                 Location/Qualifiers
REGION                  1..18
                        note = FLAG tag plus linkers
source                  1..18
                        mol_type = protein
                        organism = synthetic construct
SEQUENCE: 18
GGGGSDYKDD DDKGGGAS                                                  18

SEQ ID NO: 19           moltype = AA   length = 247
FEATURE                 Location/Qualifiers
REGION                  1..247
                        note = Single chain variable domains of R7P1D5 with linker
source                  1..247
                        mol_type = protein
                        organism = synthetic construct
SEQUENCE: 19
GEDVEQSLFL SVREGDSSVI NCTYTDSSST YLYWYKQEPG AGLQLLTYIF SNMDMKQDQR    60
LTVLLNKKDK HLSLRIADTQ TGDSAIYFCA EYSSASKIIF GSGTRLSIRP GGGGSGGGGS   120
GGGGSGGGGS GGGGSDAGVI QSPRHEVTEM GQEVTLRCKP ISGHDYLFWY RQTMMRGLEL   180
LIYFNNNVPI DDSGMPEDRF SAKMPNASFS TLKIQPSEPR DSAVYFCASR ANTGELFFGE   240
GSRLTVL                                                             247

SEQ ID NO: 20           moltype = AA   length = 18
FEATURE                 Location/Qualifiers
REGION                  1..18
                        note = Linker and Myc tag
source                  1..18
                        mol_type = protein
                        organism = synthetic construct
SEQUENCE: 20
AAAGGSGGEQ KLISEEDL                                                  18

SEQ ID NO: 21           moltype = AA   length = 7
FEATURE                 Location/Qualifiers
REGION                  1..7
                        note = CDRa2 mutant 1 (aF57Y)
source                  1..7
                        mol_type = protein
                        organism = synthetic construct
SEQUENCE: 21
IYSNMDM                                                               7
```

```
SEQ ID NO: 22            moltype = AA   length = 247
FEATURE                  Location/Qualifiers
REGION                   1..247
                         note = scTv R7P1D5S (Stabilized version of scTv R7P1D5)
source                   1..247
                         mol_type = protein
                         organism = synthetic construct
SEQUENCE: 22
GEDVEQSLFL SVREGDSAVI NCTYTDSSST YLYWYKQEPG AGLQLLTYIY SNMDMKQDQR    60
LTVLLNKKDK HLSLRIADTQ TGDSAIYFCA EYSSASKIIF GSGTRLSIRP GGGGSGGGGS   120
GGGGSGGGGS GGGGSDAGVI QSPRHEVTEM GQEVTLRCKP ISGHDYLFWY RQTMMRGLEL   180
LIYFNNNVPI DDSGMPEDRF SAKMPNASFS TLKIQPSEPR DSAVYFCASR ANTGELFFGE   240
GSRLTVL                                                            247

SEQ ID NO: 23            moltype = AA   length = 9
FEATURE                  Location/Qualifiers
REGION                   1..9
                         note = RABGAP1L-001
source                   1..9
                         mol_type = protein
                         organism = synthetic construct
SEQUENCE: 23
FLLETVVRV                                                            9

SEQ ID NO: 24            moltype = AA   length = 9
FEATURE                  Location/Qualifiers
REGION                   1..9
                         note = AXIN1-001
source                   1..9
                         mol_type = protein
                         organism = synthetic construct
SEQUENCE: 24
ILDEHVQRV                                                            9

SEQ ID NO: 25            moltype = AA   length = 9
FEATURE                  Location/Qualifiers
REGION                   1..9
                         note = ANO5-001
source                   1..9
                         mol_type = protein
                         organism = synthetic construct
SEQUENCE: 25
IVMEHVVFL                                                            9

SEQ ID NO: 26            moltype = AA   length = 9
FEATURE                  Location/Qualifiers
REGION                   1..9
                         note = TPX2-001
source                   1..9
                         mol_type = protein
                         organism = synthetic construct
SEQUENCE: 26
KILEDVVGV                                                            9

SEQ ID NO: 27            moltype = AA   length = 9
FEATURE                  Location/Qualifiers
REGION                   1..9
                         note = SYNE3-001
source                   1..9
                         mol_type = protein
                         organism = synthetic construct
SEQUENCE: 27
KLLDLQVRV                                                            9

SEQ ID NO: 28            moltype = AA   length = 9
FEATURE                  Location/Qualifiers
REGION                   1..9
                         note = MIA3-001
source                   1..9
                         mol_type = protein
                         organism = synthetic construct
SEQUENCE: 28
KVLDKVFRA                                                            9

SEQ ID NO: 29            moltype = AA   length = 9
FEATURE                  Location/Qualifiers
REGION                   1..9
                         note = HERC4-001
```

```
source                    1..9
                          mol_type = protein
                          organism = synthetic construct
SEQUENCE: 29
KVLEILHRV                                                              9

SEQ ID NO: 30             moltype = AA   length = 9
FEATURE                   Location/Qualifiers
REGION                    1..9
                          note = PSME2-001
source                    1..9
                          mol_type = protein
                          organism = synthetic construct
SEQUENCE: 30
KVLERVNAV                                                              9

SEQ ID NO: 31             moltype = AA   length = 9
FEATURE                   Location/Qualifiers
REGION                    1..9
                          note = HEATR5A-001
source                    1..9
                          mol_type = protein
                          organism = synthetic construct
SEQUENCE: 31
KVLETLVTV                                                              9

SEQ ID NO: 32             moltype = AA   length = 9
FEATURE                   Location/Qualifiers
REGION                    1..9
                          note = CNOT1-003
source                    1..9
                          mol_type = protein
                          organism = synthetic construct
SEQUENCE: 32
KVLGIVVGV                                                              9

SEQ ID NO: 33             moltype = AA   length = 9
FEATURE                   Location/Qualifiers
REGION                    1..9
                          note = TEP1-003
source                    1..9
                          mol_type = protein
                          organism = synthetic construct
SEQUENCE: 33
AVEEHVVSV                                                              9

SEQ ID NO: 34             moltype = AA   length = 9
FEATURE                   Location/Qualifiers
REGION                    1..9
                          note = PITPNM3-001
source                    1..9
                          mol_type = protein
                          organism = synthetic construct
SEQUENCE: 34
SVLEKVTRA                                                              9

SEQ ID NO: 35             moltype = AA   length = 12
FEATURE                   Location/Qualifiers
REGION                    1..12
                          note = CDRa3 mutant 1
source                    1..12
                          mol_type = protein
                          organism = synthetic construct
SEQUENCE: 35
CAEMTSESKI IF                                                         12

SEQ ID NO: 36             moltype = AA   length = 12
FEATURE                   Location/Qualifiers
REGION                    1..12
                          note = CDRa3 mutant 2
source                    1..12
                          mol_type = protein
                          organism = synthetic construct
SEQUENCE: 36
CAEFTSESKI IF                                                         12

SEQ ID NO: 37             moltype = AA   length = 12
FEATURE                   Location/Qualifiers
REGION                    1..12
```

```
                        note = CDRa3 mutant 3
source                  1..12
                        mol_type = protein
                        organism = synthetic construct
SEQUENCE: 37
CAEFNSESKI IF                                                               12

SEQ ID NO: 38           moltype = AA   length = 12
FEATURE                 Location/Qualifiers
REGION                  1..12
                        note = CDRa3 mutant 4
source                  1..12
                        mol_type = protein
                        organism = synthetic construct
SEQUENCE: 38
CAEFSSASKI IF                                                               12

SEQ ID NO: 39           moltype = AA   length = 12
FEATURE                 Location/Qualifiers
REGION                  1..12
                        note = CDRa3 mutant 5
source                  1..12
                        mol_type = protein
                        organism = synthetic construct
SEQUENCE: 39
CAEATSESKI IF                                                               12

SEQ ID NO: 40           moltype = AA   length = 272
FEATURE                 Location/Qualifiers
REGION                  1..272
                        note = R7P1D5 - alpha chain variant 1
source                  1..272
                        mol_type = protein
                        organism = synthetic construct
SEQUENCE: 40
MKTFAGFSFL FLWLQLDCMS RGEDVEQSLF LSVREGDSSV INCTYTDSSS TYLYWYKQEP            60
GAGLQLLTYI FSNMDMKQDQ RLTVLLNKKD KHLSLRIADT QTGDSAIYFC AEMTSESKII           120
FGSGTRLSIR PNIQNPDPAV YQLRDSKSSD KSVCLFTDFD SQTNVSQSKD SDVYITDKTV           180
LDMRSMDFKS NSAVAWSNKS DFACANAFNN SIIPEDTFFP SPESSCDVKL VEKSFETDTN           240
LNFQNLSVIG FRILLLKVAG FNLLMTLRLW SS                                         272

SEQ ID NO: 41           moltype = AA   length = 272
FEATURE                 Location/Qualifiers
REGION                  1..272
                        note = R7P1D5 - alpha chain variant 2
source                  1..272
                        mol_type = protein
                        organism = synthetic construct
SEQUENCE: 41
MKTFAGFSFL FLWLQLDCMS RGEDVEQSLF LSVREGDSSV INCTYTDSSS TYLYWYKQEP            60
GAGLQLLTYI FSNMDMKQDQ RLTVLLNKKD KHLSLRIADT QTGDSAIYFC AEFTSESKII           120
FGSGTRLSIR PNIQNPDPAV YQLRDSKSSD KSVCLFTDFD SQTNVSQSKD SDVYITDKTV           180
LDMRSMDFKS NSAVAWSNKS DFACANAFNN SIIPEDTFFP SPESSCDVKL VEKSFETDTN           240
LNFQNLSVIG FRILLLKVAG FNLLMTLRLW SS                                         272

SEQ ID NO: 42           moltype = AA   length = 272
FEATURE                 Location/Qualifiers
REGION                  1..272
                        note = R7P1D5 - alpha chain variant 3
source                  1..272
                        mol_type = protein
                        organism = synthetic construct
SEQUENCE: 42
MKTFAGFSFL FLWLQLDCMS RGEDVEQSLF LSVREGDSSV INCTYTDSSS TYLYWYKQEP            60
GAGLQLLTYI FSNMDMKQDQ RLTVLLNKKD KHLSLRIADT QTGDSAIYFC AEFNSESKII           120
FGSGTRLSIR PNIQNPDPAV YQLRDSKSSD KSVCLFTDFD SQTNVSQSKD SDVYITDKTV           180
LDMRSMDFKS NSAVAWSNKS DFACANAFNN SIIPEDTFFP SPESSCDVKL VEKSFETDTN           240
LNFQNLSVIG FRILLLKVAG FNLLMTLRLW SS                                         272

SEQ ID NO: 43           moltype = AA   length = 272
FEATURE                 Location/Qualifiers
REGION                  1..272
                        note = R7P1D5 - alpha chain variant 4
source                  1..272
                        mol_type = protein
                        organism = synthetic construct
SEQUENCE: 43
MKTFAGFSFL FLWLQLDCMS RGEDVEQSLF LSVREGDSSV INCTYTDSSS TYLYWYKQEP            60
GAGLQLLTYI FSNMDMKQDQ RLTVLLNKKD KHLSLRIADT QTGDSAIYFC AEFSSASKII           120
```

```
FGSGTRLSIR PNIQNPDPAV YQLRDSKSSD KSVCLFTDFD SQTNVSQSKD SDVYITDKTV   180
LDMRSMDFKS NSAVAWSNKS DFACANAFNN SIIPEDTFFP SPESSCDVKL VEKSFETDTN   240
LNFQNLSVIG FRILLLKVAG FNLLMTLRLW SS                                 272

SEQ ID NO: 44           moltype = AA  length = 272
FEATURE                 Location/Qualifiers
REGION                  1..272
                        note = R7P1D5 - alpha chain variant 5
source                  1..272
                        mol_type = protein
                        organism = synthetic construct
SEQUENCE: 44
MKTFAGFSFL FLWLQLDCMS RGEDVEQSLF LSVREGDSSV INCTYTDSSS TYLYWYKQEP    60
GAGLQLLTYI FSNMDMKQDQ RLTVLLNKKD KHLSLRIADT QTGDSAIYFC AEATSESKII   120
FGSGTRLSIR PNIQNPDPAV YQLRDSKSSD KSVCLFTDFD SQTNVSQSKD SDVYITDKTV   180
LDMRSMDFKS NSAVAWSNKS DFACANAFNN SIIPEDTFFP SPESSCDVKL VEKSFETDTN   240
LNFQNLSVIG FRILLLKVAG FNLLMTLRLW SS                                 272

SEQ ID NO: 45           moltype = AA  length = 9
FEATURE                 Location/Qualifiers
REGION                  1..9
                        note = NYESO1-001
source                  1..9
                        mol_type = protein
                        organism = synthetic construct
SEQUENCE: 45
SLLMWITQV                                                             9

SEQ ID NO: 46           moltype = AA  length = 9
FEATURE                 Location/Qualifiers
REGION                  1..9
                        note = MAG-003_A1
source                  1..9
                        mol_type = protein
                        organism = synthetic construct
SEQUENCE: 46
AVLEHVVRV                                                             9

SEQ ID NO: 47           moltype = AA  length = 9
FEATURE                 Location/Qualifiers
REGION                  1..9
                        note = MAG-003_A2
source                  1..9
                        mol_type = protein
                        organism = synthetic construct
SEQUENCE: 47
KALEHVVRV                                                             9

SEQ ID NO: 48           moltype = AA  length = 9
FEATURE                 Location/Qualifiers
REGION                  1..9
                        note = MAG-003_A3
source                  1..9
                        mol_type = protein
                        organism = synthetic construct
SEQUENCE: 48
KVAEHVVRV                                                             9

SEQ ID NO: 49           moltype = AA  length = 9
FEATURE                 Location/Qualifiers
REGION                  1..9
                        note = MAG-003_A4
source                  1..9
                        mol_type = protein
                        organism = synthetic construct
SEQUENCE: 49
KVLAHVVRV                                                             9

SEQ ID NO: 50           moltype = AA  length = 9
FEATURE                 Location/Qualifiers
REGION                  1..9
                        note = MAG-003_A5
source                  1..9
                        mol_type = protein
                        organism = synthetic construct
SEQUENCE: 50
KVLEAVVRV                                                             9

SEQ ID NO: 51           moltype = AA  length = 9
```

```
FEATURE              Location/Qualifiers
REGION               1..9
                     note = MAG-003_A6
source               1..9
                     mol_type = protein
                     organism = synthetic construct
SEQUENCE: 51
KVLEHAVRV                                                                 9

SEQ ID NO: 52        moltype = AA  length = 9
FEATURE              Location/Qualifiers
REGION               1..9
                     note = MAG-003_A7
source               1..9
                     mol_type = protein
                     organism = synthetic construct
SEQUENCE: 52
KVLEHVARV                                                                 9

SEQ ID NO: 53        moltype = AA  length = 9
FEATURE              Location/Qualifiers
REGION               1..9
                     note = MAG-003_A8
source               1..9
                     mol_type = protein
                     organism = synthetic construct
SEQUENCE: 53
KVLEHVVAV                                                                 9

SEQ ID NO: 54        moltype = AA  length = 9
FEATURE              Location/Qualifiers
REGION               1..9
                     note = MAG-003_A9
source               1..9
                     mol_type = protein
                     organism = synthetic construct
SEQUENCE: 54
KVLEHVVRA                                                                 9

SEQ ID NO: 55        moltype = AA  length = 6
FEATURE              Location/Qualifiers
REGION               1..6
                     note = CDRa1 mutant 1 (equals mutation aD27E)
source               1..6
                     mol_type = protein
                     organism = synthetic construct
SEQUENCE: 55
ESSSTY                                                                    6

SEQ ID NO: 56        moltype = AA  length = 7
FEATURE              Location/Qualifiers
REGION               1..7
                     note = CDRa2 mutant 2 (equals CDRa2 mutant 5 + mutation
                     aS65Q)
source               1..7
                     mol_type = protein
                     organism = synthetic construct
SEQUENCE: 56
IYSSQDQ                                                                   7

SEQ ID NO: 57        moltype = AA  length = 7
FEATURE              Location/Qualifiers
REGION               1..7
                     note = CDRa2 mutant 3
source               1..7
                     mol_type = protein
                     organism = synthetic construct
SEQUENCE: 57
IYSSQDV                                                                   7

SEQ ID NO: 58        moltype = AA  length = 488
FEATURE              Location/Qualifiers
REGION               1..488
                     note = 75-NU(17)-R7P1D5#1
source               1..488
                     mol_type = protein
                     organism = synthetic construct
SEQUENCE: 58
EVQLVQSGAE VKKPGASVKV SCKASGYSFT GYTMNWVRQA PGQGLEWMGL INPYKGVSTY    60
```

```
AQKFQDRVTL TVDKSTSTAY MELSSLRSED TAVYYCARSG YYGDSDWYFD VWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT SPPSPAPPVA    240
GGEDVEQSLF LSVREGDSAV INCTYTDSSS TYLYWYKQEP GAGLQLLTYI YSSQDQKQDQ    300
RLTVLLNKKD KHLSLRIADT QTGDSAIYFC AEMTSESKII FGSGTRLSIR PGGGGSGGGG    360
SGGGGSGGGG SGGGGSDAGV IQSPRHEVTE MGQEVTLRCK PIPGHDYLFW YRQTMMRGLE    420
LLIYFNNNVP IDDSGMPEDR FSAKMPNASF STLKIQPSEP RDSAVYFCAS RANTGELFFG    480
EGSRLTVL                                                             488

SEQ ID NO: 59           moltype = AA  length = 7
FEATURE                 Location/Qualifiers
REGION                  1..7
                        note = CDRa2 mutant 4
source                  1..7
                        mol_type = protein
                        organism = synthetic construct
SEQUENCE: 59
IYSSQDS                                                              7

SEQ ID NO: 60           moltype = AA  length = 488
FEATURE                 Location/Qualifiers
REGION                  1..488
                        note = 75-NU(17)-R7P1D5#20
source                  1..488
                        mol_type = protein
                        organism = synthetic construct
SEQUENCE: 60
EVQLVQSGAE VKKPGASVKV SCKASGYSFT GYTMNWVRQA PGQGLEWMGL INPYKGVSTY    60
AQKFQDRVTL TVDKSTSTAY MELSSLRSED TAVYYCARSG YYGDSDWYFD VWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT SPPSPAPPVA    240
GGEDVEQSLF LSVREGDSAV INCTYTDSSS TYLYWYKQEP GAGLQLLTYI YSSQDSKQDQ    300
RLTVLLNKKD KHLSLRIADT QTGDSAIYFC AEMTSESKII FGSGTRLSIR PGGGGSGGGG    360
SGGGGSGGGG SGGGGSDAGV IQSPRHEVTE MGQEVTLRCK PIPGHDYLFW YRQTMMRGLE    420
LLIYFCYGTP CDDSGMPEDR FSAKMPNASF STLKIQPSEP RDSAVYFCAS RADTGELFFG    480
EGSRLTVL                                                             488

SEQ ID NO: 61           moltype = AA  length = 488
FEATURE                 Location/Qualifiers
REGION                  1..488
                        note = 75-NU(17)-R7P1D5#21
source                  1..488
                        mol_type = protein
                        organism = synthetic construct
SEQUENCE: 61
EVQLVQSGAE VKKPGASVKV SCKASGYSFT GYTMNWVRQA PGQGLEWMGL INPYKGVSTY    60
AQKFQDRVTL TVDKSTSTAY MELSSLRSED TAVYYCARSG YYGDSDWYFD VWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT SPPSPAPPVA    240
GGEDVEQSLF LSVREGDSAV INCTYTDSSS TYLYWYKQEP GAGLQLLTYI YSSQDSKQDQ    300
RLTVLLNKKD KHLSLRIADT QTGDSAIYFC AEMTSESKII FGSGTRLSIR PGGGGSGGGG    360
SGGGGSGGGG SGGGGSDAGV IQSPRHEVTE MGQEVTLRCK PIPGHDYLFW YRQTMMRGLE    420
LLFYFCYGTP CDDSGMPEDR FSAKMPNASF STLKIQPSEP RDSAVYFCAS RADTGELFFG    480
EGSRLTVL                                                             488

SEQ ID NO: 62           moltype = AA  length = 5
FEATURE                 Location/Qualifiers
REGION                  1..5
                        note = CDRb1 mutant 1
source                  1..5
                        mol_type = protein
                        organism = synthetic construct
SEQUENCE: 62
PGHDY                                                                5

SEQ ID NO: 63           moltype = AA  length = 6
FEATURE                 Location/Qualifiers
REGION                  1..6
                        note = CDRb2 mutant 1
source                  1..6
                        mol_type = protein
                        organism = synthetic construct
SEQUENCE: 63
FCYGHP                                                               6

SEQ ID NO: 64           moltype = AA  length = 6
FEATURE                 Location/Qualifiers
REGION                  1..6
                        note = CDRb2 mutant 2
```

```
source                        1..6
                              mol_type = protein
                              organism = synthetic construct
SEQUENCE: 64
FCYGVP                                                                      6

SEQ ID NO: 65                 moltype = AA   length = 6
FEATURE                       Location/Qualifiers
REGION                        1..6
                              note = CDRb2 mutant 3
source                        1..6
                              mol_type = protein
                              organism = synthetic construct
SEQUENCE: 65
FCYGTP                                                                      6

SEQ ID NO: 66                 moltype = AA   length = 6
FEATURE                       Location/Qualifiers
REGION                        1..6
                              note = CDRb2 mutant 4
source                        1..6
                              mol_type = protein
                              organism = synthetic construct
SEQUENCE: 66
FCYGAP                                                                      6

SEQ ID NO: 67                 moltype = AA   length = 488
FEATURE                       Location/Qualifiers
REGION                        1..488
                              note = 75-NU(17)-R7P1D5#29
source                        1..488
                              mol_type = protein
                              organism = synthetic construct
SEQUENCE: 67
EVQLVQSGAE VKKPGASVKV SCKASGYSFT GYTMNWVRQA PGQGLEWMGL INPYKGVSTY           60
AQKFQDRVTL TVDKSTSTAY MELSSLRSED TAVYYCARSG YYGDSDWYFD VWGQGTLVTV          120
SSASTKGPSV FPLAPSSKST SGGTAALGCL VKDYFPEPVT VSWNSGALTS GVHTFPAVLQ          180
SSGLYSLSSV VTVPSSSLGT QTYICNVNHK PSNTKVDKKV EPKSCDKTHT SPPSPAPPVA          240
GGEDVEQSLF LSVREGDSSV INCTYTDSSS TYLYWYKQEP GAGPQLLTYI YSSQDQKQDQ          300
RLTVLLNKKD KHLSLRIADT QTGDSAIYFC AEMTSESKII FGSGTRLSIR PGGGGSGGGG          360
SGGGGSGGGG SGGGGSDAGV IQSPRHEVTE MGQEVTLRCK PIPGHDYLFW YRQTPGRGLE          420
LLIYFNNNVP IDDSGMPEDR FSAKMPNASF STLKIQPSEP RDSAVYFCAS RANTGELFFG          480
EGSRLTVL                                                                  488

SEQ ID NO: 68                 moltype = AA   length = 488
FEATURE                       Location/Qualifiers
REGION                        1..488
                              note = 75-NU(17)-R7P1D5#30
source                        1..488
                              mol_type = protein
                              organism = synthetic construct
SEQUENCE: 68
EVQLVQSGAE VKKPGASVKV SCKASGYSFT GYTMNWVRQA PGQGLEWMGL INPYKGVSTY           60
AQKFQDRVTL TVDKSTSTAY MELSSLRSED TAVYYCARSG YYGDSDWYFD VWGQGTLVTV          120
SSASTKGPSV FPLAPSSKST SGGTAALGCL VKDYFPEPVT VSWNSGALTS GVHTFPAVLQ          180
SSGLYSLSSV VTVPSSSLGT QTYICNVNHK PSNTKVDKKV EPKSCDKTHT SPPSPAPPVA          240
GGEDVEQSLF LSVREGDSAV INCTYTDSSS TYLYWYKQEP GAGPQLLTYI YSSQDQKQDQ          300
RLTVLLNKKD KHLSLRIADT QTGDSAIYFC AEMTSESKII FGSGTRLSIR PGGGGSGGGG          360
SGGGGSGGGG SGGGGSDAGV IQSPRHEVTE MGQEVTLRCK PIPGHDYLFW YRQTPGRGLE          420
LLIYFNNNVP IDDSGMPEDR FSAKMPNASF STLKIQPSEP RDSAVYFCAS RANTGELFFG          480
EGSRLTVL                                                                  488

SEQ ID NO: 69                 moltype = AA   length = 488
FEATURE                       Location/Qualifiers
REGION                        1..488
                              note = 75-NU(17)-R7P1D5#31
source                        1..488
                              mol_type = protein
                              organism = synthetic construct
SEQUENCE: 69
EVQLVQSGAE VKKPGASVKV SCKASGYSFT GYTMNWVRQA PGQGLEWMGL INPYKGVSTY           60
AQKFQDRVTL TVDKSTSTAY MELSSLRSED TAVYYCARSG YYGDSDWYFD VWGQGTLVTV          120
SSASTKGPSV FPLAPSSKST SGGTAALGCL VKDYFPEPVT VSWNSGALTS GVHTFPAVLQ          180
SSGLYSLSSV VTVPSSSLGT QTYICNVNHK PSNTKVDKKV EPKSCDKTHT SPPSPAPPVA          240
GGEDVEQSLF LSVREGDSSV INCTYTDSSS TYLYWYKQEP GKGPQLLTYI YSSQDQKQDQ          300
RLTVLLNKKD KHLSLRIADT QTGDSAIYFC AEMTSESKII FGSGTRLSIR PGGGGSGGGG          360
SGGGGSGGGG SGGGGSDAGV IQSPRHEVTE MGQEVTLRCK PIPGHDYLFW YRQTPGRGLE          420
LLIYFNNNVP IDDSGMPEDR FSAKMPNASF STLKIQPSEP RDSAVYFCAS RANTGELFFG          480
EGSRLTVL                                                                  488
```

```
SEQ ID NO: 70           moltype = AA  length = 6
FEATURE                 Location/Qualifiers
REGION                  1..6
                        note = CDRb2 mutant 5
source                  1..6
                        mol_type = protein
                        organism = synthetic construct
SEQUENCE: 70
FCYGMP                                                                    6

SEQ ID NO: 71           moltype = AA  length = 12
FEATURE                 Location/Qualifiers
REGION                  1..12
                        note = CDRb3 mutant 1 ( bN109D)
source                  1..12
                        mol_type = protein
                        organism = synthetic construct
SEQUENCE: 71
CASRADTGEL FF                                                            12

SEQ ID NO: 72           moltype = AA  length = 6
FEATURE                 Location/Qualifiers
REGION                  1..6
                        note = CDRa1 consensus - ACT + TCER
SITE                    1
                        note = MISC_FEATURE - wherein Xaa is any amino acid,
                         preferably D or E, more preferably E
source                  1..6
                        mol_type = protein
                        organism = synthetic construct
SEQUENCE: 72
XSSSTY                                                                    6

SEQ ID NO: 73           moltype =     length =
SEQUENCE: 73
000

SEQ ID NO: 74           moltype = AA  length = 7
FEATURE                 Location/Qualifiers
REGION                  1..7
                        note = CDRa2 consensus p1 - TCER
SITE                    7
                        note = misc_feature - Xaa is any amino acid, preferably Q,
                         V or S, preferably Q
source                  1..7
                        mol_type = protein
                        organism = synthetic construct
SEQUENCE: 74
IYSSQDX                                                                   7

SEQ ID NO: 75           moltype = AA  length = 488
FEATURE                 Location/Qualifiers
REGION                  1..488
                        note = 75-NU(17)-R7P1D5#32 heavy chain
source                  1..488
                        mol_type = protein
                        organism = synthetic construct
SEQUENCE: 75
EVQLVQSGAE VKKPGASVKV SCKASGYSFT GYTMNWVRQA PGQGLEWMGL INPYKGVSTY         60
AQKFQDRVTL TVDKSTSTAY MELSSLRSED TAVYYCARSG YYGDSDWYFD VWGQGTLVTV        120
SSASTKGPSV FPLAPSSKST SGGTAALGCL VKDYFPEPVT VSWNSGALTS GVHTFPAVLQ        180
SSGLYSLSSV VTVPSSSLGT QTYICNVNHK PSNTKVDKKV EPKSCDKTHT SPPSPAPPVA        240
GGEDVEQSLF LSVREGDSVV INCTYTDSSS TYLYWYKQEP GAGPQLLTYI YSSQDQKQDQ        300
RLTVLLNKKD KHLSLRIADT QTGDSAIYFC AEMTSESKII FGSGTRLSIR PGGGGSGGGG        360
SGGGGSGGGG SGGGGSDAGV IQSPRHEVTE MGQEVTLRCK PIPGHDYLFW YRQTPGRGLE        420
LLIYFNNNVP IDDSGMPEDR FSAKMPNASF STLKIQPSEP RDSAVYFCAS RANTGELFFG        480
EGSRLTVL                                                                488

SEQ ID NO: 76           moltype = AA  length = 488
FEATURE                 Location/Qualifiers
REGION                  1..488
                        note = 75-NU(17)-R7P1D5#2-heavy chain
source                  1..488
                        mol_type = protein
                        organism = synthetic construct
SEQUENCE: 76
EVQLVQSGAE VKKPGASVKV SCKASGYSFT GYTMNWVRQA PGQGLEWMGL INPYKGVSTY         60
AQKFQDRVTL TVDKSTSTAY MELSSLRSED TAVYYCARSG YYGDSDWYFD VWGQGTLVTV        120
```

```
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT SPPSPAPPVA    240
GGEDVEQSLF LSVREGDSAV INCTYTDSSS TYLYWYKQEP GAGLQLLTYI YSSQDSKQDQ    300
RLTVLLNKKD KHLSLRIADT QTGDSAIYFC AEMTSESKII FGSGTRLSIR PGGGGSGGGG    360
SGGGGSGGGG SGGGGSDAGV IQSPRHEVTE MGQEVTLRCK PIPGHDYLFW YRQTMMRGLE    420
LLIYFNNNVP IDDSGMPEDR FSAKMPNASF STLKIQPSEP RDSAVYFCAS RANTGELFFG    480
EGSRLTVL                                                            488
```

```
SEQ ID NO: 77              moltype = AA  length = 12
FEATURE                    Location/Qualifiers
REGION                     1..12
                           note = CDRa3 consensus ACT + TCER
SITE                       4
                           note = MISC_FEATURE - wherein Xaa is any amino acid,
                            preferably Xaa is A, F or M, more preferably M
SITE                       5
                           note = MISC_FEATURE - wherein Xaa is any amino acid,
                            preferably Xaa is S, T, or N, more preferably T
SITE                       7
                           note = MISC_FEATURE - wherein Xaa is any amino acid,
                            preferably Xaa is E or A, preferably E
source                     1..12
                           mol_type = protein
                           organism = synthetic construct
SEQUENCE: 77
CAEXXSXSKI IF                                                        12

SEQ ID NO: 78              moltype = AA  length = 5
FEATURE                    Location/Qualifiers
REGION                     1..5
                           note = CDRb1 consensus - ACT + TCER
SITE                       1
                           note = MISC_FEATURE - Xaa is any amino acid, preferably
                            P,S, more preferably P
source                     1..5
                           mol_type = protein
                           organism = synthetic construct
SEQUENCE: 78
XGHDY                                                                 5

SEQ ID NO: 79              moltype =   length =
SEQUENCE: 79
000

SEQ ID NO: 80              moltype = AA  length = 214
FEATURE                    Location/Qualifiers
REGION                     1..214
                           note = 75-NU(17)-R7P1D5x- common light chain
source                     1..214
                           mol_type = protein
                           organism = synthetic construct
SEQUENCE: 80
DIQMTQSPSS LSASVGDRVT ITCRASQDIR NYLNWYQQKP GKAPKLLIYY TSRLHSGVPS     60
RFSGSGSGTD YTLTISSLQP EDIATYFCQQ GQTLPWTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 81              moltype = AA  length = 6
FEATURE                    Location/Qualifiers
REGION                     1..6
                           note = CDRb2 consensus p3 - TCER
SITE                       5
                           note = MISC_FEATURE - Xaa is any amino acid, preferably
                            H,T, more preferably T
source                     1..6
                           mol_type = protein
                           organism = synthetic construct
SEQUENCE: 81
FCYGXP                                                                6

SEQ ID NO: 82              moltype = AA  length = 12
FEATURE                    Location/Qualifiers
REGION                     1..12
                           note = CDRb3 consensus ACT + TCER
SITE                       6
                           note = MISC_FEATURE - Xaa is any amino acid, preferably
                            N,D, preferably D
source                     1..12
                           mol_type = protein
```

-continued

```
                         organism = synthetic construct
SEQUENCE: 82
CASRAXTGEL FF                                                          12

SEQ ID NO: 83            moltype = AA   length = 24
FEATURE                  Location/Qualifiers
REGION                   1..24
                         note = FR1-a
source                   1..24
                         mol_type = protein
                         organism = synthetic construct
SEQUENCE: 83
EDVEQSLFLS VREGDSSVIN CTYT                                             24

SEQ ID NO: 84            moltype = AA   length = 17
FEATURE                  Location/Qualifiers
REGION                   1..17
                         note = FR2-a
source                   1..17
                         mol_type = protein
                         organism = synthetic construct
SEQUENCE: 84
LYWYKQEPGA GLQLLTY                                                     17

SEQ ID NO: 85            moltype = AA   length = 33
FEATURE                  Location/Qualifiers
REGION                   1..33
                         note = FR3-a
source                   1..33
                         mol_type = protein
                         organism = synthetic construct
SEQUENCE: 85
KQDQRLTVLL NKKDKHLSLR IADTQTGDSA IYF                                   33

SEQ ID NO: 86            moltype = AA   length = 10
FEATURE                  Location/Qualifiers
REGION                   1..10
                         note = FR4-a
source                   1..10
                         mol_type = protein
                         organism = synthetic construct
SEQUENCE: 86
GSGTRLSIRP                                                             10

SEQ ID NO: 87            moltype = AA   length = 26
FEATURE                  Location/Qualifiers
REGION                   1..26
                         note = FR1-b
source                   1..26
                         mol_type = protein
                         organism = synthetic construct
SEQUENCE: 87
DAGVIQSPRH EVTEMGQEVT LRCKPI                                           26

SEQ ID NO: 88            moltype = AA   length = 17
FEATURE                  Location/Qualifiers
REGION                   1..17
                         note = FR2-b
source                   1..17
                         mol_type = protein
                         organism = synthetic construct
SEQUENCE: 88
LFWYRQTMMR GLELLIY                                                     17

SEQ ID NO: 89            moltype = AA   length = 37
FEATURE                  Location/Qualifiers
REGION                   1..37
                         note = FR3-b
source                   1..37
                         mol_type = protein
                         organism = synthetic construct
SEQUENCE: 89
IDDSGMPEDR FSAKMPNASF STLKIQPSEP RDSAVYF                               37

SEQ ID NO: 90            moltype = AA   length = 9
FEATURE                  Location/Qualifiers
REGION                   1..9
                         note = FR4-b
source                   1..9
```

```
                        mol_type = protein
                        organism = synthetic construct
SEQUENCE: 90
GEGSRLTVL                                                               9

SEQ ID NO: 91           moltype = AA  length = 24
FEATURE                 Location/Qualifiers
REGION                  1..24
                        note = FR1-a(19V)
source                  1..24
                        mol_type = protein
                        organism = synthetic construct
SEQUENCE: 91
EDVEQSLFLS VREGDSVVIN CTYT                                              24

SEQ ID NO: 92           moltype = AA  length = 17
FEATURE                 Location/Qualifiers
REGION                  1..17
                        note = FR2-a (48K)
source                  1..17
                        mol_type = protein
                        organism = synthetic construct
SEQUENCE: 92
LYWYKQEPGK GLQLLTY                                                      17

SEQ ID NO: 93           moltype = AA  length = 17
FEATURE                 Location/Qualifiers
REGION                  1..17
                        note = FR2-b (54F)
source                  1..17
                        mol_type = protein
                        organism = synthetic construct
SEQUENCE: 93
LFWYRQTMMR GLELLFY                                                      17

SEQ ID NO: 94           moltype = AA  length = 37
FEATURE                 Location/Qualifiers
REGION                  1..37
                        note = FR3-b (66C)
source                  1..37
                        mol_type = protein
                        organism = synthetic construct
SEQUENCE: 94
CDDSGMPEDR FSAKMPNASF STLKIQPSEP RDSAVYF                                37

SEQ ID NO: 95           moltype = AA  length = 9
FEATURE                 Location/Qualifiers
REGION                  1..9
                        note = MUM-001
source                  1..9
                        mol_type = protein
                        organism = synthetic construct
SEQUENCE: 95
KLVEYIVKA                                                               9

SEQ ID NO: 96           moltype = AA  length = 8
FEATURE                 Location/Qualifiers
REGION                  1..8
                        note = Linker
source                  1..8
                        mol_type = protein
                        organism = synthetic construct
SEQUENCE: 96
GGGSGGGG                                                                8

SEQ ID NO: 97           moltype = AA  length = 317
FEATURE                 Location/Qualifiers
REGION                  1..317
                        note = MAGA4 (P43358)
source                  1..317
                        mol_type = protein
                        organism = synthetic construct
SEQUENCE: 97
MSSEQKSQHC KPEEGVEAQE EALGLVGAQA PTTEEQEAAV SSSSPLVPGT LEEVPAAESA       60
GPPQSPQGAS ALPTTISFTC WRQPNEGSSS QEEEGPSTSP DAESLFREAL SNKVDELAHF       120
LLRKYRAKEL VTKAEMLERV IKNYKRCFPV IFGKASESLK MIFGIDVKEV DPASNTYTLV       180
TCLGLSYDGL LGNNQIFPKT GLLIIVLGTI AMEGDSASEE EIWEELGVMG VYDGREHTVY       240
GEPRKLLTQD WVQENYLEYR QVPGSNPARY EFLWGPRALA ETSYVKVLEH VVRVNARVRI       300
AYPSLREAAL LEEEEGV                                                      317
```

```
SEQ ID NO: 98            moltype = AA   length = 318
FEATURE                  Location/Qualifiers
REGION                   1..318
                         note = MAGA8 (P43361)
source                   1..318
                         mol_type = protein
                         organism = synthetic construct
SEQUENCE: 98
MLLGQKSQRY KAEEGLQAQG EAPGLMDVQI PTAEEQKAAS SSSTLIMGTL EEVTDSGSPS   60
PPQSPEGASS SLTVTDSTLW SQSDEGSSSN EEEGPSTSPD PAHLESLFRE ALDEKVAELV  120
RFLLRKYQIK EPVTKAEMLE SVIKNYKNHF PDIFSKASEC MQVIFGIDVK EVDPAGHSYI  180
LVTCLGLSYD GLLGDDQSTP KTGLLIIVLG MILMEGSRAP EEAIWEALSV MGLYDGREHS  240
VYWKLRKLLT QEWVQENYLE YRQAPGSDPV RYEFLWGPRA LAETSYVKVL EHVVRVNARV  300
RISYPSLHEE ALGEEKGV                                                318

SEQ ID NO: 99            moltype = AA   length = 5
FEATURE                  Location/Qualifiers
REGION                   1..5
                         note = Linker
source                   1..5
                         mol_type = protein
                         organism = synthetic construct
SEQUENCE: 99
TVAAP                                                                5

SEQ ID NO: 100           moltype = AA   length = 4
FEATURE                  Location/Qualifiers
REGION                   1..4
                         note = Linker
source                   1..4
                         mol_type = protein
                         organism = synthetic construct
SEQUENCE: 100
GGGS                                                                 4

SEQ ID NO: 101           moltype = AA   length = 5
FEATURE                  Location/Qualifiers
REGION                   1..5
                         note = GGGGS
source                   1..5
                         mol_type = protein
                         organism = synthetic construct
SEQUENCE: 101
GGGGS                                                                5

SEQ ID NO: 102           moltype = AA   length = 5
FEATURE                  Location/Qualifiers
REGION                   1..5
                         note = Linker
source                   1..5
                         mol_type = protein
                         organism = synthetic construct
SEQUENCE: 102
TVLRT                                                                5

SEQ ID NO: 103           moltype = AA   length = 6
FEATURE                  Location/Qualifiers
REGION                   1..6
                         note = Linker
source                   1..6
                         mol_type = protein
                         organism = synthetic construct
SEQUENCE: 103
TVSSAS                                                               6

SEQ ID NO: 104           moltype = AA   length = 10
FEATURE                  Location/Qualifiers
REGION                   1..10
                         note = Linker
source                   1..10
                         mol_type = protein
                         organism = synthetic construct
SEQUENCE: 104
GGGGSGGGGS                                                          10

SEQ ID NO: 105           moltype = AA   length = 8
FEATURE                  Location/Qualifiers
REGION                   1..8
```

```
                                    note = Linker
source                              1..8
                                    mol_type = protein
                                    organism = synthetic construct
SEQUENCE: 105
GGGGSAAA                                                                        8

SEQ ID NO: 106              moltype = AA  length = 15
FEATURE                     Location/Qualifiers
REGION                      1..15
                            note = Linker
source                      1..15
                            mol_type = protein
                            organism = synthetic construct
SEQUENCE: 106
GGGGSGGGGS GGGGS                                                                15

SEQ ID NO: 107              moltype = AA  length = 27
FEATURE                     Location/Qualifiers
REGION                      1..27
                            note = Linker
source                      1..27
                            mol_type = protein
                            organism = synthetic construct
SEQUENCE: 107
GGGGSGGGGS GGGGSGGGGS GGGGSGS                                                   27

SEQ ID NO: 108              moltype = AA  length = 25
FEATURE                     Location/Qualifiers
REGION                      1..25
                            note = Linker
source                      1..25
                            mol_type = protein
                            organism = synthetic construct
SEQUENCE: 108
GGGGSGGGGS GGGGSGGGGS GGGGS                                                     25

SEQ ID NO: 109              moltype = AA  length = 7
FEATURE                     Location/Qualifiers
REGION                      1..7
                            note = Linker
source                      1..7
                            mol_type = protein
                            organism = synthetic construct
SEQUENCE: 109
TVLSSAS                                                                         7

SEQ ID NO: 110              moltype = AA  length = 20
FEATURE                     Location/Qualifiers
REGION                      1..20
                            note = Linker
source                      1..20
                            mol_type = protein
                            organism = synthetic construct
SEQUENCE: 110
GGGGSGGGGS GGGGSGGGGS                                                           20

SEQ ID NO: 111              moltype = AA  length = 232
FEATURE                     Location/Qualifiers
REGION                      1..232
                            note = native Fc amino acid sequence of IGHG1*01
source                      1..232
                            mol_type = protein
                            organism = synthetic construct
SEQUENCE: 111
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 112              moltype = AA  length = 229
FEATURE                     Location/Qualifiers
REGION                      1..229
                            note = Fc with knob mutation [S354C and T366W] +
source                      1..229
                            mol_type = protein
                            organism = synthetic construct
SEQUENCE: 112
EPKSSDKTHT CPPCPAPPVA GPSVFLFPPK PKDTLMISRT PEVTCVVVDV SHEDPEVKFN    60
```

```
WYVDGVEVHN AKTKPREEQY QSTYRVVSVL TVLHQDWLNG KEYKCKVSNK ALPASIEKTI    120
SKAKGQPREP QVYTLPPCRD ELTKNQVSLW CLVKGFYPSD IAVEWESNGQ PENNYKTTPP    180
VLDSDGSFFL YSKLTVDKSR WQQGNVFSCS VMHEALHNHY TQKSLSLSP                229

SEQ ID NO: 113           moltype = AA   length = 229
FEATURE                  Location/Qualifiers
REGION                   1..229
                         note = Fc hole [(Y349C, T366S, L368A and Y407V] +
source                   1..229
                         mol_type = protein
                         organism = synthetic construct
SEQUENCE: 113
EPKSSDKTHT CPPCPAPPVA GPSVFLFPPK PKDTLMISRT PEVTCVVVDV SHEDPEVKFN    60
WYVDGVEVHN AKTKPREEQY QSTYRVVSVL TVLHQDWLNG KEYKCKVSNK ALPASIEKTI    120
SKAKGQPREP QVCTLPPSRD ELTKNQVSLS CAVKGFYPSD IAVEWESNGQ PENNYKTTPP    180
VLDSDGSFFL VSKLTVDKSR WQQGNVFSCS VMHEALHNHY TQKSLSLSP                229

SEQ ID NO: 114           moltype = AA   length = 21
FEATURE                  Location/Qualifiers
REGION                   1..21
                         note = IgG1-hinge
source                   1..21
                         mol_type = protein
                         organism = synthetic construct
SEQUENCE: 114
EPKSCDKTHT CPPCPAPELL G                                              21

SEQ ID NO: 115           moltype = AA   length = 19
FEATURE                  Location/Qualifiers
REGION                   1..19
                         note = IG2-hinge
source                   1..19
                         mol_type = protein
                         organism = synthetic construct
SEQUENCE: 115
ERKCCVECPP CPAPPVAGP                                                 19

SEQ ID NO: 116           moltype = AA   length = 53
FEATURE                  Location/Qualifiers
REGION                   1..53
                         note = IG3-hinge
source                   1..53
                         mol_type = protein
                         organism = synthetic construct
SEQUENCE: 116
ELKTPLGDTT HTCPRCPEPK SCDTPPPCPR CPEPKSCDTP PPCPRCPAPE LLG           53

SEQ ID NO: 117           moltype = AA   length = 18
FEATURE                  Location/Qualifiers
REGION                   1..18
                         note = IG4-hinge
source                   1..18
                         mol_type = protein
                         organism = synthetic construct
SEQUENCE: 117
ESKYGPPCPS CPAPEFLG                                                  18

SEQ ID NO: 118           moltype = AA   length = 109
FEATURE                  Location/Qualifiers
REGION                   1..109
                         note = R7P1D5_aMTSE
source                   1..109
                         mol_type = protein
                         organism = synthetic construct
SEQUENCE: 118
EDVEQSLFLS VREGDSSVIN CTYTDSSSTY LYWYKQEPGA GLQLLTYIFS NMDMKQDQRL    60
TVLLNKKDKH LSLRIADTQT GDSAIYFCAE MTSESKIIFG SGTRLSIRP                109

SEQ ID NO: 119           moltype = AA   length = 109
FEATURE                  Location/Qualifiers
REGION                   1..109
                         note = R7P1D5_aFTSE
source                   1..109
                         mol_type = protein
                         organism = synthetic construct
SEQUENCE: 119
EDVEQSLFLS VREGDSSVIN CTYTDSSSTY LYWYKQEPGA GLQLLTYIFS NMDMKQDQRL    60
TVLLNKKDKH LSLRIADTQT GDSAIYFCAE FTSESKIIFG SGTRLSIRP                109
```

```
SEQ ID NO: 120            moltype = AA  length = 109
FEATURE                   Location/Qualifiers
REGION                    1..109
                          note = R7P1D5_aFNSE
source                    1..109
                          mol_type = protein
                          organism = synthetic construct
SEQUENCE: 120
EDVEQSLFLS VREGDSSVIN CTYTDSSSTY LYWYKQEPGA GLQLLTYIFS NMDMKQDQRL    60
TVLLNKKDKH LSLRIADTQT GDSAIYFCAE FNSESKIIFG SGTRLSIRP              109

SEQ ID NO: 121            moltype = AA  length = 109
FEATURE                   Location/Qualifiers
REGION                    1..109
                          note = R7P1D5_aFSSA
source                    1..109
                          mol_type = protein
                          organism = synthetic construct
SEQUENCE: 121
EDVEQSLFLS VREGDSSVIN CTYTDSSSTY LYWYKQEPGA GLQLLTYIFS NMDMKQDQRL    60
TVLLNKKDKH LSLRIADTQT GDSAIYFCAE FSSASKIIFG SGTRLSIRP              109

SEQ ID NO: 122            moltype = AA  length = 109
FEATURE                   Location/Qualifiers
REGION                    1..109
                          note = R7P1D5_aATSE
source                    1..109
                          mol_type = protein
                          organism = synthetic construct
SEQUENCE: 122
EDVEQSLFLS VREGDSSVIN CTYTDSSSTY LYWYKQEPGA GLQLLTYIFS NMDMKQDQRL    60
TVLLNKKDKH LSLRIADTQT GDSAIYFCAE ATSESKIIFG SGTRLSIRP              109

SEQ ID NO: 123            moltype = AA  length = 214
FEATURE                   Location/Qualifiers
REGION                    1..214
                          note = 75-NU (V9) light chain for CR7P1D5S
source                    1..214
                          mol_type = protein
                          organism = synthetic construct
SEQUENCE: 123
DIQMTQSPSS LSASVGDRVT ITCRASQDIR NYLNWYQQKP GKAPKLLIYY TSRLESGVPS    60
RFSGSGSGTD YTLTISSLQP EDFATYYCQQ GNTLPWTFGQ GTKVEIKRTV AAPSVFIFPP   120
SDEQLKSGTA SVVCLLNNFY PREAKVQWKV DNALQSGNSQ ESVTEQDSKD STYSLSNTLT   180
LSKADYEKHK VYACEVTHQG LSSPVTKSFN RGEC                              214

SEQ ID NO: 124            moltype = AA  length = 487
FEATURE                   Location/Qualifiers
REGION                    1..487
                          note = 75-NU(V9)-CR7P1D5S (HC)
source                    1..487
                          mol_type = protein
                          organism = synthetic construct
SEQUENCE: 124
EVQLVESGGG LVQPGGSLRL SCAASGYSFT GYTMNWVRQA PGKGLEWVAL INPYKGVSTY    60
NQKFKDRFTI SVDKSKNTAY LQMNSLRAED TAVYYCARSG YYGDSDWYFD VWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT SPPSPAPPVA   240
GEDVEQSLFL SVREGDSAVI NCTYTDSSST TLYWYKQEPG AGLQLLTYIY SNMDMKQDQR   300
LTVLLNKKDK HLSLRIADTQ TGDSAIYFCA EYSSASKIIF GSGTRLSIRP GGGGSGGGGS   360
GGGGSGGGGS GGGGSDAGVI QSPRHEVTEM GQEVTLRCKP ISGHDYLFWY RQTMMRGLEL   420
LIYFNNNVPI DDSGMPEDRF SAKMPNASFS TLKIQPSEPR DSAVYFCASR ANTGELFFGE   480
GSRLTVL                                                            487

SEQ ID NO: 125            moltype = AA  length = 488
FEATURE                   Location/Qualifiers
REGION                    1..488
                          note = 75-NU(Var17)-CR7P1D5#19 (HC)
source                    1..488
                          mol_type = protein
                          organism = synthetic construct
SEQUENCE: 125
EVQLVQSGAE VKKPGASVKV SCKASGYSFT GYTMNWVRQA PGQGLEWMGL INPYKGVSTY    60
AQKFQDRVTL TVDKSTSTAY MELSSLRSED TAVYYCARSG YYGDSDWYFD VWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT SPPSPAPPVA   240
GGEDVEQSLF LSVREGDSAV INCTYTDSSS TLYWYKQEP GAGLQLLTYI YSSQDSKQDQ    300
RLTVLLNKKD KHLSLRIADT QTGDSAIYFC AEMTSESKII FGSGTRLSIR PGGGGSGGGG   360
SGGGGSGGGG SGGGGSDAGV IQSPRHEVTE MGQEVTLRCK PIPGHDYLFW YRQTMMRGLE   420
```

```
LLFYFCYGTP CDDSGMPEDR FSAKMPNASF STLKIQPSEP RDSAVYFCAS RANTGELFFG    480
EGSRLTVL                                                             488

SEQ ID NO: 126           moltype = AA  length = 488
FEATURE                  Location/Qualifiers
REGION                   1..488
                         note = 75-NU(Var17)-CR7P1D5I (HC)
source                   1..488
                         mol_type = protein
                         organism = synthetic construct
SEQUENCE: 126
EVQLVQSGAE VKKPGASVKV SCKASGYSFT GYTMNWVRQA PGQGLEWMGL INPYKGVSTY    60
AQKFQDRVTL TVDKSTSTAY MELSSLRSED TAVYYCARSG YYGDSDWYFD VWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT SPPSPAPPVA    240
GGEDVEQSLF LSVREGDSAV INCTYTDSSS TYLYWYKQEP GAGLQLLTYI YSSQDSKQDQ    300
RLTVLLNKKD KHLSLRIADT QTGDSAIYFC AEMTSESKII FGSGTRLSIR PGGGGSGGGG    360
SGGGGSGGGG SGGGGSDAGV IQSPRHEVTE MGQEVTLRCK PIPGHDYLFW YRQTMMRGLE    420
LLIYFCYGTP CDDSGMPEDR FSAKMPNASF STLKIQPSEP RDSAVYFCAS RANTGELFFG    480
EGSRLTVL                                                             488

SEQ ID NO: 127           moltype = AA  length = 453
FEATURE                  Location/Qualifiers
REGION                   1..453
                         note = 100(A)-NU(V17)-R7P1D5#114-iso0-dSFcKO-GK (first
                         polypeptide (alpha-VL))
source                   1..453
                         mol_type = protein
                         organism = synthetic construct
SEQUENCE: 127
EDVEQSLFLS VREGDSVVIN CTYTDSSSTY LYWYKQEPGK GLQLLTYIYS SQDSKQDQRL    60
TVLLNKKDKH LSLRIADTQT GDSAIYFCAE MTSESKIIFG SGTRLSIRPG GGSGGGGDIQ    120
MTQSPSSLSA SVGDRVTITC RASQDIRNYL NWYQQKPGKA PKLLIYYTSR LHSGVPSRFS    180
GSGSGTDYTL TISSLQPEDI ATYFCQQGQT LPWTFGQGTK VEIKEPKSSD KTHTCPPCPA    240
PPVAGPSVFL FPPKPKDTLM ISRTPEVTCV VVDVSHEDPE VKFNWYVDGV EVHNAKTKPR    300
EEQYQSTYRV VSVLTVLHQD WLNGKEYKCK VSNKALPASI EKTISKAKGQ PREPQVYTLP    360
PCRDELTKNQ VSLWCLVKGF YPSDIAVEWE SNGQPENNYK TTPPVLDSDG SFFLYSKLTV    420
DKSRWQQGNV FSCSVMHEAL HNHYTQKSLS LSP                                 453

SEQ ID NO: 128           moltype = AA  length = 471
FEATURE                  Location/Qualifiers
REGION                   1..471
                         note = 100(A)-NU(V17)-R7P1D5#112-dsFcKO-GK (VH-beta)
source                   1..471
                         mol_type = protein
                         organism = synthetic construct
SEQUENCE: 128
EVQLVQSGAE VKKPGASVKV SCKASGYSFT GYTMNWVRQA PGQGLEWMGL INPYKGVSTY    60
AQKFQDRVTL TVDKSTSTAY MELSSLRSED TAVYYCARSG YYGDSDWYFD VWGQGTLVTV    120
SSGGGSGGGG DAGVIQSPRH EVTEMGQEVT LRCKPIPGHD YLFWYRQTMM RGLELLFYFC    180
YGTPCDDSGM PEDRFSAKMP NASFSTLKIQ PSEPRDSAVY FCASRANTGE LFFGEGSRLT    240
VLEPKSSDKT HTCPPCPAPP VAGPSVFLFP PKPKDTLMIS RTPEVTCVVV DVSHEDPEVK    300
FNWYVDGVEV HNAKTKPREE QYQSTYRVVS VLTVLHQDWL NGKEYKCKVS NKALPASIEK    360
TISKAKGQPR EPQVCTLPPS RDELTKNQVS LSCAVKGFYP SDIAVEWESN GQPENNYKTT    420
PPVLDSDGSF FLVSKLTVDK SRWQQGNVFS CSVMHEALHN HYTQKSLSLS P             471

SEQ ID NO: 129           moltype = AA  length = 9
FEATURE                  Location/Qualifiers
REGION                   1..9
                         note = ZFC-001
source                   1..9
                         mol_type = protein
                         organism = synthetic construct
SEQUENCE: 129
KLQEQIHRV                                                            9

SEQ ID NO: 130           moltype = AA  length = 471
FEATURE                  Location/Qualifiers
REGION                   1..471
                         note = 100(A)-NU(V17)-R7P1D5#114-dsFcKO-GK (VH-beta)
source                   1..471
                         mol_type = protein
                         organism = synthetic construct
SEQUENCE: 130
EVQLVQSGAE VKKPGASVKV SCKASGYSFT GYTMNWVRQA PGQGLEWMGL INPYKGVSTY    60
AQKFQDRVTL TVDKSTSTAY MELSSLRSED TAVYYCARSG YYGDSDWYFD VWGQGTLVTV    120
SSGGGSGGGG DAGVIQSPRH EVTEMGQEVT LRCKPIPGHD YLFWYRQTMM RGLELLFYFC    180
YGTPCDDSGM PEDRFSAKMP NASFSTLKIQ PSEPRDSAVY FCASRADTGE LFFGEGSRLT    240
VLEPKSSDKT HTCPPCPAPP VAGPSVFLFP PKPKDTLMIS RTPEVTCVVV DVSHEDPEVK    300
```

```
FNWYVDGVEV HNAKTKPREE QYQSTYRVVS VLTVLHQDWL NGKEYKCKVS NKALPASIEK    360
TISKAKGQPR EPQVCTLPPS RDELTKNQVS LSCAVKGFYP SDIAVEWESN GQPENNYKTT    420
PPVLDSGSF  FLVSKLTVDK SRWQQGNVFS CSVMHEALHN HYTQKSLSLS P             471

SEQ ID NO: 131              moltype = AA   length = 453
FEATURE                     Location/Qualifiers
REGION                      1..453
                            note = 100(A)-NU(V17)-R7P1D5#114-iso1-dsFcKO-GK (alpha-VL)
source                      1..453
                            mol_type = protein
                            organism = synthetic construct
SEQUENCE: 131
EDVEQSLFLS VREGDSVVIN CTYTDSSSTY LYWYKQEPGK GLQLLTYIYS SQDQKQDQRL     60
TVLLNKKDKH LSLRIADTQT GDSAIYFCAE MTSESKIIFG SGTRLSIRPG GGSGGGGDIQ    120
MTQSPSSLSA SVGDRVTITC RASQDIRNYL NWYQQKPGKA PKLLIYYTSR LHSGVPSRFS    180
GSGSGTDYTL TISSLQPEDI ATYFCQQGQT LPWTFGQGTK VEIKEPKSSD KTHTCPPCPA    240
PPVAGPSVFL FPPKPKDTLM ISRTPEVTCV VVDVSHEDPE VKFNWYVDGV EVHNAKTKPR    300
EEQYQSTYRV VSVLTVLHQD WLNGKEYKCK VSNKALPASI EKTISKAKGQ PREPQVYTLP    360
PCRDELTKNQ VSLWCLVKGF YPSDIAVEWE SNGQPENNYK TTPPVLDSDG SFFLYSKLTV    420
DKSRWQQGNV FSCSVMHEAL HNHYTQKSLS LSP                                453

SEQ ID NO: 132              moltype = AA   length = 274
FEATURE                     Location/Qualifiers
REGION                      1..274
                            note = 1G4 alpha chain
source                      1..274
                            mol_type = protein
                            organism = synthetic construct
SEQUENCE: 132
METLLGLLIL WLQLQWVSSK QEVTQIPAAL SVPEGENLVL NCSFTDSAIY NLQWFRQDPG     60
KGLTSLLLIQ SSQREQTSGR LNASLDKSSG RSTLYIAASQ PGDSATYLCA VRPTSGGSYI    120
PTFGRGTSLI VHPYIQNPDP AVYQLRDSKS SDKSVCLFTD FDSQTNVSQS KDSDVYITDK    180
TVLDMRSMDF KSNSAVAWSN KSDFACANAF NNSIIPEDTF FPSPESSCDV KLVEKSFETD    240
TNLNFQNLSV IGFRILLLKV AGFNLLMTLR LWSS                                274

SEQ ID NO: 133              moltype = AA   length = 453
FEATURE                     Location/Qualifiers
REGION                      1..453
                            note = 100(A)-NU(V17)-R7P1D5#114-iso2-dsFcKO-GK (alpha-VL)
source                      1..453
                            mol_type = protein
                            organism = synthetic construct
SEQUENCE: 133
EDVEQSLFLS VREGDSVVIN CTYTESSSTY LYWYKQEPGK GLQLLTYIYS SQDQKQDQRL     60
TVLLNKKDKH LSLRIADTQT GDSAIYFCAE MTSESKIIFG SGTRLSIRPG GGSGGGGDIQ    120
MTQSPSSLSA SVGDRVTITC RASQDIRNYL NWYQQKPGKA PKLLIYYTSR LHSGVPSRFS    180
GSGSGTDYTL TISSLQPEDI ATYFCQQGQT LPWTFGQGTK VEIKEPKSSD KTHTCPPCPA    240
PPVAGPSVFL FPPKPKDTLM ISRTPEVTCV VVDVSHEDPE VKFNWYVDGV EVHNAKTKPR    300
EEQYQSTYRV VSVLTVLHQD WLNGKEYKCK VSNKALPASI EKTISKAKGQ PREPQVYTLP    360
PCRDELTKNQ VSLWCLVKGF YPSDIAVEWE SNGQPENNYK TTPPVLDSDG SFFLYSKLTV    420
DKSRWQQGNV FSCSVMHEAL HNHYTQKSLS LSP                                453

SEQ ID NO: 134              moltype = AA   length = 311
FEATURE                     Location/Qualifiers
REGION                      1..311
                            note = 1G4 beta chain
source                      1..311
                            mol_type = protein
                            organism = synthetic construct
SEQUENCE: 134
MSIGLLCCAA LSLLWAGPVN AGVTQTPKFQ VLKTGQSMTL QCAQDMNHEY MSWYRQDPGM     60
GLRLIHYSVG AGITDQGEVP NGYNVSRSTT EDFPLRLLSA APSQTSVYFC ASSYVGNTGE    120
LFFGEGSRLT VLEDLKNVFP PEVAVFEPSE AEISHTQKAT LVCLATGFYP DHVELSWWVN    180
GKEVHSGVST DPQPLKEQPA LNDSRYCLSS RLRVSATFWQ NPRNHFRCQV QFYGLSENDE    240
WTQDRAKPVT QIVSAEAWGR ADCGFTSESY QQGVLSATIL YEILLGKATL YAVLVSALVL    300
MAMVKRKDSR G                                                        311

SEQ ID NO: 135              moltype = AA   length = 466
FEATURE                     Location/Qualifiers
REGION                      1..466
                            note = 100(D)-NB(V36)-R7P1D5#114-iso0-dsFcKO-GK (alpha-VH)
source                      1..466
                            mol_type = protein
                            organism = synthetic construct
SEQUENCE: 135
EDVEQSLFLS VREGDSVVIN CTYTDSSSTY LYWYKQEPGK GLQLLTYIYS SQDSKQDQRL     60
TVLLNKKDKH LSLRIADTQT GDSAIYFCAE MTSESKIIFG SGTRLSIRPG GGSGGGGEVQ    120
LVQSGAEVKK PGASVKVSCK ASGYKFTSYV MHWVRQAPGQ GLEWMGYINP YNDVTKYAEK    180
FQGRVTLTSD TSTSTAYMEL SSLRSEDTAV HYCARGSYYD YEGFVYWGQG TLVTVSSEPK    240
```

```
SSDKTHTCPP CPAPPVAGPS VFLFPPKPKD TLMISRTPEV TCVVVDVSHE DPEVKFNWYV   300
DGVEVHNAKT KPREEQYQST YRVVSVLTVL HQDWLNGKEY KCKVSNKALP ASIEKTISKA   360
KGQPREPQVC TLPPSRDELT KNQVSLSCAV KGFYPSDIAV EWESNGQPEN NYKTTPPVLD   420
SDGSFFLVSK LTVDKSRWQQ GNVFSCSVMH EALHNHYTQK SLSLSP                 466

SEQ ID NO: 136           moltype = AA   length = 455
FEATURE                  Location/Qualifiers
REGION                   1..455
                         note = 100(D)-NB(V36)-R7P1D5#114-dsFcKO-GK (VL-beta)
source                   1..455
                         mol_type = protein
                         organism = synthetic construct
SEQUENCE: 136
QIQMTQSPSS LSASVGDRVT ITCSATSSVS YMHWYQQKPG KAPKRWIYDT SKLASGVPSR    60
FSGSGSGTDY TLTISSLQPE DAATYYCQQW SSNPLTFGGG TKVEIKGGGS GGGGDAGVIQ   120
SPRHEVTEMG QEVTLRCKPI PGHDYLFWYR QTMMRGLELL FYFCYGTPCD DSGMPEDRFS   180
AKMPNASFST LKIQPSEPRD SAVYFCASRA DTGELFFGEG SRLTVLEPKS SDKTHTCPPC   240
PAPPVAGPSV FLFPPKPKDT LMISRTPEVT CVVVDVSHED PEVKFNWYVD GVEVHNAKTK   300
PREEQYQSTY RVVSVLTVLH QDWLNGKEYK CKVSNKALPA SIEKTISKAK GQPREPQVYT   360
LPPCRDELTK NQVSLWCLVK GFYPSDIAVE WESNGQPENN YKTTPPVLDS DGSFFLYSKL   420
TVDKSRWQQG NVFSCSVMHE ALHNHYTQKS LSLSP                             455

SEQ ID NO: 137           moltype = AA   length = 466
FEATURE                  Location/Qualifiers
REGION                   1..466
                         note = 100(D)-NB(V36)-R7P1D5#114_iso1-dsFcKO-GK (alpha-VH)
source                   1..466
                         mol_type = protein
                         organism = synthetic construct
SEQUENCE: 137
EDVEQSLFLS VREGDSVVIN CTYTDSSSTY LYWYKQEPGK GLQLLTYIYS SQDQKQDQRL    60
TVLLNKKDKH LSLRIADTQT GDSAIYFCAE MTSESKIIFG SGTRLSIRPG GGSGGGGEVQ   120
LVQSGAEVKK PGASVKVSCK ASGYKFTSYV MHWVRQAPGQ GLEWMGYINP YNDVTKYAEK   180
FQGRVTLTSD TSTSTAYMEL SSLRSEDTAV HYCARGSYYD YEGFVYWGQG TLVTVSSEPK   240
SSDKTHTCPP CPAPPVAGPS VFLFPPKPKD TLMISRTPEV TCVVVDVSHE DPEVKFNWYV   300
DGVEVHNAKT KPREEQYQST YRVVSVLTVL HQDWLNGKEY KCKVSNKALP ASIEKTISKA   360
KGQPREPQVC TLPPSRDELT KNQVSLSCAV KGFYPSDIAV EWESNGQPEN NYKTTPPVLD   420
SDGSFFLVSK LTVDKSRWQQ GNVFSCSVMH EALHNHYTQK SLSLSP                 466

SEQ ID NO: 138           moltype = AA   length = 109
FEATURE                  Location/Qualifiers
REGION                   1..109
                         note = R7P1D5# 114-iso0-Valpha
source                   1..109
                         mol_type = protein
                         organism = synthetic construct
SEQUENCE: 138
EDVEQSLFLS VREGDSVVIN CTYTDSSSTY LYWYKQEPGK GLQLLTYIYS SQDSKQDQRL    60
TVLLNKKDKH LSLRIADTQT GDSAIYFCAE MTSESKIIFG SGTRLSIRP              109

SEQ ID NO: 139           moltype = AA   length = 466
FEATURE                  Location/Qualifiers
REGION                   1..466
                         note = 100(D)-NB(V36)-R7P1D5#114_iso2-dsFcKO-GK (alpha-VH)
source                   1..466
                         mol_type = protein
                         organism = synthetic construct
SEQUENCE: 139
EDVEQSLFLS VREGDSVVIN CTYTESSSTY LYWYKQEPGK GLQLLTYIYS SQDQKQDQRL    60
TVLLNKKDKH LSLRIADTQT GDSAIYFCAE MTSESKIIFG SGTRLSIRPG GGSGGGGEVQ   120
LVQSGAEVKK PGASVKVSCK ASGYKFTSYV MHWVRQAPGQ GLEWMGYINP YNDVTKYAEK   180
FQGRVTLTSD TSTSTAYMEL SSLRSEDTAV HYCARGSYYD YEGFVYWGQG TLVTVSSEPK   240
SSDKTHTCPP CPAPPVAGPS VFLFPPKPKD TLMISRTPEV TCVVVDVSHE DPEVKFNWYV   300
DGVEVHNAKT KPREEQYQST YRVVSVLTVL HQDWLNGKEY KCKVSNKALP ASIEKTISKA   360
KGQPREPQVC TLPPSRDELT KNQVSLSCAV KGFYPSDIAV EWESNGQPEN NYKTTPPVLD   420
SDGSFFLVSK LTVDKSRWQQ GNVFSCSVMH EALHNHYTQK SLSLSP                 466

SEQ ID NO: 140           moltype = AA   length = 5
FEATURE                  Location/Qualifiers
REGION                   1..5
                         note = Linker
source                   1..5
                         mol_type = protein
                         organism = synthetic construct
SEQUENCE: 140
GGSGG                                                               5

SEQ ID NO: 141           moltype = AA   length = 10
FEATURE                  Location/Qualifiers
```

```
REGION                      1..10
                            note = Linker
source                      1..10
                            mol_type = protein
                            organism = synthetic construct
SEQUENCE: 141
GGSGGGGSGG                                                                    10

SEQ ID NO: 142              moltype = AA  length = 471
FEATURE                     Location/Qualifiers
REGION                      1..471
                            note = 100(A)-NU(V23)-R7P1D5#114_dsFcKO-GK (VH-beta)
source                      1..471
                            mol_type = protein
                            organism = synthetic construct
SEQUENCE: 142
EVQLVQSGAE VKKPGASVKV SCKASGYSFT EYTMNWVRQA PGQGLEWMGL INPQKGVSTY              60
AQKFQDRVTL TVDKSTSTAY MELSSLRSED TAVYYCARSG YYGDSDWYFD VWGQGTLVTV             120
SSGGGSGGGG DAGVIQSPRH EVTEMGQEVT LRCKPIPGHD YLFWYRQTMM RGLELLFYFC             180
YGTPCDDSGM PEDRFSAKMP NASFSTLKIQ PSEPRDSAVY FCASRADTGE LFFGEGSRLT             240
VLEPKSSDKT HTCPPCPAPP VAGPSVFLFP PKPKDTLMIS RTPEVTCVVV DVSHEDPEVK             300
FNWYVDGVEV HNAKTKPREE QYQSTYRVVS VLTVLHQDWL NGKEYKCKVS NKALPASIEK             360
TISKAKGQPR EPQVCTLPPS RDELTKNQVS LSCAVKGFYP SDIAVEWESN GQPENNYKTT             420
PPVLDSDGSF FLVSKLTVDK SRWQQGNVFS CSVMHEALHN HYTQKSLSLS P                     471

SEQ ID NO: 143              moltype = AA  length = 15
FEATURE                     Location/Qualifiers
REGION                      1..15
                            note = Linker
source                      1..15
                            mol_type = protein
                            organism = synthetic construct
SEQUENCE: 143
GGSGGGGSGG GGSGG                                                              15

SEQ ID NO: 144              moltype = AA  length = 20
FEATURE                     Location/Qualifiers
REGION                      1..20
                            note = Linker
source                      1..20
                            mol_type = protein
                            organism = synthetic construct
SEQUENCE: 144
GGSGGGGSGG GGSGGGGSGG                                                         20

SEQ ID NO: 145              moltype = AA  length = 25
FEATURE                     Location/Qualifiers
REGION                      1..25
                            note = Linker
source                      1..25
                            mol_type = protein
                            organism = synthetic construct
SEQUENCE: 145
GGSGGGGSGG GGSGGGGSGG GGSGG                                                   25

SEQ ID NO: 146              moltype = AA  length = 17
FEATURE                     Location/Qualifiers
REGION                      1..17
                            note = Linker
source                      1..17
                            mol_type = protein
                            organism = synthetic construct
SEQUENCE: 146
GSADDAKKDA AKKDGKS                                                            17

SEQ ID NO: 147              moltype = AA  length = 25
FEATURE                     Location/Qualifiers
REGION                      1..25
                            note = Linker
source                      1..25
                            mol_type = protein
                            organism = synthetic construct
SEQUENCE: 147
GGQGSGGTGS GGQGSGGTGS GGQGS                                                   25

SEQ ID NO: 148              moltype = AA  length = 7
FEATURE                     Location/Qualifiers
REGION                      1..7
                            note = Linker
```

```
source                     1..7
                           mol_type = protein
                           organism = synthetic construct
SEQUENCE: 148
GGGGSGT                                                                   7

SEQ ID NO: 149             moltype = AA  length = 112
FEATURE                    Location/Qualifiers
REGION                     1..112
                           note = R7P1D5#112-Vbeta
source                     1..112
                           mol_type = protein
                           organism = synthetic construct
SEQUENCE: 149
DAGVIQSPRH EVTEMGQEVT LRCKPIPGHD YLFWYRQTMM RGLELLFYFC YGTPCDDSGM    60
PEDRFSAKMP NASFSTLKIQ PSEPRDSAVY FCASRANTGE LFFGEGSRLT VL           112

SEQ ID NO: 150             moltype = AA  length = 112
FEATURE                    Location/Qualifiers
REGION                     1..112
                           note = R7P1D5#114 VBETA
source                     1..112
                           mol_type = protein
                           organism = synthetic construct
SEQUENCE: 150
DAGVIQSPRH EVTEMGQEVT LRCKPIPGHD YLFWYRQTMM RGLELLFYFC YGTPCDDSGM    60
PEDRFSAKMP NASFSTLKIQ PSEPRDSAVY FCASRADTGE LFFGEGSRLT VL           112

SEQ ID NO: 151             moltype = AA  length = 109
FEATURE                    Location/Qualifiers
REGION                     1..109
                           note = R7P1D5#114-iso1-Valpha
source                     1..109
                           mol_type = protein
                           organism = synthetic construct
SEQUENCE: 151
EDVEQSLFLS VREGDSVVIN CTYTDSSSTY LYWYKQEPGK GLQLLTYIYS SQDQKQDQRL    60
TVLLNKKDKH LSLRIADTQT GDSAIYFCAE MTSESKIIFG SGTRLSIRP              109

SEQ ID NO: 152             moltype = AA  length = 109
FEATURE                    Location/Qualifiers
REGION                     1..109
                           note = R7P1D5#114-iso2-Valpha100
source                     1..109
                           mol_type = protein
                           organism = synthetic construct
SEQUENCE: 152
EDVEQSLFLS VREGDSVVIN CTYTESSSTY LYWYKQEPGK GLQLLTYIYS SQDQKQDQRL    60
TVLLNKKDKH LSLRIADTQT GDSAIYFCAE MTSESKIIFG SGTRLSIRP              109

SEQ ID NO: 153             moltype = AA  length = 107
FEATURE                    Location/Qualifiers
REGION                     1..107
                           note = UCHT1(V17) VL
source                     1..107
                           mol_type = protein
                           organism = synthetic construct
SEQUENCE: 153
DIQMTQSPSS LSASVGDRVT ITCRASQDIR NYLNWYQQKP GKAPKLLIYY TSRLHSGVPS    60
RFSGSGSGTD YTLTISSLQP EDIATYFCQQ GQTLPWTFGQ GTKVEIK                107

SEQ ID NO: 154             moltype = AA  length = 122
FEATURE                    Location/Qualifiers
REGION                     1..122
                           note = UCHT1(V17) VH
source                     1..122
                           mol_type = protein
                           organism = synthetic construct
SEQUENCE: 154
EVQLVQSGAE VKKPGASVKV SCKASGYSFT GYTMNWVRQA PGQGLEWMGL INPYKGVSTY    60
AQKFQDRVTL TVDKSTSTAY MELSSLRSED TAVYYCARSG YYGDSDWYFD VWGQGTLVTV   120
SS                                                                 122

SEQ ID NO: 155             moltype = AA  length = 12
FEATURE                    Location/Qualifiers
REGION                     1..12
                           note = Linker
source                     1..12
                           mol_type = protein
```

```
                        organism = synthetic construct
SEQUENCE: 155
GGGGSGGGGS GT                                                            12

SEQ ID NO: 156          moltype = AA   length = 122
FEATURE                 Location/Qualifiers
REGION                  1..122
                        note = UCHT1(23) VH
source                  1..122
                        mol_type = protein
                        organism = synthetic construct
SEQUENCE: 156
EVQLVQSGAE VKKPGASVKV SCKASGYSFT EYTMNWVRQA PGQGLEWMGL INPQKGVSTY         60
AQKFQDRVTL TVDKSTSTAY MELSSLRSED TAVYYCARSG YYGDSDWYFD VWGQGTLVTV        120
SS                                                                      122

SEQ ID NO: 157          moltype = AA   length = 106
FEATURE                 Location/Qualifiers
REGION                  1..106
                        note = BMA(10) VL
source                  1..106
                        mol_type = protein
                        organism = synthetic construct
SEQUENCE: 157
QIQMTQSPSS LSASVGDRVT ITCSATSSVS YMHWYQQKPG KAPKRWIYDT SKLASGVPSR         60
FSGSGSGTDY TLTISSLQPE DAATYYCQQW SSNPLTFGGG TKVEIK                      106

SEQ ID NO: 158          moltype = AA   length = 120
FEATURE                 Location/Qualifiers
REGION                  1..120
                        note = BMA(10) VH
source                  1..120
                        mol_type = protein
                        organism = synthetic construct
SEQUENCE: 158
EVQLVQSGAE VKKPGASVKV SCKASGYKFT SYVMHWVRQA PGQGLEWMGY INPYNDVTKY         60
AEKFQGRVTL TSDTSTSTAY MELSSLRSED TAVHYCARGS YYDYDGFVYW GQGTLVTVSS        120

SEQ ID NO: 159          moltype = AA   length = 106
FEATURE                 Location/Qualifiers
REGION                  1..106
                        note = BMA(36) VL
source                  1..106
                        mol_type = protein
                        organism = synthetic construct
SEQUENCE: 159
QIQMTQSPSS LSASVGDRVT ITCSATSSVS YMHWYQQKPG KAPKRWIYDT SKLASGVPSR         60
FSGSGSGTDY TLTISSLQPE DAATYYCQQW SSNPLTFGGG TKVEIK                      106

SEQ ID NO: 160          moltype = AA   length = 120
FEATURE                 Location/Qualifiers
REGION                  1..120
                        note = BMA(36)- VH
source                  1..120
                        mol_type = protein
                        organism = synthetic construct
SEQUENCE: 160
EVQLVQSGAE VKKPGASVKV SCKASGYKFT SYVMHWVRQA PGQGLEWMGY INPYNDVTKY         60
AEKFQGRVTL TSDTSTSTAY MELSSLRSED TAVHYCARGS YYDYEGFVYW GQGTLVTVSS        120

SEQ ID NO: 161          moltype = AA   length = 17
FEATURE                 Location/Qualifiers
REGION                  1..17
                        note = Linker
source                  1..17
                        mol_type = protein
                        organism = synthetic construct
SEQUENCE: 161
GGGGSGGGGS GGGGSGT                                                       17

SEQ ID NO: 162          moltype = AA   length = 122
FEATURE                 Location/Qualifiers
REGION                  1..122
                        note = UCHT1(17opt) VH
source                  1..122
                        mol_type = protein
                        organism = synthetic construct
SEQUENCE: 162
EVQLVQSGAE VKKPGASVKV SCKASGYSFT GYTMNWVRQA PGQGLEWMGL INPYKGVSTY         60
```

```
AQKFQDRVTL TVDKSTSTAY MELSSLRSED TAVYYCARSG YYGESDWYFD VWGQGTLVTV    120
SS                                                                  122

SEQ ID NO: 163          moltype = AA  length = 22
FEATURE                 Location/Qualifiers
REGION                  1..22
                        note = Linker
source                  1..22
                        mol_type = protein
                        organism = synthetic construct
SEQUENCE: 163
GGGGSGGGGS GGGGSGGGGS GT                                            22

SEQ ID NO: 164          moltype = AA  length = 122
FEATURE                 Location/Qualifiers
REGION                  1..122
                        note = UCHT1(21) VH
source                  1..122
                        mol_type = protein
                        organism = synthetic construct
SEQUENCE: 164
EVQLVQSGAE VKKPGASVKV SCKASGYSFT GYTMNWVRQA PGQGLEWMGL INPQKGVSTY    60
AQKFQDRVTL TVDKSTSTAY MELSSLRSED TAVYYCARSG YYGDSDWYFD VWGQGTLVTV    120
SS                                                                  122

SEQ ID NO: 165          moltype = AA  length = 27
FEATURE                 Location/Qualifiers
REGION                  1..27
                        note = Linker
source                  1..27
                        mol_type = protein
                        organism = synthetic construct
SEQUENCE: 165
GGGGSGGGGS GGGGSGGGGS GGGGSGT                                       27

SEQ ID NO: 166          moltype = AA  length = 471
FEATURE                 Location/Qualifiers
REGION                  1..471
                        note = 100(A)-NU(V21)-R7P1D5#114-dsFcKO-GK (VH-beta)
source                  1..471
                        mol_type = protein
                        organism = synthetic construct
SEQUENCE: 166
EVQLVQSGAE VKKPGASVKV SCKASGYSFT GYTMNWVRQA PGQGLEWMGL INPQKGVSTY    60
AQKFQDRVTL TVDKSTSTAY MELSSLRSED TAVYYCARSG YYGDSDWYFD VWGQGTLVTV    120
SSGGGGSGGGG DAGVIQSPRH EVTEMGQEVT LRCKPIPGHD YLFWYRQTMM RGLELLFYFC   180
YGTPCDDSGM PEDRFSAKMP NASFSTLKIQ PSEPRDSAVY FCASRADTGE LFFGEGSRLT    240
VLEPKSSDKT HTCPPCPAPP VAGPSVFLFP PKPKDTLMIS RTPEVTCVVV DVSHEDPEVK    300
FNWYVDGVEV HNAKTKPREE QYQSTYRVVS VLTVLHQDWL NGKEYKCKVS NKALPASIEK    360
TISKAKGQPR EPQVCTLPPS RDELTKNQVS LSCAVKGFYP SDIAVEWESN GQPENNYKTT    420
PPVLDSDGSF FLVSKLTVDK SRWQQGNVFS CSVMHEALHN HYTQKSLSLS P            471

SEQ ID NO: 167          moltype = AA  length = 471
FEATURE                 Location/Qualifiers
REGION                  1..471
                        note = 100(A)-NU(V17opt)-R7P1D5#114-dsFcKO-GK (VH-beta)
source                  1..471
                        mol_type = protein
                        organism = synthetic construct
SEQUENCE: 167
EVQLVQSGAE VKKPGASVKV SCKASGYSFT GYTMNWVRQA PGQGLEWMGL INPYKGVSTY    60
AQKFQDRVTL TVDKSTSTAY MELSSLRSED TAVYYCARSG YYGESDWYFD VWGQGTLVTV    120
SSGGGGSGGGG DAGVIQSPRH EVTEMGQEVT LRCKPIPGHD YLFWYRQTMM RGLELLFYFC   180
YGTPCDDSGM PEDRFSAKMP NASFSTLKIQ PSEPRDSAVY FCASRADTGE LFFGEGSRLT    240
VLEPKSSDKT HTCPPCPAPP VAGPSVFLFP PKPKDTLMIS RTPEVTCVVV DVSHEDPEVK    300
FNWYVDGVEV HNAKTKPREE QYQSTYRVVS VLTVLHQDWL NGKEYKCKVS NKALPASIEK    360
TISKAKGQPR EPQVCTLPPS RDELTKNQVS LSCAVKGFYP SDIAVEWESN GQPENNYKTT    420
PPVLDSDGSF FLVSKLTVDK SRWQQGNVFS CSVMHEALHN HYTQKSLSLS P            471

SEQ ID NO: 168          moltype = AA  length = 9
FEATURE                 Location/Qualifiers
REGION                  1..9
                        note = PRAME-004
source                  1..9
                        mol_type = protein
                        organism = synthetic construct
SEQUENCE: 168
SLLQHLIGL                                                           9
```

```
SEQ ID NO: 169              moltype = AA  length = 461
FEATURE                     Location/Qualifiers
REGION                      1..461
                            note = 100(A)-NU(17)-PRAME-dsFcKO-GK (alpha-VL)
source                      1..461
                            mol_type = protein
                            organism = synthetic construct
SEQUENCE: 169
QKEVEQNSGP LSVPEGAIAS LNCTYSDRGS QSFFWYRQYS GKSPELIMSI YQEGDKEDGR   60
FTAQLNKASQ YVSLLIRDSQ PSDSATYLCA AVIDNDQGGI LTFGTGTRLT IIPNIQNGGG  120
SGGGGDIQMT QSPSSLSASV GDRVTITCRA SQDIRNYLNW YQQKPGKAPK LLIYYTSRLH  180
SGVPSRFSGS GSGTDYTLTI SSLQPEDIAT YFCQQGQTLP WTFGQGTKVE IKEPKSSDKT  240
HTCPPCPAPP VAGPSVFLFP PKPKDTLMIS RTPEVTCVVV DVSHEDPEVK FNWYVDGVEV  300
HNAKTKPREE QYQSTYRVVS VLTVLHQDWL NGKEYKCKVS NKALPASIEK TISKAKGQPR  360
EPQVYTLPPC RDELTKNQVS LWCLVKGFYP SDIAVEWESN GQPENNYKTT PPVLDSDGSF  420
FLYSKLTVDK SRWQQGNVFS CSVMHEALHN HYTQKSLSLS P                     461

SEQ ID NO: 170              moltype = AA  length = 477
FEATURE                     Location/Qualifiers
REGION                      1..477
                            note = 100(A)-NU(17)-PRAME-dsFcKO-GK (VH-beta)
source                      1..477
                            mol_type = protein
                            organism = synthetic construct
SEQUENCE: 170
EVQLVQSGAE VKKPGASVKV SCKASGYSFT GYTMNWVRQA PGQGLEWMGL INPYKGVSTY   60
AQKFQDRVTL TVDKSTSTAY MELSSLRSED TAVYYCARSG YYGDSDWYFD VWGQGTLVTV  120
SSGGGSGGGG KAGVTQTPRY LIKTRGQQVT LSCSPIPGHR AVSWYQQTPG QGLQFLFEYV  180
HGEERNKGNF PGRFSGRQFS NSSSEMNISN LELGDSALYL CASSPWDSPN VQYFGPGTRL  240
TVTEDLKNEP KSSDKTHTCP PCPAPPVAGP SVFLFPPKPK DTLMISRTPE VTCVVVDVSH  300
EDPEVKFNWY VDGVEVHNAK TKPREEQYQS TYRVVSVLTV LHQDWLNGKE YKCKVSNKAL  360
PASIEKTISK AKGQPREPQV CTLPPSRDEL TKNQVSLSCA VKGFYPSDIA VEWESNGQPE  420
NNYKTTPPVL DSDGSFFLVS KLTVDKSRWQ QGNVFSCSVM HEALHNHYTQ KSLSLSP    477

SEQ ID NO: 171              moltype = AA  length = 9
FEATURE                     Location/Qualifiers
source                      1..9
                            mol_type = protein
                            organism = Homo sapiens
SEQUENCE: 171
KLLDLMPRL                                                           9

SEQ ID NO: 172              moltype = AA  length = 9
FEATURE                     Location/Qualifiers
source                      1..9
                            mol_type = protein
                            organism = Homo sapiens
SEQUENCE: 172
KLLSYIQRL                                                           9

SEQ ID NO: 173              moltype = AA  length = 9
FEATURE                     Location/Qualifiers
source                      1..9
                            mol_type = protein
                            organism = Homo sapiens
SEQUENCE: 173
SIIGRLLEV                                                           9

SEQ ID NO: 174              moltype = AA  length = 9
FEATURE                     Location/Qualifiers
source                      1..9
                            mol_type = protein
                            organism = Homo sapiens
SEQUENCE: 174
KIYEGQVEV                                                           9

SEQ ID NO: 175              moltype = AA  length = 9
FEATURE                     Location/Qualifiers
source                      1..9
                            mol_type = protein
                            organism = Homo sapiens
SEQUENCE: 175
ILLEHNYAL                                                           9

SEQ ID NO: 176              moltype = AA  length = 9
FEATURE                     Location/Qualifiers
source                      1..9
                            mol_type = protein
                            organism = Homo sapiens
```

```
SEQUENCE: 176
ALSNLEVKL                                                                       9

SEQ ID NO: 177          moltype = AA  length = 9
FEATURE                 Location/Qualifiers
source                  1..9
                        mol_type = protein
                        organism = Homo sapiens
SEQUENCE: 177
LLDVPTAAV                                                                       9

SEQ ID NO: 178          moltype = AA  length = 9
FEATURE                 Location/Qualifiers
source                  1..9
                        mol_type = protein
                        organism = Homo sapiens
SEQUENCE: 178
ILDQKINEV                                                                       9

SEQ ID NO: 179          moltype = AA  length = 9
FEATURE                 Location/Qualifiers
source                  1..9
                        mol_type = protein
                        organism = Homo sapiens
SEQUENCE: 179
KLLPYIVGV                                                                       9

SEQ ID NO: 180          moltype = AA  length = 9
FEATURE                 Location/Qualifiers
source                  1..9
                        mol_type = protein
                        organism = Homo sapiens
SEQUENCE: 180
KLGSVPVTV                                                                       9

SEQ ID NO: 181          moltype = AA  length = 9
FEATURE                 Location/Qualifiers
source                  1..9
                        mol_type = protein
                        organism = Homo sapiens
SEQUENCE: 181
KLFGHLTSA                                                                       9

SEQ ID NO: 182          moltype = AA  length = 9
FEATURE                 Location/Qualifiers
source                  1..9
                        mol_type = protein
                        organism = Homo sapiens
SEQUENCE: 182
KTLSAILRI                                                                       9
```

What is claimed is:

1. A protein that binds both (a) a complex of MAGE-A and human major histocompatibility complex (MHC) protein and (b) a TCRαβ, wherein said protein comprises
    (a) a first polypeptide comprising
        an amino acid sequence that is at least 98% identical to SEQ ID NO: 136 comprising (1) a beta variable (Vβ) domain comprising
            (i) a CDR1 comprising the amino acid sequence of SEQ ID NO: 62,
            (ii) a CDR2 comprising the amino acid sequence of SEQ ID NO: 65, and
            (iii) a CDR3 comprising the amino acid sequence of SEQ ID NO: 71; and
        (2) an antibody light chain variable (VL) domain comprising the amino acid sequence of SEQ ID NO: 159; and
    (b) a second polypeptide comprising
        an amino acid sequence that is at least 98% identical to SEQ ID NO: 137 comprising (1) an alpha variable (Vα) domain comprising
            (i) a CDR1 comprising the amino acid sequence of SEQ ID NO: 5,
            (ii) a CDR2 comprising the amino acid sequence of SEQ ID NO: 56, and
            (iii) a CDR3 comprising the amino acid sequence of SEQ ID NO: 35, and
        (2) an antibody heavy chain variable (VH) domain comprising the amino acid sequence of SEQ ID NO: 160; and wherein
    the Vα and the Vβ form a binding site that binds to the MAGE-A/MHC complex and the VL and VH form a binding site that binds to the TCRαβ.

2. The protein of claim 1, wherein the first polypeptide comprises an amino acid sequence that is at least 99% identical to SEQ ID NO: 136 and the second polypeptide comprises an amino acid sequence that is at least 99% identical to SEQ ID NO: 137.

3. A pharmaceutical composition comprising the protein of claim 1 and a pharmaceutically acceptable carrier, diluent, stabilizer, and/or excipient.

4. A pharmaceutical composition comprising the protein of claim 1, wherein the protein is dissolved or dispersed in a pharmaceutically acceptable carrier or aqueous medium.

5. The protein of claim 1, wherein the Vβ domain comprises an amino acid sequence that is at least 98% identical to the amino acid sequence of SEQ ID NO: 150 and the Vα domain comprises an amino acid sequence that is at least 98% identical to the amino acid sequence of SEQ ID NO: 151.

6. The protein of claim 1, wherein the Vβ domain comprises an amino acid sequence that is at least 99% identical to the amino acid sequence of SEQ ID NO: 150 and the Vα domain comprises an amino acid sequence that is at least 99% identical to the amino acid sequence of SEQ ID NO: 151.

7. The protein of claim 1, wherein the Vβ domain comprises the amino acid sequence of SEQ ID NO: 150 and the Vα domain comprises the amino acid sequence of SEQ ID NO: 151.

8. The protein of claim 1, wherein the first polypeptide comprises an N-linked glycosylation at residue 185 of SEQ ID NO: 136 and/or the second polypeptide comprises an N-linked glycosylation at residue 20 of SEQ ID NO: 137.

* * * * *